US011612661B2

(12) United States Patent
Mercado et al.

(10) Patent No.: US 11,612,661 B2
(45) Date of Patent: Mar. 28, 2023

(54) CONOTOXIN PEPTIDE ANALOGS AND USES FOR THE TREATMENT OF PAIN AND INFLAMMATORY CONDITIONS

(71) Applicant: Kineta Chronic Pain, LLC, Seattle, WA (US)

(72) Inventors: Jose Mercado, Seattle, WA (US); Eric J. Tarcha, Sammamish, WA (US); Jeffrey J. Posakony, Seattle, WA (US); Shawn Iadonato, Seattle, WA (US)

(73) Assignee: Kineta Chronic Pain, LLC, Seattle, WA (US)

( * ) Notice: Subject to any disclaimer, the term of this patent is extended or adjusted under 35 U.S.C. 154(b) by 0 days.

(21) Appl. No.: 16/734,151

(22) Filed: Jan. 3, 2020

(65) Prior Publication Data

US 2020/0237924 A1 Jul. 30, 2020

Related U.S. Application Data

(60) Provisional application No. 62/788,559, filed on Jan. 4, 2019.

(51) Int. Cl.

| | |
|---|---|
| ***A61K 38/00*** | (2006.01) |
| ***A61K 47/60*** | (2017.01) |
| ***A61P 25/02*** | (2006.01) |
| ***C07K 7/08*** | (2006.01) |

(52) U.S. Cl.

CPC .............. *A61K 47/60* (2017.08); *A61P 25/02* (2018.01); *C07K 7/08* (2013.01); *A61K 38/00* (2013.01)

(58) Field of Classification Search

CPC ......... A61K 38/00; A61K 47/60; A61P 25/02; C07K 7/08; C07K 14/43504

See application file for complete search history.

(56) References Cited

U.S. PATENT DOCUMENTS

| | | | |
|---|---|---|---|
| 11,014,970 | B2 | 5/2021 | Posakony |
| 2010/0022749 | A1 | 1/2010 | Robinson et al. |
| 2011/0195909 | A1 | 8/2011 | Lewis et al. |
| 2012/0190827 | A1 | 7/2012 | Sheffer et al. |
| 2012/0220539 | A1 | 8/2012 | McIntosh et al. |
| 2014/0323701 | A1 | 10/2014 | Nash et al. |
| 2018/0362599 | A1 | 12/2018 | Posakony et al. |

FOREIGN PATENT DOCUMENTS

| | | | | | |
|---|---|---|---|---|---|
| WO | WO 2008011006 | A2 | | 1/2008 | |
| WO | WO 2009126292 | A2 | | 10/2009 | |
| WO | WO 2014194284 | A1 | | 12/2014 | |
| WO | WO-2016073949 | A1 | * | 5/2016 | ............ A61K 47/60 |
| WO | WO 2016073949 | A1 | | 5/2016 | |

OTHER PUBLICATIONS

Baker et al. Bioconjugate Chem. 2006, 17, 179-188. N-Terminally PEGylated Human Interferon-â-1a with Improved Pharmacokinetic Properties and in Vivo Efficacy in a Melanoma Angiogenesis Model (Year: 2006).*

Zhao et al. Mar Drugs. Jun. 2019; 17(6): 342. DSPE-PEG Modification of α-Conotoxin TxID (Year: 2019).*

Bailon et al. PEG-modifi ed biopharmaceuticals. Expert Opin. Drug Deliv. (2009) 6(1) (Year: 2009).*

Chhabra et al., 2014, "Dicarbo Analogues of α-Conotoxin RgIA Structure, Stability, and Activity at Potential Pain Targets," Journal of Medicial Chemsitry, 57(23):9933-9944.

Amendments filed in European Application No. 15856496.3 dated Jan. 8, 2018, 401 pages.

Ellsion et al., 2006, "α-RgIA: A Novel Conotoxin That Specifically and Potently Blocks the α9α10 nAChR," Biochemistry, 45(5):1511-1517.

Gori et al., 2015, "Stabilization of the Cysteine-Rich Conotoxin MrIA by Using a 1,2,3-Triazole as a Disulfide Bond Mimetic," Angew. Chem. Int. Ed., 54(4):1361-1364.

Hargittai et al., 2000, "Chemical Syntheses and Biological Activities of Lactam Analogues of α-Conotoxin SI," Journal of Medicinal Chemistry, 43(25):4787-4792.

Harris, et al., 2003, "Effect of Pegylation on Pharmaceuticals," Nature Reviews Drug Discovery, 2(3):214-221.

Holland-Nell et al., 2011, "Maintaining Biological Activity by Using Triazoles as Disulfide Bond Mimetics," Angew. Chem. Int. Ed., 50(22):5204-5206.

International Search Report and Written Opinion of corresponding Interantional Patent Application No. PCT/US2019/012307 dated Sep. 24, 2019 (17 pages).

Kowalczyk, et al., 2012, "Synthesis and evaluation of disulfide bond mimetics of amylin-(1-8) as agents to treat osteoporosis," Bioorg. Med. Chem., 20:2661-2668.

Pasut et al., 2012, "State of the art in PEGylation: The great versatility, achieved after forty years of research," Journal of Controlled Release, 161(2):461-472.

Romero et al, 2017, "Inhibition of α9α10 nicotinic acetylcholine receptors prevents chemotherapy-induced neuropathic pain," Proc. Natl. Acad. Sci., 114(10):E1825-E1832.

Veronese et al., 2005, "PEGylation, successful approach to drug delivery," Drug Discovery Today 10(21):1451-1458.

(Continued)

*Primary Examiner* — Aradhana Sasan
*Assistant Examiner* — Mercy H Sabila
(74) *Attorney, Agent, or Firm* — McCarter & English, LLP; Marcie B. Clarke

(57) ABSTRACT

Provided herein are alpha-conotoxin peptide analogs, including alpha-conotoxin peptide analogs that are covalently attached to polyethylene glycol (PEG), and pharmaceutical compositions of such alpha-conotoxin peptide analogs. Also provided herein are methods of treating or preventing a condition conducive to treatment or prevention by inhibition of an α9-containing nicotinic acetylcholine receptor (nAChR) (e.g., the α9α10 subtype of the nAChR) in a subject.

28 Claims, 17 Drawing Sheets

Figure 1A:
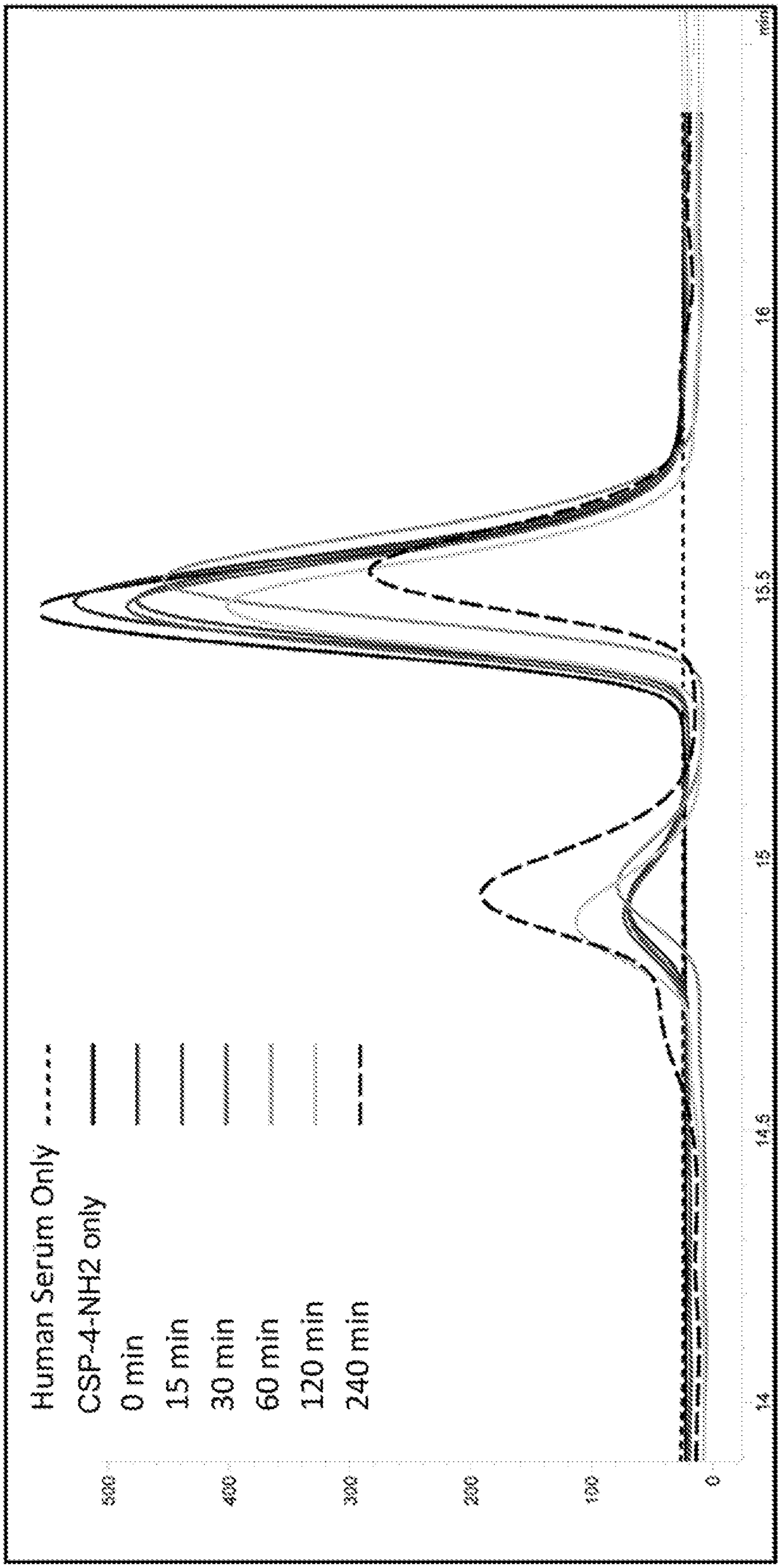

Specification includes a Sequence Listing.

(56) References Cited

OTHER PUBLICATIONS

Vincler et al, 2006, "Molecular Mechanism for Analgesia Involving Specific Antagonism of α9α10 Nicotinic Acetylcholine Receptors," Proc. Natl. Acad. Sci., 103(47):17880-17884.

Fishburn, 2008, "The Pharmacology of PEGylation: Balancing PD with PK to Generate Novel Therapeutics," Journal of Pharmaceutical Sciences, 97(10):4167-4183.

Harris et al., 2001, "Pegylation, A Novel Process for Modifying Pharmacokinetics," Clinical Pharmacokinetics, 40(7):539-551.

Parrott et al., 2011, "Drug delivery: Relieving PEGylation," Nature Chemistry, 4(1):13-14.

Kasheverov et al., "Rational Design of New Ligands for Nicotinic Receptors on the Basis of α Conotoxin PnIA," Biochemishy, Biophysics and Molecular Biology, 2015, 461(4):476-479 (in Russian).

Leipold et al., Molecular interaction of delta-conotoxins with voltage-gated sodium channels. FEBS Lett. Jul. 18, 2005;579(18):3881-4.

Li et al., Using the deadly mu-conotoxins as probes of voltage-gated sodium channels. Toxicon. Aug. 2004;44(2):117-22.

Lu et al., Linkers Having a Crucial Role in Antibody-Drug Conjugates. Int J Mol Sci. Apr. 14, 2016;17(4):561.

Nicke et al., Alpha-conotoxins as tools for the elucidation of structure and function of neuronal nicotinic acetylcholine receptor subtypes. Eur J Biochem Jun. 2004;271(12):2305-19.

Nielsen et al., Structure-activity relationships of omega-conotoxins at N-type voltage-sensitive calcium channels. J Mol Recognit. Mar.-Apr. 2000;13(2):55-70.

Paukov et al., Pathology. Chapter 6: Inflammation. General Characteristics of Inflammation. 1989. pp. 98-105.

Shon et al., kappa-Conotoxin PVIIA is a peptide inhibiting the shaker K+ channel. J Biol Chem. Jan. 2, 1998;273(1):33-8.

Treetharnmathurot et al., Effect of PEG molecular weight and linking chemistry on the biological activity and thermal stability of PEGylated trypsin. Int J Pharm. Jun. 5, 2008;357(1-2):252-9.

Russian Office Action for Application No. 2021123047, dated Oct. 31, 2022, 21 pages.

* cited by examiner

SEQUENCE LISTING

<160> NUMBER OF SEQ ID NOS: 107

<210> SEQ ID NO 1
<211> LENGTH: 13
<212> TYPE: PRT
<213> ORGANISM: Conus regius
<220> FEATURE:
<223> OTHER INFORMATION: native RgIA

<400> SEQUENCE: 1

Gly Cys Cys Ser Asp Pro Arg Cys Arg Tyr Arg Cys Arg
1               5                   10

<210> SEQ ID NO 2
<211> LENGTH: 12
<212> TYPE: PRT
<213> ORGANISM: Conus regius
<220> FEATURE:
<223> OTHER INFORMATION: native ImI

<400> SEQUENCE: 2

Gly Cys Cys Ser Asp Pro Arg Cys Ala Trp Arg Cys
1               5                   10

<210> SEQ ID NO 3
<211> LENGTH: 15
<212> TYPE: PRT
<213> ORGANISM: Conus regius
<220> FEATURE:
<223> OTHER INFORMATION: Vc1.1

<400> SEQUENCE: 3

Gly Cys Cys Ser Asp Pro Arg Cys Asn Tyr Asp His Pro Glu Ile
1 5 10 15

<210> SEQ ID NO 4
<211> LENGTH: 13
<212> TYPE: PRT
<213> ORGANISM: Artificial Sequence
<220> FEATURE:
<223> OTHER INFORMATION: CSP-4-OH
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr

<400> SEQUENCE: 4

Gly Cys Cys Thr Asp Pro Arg Cys Xaa Xaa Gln Cys Tyr
1 5 10

<210> SEQ ID NO 5
<211> LENGTH: 12
<212> TYPE: PRT
<213> ORGANISM: Artificial Sequence
<220> FEATURE:
<223> OTHER INFORMATION: CSP-4-desTyr-OH
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr

<400> SEQUENCE: 5

Gly Cys Cys Thr Asp Pro Arg Cys Xaa Xaa Gln Cys
1 5 10

<210> SEQ ID NO 6
<211> LENGTH: 13
<212> TYPE: PRT
<213> ORGANISM: Artificial Sequence
<220> FEATURE:
<223> OTHER INFORMATION: Conotoxin peptide analog Ia
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 6

Gly Cys Xaa Thr Asp Pro Arg Cys Xaa Trp Gln Xaa Tyr
1 5 10

<210> SEQ ID NO 7
<211> LENGTH: 13
<212> TYPE: PRT
<213> ORGANISM: Artificial Sequence
<220> FEATURE:
<223> OTHER INFORMATION: Compound 3
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 7

Gly Cys Xaa Thr Asp Pro Arg Cys Xaa Trp Gln Xaa Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Compound 4
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 8

Gly Cys Xaa Thr Asp Pro Arg Cys Xaa Trp Gln Xaa Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Conotoxin peptide analog Ia'
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
      (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: AMIDATION

<400> SEQUENCE: 9

Gly Cys Xaa Thr Asp Pro Arg Cys Xaa Trp Gln Xaa Tyr
1 5 10

<210> SEQ ID NO 10
<211> LENGTH: 13
<212> TYPE: PRT
<213> ORGANISM: Artificial Sequence
<220> FEATURE:
<223> OTHER INFORMATION: Intermediate conotoxin peptide analog Ya'
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: AMIDATION

<400> SEQUENCE: 10

Gly Cys Xaa Thr Asp Pro Arg Cys Xaa Trp Gln Xaa Tyr
1 5 10

<210> SEQ ID NO 11
<211> LENGTH: 13
<212> TYPE: PRT
<213> ORGANISM: Artificial Sequence
<220> FEATURE:
<223> OTHER INFORMATION: Intermediate conotoxin peptide analog Za'
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: AMIDATION

<400> SEQUENCE: 11

Gly Cys Xaa Thr Asp Pro Arg Cys Xaa Trp Gln Xaa Tyr
1 5 10

<210> SEQ ID NO 12
<211> LENGTH: 13
<212> TYPE: PRT
<213> ORGANISM: Artificial Sequence
<220> FEATURE:

<223> OTHER INFORMATION: Conotoxin peptide analog Ib
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 12

```
Gly Cys Xaa Thr Asp Pro Arg Cys Xaa Xaa Gln Xaa Tyr
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Intermediate conotoxin peptide analog Yb
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 13

```
Gly Cys Xaa Thr Asp Pro Arg Cys Xaa Xaa Gln Xaa Tyr
1               5                   10
```

<210> SEQ ID NO 14
<211> LENGTH: 13
<212> TYPE: PRT
<213> ORGANISM: Artificial Sequence
<220> FEATURE:
<223> OTHER INFORMATION: Intermediate conotoxin peptide analog Zb
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:

<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 14

Gly Cys Xaa Thr Asp Pro Arg Cys Xaa Xaa Gln Xaa Tyr
1 5 10

<210> SEQ ID NO 15
<211> LENGTH: 13
<212> TYPE: PRT
<213> ORGANISM: Artificial Sequence
<220> FEATURE:
<223> OTHER INFORMATION: Conotoxin peptide analog Ib'
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: AMIDATION

<400> SEQUENCE: 15

Gly Cys Xaa Thr Asp Pro Arg Cys Xaa Xaa Gln Xaa Tyr
1 5 10

<210> SEQ ID NO 16
<211> LENGTH: 13
<212> TYPE: PRT
<213> ORGANISM: Artificial Sequence
<220> FEATURE:
<223> OTHER INFORMATION: Intermediate conotoxin peptide analog Yb'
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES

<222> LOCATION: (13)..(13)
<223> OTHER INFORMATION: AMIDATION

<400> SEQUENCE: 16

Gly Cys Xaa Thr Asp Pro Arg Cys Xaa Xaa Gln Xaa Tyr
1 5 10

<210> SEQ ID NO 17
<211> LENGTH: 13
<212> TYPE: PRT
<213> ORGANISM: Artificial Sequence
<220> FEATURE:
<223> OTHER INFORMATION: Intermediate conotoxin peptide analog Zb'
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: AMIDATION

<400> SEQUENCE: 17

Gly Cys Xaa Thr Asp Pro Arg Cys Xaa Xaa Gln Xaa Tyr
1 5 10

<210> SEQ ID NO 18
<211> LENGTH: 13
<212> TYPE: PRT
<213> ORGANISM: Artificial Sequence
<220> FEATURE:
<223> OTHER INFORMATION: Conotoxin peptide analog Ic
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: (S)-Propargyl glycine at position 2 and
(S)-5-azidonorvaline at position 8 form a triazole bridge
<220> FEATURE:
<221> NAME/KEY: MOD_RES
<222> LOCATION: (2)..(2)
<223> OTHER INFORMATION: Xaa = (S)-propargyl glycine
<220> FEATURE:
<221> NAME/KEY: MOD_RES
<222> LOCATION: (8)..(8)
<223> OTHER INFORMATION: Xaa = (S)-5-azidonorvaline
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 18

Gly Xaa Cys Thr Asp Pro Arg Xaa Xaa Xaa Gln Cys Tyr
1 5 10

<210> SEQ ID NO 19
<211> LENGTH: 13
<212> TYPE: PRT
<213> ORGANISM: Artificial Sequence
<220> FEATURE:
<223> OTHER INFORMATION: Intermediate conotoxin peptide analog Yc
<220> FEATURE:
<221> NAME/KEY: MOD_RES
<222> LOCATION: (2)..(2)
<223> OTHER INFORMATION: Xaa = (S)-propargyl glycine
<220> FEATURE:
<221> NAME/KEY: MOD_RES
<222> LOCATION: (8)..(8)
<223> OTHER INFORMATION: Xaa = (S)-5-azidonorvaline
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 19

Gly Xaa Cys Thr Asp Pro Arg Xaa Xaa Xaa Gln Cys Tyr
1 5 10

<210> SEQ ID NO 20
<211> LENGTH: 13
<212> TYPE: PRT
<213> ORGANISM: Artificial Sequence
<220> FEATURE:
<223> OTHER INFORMATION: Intermediate conotoxin peptide analog Zc
<220> FEATURE:
<221> NAME/KEY: DISULFID
<222> LOCATION: (3)..(12)
<220> FEATURE:
<221> NAME/KEY: MOD_RES
<222> LOCATION: (2)..(2)
<223> OTHER INFORMATION: Xaa = (S)-propargyl glycine
<220> FEATURE:
<221> NAME/KEY: MOD_RES
<222> LOCATION: (8)..(8)
<223> OTHER INFORMATION: Xaa = (S)-5-azidonorvaline
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 20

Gly Xaa Cys Thr Asp Pro Arg Xaa Xaa Xaa Gln Cys Tyr
1 5 10

<210> SEQ ID NO 21
<211> LENGTH: 13
<212> TYPE: PRT

```
<213> ORGANISM: Artificial Sequence
<220> FEATURE:
<223> OTHER INFORMATION: Conotoxin peptide analog Id
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: (S)-5-Azidonorvaline at position 2 and
      (S)-propargyl glycine at position 8 form a triazole bridge
<220> FEATURE:
<221> NAME/KEY: MOD_RES
<222> LOCATION: (2)..(2)
<223> OTHER INFORMATION: Xaa = (S)-5-azidonorvaline
<220> FEATURE:
<221> NAME/KEY: MOD_RES
<222> LOCATION: (8)..(8)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 21

Gly Xaa Cys Thr Asp Pro Arg Xaa Xaa Xaa Gln Cys Tyr
1               5                   10


<210> SEQ ID NO 22
<211> LENGTH: 13
<212> TYPE: PRT
<213> ORGANISM: Artificial Sequence
<220> FEATURE:
<223> OTHER INFORMATION: Intermediate conotoxin peptide analog Yd
<220> FEATURE:
<221> NAME/KEY: MOD_RES
<222> LOCATION: (2)..(2)
<223> OTHER INFORMATION: Xaa = (S)-5-azidonorvaline
<220> FEATURE:
<221> NAME/KEY: MOD_RES
<222> LOCATION: (8)..(8)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 22

Gly Xaa Cys Thr Asp Pro Arg Xaa Xaa Xaa Gln Cys Tyr
1               5                   10


<210> SEQ ID NO 23
<211> LENGTH: 13
<212> TYPE: PRT
<213> ORGANISM: Artificial Sequence
<220> FEATURE:
<223> OTHER INFORMATION: Intermediate conotoxin peptide analog Zd
<220> FEATURE:
<221> NAME/KEY: DISULFID
```

```
<222> LOCATION: (3)..(12)
<220> FEATURE:
<221> NAME/KEY: MOD_RES
<222> LOCATION: (2)..(2)
<223> OTHER INFORMATION: Xaa = (S)-5-azidonorvaline
<220> FEATURE:
<221> NAME/KEY: MOD_RES
<222> LOCATION: (8)..(8)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 23

Gly Xaa Cys Thr Asp Pro Arg Xaa Xaa Xaa Gln Cys Tyr
1               5                   10


<210> SEQ ID NO 24
<211> LENGTH: 13
<212> TYPE: PRT
<213> ORGANISM: Artificial Sequence
<220> FEATURE:
<223> OTHER INFORMATION: Conotoxin peptide analog Ie
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-5-Azidonorvaline at position 3 and
      (S)-propargyl glycine at position 12 form a triazole bridge
<220> FEATURE:
<221> NAME/KEY: MOD_RES
<222> LOCATION: (3)..(3)
<223> OTHER INFORMATION: Xaa = (S)-5-azidonorvaline
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-propargyl glycine
<220> FEATURE:
<221> NAME/KEY: MOD_RES
<222> LOCATION: (13)..(13)
<223> OTHER INFORMATION: AMIDATION

<400> SEQUENCE: 24

Gly Cys Xaa Thr Asp Pro Arg Cys Xaa Xaa Gln Xaa Tyr
1               5                   10


<210> SEQ ID NO 25
<211> LENGTH: 13
<212> TYPE: PRT
<213> ORGANISM: Artificial Sequence
<220> FEATURE:
<223> OTHER INFORMATION: Intermediate conotoxin peptide analog Ye
<220> FEATURE:
<221> NAME/KEY: MOD_RES
<222> LOCATION: (3)..(3)
<223> OTHER INFORMATION: Xaa = (S)-5-azidonorvaline
```

<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-propargyl glycine
<220> FEATURE:
<221> NAME/KEY: MOD_RES
<222> LOCATION: (13)..(13)
<223> OTHER INFORMATION: AMIDATION

<400> SEQUENCE: 25

Gly Cys Xaa Thr Asp Pro Arg Cys Xaa Xaa Gln Xaa Tyr
1 5 10

<210> SEQ ID NO 26
<211> LENGTH: 13
<212> TYPE: PRT
<213> ORGANISM: Artificial Sequence
<220> FEATURE:
<223> OTHER INFORMATION: Intermediate conotoxin peptide analog Ze
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-5-azidonorvaline
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-propargyl glycine
<220> FEATURE:
<221> NAME/KEY: MOD_RES
<222> LOCATION: (13)..(13)
<223> OTHER INFORMATION: AMIDATION

<400> SEQUENCE: 26

Gly Cys Xaa Thr Asp Pro Arg Cys Xaa Xaa Gln Xaa Tyr
1 5 10

<210> SEQ ID NO 27
<211> LENGTH: 13
<212> TYPE: PRT
<213> ORGANISM: Artificial Sequence
<220> FEATURE:
<223> OTHER INFORMATION: Conotoxin peptide analog If
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-3-azido-alanine at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-3-azido-alanine
<220> FEATURE:
<221> NAME/KEY: MOD_RES
<222> LOCATION: (13)..(13)
<223> OTHER INFORMATION: AMIDATION

<400> SEQUENCE: 27

Gly Cys Xaa Thr Asp Pro Arg Cys Xaa Xaa Gln Xaa Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Intermediate conotoxin peptide analog Yf
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-3-azido-alanine
<220> FEATURE:
<221> NAME/KEY: MOD_RES
<222> LOCATION: (13)..(13)
<223> OTHER INFORMATION: AMIDATION

<400> SEQUENCE: 28

Gly Cys Xaa Thr Asp Pro Arg Cys Xaa Xaa Gln Xaa Tyr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Intermediate conotoxin peptide analog Zf
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-3-azido-alanine
<220> FEATURE:
<221> NAME/KEY: MOD_RES
<222> LOCATION: (13)..(13)
<223> OTHER INFORMATION: AMIDATION

<400> SEQUENCE: 29

Gly Cys Xaa Thr Asp Pro Arg Cys Xaa Xaa Gln Xaa Tyr
1 5 10

<210> SEQ ID NO 30
<211> LENGTH: 13
<212> TYPE: PRT
<213> ORGANISM: Artificial Sequence
<220> FEATURE:
<223> OTHER INFORMATION: Conotoxin peptide analog Ig
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Homopropargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 30

Gly Cys Xaa Thr Asp Pro Arg Cys Xaa Trp Gln Xaa Tyr
1 5 10

<210> SEQ ID NO 31
<211> LENGTH: 13
<212> TYPE: PRT
<213> ORGANISM: Artificial Sequence
<220> FEATURE:
<223> OTHER INFORMATION: Intermediate conotoxin peptide analog Yg
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 31

Gly Cys Xaa Thr Asp Pro Arg Cys Xaa Trp Gln Xaa Tyr
1 5 10

<210> SEQ ID NO 32
<211> LENGTH: 13
<212> TYPE: PRT
<213> ORGANISM: Artificial Sequence
<220> FEATURE:
<223> OTHER INFORMATION: Intermediate conotoxin peptide analog Zg
<220> FEATURE:
<221> NAME/KEY: DISULFID
<222> LOCATION: (2)..(8)
<220> FEATURE:

<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 32

Gly Cys Xaa Thr Asp Pro Arg Cys Xaa Trp Gln Xaa Tyr
1 5 10

<210> SEQ ID NO 33
<211> LENGTH: 13
<212> TYPE: PRT
<213> ORGANISM: Artificial Sequence
<220> FEATURE:
<223> OTHER INFORMATION: Conotoxin peptide analog Ih
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Homopropargyl glycine at position 3 and (S)-gamma-azido-homoalanine at position 12 form a triazole bridge
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-gamma-azido-homoalanine

<400> SEQUENCE: 33

Gly Cys Xaa Thr Asp Pro Arg Cys Xaa Trp Gln Xaa Tyr
1 5 10

<210> SEQ ID NO 34
<211> LENGTH: 13
<212> TYPE: PRT
<213> ORGANISM: Artificial Sequence
<220> FEATURE:
<223> OTHER INFORMATION: Intermediate conotoxin peptide analog Yh
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-gamma-azido-homoalanine

<400> SEQUENCE: 34

Gly Cys Xaa Thr Asp Pro Arg Cys Xaa Trp Gln Xaa Tyr
1 5 10

<210> SEQ ID NO 35
<211> LENGTH: 13
<212> TYPE: PRT

<213> ORGANISM: Artificial Sequence
<220> FEATURE:
<223> OTHER INFORMATION: Intermediate conotoxin peptide analog Zh
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-gamma-azido-homoalanine

<400> SEQUENCE: 35

Gly Cys Xaa Thr Asp Pro Arg Cys Xaa Trp Gln Xaa Tyr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Conotoxin peptide analog Ii
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Gamma-azido-homoalanine at position 3 and
      (S)-homopropargyl glycine at position 12 form a triazole bridge
<220> FEATURE:
<221> NAME/KEY: MOD_RES
<222> LOCATION: (3)..(3)
<223> OTHER INFORMATION: Xaa = (S)-gamma-azido-homoalanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-homopropargyl glycine

<400> SEQUENCE: 36

Gly Cys Xaa Thr Asp Pro Arg Cys Xaa Trp Gln Xaa Tyr
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Intermediate conotoxin peptide analog Yi
<220> FEATURE:
<221> NAME/KEY: MOD_RES
<222> LOCATION: (3)..(3)
<223> OTHER INFORMATION: Xaa = (S)-gamma-azido-homoalanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-homopropargyl glycine

<400> SEQUENCE: 37

```
Gly Cys Xaa Thr Asp Pro Arg Cys Xaa Trp Gln Xaa Tyr
1               5                   10


<210> SEQ ID NO 38
<211> LENGTH: 13
<212> TYPE: PRT
<213> ORGANISM: Artificial Sequence
<220> FEATURE:
<223> OTHER INFORMATION: Intermediate conotoxin peptide analog Zi
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-gamma-azido-homoalanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-homopropargyl glycine

<400> SEQUENCE: 38

Gly Cys Xaa Thr Asp Pro Arg Cys Xaa Trp Gln Xaa Tyr
1               5                   10


<210> SEQ ID NO 39
<211> LENGTH: 13
<212> TYPE: PRT
<213> ORGANISM: Artificial Sequence
<220> FEATURE:
<223> OTHER INFORMATION: Conotoxin peptide analog Ij
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Bis-homopropargyl glycine at position 3 and
      (S)-3-azido-alanine at position 12 form a triazole bridge
<220> FEATURE:
<221> NAME/KEY: MOD_RES
<222> LOCATION: (3)..(3)
<223> OTHER INFORMATION: Xaa = (S)-bis-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-3-azido-alanine

<400> SEQUENCE: 39

Gly Cys Xaa Thr Asp Pro Arg Cys Xaa Trp Gln Xaa Tyr
1               5                   10


<210> SEQ ID NO 40
<211> LENGTH: 13
<212> TYPE: PRT
<213> ORGANISM: Artificial Sequence
<220> FEATURE:
<223> OTHER INFORMATION: Intermediate conotoxin peptide analog Yj
<220> FEATURE:
<221> NAME/KEY: MOD_RES
<222> LOCATION: (3)..(3)
<223> OTHER INFORMATION: Xaa = (S)-bis-homopropargyl glycine
<220> FEATURE:
<221> NAME/KEY: MOD_RES
<222> LOCATION: (9)..(9)
<223> OTHER INFORMATION: Xaa = Citrulline
```

<220> FEATURE:
<221> NAME/KEY: MOD_RES
<222> LOCATION: (12)..(12)
<223> OTHER INFORMATION: Xaa = (S)-3-azido-alanine

<400> SEQUENCE: 40

Gly Cys Xaa Thr Asp Pro Arg Cys Xaa Trp Gln Xaa Tyr
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Intermediate conotoxin peptide analog Zj
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-bis-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-3-azido-alanine

<400> SEQUENCE: 41

Gly Cys Xaa Thr Asp Pro Arg Cys Xaa Trp Gln Xaa Tyr
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Conotoxin peptide analog Ik
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-3-Azido-alanine at position 3 and (S)-bis-
homopropargyl glycine at position 12 form a triazole bridge
<220> FEATURE:
<221> NAME/KEY: MOD_RES
<222> LOCATION: (3)..(3)
<223> OTHER INFORMATION: Xaa = (S)-3-azido-alanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-bis-homopropargyl glycine

<400> SEQUENCE: 42

Gly Cys Xaa Thr Asp Pro Arg Cys Xaa Trp Gln Xaa Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Intermediate conotoxin peptide analog Yk
<220> FEATURE:

-continued

<221> NAME/KEY: MOD_RES
<222> LOCATION: (3)..(3)
<223> OTHER INFORMATION: Xaa = (S)-3-azido-alanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-bis-homopropargyl glycine

<400> SEQUENCE: 43

Gly Cys Xaa Thr Asp Pro Arg Cys Xaa Trp Gln Xaa Tyr
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Intermediate conotoxin peptide analog Zk
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-3-azido-alanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-bis-homopropargyl glycine

<400> SEQUENCE: 44

Gly Cys Xaa Thr Asp Pro Arg Cys Xaa Trp Gln Xaa Tyr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Conotoxin peptide analog Il
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 45

Gly Cys Xaa Thr Asp Pro Arg Cys Xaa Trp Gln Xaa Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Intermediate conotoxin peptide analog Y1
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 46

Gly Cys Xaa Thr Asp Pro Arg Cys Xaa Trp Gln Xaa Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Intermediate conotoxin peptide analog Z1
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 47

Gly Cys Xaa Thr Asp Pro Arg Cys Xaa Trp Gln Xaa Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Conotoxin peptide analog Im
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

```
<220> FEATURE:
<221> NAME/KEY: MOD_RES
<222> LOCATION: (13)..(13)
<223> OTHER INFORMATION: Xaa = D-Tyr

<400> SEQUENCE: 48

Gly Cys Xaa Thr Asp Pro Arg Cys Xaa Trp Gln Xaa Xaa
1               5                   10


<210> SEQ ID NO 49
<211> LENGTH: 13
<212> TYPE: PRT
<213> ORGANISM: Artificial Sequence
<220> FEATURE:
<223> OTHER INFORMATION: Intermediate conotoxin peptide analog Ym
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Tyr

<400> SEQUENCE: 49

Gly Cys Xaa Thr Asp Pro Arg Cys Xaa Trp Gln Xaa Xaa
1               5                   10


<210> SEQ ID NO 50
<211> LENGTH: 13
<212> TYPE: PRT
<213> ORGANISM: Artificial Sequence
<220> FEATURE:
<223> OTHER INFORMATION: Intermediate conotoxin peptide analog Zm
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Tyr

<400> SEQUENCE: 50

Gly Cys Xaa Thr Asp Pro Arg Cys Xaa Trp Gln Xaa Xaa
1               5                   10


<210> SEQ ID NO 51
<211> LENGTH: 14
<212> TYPE: PRT
<213> ORGANISM: Artificial Sequence
<220> FEATURE:
<223> OTHER INFORMATION: Conotoxin peptide analog In
<220> FEATURE:
```

<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Gly

<400> SEQUENCE: 51

Gly Cys Xaa Thr Asp Pro Arg Cys Xaa Trp Gln Xaa Tyr Xaa
1 5 10

<210> SEQ ID NO 52
<211> LENGTH: 14
<212> TYPE: PRT
<213> ORGANISM: Artificial Sequence
<220> FEATURE:
<223> OTHER INFORMATION: Intermediate conotoxin peptide analog Yn
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa c= (S)-5-azidonorvaline
<220> FEATURE:
<221> NAME/KEY: MOD_RES
<222> LOCATION: (14)..(14)
<223> OTHER INFORMATION: Xaa = N-Me-Gly

<400> SEQUENCE: 52

Gly Cys Xaa Thr Asp Pro Arg Cys Xaa Trp Gln Xaa Tyr Xaa
1 5 10

<210> SEQ ID NO 53
<211> LENGTH: 14
<212> TYPE: PRT
<213> ORGANISM: Artificial Sequence
<220> FEATURE:
<223> OTHER INFORMATION: Intermediate conotoxin peptide analog Zn
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)

-continued

<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Gly

<400> SEQUENCE: 53

Gly Cys Xaa Thr Asp Pro Arg Cys Xaa Trp Gln Xaa Tyr Xaa
1 5 10

<210> SEQ ID NO 54
<211> LENGTH: 14
<212> TYPE: PRT
<213> ORGANISM: Artificial Sequence
<220> FEATURE:
<223> OTHER INFORMATION: Conotoxin peptide analog Io
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = D-Tyr

<400> SEQUENCE: 54

Gly Cys Xaa Thr Asp Pro Arg Cys Xaa Trp Gln Xaa Tyr Xaa
1 5 10

<210> SEQ ID NO 55
<211> LENGTH: 14
<212> TYPE: PRT
<213> ORGANISM: Artificial Sequence
<220> FEATURE:
<223> OTHER INFORMATION: Intermediate conotoxin peptide analog Yo
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = D-Tyr

<400> SEQUENCE: 55

Gly Cys Xaa Thr Asp Pro Arg Cys Xaa Trp Gln Xaa Tyr Xaa
1 5 10

<210> SEQ ID NO 56

<211> LENGTH: 14
<212> TYPE: PRT
<213> ORGANISM: Artificial Sequence
<220> FEATURE:
<223> OTHER INFORMATION: Intermediate conotoxin peptide analog Zo
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = D-Tyr

<400> SEQUENCE: 56

Gly Cys Xaa Thr Asp Pro Arg Cys Xaa Trp Gln Xaa Tyr Xaa
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Conotoxin peptide analog Ip
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Tyr

<400> SEQUENCE: 57

Gly Cys Xaa Thr Asp Pro Arg Cys Xaa Trp Gln Xaa Tyr Xaa
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Intermediate conotoxin peptide analog Yp
<220> FEATURE:
<221> NAME/KEY: MOD_RES
<222> LOCATION: (3)..(3)
<223> OTHER INFORMATION: Xaa = (S)-propargyl glycine
<220> FEATURE:

<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Tyr

<400> SEQUENCE: 58

Gly Cys Xaa Thr Asp Pro Arg Cys Xaa Trp Gln Xaa Tyr Xaa
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Intermediate conotoxin peptide analog Zp
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Tyr

<400> SEQUENCE: 59

Gly Cys Xaa Thr Asp Pro Arg Cys Xaa Trp Gln Xaa Tyr Xaa
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Conotoxin peptide analog Iq
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
      (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 60

-continued

Gly Cys Xaa Thr Asp Pro Arg Cys Xaa Trp Gln Xaa
1 5 10

<210> SEQ ID NO 61
<211> LENGTH: 12
<212> TYPE: PRT
<213> ORGANISM: Artificial Sequence
<220> FEATURE:
<223> OTHER INFORMATION: Intermediate conotoxin peptide analog Yq
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 61

Gly Cys Xaa Thr Asp Pro Arg Cys Xaa Trp Gln Xaa
1 5 10

<210> SEQ ID NO 62
<211> LENGTH: 12
<212> TYPE: PRT
<213> ORGANISM: Artificial Sequence
<220> FEATURE:
<223> OTHER INFORMATION: Intermediate conotoxin peptide analog Zq
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 62

Gly Cys Xaa Thr Asp Pro Arg Cys Xaa Trp Gln Xaa
1 5 10

<210> SEQ ID NO 63
<211> LENGTH: 13
<212> TYPE: PRT
<213> ORGANISM: Artificial Sequence
<220> FEATURE:
<223> OTHER INFORMATION: Conotoxin peptide analog Ir
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Tyr

<400> SEQUENCE: 63

Gly Cys Xaa Thr Asp Pro Arg Cys Xaa Trp Gln Xaa Xaa
1 5 10

<210> SEQ ID NO 64
<211> LENGTH: 13
<212> TYPE: PRT
<213> ORGANISM: Artificial Sequence
<220> FEATURE:
<223> OTHER INFORMATION: Intermediate conotoxin peptide analog Yr
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Tyr

<400> SEQUENCE: 64

Gly Cys Xaa Thr Asp Pro Arg Cys Xaa Trp Gln Xaa Xaa
1 5 10

<210> SEQ ID NO 65
<211> LENGTH: 13
<212> TYPE: PRT
<213> ORGANISM: Artificial Sequence
<220> FEATURE:
<223> OTHER INFORMATION: Intermediate conotoxin peptide analog Zr
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Tyr

<400> SEQUENCE: 65

Gly Cys Xaa Thr Asp Pro Arg Cys Xaa Trp Gln Xaa Xaa
1 5 10

<210> SEQ ID NO 66
<211> LENGTH: 13
<212> TYPE: PRT

<213> ORGANISM: Artificial Sequence
<220> FEATURE:
<223> OTHER INFORMATION: Conotoxin peptide analog Is
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Arg

<400> SEQUENCE: 66

Gly Cys Xaa Thr Asp Pro Arg Cys Xaa Trp Gln Xaa Xaa
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Intermediate conotoxin peptide analog Ys
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Arg

<400> SEQUENCE: 67

Gly Cys Xaa Thr Asp Pro Arg Cys Xaa Trp Gln Xaa Xaa
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Intermediate conotoxin peptide analog Zs
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)

```
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Arg

<400> SEQUENCE: 68

Gly Cys Xaa Thr Asp Pro Arg Cys Xaa Trp Gln Xaa Xaa
1               5                   10


<210> SEQ ID NO 69
<211> LENGTH: 13
<212> TYPE: PRT
<213> ORGANISM: Artificial Sequence
<220> FEATURE:
<223> OTHER INFORMATION: Conotoxin peptide analog It
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
      (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-D-Tyr

<400> SEQUENCE: 69

Gly Cys Xaa Thr Asp Pro Arg Cys Xaa Trp Gln Xaa Xaa
1               5                   10


<210> SEQ ID NO 70
<211> LENGTH: 13
<212> TYPE: PRT
<213> ORGANISM: Artificial Sequence
<220> FEATURE:
<223> OTHER INFORMATION: Intermediate conotoxin peptide analog Yt
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-D-Tyr

<400> SEQUENCE: 70

Gly Cys Xaa Thr Asp Pro Arg Cys Xaa Trp Gln Xaa Xaa
```

1 5 10

<210> SEQ ID NO 71
<211> LENGTH: 13
<212> TYPE: PRT
<213> ORGANISM: Artificial Sequence
<220> FEATURE:
<223> OTHER INFORMATION: Intermediate conotoxin peptide analog Zt
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-D-Tyr

<400> SEQUENCE: 71

Gly Cys Xaa Thr Asp Pro Arg Cys Xaa Trp Gln Xaa Xaa
1 5 10

<210> SEQ ID NO 72
<211> LENGTH: 13
<212> TYPE: PRT
<213> ORGANISM: Artificial Sequence
<220> FEATURE:
<223> OTHER INFORMATION: Conotoxin peptide analog Iu
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = beta-Tyr

<400> SEQUENCE: 72

Gly Cys Xaa Thr Asp Pro Arg Cys Xaa Trp Gln Xaa Xaa
1 5 10

<210> SEQ ID NO 73
<211> LENGTH: 13
<212> TYPE: PRT
<213> ORGANISM: Artificial Sequence
<220> FEATURE:
<223> OTHER INFORMATION: Intermediate conotoxin peptide analog Yu
<220> FEATURE:

```
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = beta-Tyr

<400> SEQUENCE: 73

Gly Cys Xaa Thr Asp Pro Arg Cys Xaa Trp Gln Xaa Xaa
1               5                   10


<210> SEQ ID NO 74
<211> LENGTH: 13
<212> TYPE: PRT
<213> ORGANISM: Artificial Sequence
<220> FEATURE:
<223> OTHER INFORMATION: Intermediate conotoxin peptide analog Zu
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = beta-Tyr

<400> SEQUENCE: 74

Gly Cys Xaa Thr Asp Pro Arg Cys Xaa Trp Gln Xaa Xaa
1               5                   10


<210> SEQ ID NO 75
<211> LENGTH: 13
<212> TYPE: PRT
<213> ORGANISM: Artificial Sequence
<220> FEATURE:
<223> OTHER INFORMATION: Conotoxin peptide analog Iv
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
      (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
```

<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Arg

<400> SEQUENCE: 75

Gly Cys Xaa Thr Asp Pro Arg Cys Xaa Trp Gln Xaa Xaa
1 5 10

<210> SEQ ID NO 76
<211> LENGTH: 13
<212> TYPE: PRT
<213> ORGANISM: Artificial Sequence
<220> FEATURE:
<223> OTHER INFORMATION: Intermediate conotoxin peptide analog Yv
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Arg

<400> SEQUENCE: 76

Gly Cys Xaa Thr Asp Pro Arg Cys Xaa Trp Gln Xaa Xaa
1 5 10

<210> SEQ ID NO 77
<211> LENGTH: 13
<212> TYPE: PRT
<213> ORGANISM: Artificial Sequence
<220> FEATURE:
<223> OTHER INFORMATION: Intermediate conotoxin peptide analog Zv
<220> FEATURE:
<221> NAME/KEY: DISULFID
<222> LOCATION: (2)..(8)
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = N-Me-Arg

<400> SEQUENCE: 77

Gly Cys Xaa Thr Asp Pro Arg Cys Xaa Trp Gln Xaa Xaa
1 5 10

<210> SEQ ID NO 78
<211> LENGTH: 13
<212> TYPE: PRT
<213> ORGANISM: Artificial Sequence
<220> FEATURE:
<223> OTHER INFORMATION: Conotoxin peptide analog Iw
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Glu at position 3 and Lys at position 12
form a lactam bridge
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 78

Gly Cys Glu Thr Asp Pro Arg Cys Xaa Xaa Gln Lys Tyr
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Intermediate X1
<220> FEATURE:
<221> NAME/KEY: MISC_FEATURE
<222> LOCATION: (13)..(13)
<223> OTHER INFORMATION: Tyr at position 13 is attached to a
Rink amide MBHA resin
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr

<400> SEQUENCE: 79

Gly Cys Glu Thr Asp Pro Arg Cys Xaa Xaa Gln Lys Tyr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Intermediate X2
<220> FEATURE:
<221> NAME/KEY: MISC_FEATURE
<222> LOCATION: (3)..(12)
<223> OTHER INFORMATION: Glu at position 3 and Lys at position 12
form a lactam bridge
<220> FEATURE:
<221> NAME/KEY: MISC_FEATURE
<222> LOCATION: (13)..(13)
<223> OTHER INFORMATION: Tyr at position 13 is attached to a Rink
amide MBHA resin
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr

<400> SEQUENCE: 80

```
Gly Cys Glu Thr Asp Pro Arg Cys Xaa Xaa Gln Lys Tyr
1               5                   10


<210> SEQ ID NO 81
<211> LENGTH: 13
<212> TYPE: PRT
<213> ORGANISM: Artificial Sequence
<220> FEATURE:
<223> OTHER INFORMATION: Intermediate X3
<220> FEATURE:
<221> NAME/KEY: MISC_FEATURE
<222> LOCATION: (3)..(12)
<223> OTHER INFORMATION: Glu at position 3 and Lys at position 12
      form a lactam bridge
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 81

Gly Cys Glu Thr Asp Pro Arg Cys Xaa Xaa Gln Lys Tyr
1               5                   10


<210> SEQ ID NO 82
<211> LENGTH: 13
<212> TYPE: PRT
<213> ORGANISM: Artificial Sequence
<220> FEATURE:
<223> OTHER INFORMATION: Conotoxin peptide analog Ix
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Lys at position 3 and Glu at position 12
      form a lactam bridge
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 82

Gly Cys Lys Thr Asp Pro Arg Cys Xaa Xaa Gln Glu Tyr
1               5                   10


<210> SEQ ID NO 83
<211> LENGTH: 13
<212> TYPE: PRT
<213> ORGANISM: Artificial Sequence
<220> FEATURE:
<223> OTHER INFORMATION: PEGylated conotoxin peptide analog IIa
<220> FEATURE:
<221> NAME/KEY: MISC_FEATURE
<222> LOCATION: (1)..(1)
<223> OTHER INFORMATION: Gly at position 1 is attached to a linear
      30 kDa mPEG polymer via a valerate linker
```

<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 83

```
Gly Cys Xaa Thr Asp Pro Arg Cys Xaa Trp Gln Xaa Tyr
1               5                   10
```

<210> SEQ ID NO 84
<211> LENGTH: 13
<212> TYPE: PRT
<213> ORGANISM: Artificial Sequence
<220> FEATURE:
<223> OTHER INFORMATION: PEGylated conotoxin peptide analog IVa
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a butylene linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 84

```
Gly Cys Xaa Thr Asp Pro Arg Cys Xaa Trp Gln Xaa Tyr
1               5                   10
```

<210> SEQ ID NO 85
<211> LENGTH: 13
<212> TYPE: PRT
<213> ORGANISM: Artificial Sequence
<220> FEATURE:
<223> OTHER INFORMATION: PEGylated conotoxin peptide analog Va
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Tyr at position 13 is attached to a linear 30 kDa mPEG polymer via a amidopropyl linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 85

Gly Cys Xaa Thr Asp Pro Arg Cys Xaa Trp Gln Xaa Tyr
1 5 10

<210> SEQ ID NO 86
<211> LENGTH: 13
<212> TYPE: PRT
<213> ORGANISM: Artificial Sequence
<220> FEATURE:
<223> OTHER INFORMATION: PEGylated conotoxin peptide analog VIa
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: Arg at position 7 is attached to a linear 30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 86

Gly Cys Xaa Thr Asp Pro Arg Cys Xaa Trp Gln Xaa Tyr
1 5 10

<210> SEQ ID NO 87
<211> LENGTH: 13
<212> TYPE: PRT
<213> ORGANISM: Artificial Sequence
<220> FEATURE:
<223> OTHER INFORMATION: PEGylated conotoxin peptide analog VII
<220> FEATURE:
<221> NAME/KEY: MISC_FEATURE
<222> LOCATION: (1)..(1)

<223> OTHER INFORMATION: Gly at position 1 is attached to a linear
      20 kDa mPEG polymer via a valerate linker
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 87

Gly Cys Cys Thr Asp Pro Arg Cys Xaa Xaa Gln Cys Tyr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: PEGylated conotoxin peptide analog VIII
<220> FEATURE:
<221> NAME/KEY: MISC_FEATURE
<222> LOCATION: (1)..(1)
<223> OTHER INFORMATION: Gly at position 1 is attached to a linear
      20 kDa mPEG polymer via a butylene linker
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 88

Gly Cys Cys Thr Asp Pro Arg Cys Xaa Xaa Gln Cys Tyr
1               5                   10

<210> SEQ ID NO 89
<211> LENGTH: 13
<212> TYPE: PRT
<213> ORGANISM: Artificial Sequence
<220> FEATURE:
<223> OTHER INFORMATION: PEGylated conotoxin peptide analog IX
<220> FEATURE:
<221> NAME/KEY: MISC_FEATURE
<222> LOCATION: (1)..(1)
<223> OTHER INFORMATION: Gly at position 1 is attached to a branched
      20 kDa mPEG polymer via a propyl amine linker
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 89

Gly Cys Cys Thr Asp Pro Arg Cys Xaa Xaa Gln Cys Tyr
1               5                   10

<210> SEQ ID NO 90
<211> LENGTH: 13
<212> TYPE: PRT
<213> ORGANISM: Artificial Sequence
<220> FEATURE:
<223> OTHER INFORMATION: PEGylated conotoxin peptide analog X
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MISC_FEATURE
<222> LOCATION: (1)..(1)
<223> OTHER INFORMATION: Gly at position 1 is attached to a branched
20 kDa mPEG polymer via a carbamate linker
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 90

Gly Cys Cys Thr Asp Pro Arg Cys Xaa Xaa Gln Cys Tyr
1               5                   10

<210> SEQ ID NO 91
<211> LENGTH: 13
<212> TYPE: PRT
<213> ORGANISM: Artificial Sequence
<220> FEATURE:
<223> OTHER INFORMATION: PEGylated conotoxin peptide analog XI
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 91

Gly Cys Cys Thr Asp Pro Arg Cys Xaa Xaa Gln Cys Tyr
1 5 10

<210> SEQ ID NO 92
<211> LENGTH: 13
<212> TYPE: PRT
<213> ORGANISM: Artificial Sequence
<220> FEATURE:
<223> OTHER INFORMATION: PEGylated conotoxin peptide analog XII
<220> FEATURE:
<221> NAME/KEY: MISC_FEATURE
<222> LOCATION: (1)..(1)
<223> OTHER INFORMATION: Gly at position 1 is attached to a linear
40 kDa mPEG polymer via a valerate linker
<220> FEATURE:
<221> NAME/KEY: DISULFID
<222> LOCATION: (2)..(8)
<220> FEATURE:
<221> NAME/KEY: DISULFID
<222> LOCATION: (3)..(12)
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (13)..(13)
<223> OTHER INFORMATION: AMIDATION

<400> SEQUENCE: 92

Gly Cys Cys Thr Asp Pro Arg Cys Xaa Xaa Gln Cys Tyr
1 5 10

<210> SEQ ID NO 93
<211> LENGTH: 14
<212> TYPE: PRT
<213> ORGANISM: Artificial Sequence
<220> FEATURE:
<223> OTHER INFORMATION: Formula I
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Xaa3 and Xaa12 form a triazole bridge
<220> FEATURE:
<221> NAME/KEY: VARIANT
<222> LOCATION: (3)..(3)
<223> OTHER INFORMATION: Xaa = an unnatural amino acid that forms a
triazole bridge with the residue at position 12
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: VARIANT
<222> LOCATION: (12)..(12)
<223> OTHER INFORMATION: Xaa = an unnatural amino acid that forms a
triazole bridge with the residue at position 3
<220> FEATURE:
<221> NAME/KEY: VARIANT
<222> LOCATION: (13)..(13)

<223> OTHER INFORMATION: Xaa can be Tyr, Phe, Trp, D-Tyr, D-Phe or D-Trp
<220> FEATURE:
<221> NAME/KEY: VARIANT
<222> LOCATION: (14)..(14)
<223> OTHER INFORMATION: Xaa can be N-Me-Gly, D-Tyr, N-Me-Tyr or absent

<400> SEQUENCE: 93

Gly Cys Xaa Thr Asp Pro Arg Cys Xaa Trp Gln Xaa Xaa Xaa
1 5 10

<210> SEQ ID NO 94
<211> LENGTH: 13
<212> TYPE: PRT
<213> ORGANISM: Artificial Sequence
<220> FEATURE:
<223> OTHER INFORMATION: Formula Ia
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 94

Gly Cys Xaa Thr Asp Pro Arg Cys Xaa Trp Gln Xaa Tyr
1 5 10

<210> SEQ ID NO 95
<211> LENGTH: 13
<212> TYPE: PRT
<213> ORGANISM: Artificial Sequence
<220> FEATURE:
<223> OTHER INFORMATION: PEGylated conotoxin peptide analog IIg
<220> FEATURE:
<221> NAME/KEY: MISC_FEATURE
<222> LOCATION: (1)..(1)
<223> OTHER INFORMATION: Gly at position 1 is attached to a linear 30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-homopropargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 95

-continued

Gly Cys Xaa Thr Asp Pro Arg Cys Xaa Trp Gln Xaa Tyr
1 5 10

<210> SEQ ID NO 96
<211> LENGTH: 13
<212> TYPE: PRT
<213> ORGANISM: Artificial Sequence
<220> FEATURE:
<223> OTHER INFORMATION: PEGylated conotoxin peptide analog IIh
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Homopropargyl glycine at position 3 and
(S)-gamma-azido-homoalanine at position 12 form a triazole bridge
<220> FEATURE:
<221> NAME/KEY: MOD_RES
<222> LOCATION: (3)..(3)
<223> OTHER INFORMATION: Xaa = (S)-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-gamma-azido-homoalanine

<400> SEQUENCE: 96

Gly Cys Xaa Thr Asp Pro Arg Cys Xaa Trp Gln Xaa Tyr
1 5 10

<210> SEQ ID NO 97
<211> LENGTH: 13
<212> TYPE: PRT
<213> ORGANISM: Artificial Sequence
<220> FEATURE:
<223> OTHER INFORMATION: PEGylated conotoxin peptide analog IIi
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Gamma-azido-homoalanine at position 3 and
(S)-homopropargyl glycine at position 12 form a triazole bridge
<220> FEATURE:
<221> NAME/KEY: MOD_RES
<222> LOCATION: (3)..(3)
<223> OTHER INFORMATION: Xaa = (S)-gamma-azido-homoalanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-homopropargyl glycine

<400> SEQUENCE: 97

Gly Cys Xaa Thr Asp Pro Arg Cys Xaa Trp Gln Xaa Tyr
1 5 10

<210> SEQ ID NO 98
<211> LENGTH: 13
<212> TYPE: PRT
<213> ORGANISM: Artificial Sequence
<220> FEATURE:
<223> OTHER INFORMATION: PEGylated conotoxin peptide analog IIk
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-3-Azido-alanine at position 3 and (S)-bis-
homopropargyl glycine at position 12 form a triazole bridge
<220> FEATURE:
<221> NAME/KEY: MOD_RES
<222> LOCATION: (3)..(3)
<223> OTHER INFORMATION: Xaa = (S)-3-azido-alanine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-bis-homopropargyl glycine

<400> SEQUENCE: 98

```
Gly Cys Xaa Thr Asp Pro Arg Cys Xaa Trp Gln Xaa Tyr
1               5                   10
```

<210> SEQ ID NO 99
<211> LENGTH: 13
<212> TYPE: PRT
<213> ORGANISM: Artificial Sequence
<220> FEATURE:
<223> OTHER INFORMATION: PEGylated conotoxin peptide analog IIl
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 99

```
Gly Cys Xaa Thr Asp Pro Arg Cys Xaa Trp Gln Xaa Phe
1               5                   10
```

<210> SEQ ID NO 100
<211> LENGTH: 13

<212> TYPE: PRT
<213> ORGANISM: Artificial Sequence
<220> FEATURE:
<223> OTHER INFORMATION: PEGylated conotoxin peptide analog IIm
<220> FEATURE:
<221> NAME/KEY: MISC_FEATURE
<222> LOCATION: (1)..(1)
<223> OTHER INFORMATION: Gly at position 1 is attached to a linear 30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (13)..(13)
<223> OTHER INFORMATION: Xaa = D-Tyr

<400> SEQUENCE: 100

Gly Cys Xaa Thr Asp Pro Arg Cys Xaa Trp Gln Xaa Xaa
1               5                   10

<210> SEQ ID NO 101
<211> LENGTH: 14
<212> TYPE: PRT
<213> ORGANISM: Artificial Sequence
<220> FEATURE:
<223> OTHER INFORMATION: PEGylated conotoxin peptide analog IIn
<220> FEATURE:
<221> NAME/KEY: MISC_FEATURE
<222> LOCATION: (1)..(1)
<223> OTHER INFORMATION: Gly at position 1 is attached to a linear 30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = N-Me-Gly

<400> SEQUENCE: 101

Gly Cys Xaa Thr Asp Pro Arg Cys Xaa Trp Gln Xaa Tyr Xaa 1               5                   10

<210> SEQ ID NO 102
<211> LENGTH: 14
<212> TYPE: PRT
<213> ORGANISM: Artificial Sequence
<220> FEATURE:
<223> OTHER INFORMATION: PEGylated conotoxin peptide analog IIo
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)
<223> OTHER INFORMATION: Xaa = D-Tyr

<400> SEQUENCE: 102

Gly Cys Xaa Thr Asp Pro Arg Cys Xaa Trp Gln Xaa Tyr Xaa
1               5                   10

<210> SEQ ID NO 103
<211> LENGTH: 14
<212> TYPE: PRT
<213> ORGANISM: Artificial Sequence
<220> FEATURE:
<223> OTHER INFORMATION: PEGylated conotoxin peptide analog IIp
<220> FEATURE:
<221> NAME/KEY: MISC_FEATURE
<222> LOCATION: (1)..(1)
<223> OTHER INFORMATION: Gly at position 1 is attached to a linear
30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and
(S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (12)..(12)
<223> OTHER INFORMATION: Xaa = (S)-5-azidonorvaline
<220> FEATURE:
<221> NAME/KEY: MOD_RES
<222> LOCATION: (14)..(14)

<223> OTHER INFORMATION: Xaa = N-Me-Tyr

<400> SEQUENCE: 103

Gly Cys Xaa Thr Asp Pro Arg Cys Xaa Trp Gln Xaa Tyr Xaa
1 5 10

<210> SEQ ID NO 104
<211> LENGTH: 13
<212> TYPE: PRT
<213> ORGANISM: Artificial Sequence
<220> FEATURE:
<223> OTHER INFORMATION: Formula Ib
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 104

Gly Cys Xaa Thr Asp Pro Arg Cys Xaa Xaa Gln Xaa Tyr
1 5 10

<210> SEQ ID NO 105
<211> LENGTH: 13
<212> TYPE: PRT
<213> ORGANISM: Artificial Sequence
<220> FEATURE:
<223> OTHER INFORMATION: PEGylated conotoxin peptide analog IIb
<220> FEATURE:
<221> NAME/KEY: MISC_FEATURE
<222> LOCATION: (1)..(1)
<223> OTHER INFORMATION: Gly at position 1 is attached to a linear 30 kDa mPEG polymer via a valerate linker
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: (S)-Propargyl glycine at position 3 and (S)-5-azidonorvaline at position 12 form a triazole bridge
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)

<223> OTHER INFORMATION: Xaa = (S)-5-azidonorvaline

<400> SEQUENCE: 105

Gly Cys Xaa Thr Asp Pro Arg Cys Xaa Xaa Gln Xaa Tyr
1 5 10

<210> SEQ ID NO 106
<211> LENGTH: 14
<212> TYPE: PRT
<213> ORGANISM: Artificial Sequence
<220> FEATURE:
<223> OTHER INFORMATION: Intermediate conotoxin peptide analog
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Xaa3 and Xaa12 form a triazole bridge
<220> FEATURE:
<221> NAME/KEY: MISC_FEATURE
<222> LOCATION: (3)..(12)
<223> OTHER INFORMATION: When Xaa3 is (S)-propargyl glycine, (S)-homopropargyl glycine, or (S)-bis-homopropargyl glycine, Xaa12 is (S)-gamma-azido-homoalanine or (S)-5-azidonorvaline
<220> FEATURE:
<221> NAME/KEY: MISC_FEATURE
<222> LOCATION: (3)..(12)
<223> OTHER INFORMATION: When Xaa3 is (S)-3-azido-alanine, (S)-gamma-azido-homoalanine, or (S)-5-azidonorvaline, Xaa12 is (S)-homopropargyl glycine or (S)-bis-homopropargyl glycine
<220> FEATURE:
<221> NAME/KEY: VARIANT
<222> LOCATION: (3)..(3)
<223> OTHER INFORMATION: Xaa can be (S)-propargyl glycine, (S)-3-azido-alanine, (S)-homopropargyl glycine, (S)-gamma-azido-homoalanine, (S)-5-azidonorvaline or (S)-bis-homopropargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: VARIANT
<222> LOCATION: (12)..(12)
<223> OTHER INFORMATION: Xaa can be (S)-homopropargyl glycine, (S)-gamma-azido-homoalanine, (S)-5-azidonorvaline or (S)-bis-homopropargyl glycine
<220> FEATURE:
<221> NAME/KEY: VARIANT
<222> LOCATION: (13)..(13)
<223> OTHER INFORMATION: Xaa can be Tyr, Phe, Trp, D-Tyr, D-Phe or D-Trp
<220> FEATURE:
<221> NAME/KEY: VARIANT
<222> LOCATION: (14)..(14)
<223> OTHER INFORMATION: Xaa can be N-Me-Gly, D-Tyr, N-Me-Tyr or absent

<400> SEQUENCE: 106

Gly Cys Xaa Thr Asp Pro Arg Cys Xaa Trp Gln Xaa Xaa Xaa
1 5 10

-continued

```
<210> SEQ ID NO 107
<211> LENGTH: 13
<212> TYPE: PRT
<213> ORGANISM: Artificial Sequence
<220> FEATURE:
<223> OTHER INFORMATION: Intermediate conotoxin peptide analog
<220> FEATURE:
<221> NAME/KEY: MOD_RES
<222> LOCATION: (3)..(3)
<223> OTHER INFORMATION: Xaa = (S)-propargyl glycine
<220> FEATURE:
<221> NAME/KEY: MOD_RES
<222> LOCATION: (9)..(9)
<223> OTHER INFORMATION: Xaa = Citrulline
<220> FEATURE:
<221> NAME/KEY: MOD_RES
<222> LOCATION: (10)..(10)
<223> OTHER INFORMATION: Xaa = 3-I-Tyr
<220> FEATURE:
<221> NAME/KEY: MOD_RES
<222> LOCATION: (12)..(12)
<223> OTHER INFORMATION: Xaa = (S)-5-azidonorvaline

<400> SEQUENCE: 107

Gly Cys Xaa Thr Asp Pro Arg Cys Xaa Xaa Gln Xaa Tyr
1               5                   10
```

CONOTOXIN PEPTIDE ANALOGS AND USES FOR THE TREATMENT OF PAIN AND INFLAMMATORY CONDITIONS

CROSS REFERENCE TO RELATED APPLICATIONS

This application claims the benefit of U.S. Provisional Application No. 62/788,559, filed Jan. 4, 2019, which is incorporated by reference herein in its entirety.

REFERENCE TO SEQUENCE LISTING SUBMITTED ELECTRONICALLY

This application incorporates by reference a Sequence Listing submitted with this application as a text file entitled "SEQ_LISTING_14520-002-999.txt" created on Jan. 2, 2020 and having a size of 68,428 bytes.

1. FIELD

Provided herein are alpha-conotoxin peptide analogs, including alpha-conotoxin peptide analogs that are covalently attached to polyethylene glycol (PEG), and pharmaceutical compositions of such alpha-conotoxin peptide analogs. Also provided herein are methods of treating or preventing a condition conducive to treatment or prevention by inhibition of an α9-containing nicotinic acetylcholine receptor (nAChR) (e.g., the α9α10 subtype of the nAChR) in a subject.

2. BACKGROUND

Predatory marine snails in the genus Conus have venoms that are rich in neuropharmacologically active peptides (conotoxin peptides or conotoxins) (Olivera et al., 1990, Science 249:257-263). There are approximately 500 species in Conus, and among those that have been examined so far, a conserved feature is the presence of alpha-conotoxin peptides in their venom. Native alpha-conotoxin peptides are highly disulfide cross-linked peptides with a C1-C3 and C2-C4 disulfide bridge pattern (Azam and McIntosh, 2009, Acta Pharmacol. Sin. 30:771-783).

Alpha-conotoxin peptides have generally been shown to be nicotinic acetylcholine receptor (nAChR) antagonists (Nicke et al., 2004, Eur. J. Biochem. 271:2305-2319). nAChRs are pentameric ligand-gated ion channels assembled from one or more a subunits (α1-α10) either alone or together with one or more non-α subunits (β1-β4) (Sine and Engel, 2006, Nature 440:448-455).

The α9α10 nAChR subunits are expressed in diverse tissues. In the inner ear, α9α10 nAChRs mediate synaptic transmission between efferent olivocochlear fibers and cochlear hair cells (Vetter et al., 1999, Neuron 23:93-103). The α9α10 subunits are also found in dorsal root ganglion neurons (Lips et al., 2002, Neuroscience 115:1-5), lymphocytes (Peng et al., 2004, Life. Sci. 76:263-280), skin keratinocytes (Nguyen et al., 2000, Am. J. Pathol. 157:1377-1391), and the pars tuberalis of the pituitary (Elgoyhen et al., 1994, Cell 79:705-715; Zuo et al., 1999, Proc. Natl. Acad. Sci. USA 96:14100-14105).

Compounds that have a pharmacological profile that includes α9α10 antagonist activity prevent or attenuate the expression of pain in several rodent models, including neuropathic pain induced by chemotherapy, traumatic nerve injury, and diabetes (see Hone and McIntosh, 2018, FEBS Lett. 592:1045-1062).

Native conotoxin peptide RgIA has the amino acid sequence Gly-Cys-Cys-Ser-Asp-Pro-Arg-Cys-Arg-Tyr-Arg-Cys-Arg (SEQ ID NO:1) (Ellison et al., 2008, J. Mol. Biol. 377:1216-1227). Alpha-conotoxin peptide RgIA has been shown to block α9α10 nAChR activity (Romero et al., 2017, Proc. Natl. Acad. Sci. USA 14:E1825-E1832).

RgIA belongs to the α-4/3 family of α-conotoxins. The native structure of RgIA is characterized by two compact intra-cysteine loops defined by two disulfide bonds formed between Cys2-Cys8 (sometimes referred CysI-CysIII) and Cys3-Cys12 (sometimes referred to CysII-CysIV) (Ellison et al, 2008, J. Mol. Biol. 377:1216-1227; Armishaw, 2010, Toxins 2:1471-1499). In the α-conotoxins, the first and second cysteine residues are always adjacent, but the number of amino acid residues between the second and third cysteine, and between the third and fourth cysteine residues can vary. This gives rise to two loops of intervening amino acids denoted loop 1 or the m-loop and loop 2 or the n-loop. In RgIA, loop 1 contains 4 amino acids and loop 2 contains 3 amino acids. The disulfide bonds and therefore the secondary structure of α-conotoxins are unstable and subject to rearrangement (Armishaw, 2010, Toxins 2:1471-1499).

The two disulfide bonds of the α-conopeptide are subject to rearrangement and can form alternative three-dimensional structures including a ribbon form (disulfide bonds Cys-2-Cys12 and Cys3-Cys8) and a bead form (disulfide bonds Cys2-Cys3 and Cys8-Cys12). While the native or globular form of the peptide is active on the α9α10-nAChr, neither the ribbon or bead form are thought to be active (Dekan et al., 2011, J. Am. Chem. Soc. 133:15866-15869; Armishaw et al., 2006, J. Bio. Chem. 281:14136-14143).

Hargittai et al. evaluated four lactam-bridged derivatives of the alpha-conotoxin SI, and only one of the four lactam-bridged derivatives did not lose significant activity in binding to BC3H1 cells (Hargittai et al., 2000, J. Med. Chem. 43:4787-4792). Bondebjerg et al. evaluated synthesized thioether mimetics of the alpha-conotoxin GI and found that the two isomers tested had significantly less pharmacologic activity than the native peptide (Bondebjerg et al., 2003, ChemBioChem 4:186-194). Non-reducible dicarba analogs of alpha-ImI were evaluated and in both instances found to have an approximately 10-fold reduction in pharmacological activity (MacRaild et al., 2009, J. Med. Chem. 52:755-762). Certain specific selenocysteine and cystathionine derivatives of ImI retained activity in blocking the rat α7 nAChR (Dekan et al., 2011, J. Am. Chem. Soc. 133:15866-15869; Armishaw et al., 2006, J. Bio. Chem. 281:14136 14143).

van Lierop evaluated dicarba substitutions of the disulfide bonds of alpha-conotoxin Vc1.1 and found that the [2,8]-cis and [2,8]-trans dicarba analogs had no activity on the rat α9α10 nAChr, whereas the [3,16]-cis and [3,16]-trans isomers of Vc1.1 had greatly reduced (10-100-fold) activity on rat α9α10 nAChR (van Lierop et al., 2013, ACS Chemical Biology 8:1815-1821). Yu et al created N-terminal to C-terminal peptide-linked derivatives of Vc1.1 that had one or more cysteine residues replaced with His or Phe. These derivatives had significantly reduced potency (20 to 40-fold lower) on the human α9α10 nAChR relative to native Vc1.1 (Yu et al. 2015, Sci. Rep. 5:13264.). In a separate study by the same group, substitution of Cys2 to His and Cys8 to Phe in Vc1.1 in the absence of N- to C-terminal cyclization also resulted in loss of activity on the human α9α10 nAChR, despite analysis that demonstrated conservation of secondary structure (Tabassum et al. 2017, ACS Omega 2:4621-4631).

Similar efforts have been explored to replace the disulfide bonds in RgIA with dicarba linkages (Chhabra et al., 2014, J. Med. Chem. 57:993-9944). While this study found that dicarba analogs of RgIA were synthetically feasible, NMR-based structural comparisons of native RgIA to the dicarba analogs demonstrated significant structural differences in the second loop of the peptides. Consistent with these structural differences and observations from the related Vc1.1, the [2,8]-cis and [2,8]-trans dicarba analogs of RgIA had no activity on the rat α9α10 nAChR, whereas the [3,12]-cis and [3,12]-trans isomers both had >100-fold reductions in inhibition of acetylcholine-evoked α9α10 currents. Chhabra et al. did not evaluate the activities of dicarba-bridged RgIA analogs on the human α9α10 nAChR.

Knuhtsen et al. (Knuhtsen et al., Chemical Science, 2019, Advance Article) studied analogs of the alpha-conotoxin GI, in which the Cys2-Cys7 or Cys3-Cys13 disulfide bonds were replaced with 1,5-disubstituted 1,2,3-triazole bridges.

Native RgIA has approximately 300-fold lower affinity for the human than the rat α9α10 nAChR, and this difference in affinity has been mapped to variation in the amino acid sequence of the alpha 9 subunit within the RgIA binding pocket (Azam et al., 2015, Mol. Pharmacol. 87:855-864).

Conotoxin peptide analogs of RgIA have been reported (WO 2008/011006; Romero et al., 2017, Proc. Natl. Acad. Sci. USA 14:E1825-E1832; WO 2016/073949).

Studies have demonstrated a greater degree of structural flexibility in loop 2 of RgIA, especially around the carboxy-terminus, and the importance of loop 2 residues in human receptor binding interactions (Clark et al., 2008, FEBS Lett. 582(5):597-602). NMR spectroscopy also indicates that Cys12 of RgIA may interact with Tyr10 in the wild type or native peptide (Ellison et al, 2008, J. Mol. Biol. 377:1216-1227; Armishaw, 2010, Toxins 2:1471-1499).

Conotoxin peptides and their analogs are competitive inhibitors of the α9α10 nAChR and they bind at the ACh binding site, i.e., at the interface between adjacent subunits. The subunit interfaces buries to a 1.4 Å probe radius, a surface area of ~1300 Å, where these conotoxins interact with residues between subunits encompassing distances less than 5 Å (Hansen et al., 2005, EMBO J., 24(20):3635-3646).

Amino acid comparison with other known nAChR subunits indicates that α9α10 nAChRs are closely related to α7 nAChR (Elgoyhen et al., 1994, Cell 79(4):705-715; Lustig et al., 2001, Genomics, 73(3):272-283; Sgard et al., 2002, Mol. Pharmacol. 61(1):150-159). The α7 nAChR has pleiotropic effects in the nervous system (Ellison et al., 2008, J. Mol. Biol. 377:1216-1227; Armishaw, 2010, Toxins 2:1471-1499).

Non-covalent or covalent attachment to polyethylene glycol polymer(s) (PEGylation) can change the physical and chemical properties of a biomolecule such as a peptide, such as its conformation, electrostatic binding, and hydrophobicity (Veronese and Mero, 2008, BioDrugs, 22:315-329; see also Harris et al., 2001, Clin. Pharmacokinet. 40:539-551).

PEGylation of a therapeutic protein often leads to a loss in its binding affinity due to the steric hindrance of the PEG polymer to the drug-target binding interaction (Fishburn, 2008, J. Pharm. Sci. 97:4167-4183). PEGylated therapeutic proteins can lose biological activity or potency, either through steric effects or through hydrophobic-hydrophobic interactions between the PEG and hydrophobic domains within the protein (Parrott and DeSimone, 2011, Nat. Chem. 4:13-14).

Studies have indicated that antagonists of α9-containing nAChRs exhibit analgesic activity in animal models of neuropathic pain (Hone, et al., 2018, British Journal of Pharmacology, 175:1915-1927). Studies have also shown that inhibition of the α9α10 nAChR in rodents prevents chemotherapy-induced neuropathic pain (Romero et al., 2018, Proc. Natl. Acad. Sci. USA 114(10):E1825-E1832). See also, Mohammadi and Christie, 2014, Molecular Pain, 10:64-72; Simard et al., 2013, Immunology and Cell Biology, 91:195-200.

There is an unmet medical need for conotoxin peptide analogs with enhanced metabolic stability while maintaining sufficient antagonist activity on α9-containing nAChRs. The conotoxin peptide analogs of the present invention meet these needs.

Citation of a reference herein shall not be construed as an admission that such is prior art to the present disclosure.

3. SUMMARY OF THE INVENTION

The present disclosure provides conotoxin peptide analogs of Formula (I) (SEQ ID NO:93):

(I)

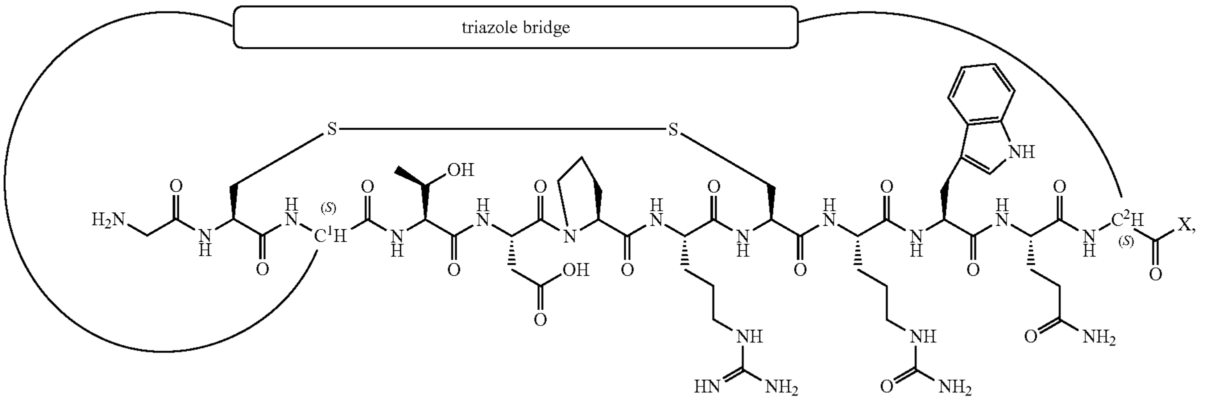

or a pharmaceutically acceptable salt thereof, wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr;

wherein the C-terminus of the conotoxin peptide analog is a carboxylic acid or an amide group.

In a specific embodiment, the triazole bridge is

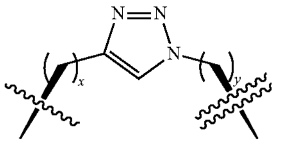

or

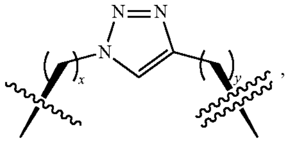

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog; and wherein x is 1, 2, 3, or 4; and y is 2, 3 or 4.

In a specific embodiment, wherein the triazole bridge is

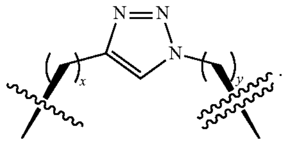

.

In a specific embodiment, the triazole bridge is

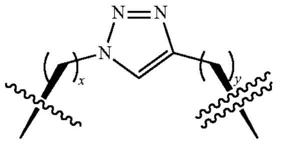

.

In a specific embodiment, x is 1, 2, or 3.

In a specific embodiment, x is 1.

In a specific embodiment, y is 2 or 3.

In a specific embodiment, y is 3.

In a specific embodiment, x is 1, 2, or 3, and y is 2 or 3.

In a specific embodiment, x is 1 and y is 3.

In a specific embodiment, x is 2, and y is 3.

In a specific embodiment, x is 2, and y is 2.

In a specific embodiment, x is 1, and y is 3.

In a specific embodiment, x is 2, and y is 2.

In a specific embodiment, the triazole bridge is

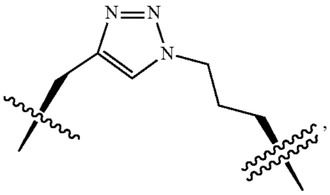

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog.

In a specific embodiment, X is $X_{AA}^1$.

In a specific embodiment, X is $X_{AA}^1X_{AA}^2$.

In a specific embodiment, $X_{AA}^1$ is selected from the group consisting of Tyr, D-Tyr and Phe.

In a specific embodiment, X is Tyr.

In a specific embodiment, the C-terminus of the conotoxin peptide analog is OH.

In a specific embodiment, the C-terminus of the conotoxin peptide analog is $NH_2$.

In a specific embodiment, the conotoxin peptide analog is of Formula (Ia) (SEQ ID NO:94)

(Ia)

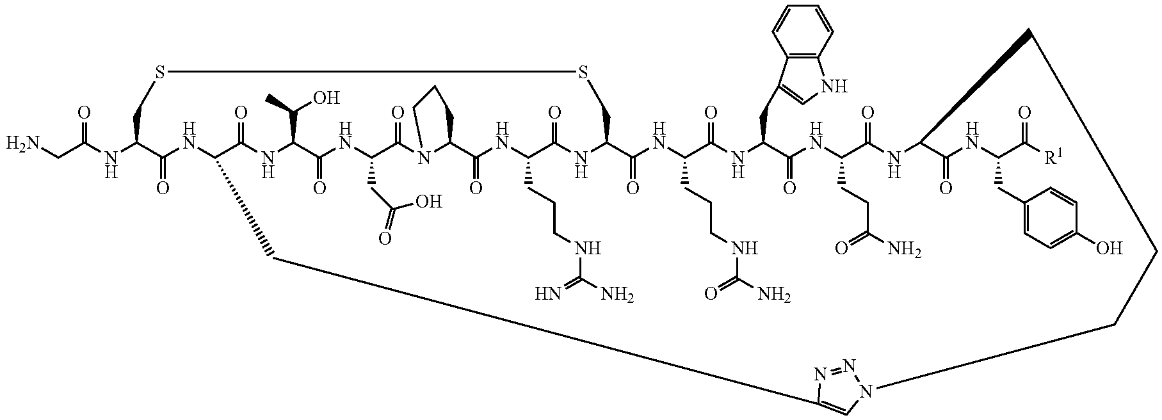

, wherein $R^1$ is OH or $NH_2$.
In a specific embodiment, $R^1$ is OH.
In a specific embodiment, $R^1$ is $NH_2$.
In a specific embodiment, the conotoxin peptide analog is of Formula (Ig) (SEQ ID NO:30):
(Ig)
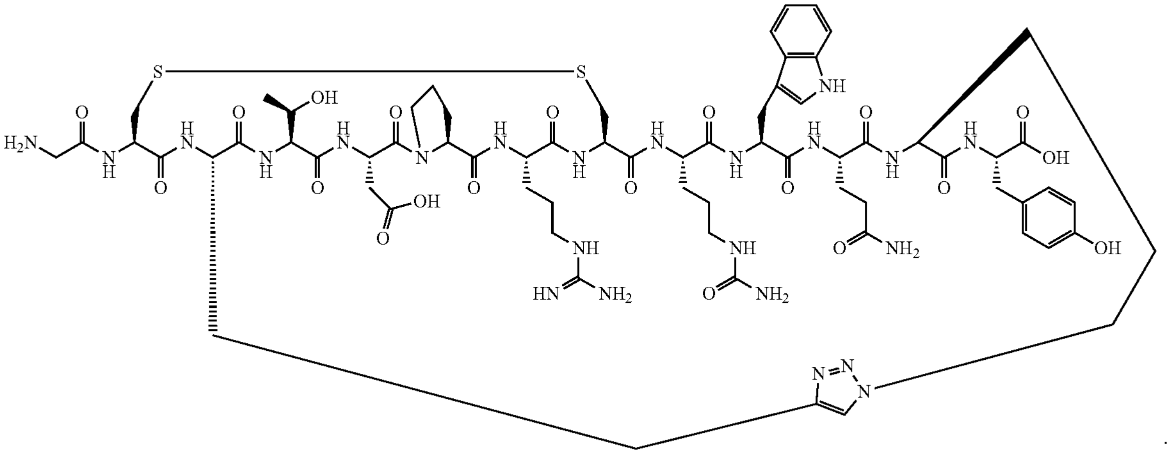
In a specific embodiment, the conotoxin peptide analog is of Formula (Ih) (SEQ ID NO:33):
(Ih)
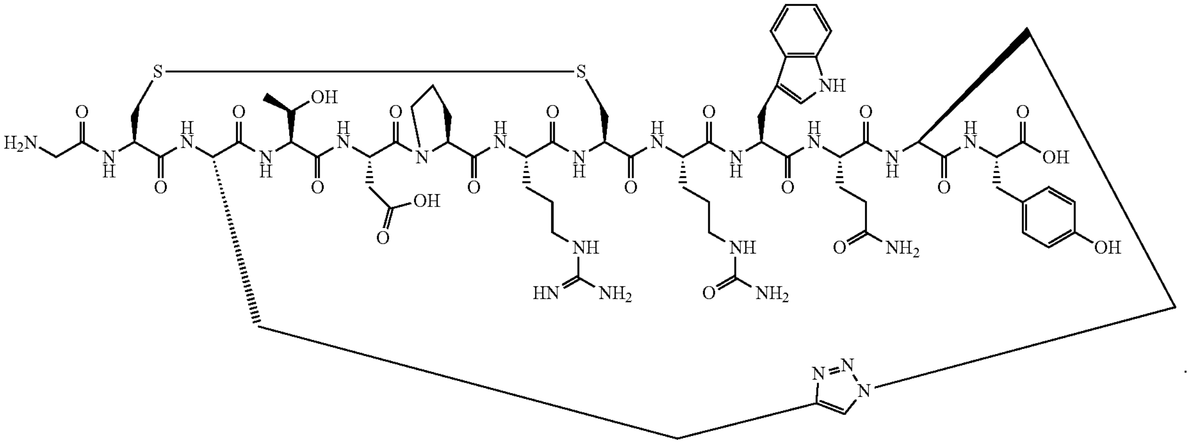

In a specific embodiment, the conotoxin peptide analog is of Formula (Ii) (SEQ ID NO:36):
(Ii)
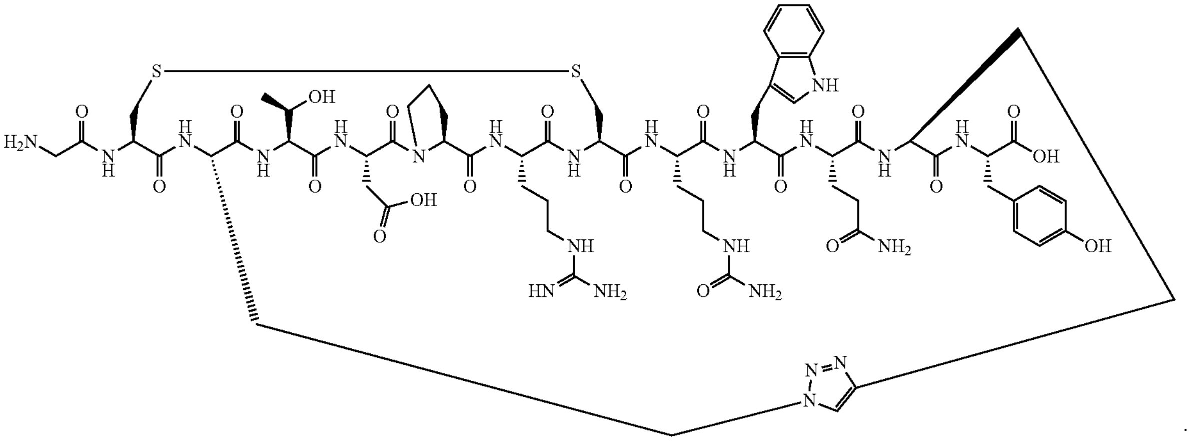
In a specific embodiment, the conotoxin peptide analog is of Formula (Ik) (SEQ ID NO:42):
(Ik)
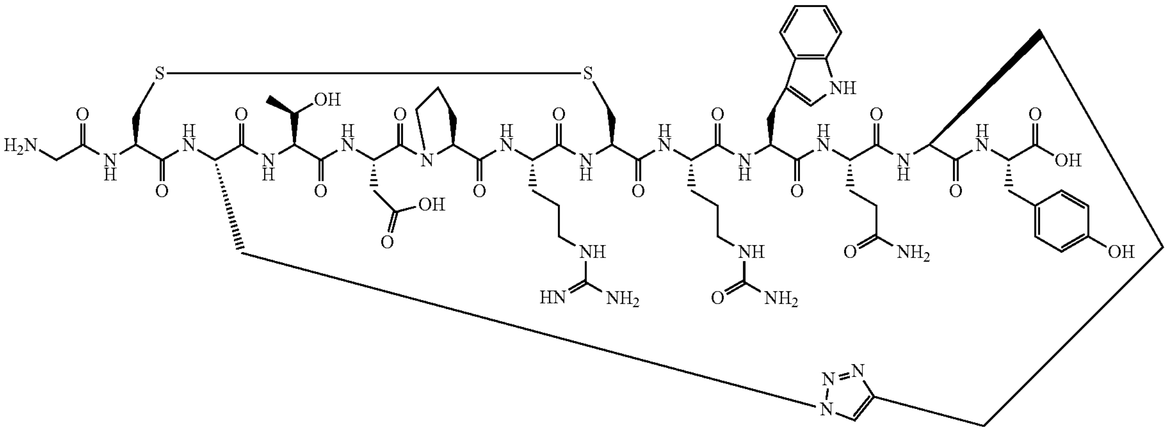

In a specific embodiment, the conotoxin peptide analog is of Formula (Il) (SEQ ID NO:45):
(Il)
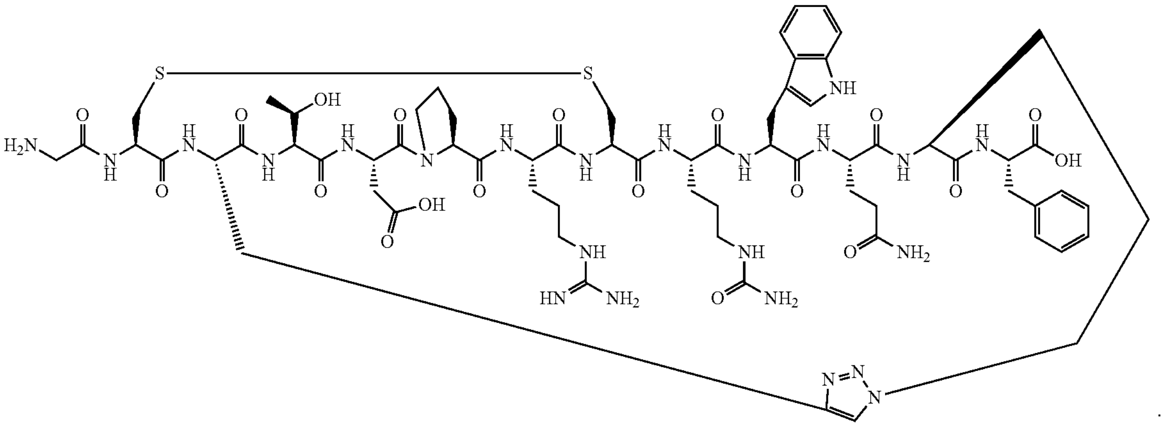
In a specific embodiment, the conotoxin peptide analog is of Formula (Im) (SEQ ID NO:48)
(Im)
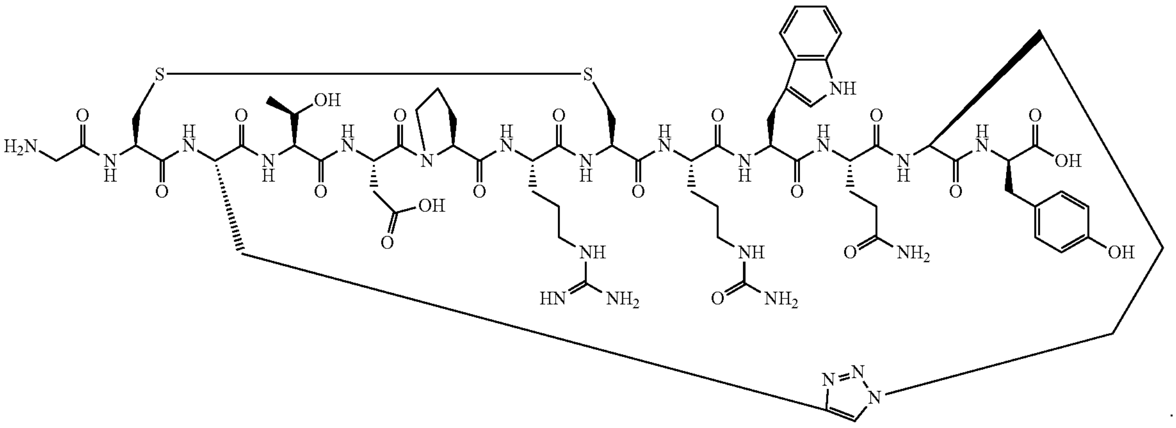

In a specific embodiment, the conotoxin peptide analog is of Formula (In) (SEQ ID NO:51)
(In)
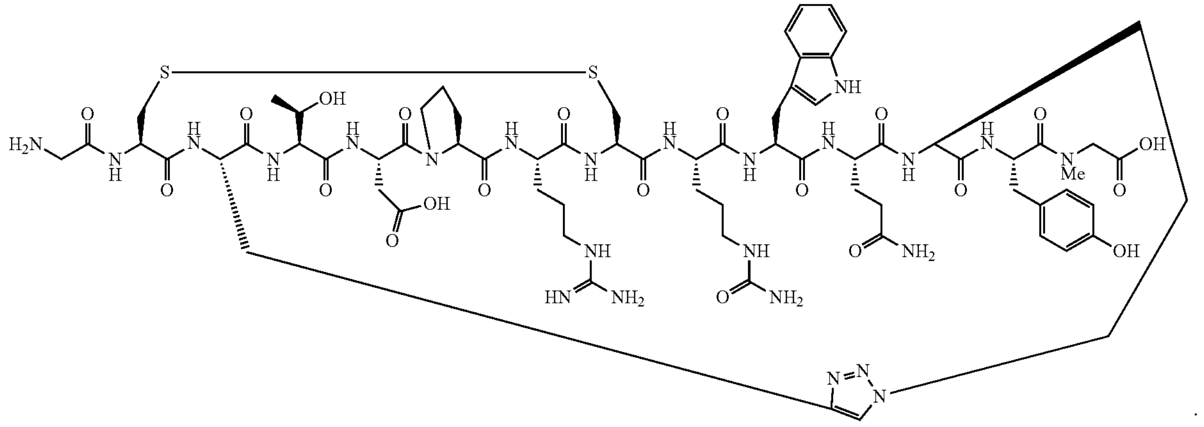
In a specific embodiment, the conotoxin peptide analog is of Formula (Io) (SEQ ID NO:54)
(Io)
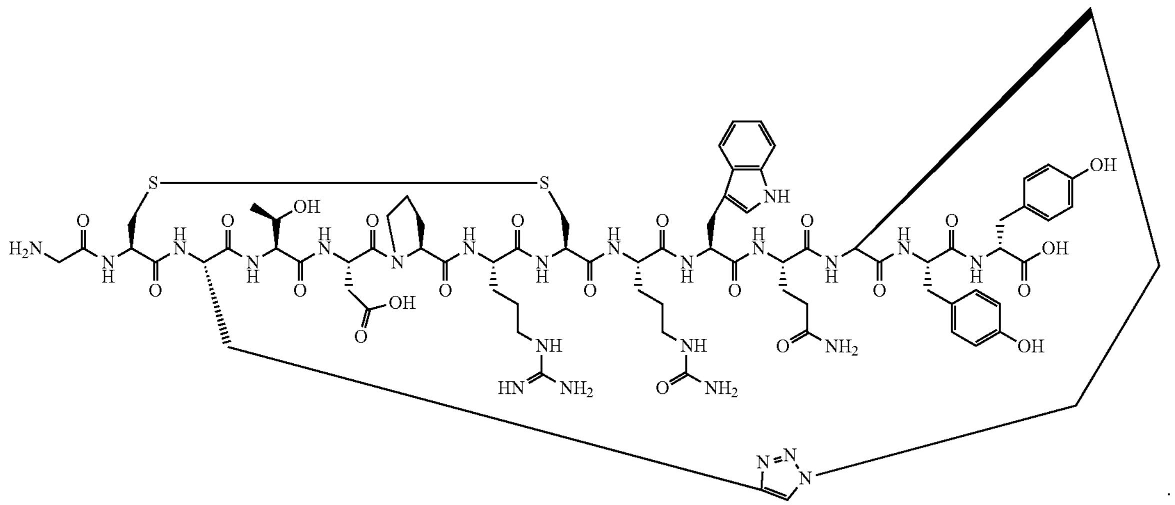

In a specific embodiment, the conotoxin peptide analog is of Formula (Ip) (SEQ ID NO:57)

(Ip)

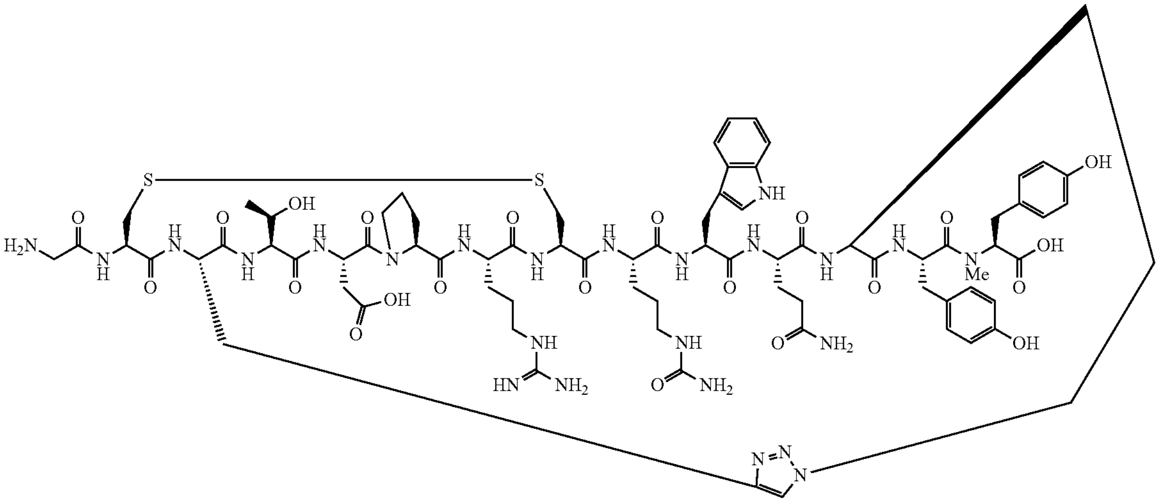

.

Also provided herein are PEGylated conotoxin peptide analogs or pharmaceutically acceptable salt thereof, wherein the conotoxin peptide analog is of Formula (I) (SEQ ID NO:93):

(I)

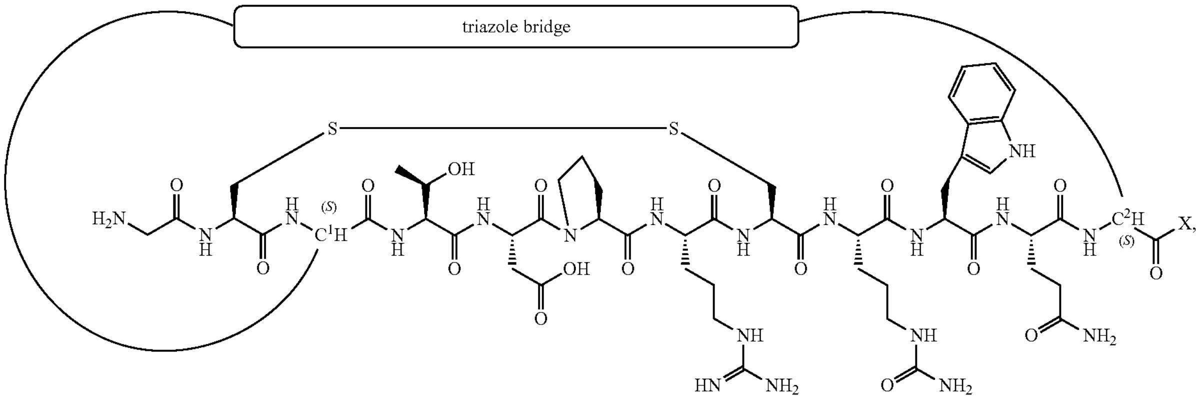

wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr;

wherein the C-terminus of the conotoxin peptide analog is a carboxylic acid or an amide group; and wherein the conotoxin peptide analog is covalently attached directly or via a linking group to one or more polyethylene glycol (PEG) polymers.

In a specific embodiment, the triazole bridge is

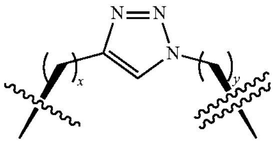

or

-continued

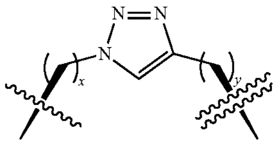

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog; and wherein x is 1, 2, 3, or 4; and y is 2, 3 or 4.

In a specific embodiment, wherein the triazole bridge is

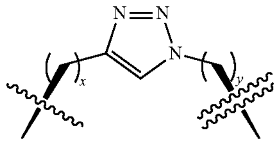

.

In a specific embodiment, the triazole bridge is

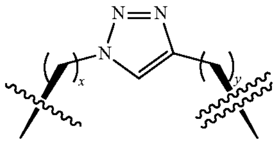

.

In a specific embodiment, x is 1, 2, or 3.

In a specific embodiment, x is 1.

In a specific embodiment, y is 2 or 3.

In a specific embodiment, y is 3.

In a specific embodiment, x is 1, 2, or 3, and y is 2 or 3.

In a specific embodiment, x is 1 and y is 3.

In a specific embodiment, x is 2 and y is 3.

In a specific embodiment, x is 2 and y is 2.

In a specific embodiment, x is 1 and y is 3.

In a specific embodiment, x is 2 and y is 2.

In a specific embodiment, the triazole bridge is

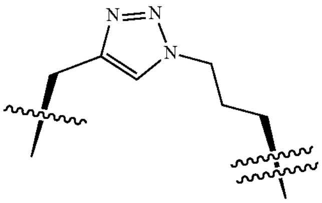

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog.

In a specific embodiment, X is $X_{AA}^1$.

In a specific embodiment, X is $X_{AA}^1X_{AA}^2$.

In a specific embodiment, $X_{AA}^1$ is selected from the group consisting of Tyr, D-Tyr and Phe.

In a specific embodiment, X is Tyr.

In a specific embodiment, the C-terminus of the conotoxin peptide analog is OH.

In a specific embodiment, the C-terminus of the conotoxin peptide analog is $NH_2$.

In a specific embodiment, the conotoxin peptide analog is of Formula (Ia) (SEQ ID NO:94)

(Ia)

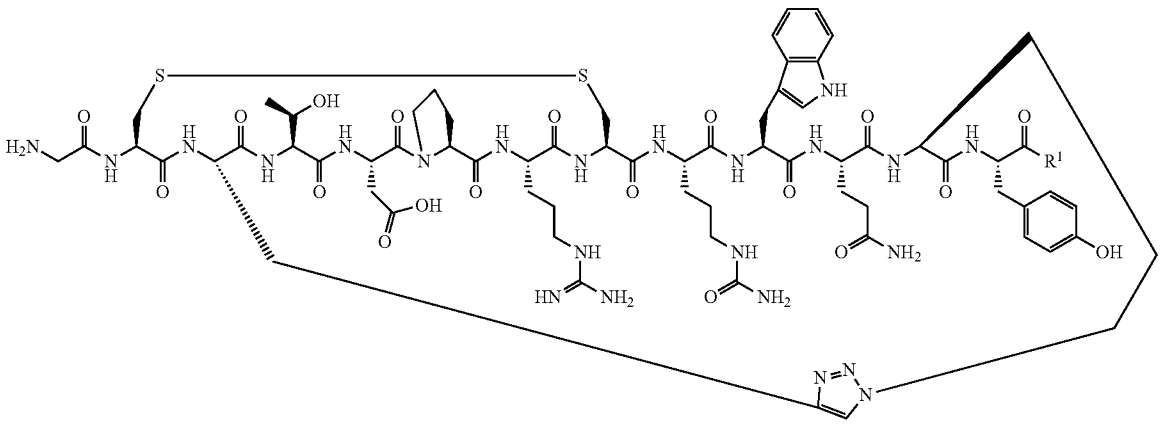

.

In a specific embodiment, $R^1$ is OH.
In a specific embodiment, $R^1$ is $NH_2$.
In a specific embodiment, the conotoxin peptide analog is of Formula (Ig) (SEQ ID NO:30):
(Ig)
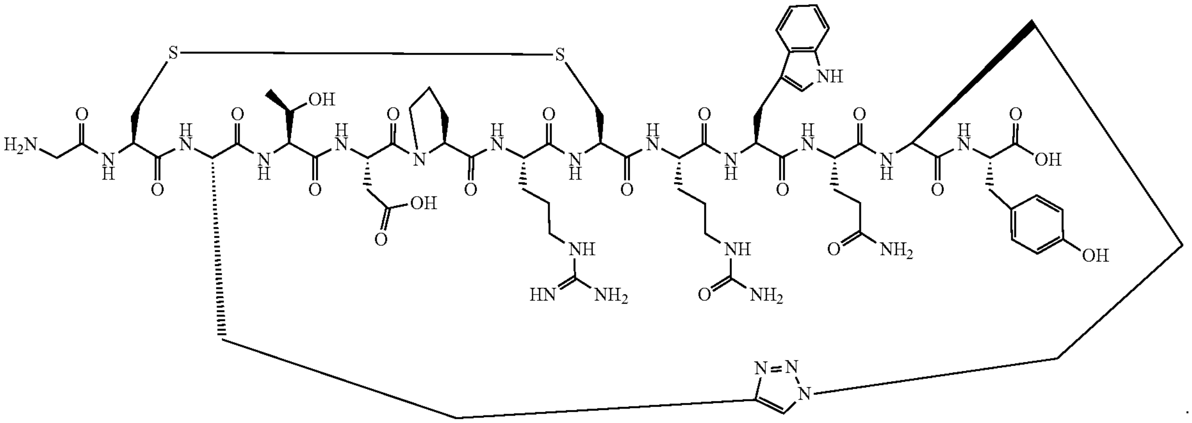
In a specific embodiment, the conotoxin peptide analog is of Formula (Ih) (SEQ ID NO:33):
(Ih)
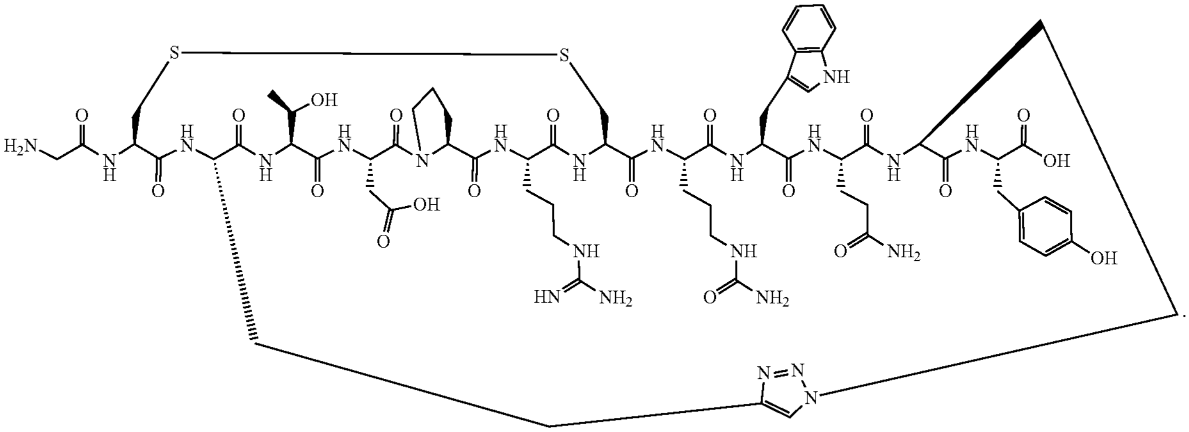

In a specific embodiment, the conotoxin peptide analog is of Formula (Ii) (SEQ ID NO:36):
(Ii)
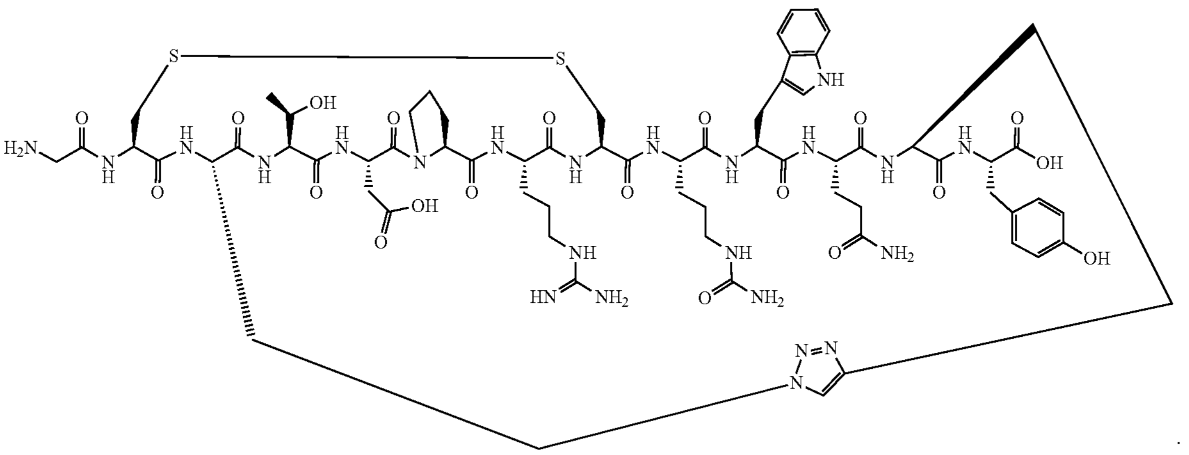
In a specific embodiment, the conotoxin peptide analog is of Formula (Ik) (SEQ ID NO:42):
(Ik)
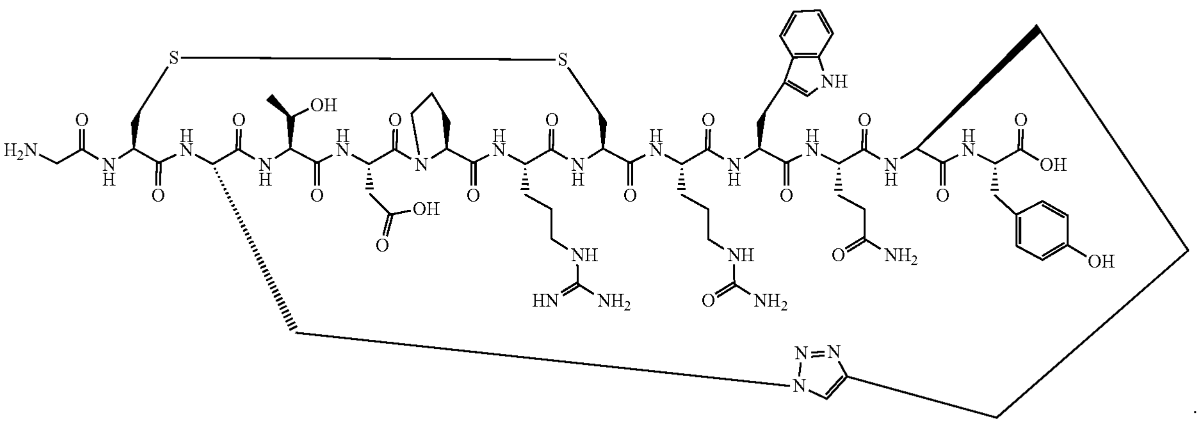

In a specific embodiment, the conotoxin peptide analog is of Formula (Il) (SEQ ID NO:45):
(Il)
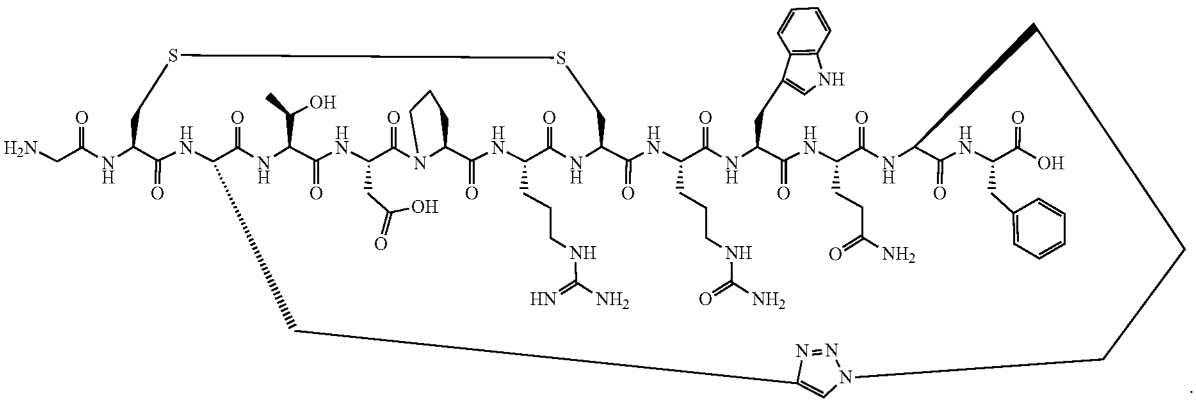
.
In a specific embodiment, the conotoxin peptide analog is of Formula (Im) (SEQ ID NO:48)
(Im)
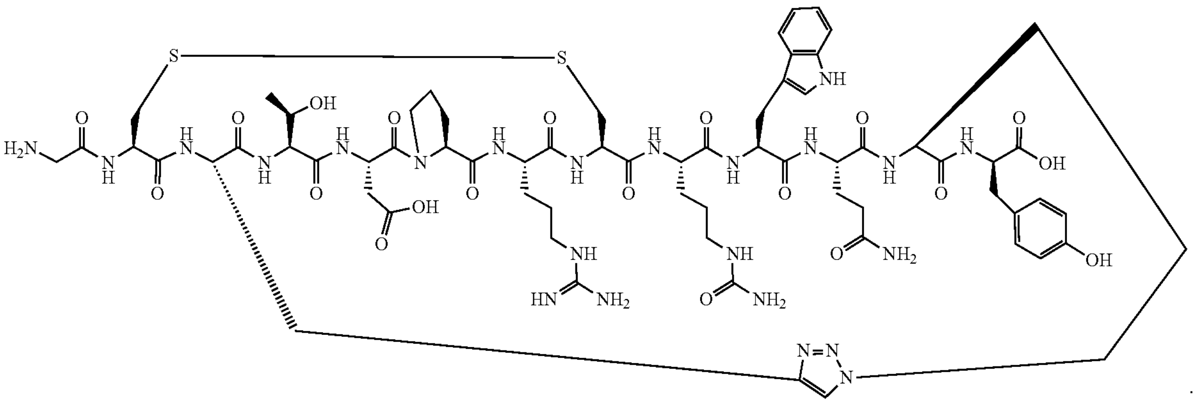
.
In a specific embodiment, the conotoxin peptide analog is of Formula (In) (SEQ ID NO:51)
(In)
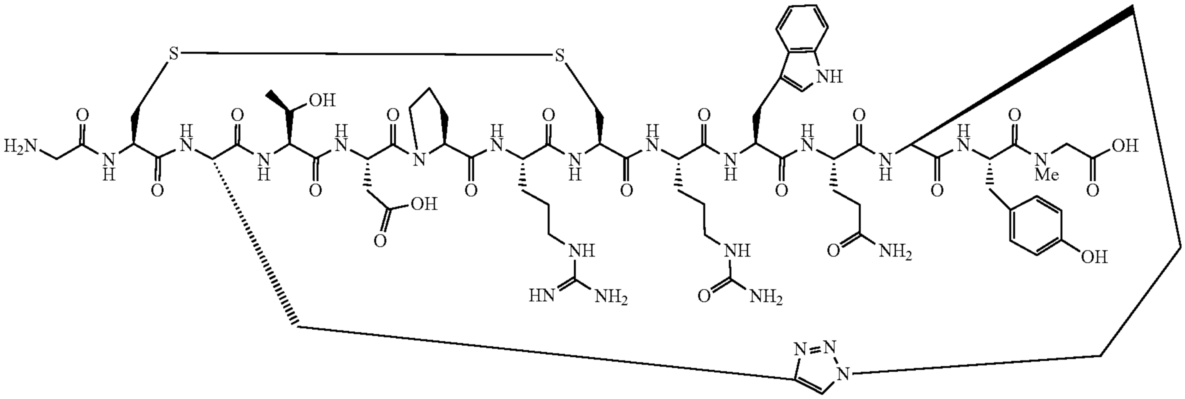
.

In a specific embodiment, the conotoxin peptide analog is of Formula (Io) (SEQ ID NO:54)

(Io)

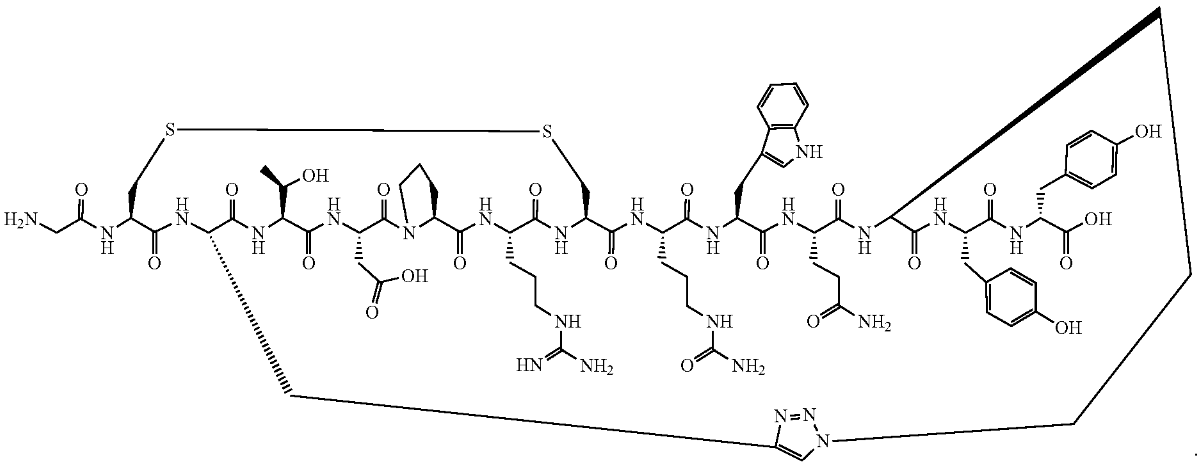

In a specific embodiment, the conotoxin peptide analog is of Formula (Ip) (SEQ ID NO:57)

(Ip)

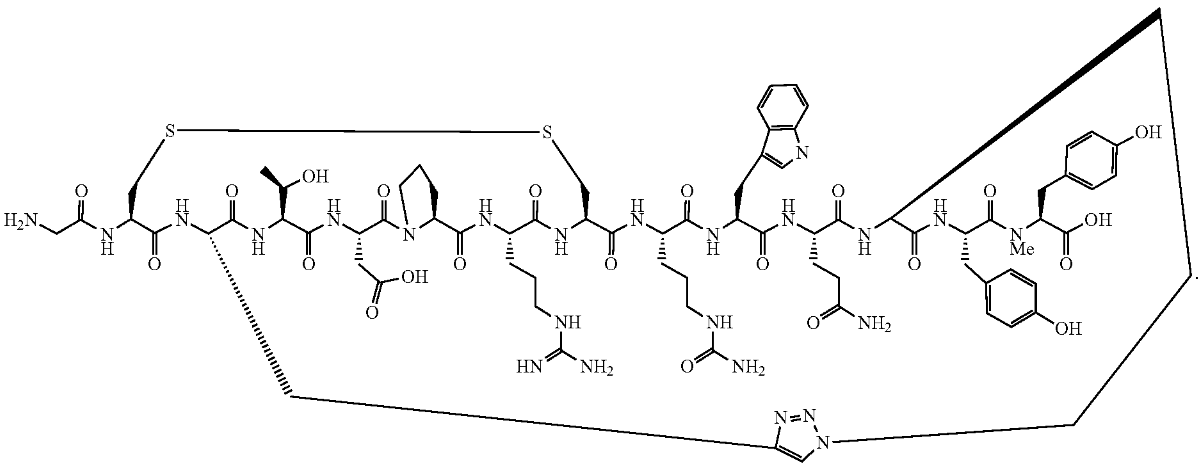

In a specific embodiment, the conotoxin peptide analog is covalently attached to one PEG polymer.

In a specific embodiment, the PEG polymer is covalently attached to the N-terminus of the conotoxin peptide analog.

In a specific embodiment, the PEG polymer is covalently attached to the C-terminus of the conotoxin peptide analog.

In a specific embodiment, the PEG polymer is covalently attached to an amino acid residue position that is not the N-terminus or the C-terminus of the conotoxin peptide analog.

In a specific embodiment, the PEG polymer is covalently attached to the conotoxin peptide analog via a linking group.

In a specific embodiment, the linking group is a valerate linker having a formula of

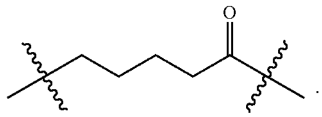 [SMILES: *CCCCC(*)=O]

In a specific embodiment, the linking group is a butylene.

In a specific embodiment, the linking group is a carbonyl.

In a specific embodiment, the PEG polymer is a linear or branched PEG polymer.

In a specific embodiment, the PEG polymer is a linear PEG polymer.

In a specific embodiment, the PEG polymer has molecular weight in the range of 10 kDa and 40 kDa.

In a specific embodiment, the PEG polymer is a linear 30 kDa PEG polymer.

In a specific embodiment, the PEG polymer is a linear 30 kDa mPEG polymer.

In a specific embodiment, the PEGylated conotoxin peptide analog is of Formula (IIa) (SEQ ID NO:83):

(IIa)

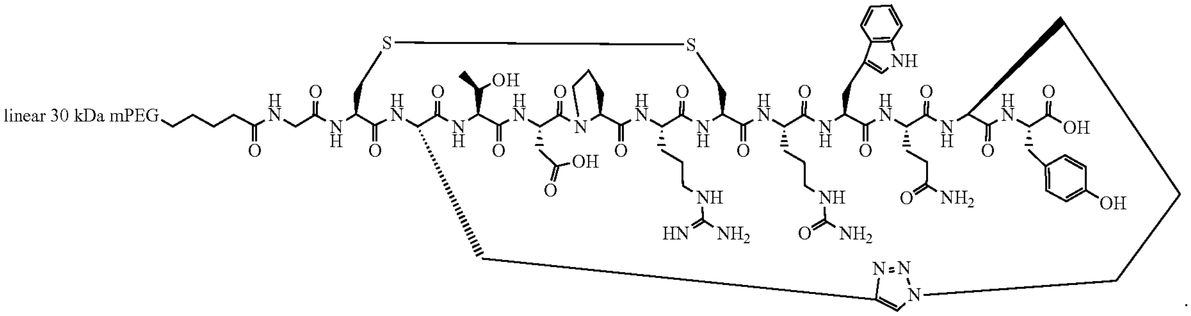

.

In a specific embodiment, the PEGylated conotoxin peptide analog is of Formula (IIg) (SEQ ID NO:95):

(IIg)

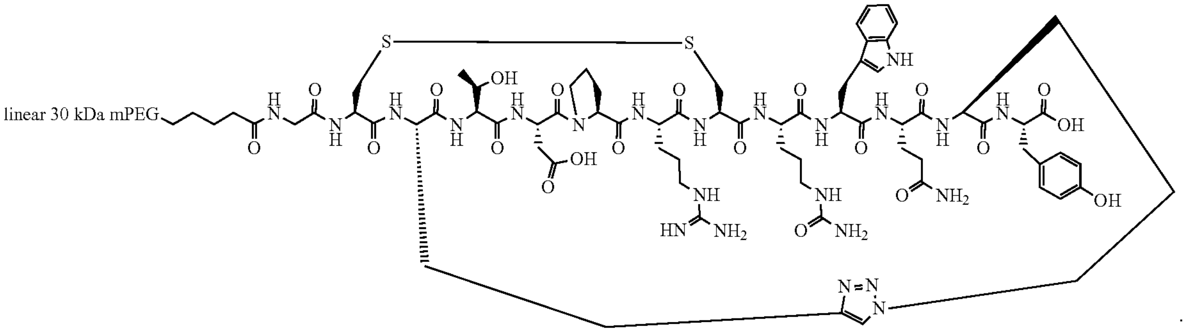

.

In a specific embodiment, the PEGylated conotoxin peptide analog is of Formula (IIh) (SEQ ID NO:96):

(IIh)

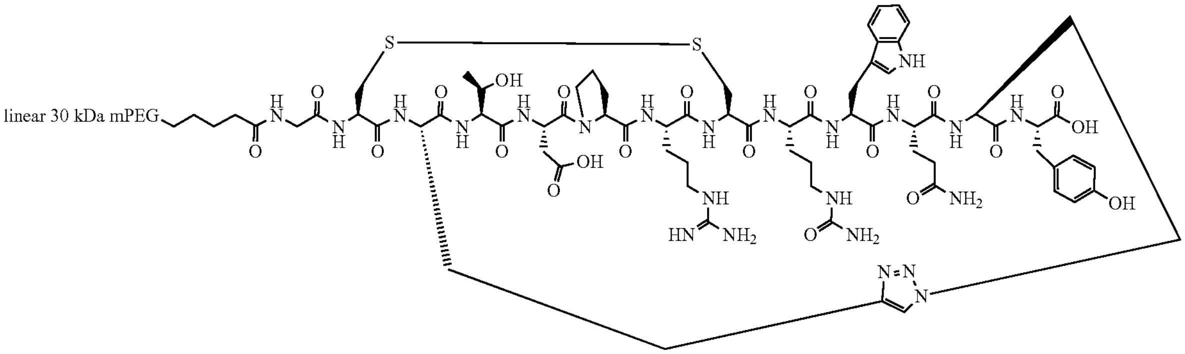

.

In a specific embodiment, the PEGylated conotoxin peptide analog is of Formula (IIi) (SEQ ID NO:97):
(IIi)
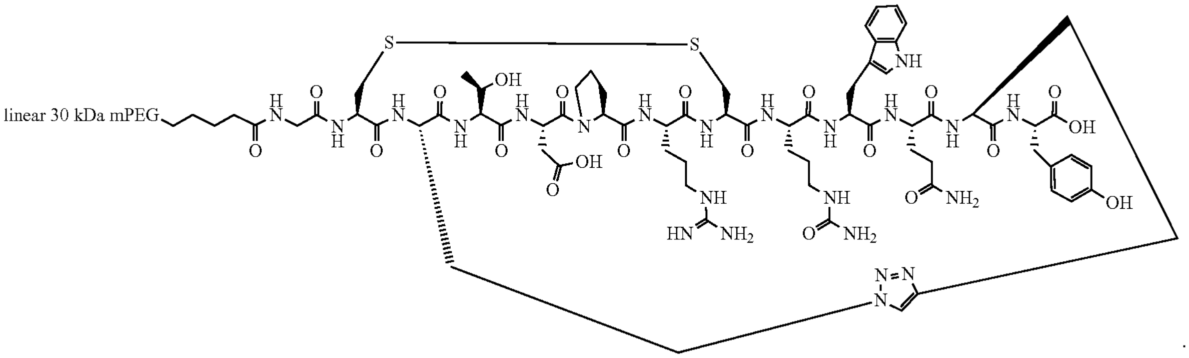
.
In a specific embodiment, the PEGylated conotoxin peptide analog is of Formula (IIk) (SEQ ID NO:98):
(IIk)
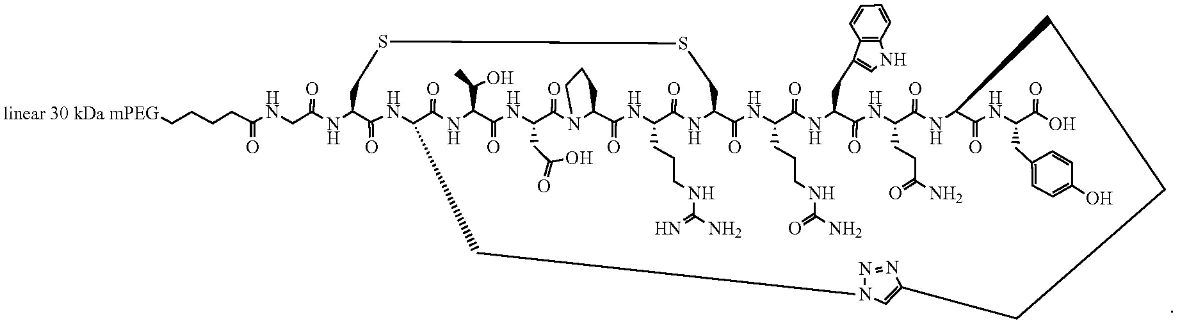
.
In a specific embodiment, the PEGylated conotoxin peptide analog is of Formula (III) (SEQ ID NO:99):
(III)
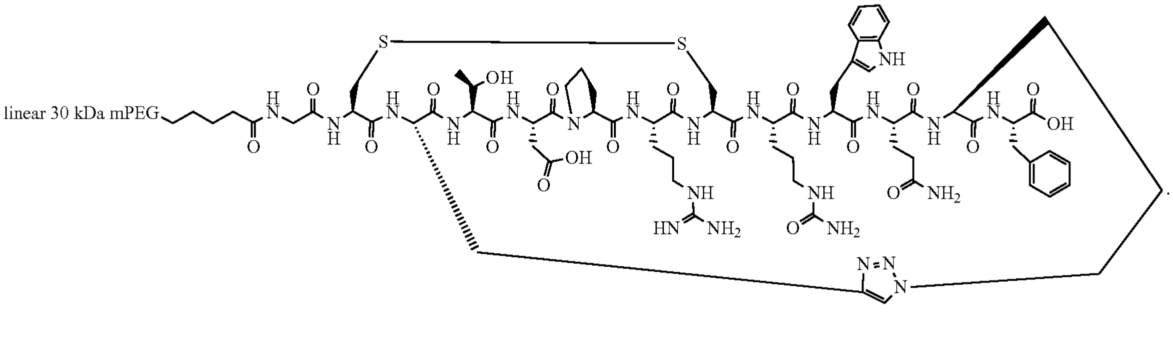
.

In a specific embodiment, the PEGylated conotoxin peptide analog is of Formula (IIm) (SEQ ID NO:100):
(IIm)
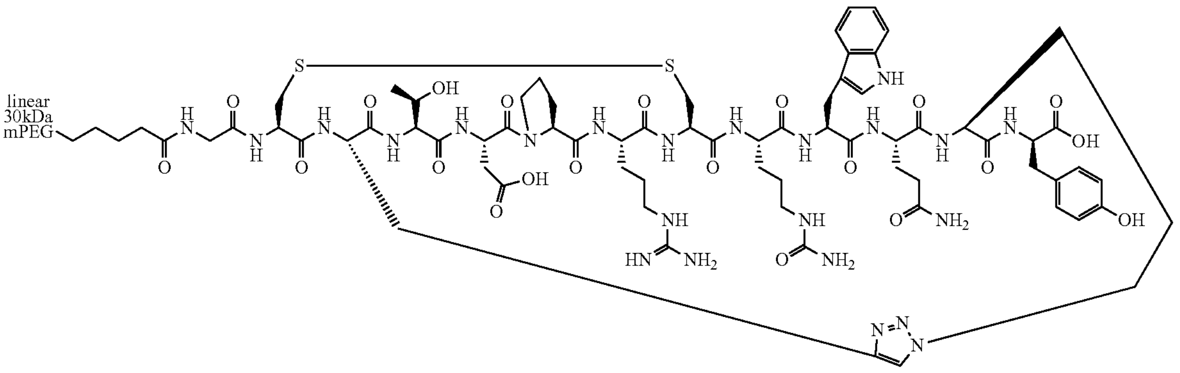
.
In a specific embodiment, the PEGylated conotoxin peptide analog is of Formula (IIn) (SEQ ID NO:101):
(IIn)
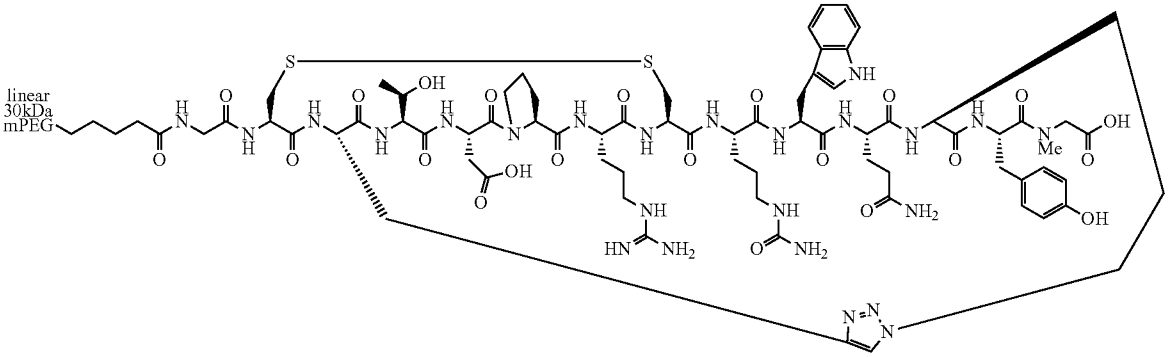
.
In a specific embodiment, the PEGylated conotoxin peptide analog is of Formula (IIo) (SEQ ID NO:102):
(IIo)
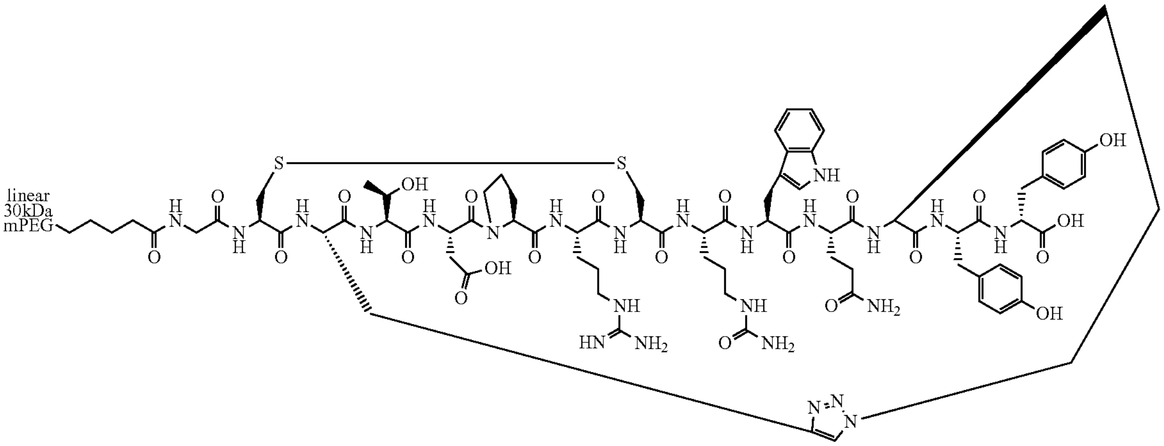
.

In a specific embodiment, the PEGylated conotoxin peptide analog is of Formula (IIp) (SEQ ID NO:103):

(IIp)

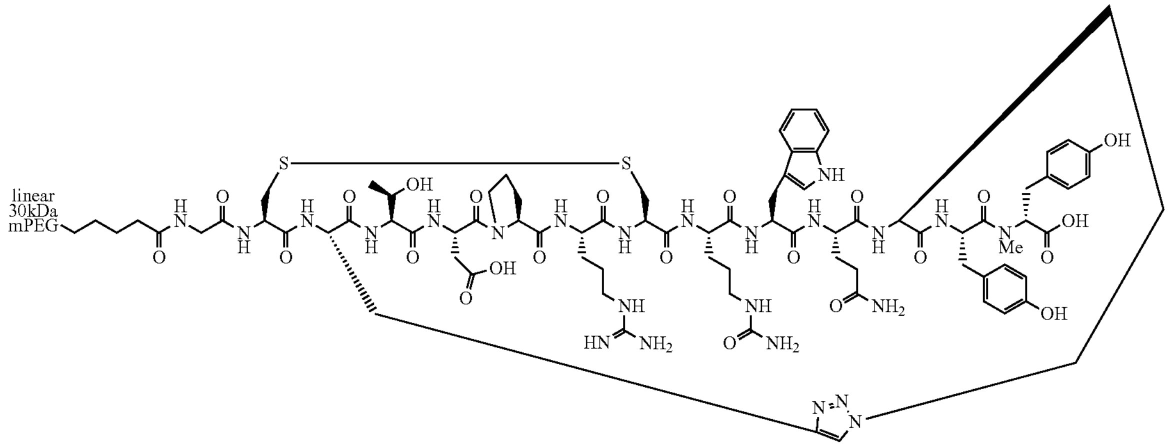

.

Also provided herein are conotoxin peptide analogs of Formula (Ib) (SEQ ID NO:104):

(Ib)

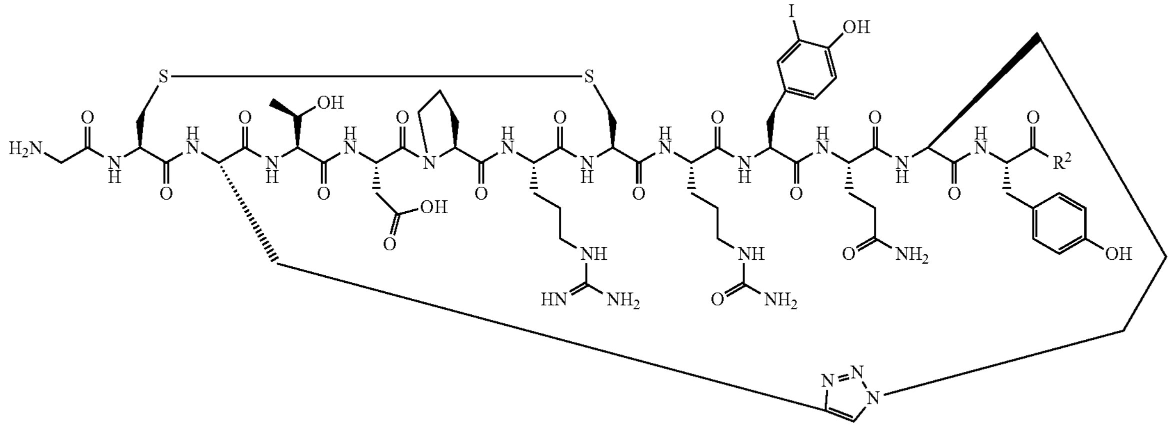

, or a pharmaceutically acceptable salt thereof, wherein $R^2$ is OH or $NH_2$.

In a specific embodiment, $R^2$ is OH.

In a specific embodiment, $R^2$ is $NH_2$.

Also provided herein are PEGylated conotoxin peptide analogs or a pharmaceutically acceptable salt thereof, wherein the conotoxin peptide analog is of Formula (Ib) (SEQ ID NO:104):

(Ib)

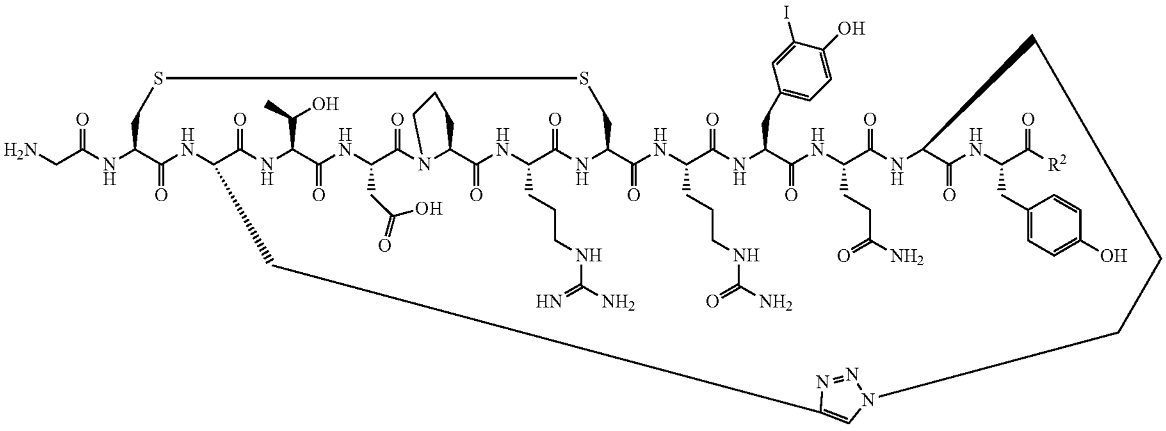

, wherein $R^2$ is OH or $NH_2$; and wherein the conotoxin peptide analog is covalently attached directly or via a linking group to one or more polyethylene glycol (PEG) polymers.

In a specific embodiment, $R^2$ is OH.

In a specific embodiment, $R^2$ is $NH_2$.

In a specific embodiment, the conotoxin peptide analog is covalently attached to one PEG polymer.

In a specific embodiment, the PEG polymer is covalently attached to the N-terminus of the conotoxin peptide analog.

In a specific embodiment, the PEG polymer is covalently attached to the C-terminus of the conotoxin peptide analog.

In a specific embodiment, the PEG polymer is covalently attached to an amino acid residue position that is not the N-terminus or the C-terminus of the conotoxin peptide analog.

In a specific embodiment, the PEG polymer is covalently attached to the conotoxin peptide analog via a linking group.

In a specific embodiment, the linking group is a valerate linker having a formula of

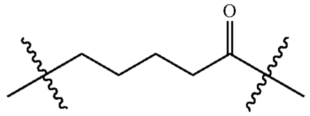

.

In a specific embodiment, the linking group is a butylene.

In a specific embodiment, the linking group is a carbonyl.

In a specific embodiment, the PEG polymer is a linear or branched PEG polymer.

In a specific embodiment, the PEG polymer is a linear PEG polymer.

In a specific embodiment, the PEG polymer has molecular weight in the range of 10 kDa and 40 kDa.

In a specific embodiment, the PEG polymer is a linear 30 kDa PEG polymer.

In a specific embodiment, the PEG polymer is a linear 30 kDa mPEG polymer.

In a specific embodiment, the PEGylated conotoxin peptide analog is of Formula (IIb) (SEQ ID NO:105):

(IIb)

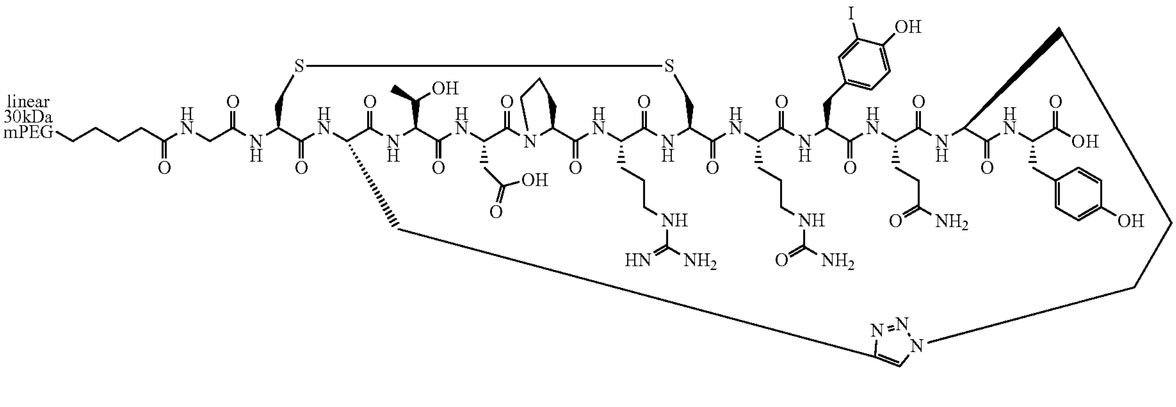

.

Also provided herein are conotoxin peptide analogs selected from the group consisting of conotoxin peptide analogs Ia, Ia', Ib, Ib', Ic, Id, Ie, If, Ig, Ih, Ii, Ij, Ik, Il, Im, In, Io, Ip, Iq, Ir, Is, It, Iu, and Iv, or a pharmaceutically acceptable salt thereof.

In a specific embodiment, the conotoxin peptide analog is selected from the group consisting of conotoxin peptide analogs Ia, Ia', Ib, Ib', Ig, Ih, Ii, Ik, Il, Im, In, Io, and Ip.

In a specific embodiment, the conotoxin peptide analog is selected from the group consisting of conotoxin peptide analogs Ia, Ia', Ib, and Ib'.

Also provided herein are pharmaceutical compositions comprising a conotoxin peptide analog or pharmaceutically acceptable salt thereof, or a PEGylated conotoxin peptide analog or pharmaceutically acceptable salt thereof described herein, and optionally a pharmaceutically acceptable carrier.

Also provided herein are methods of treating or preventing a condition conducive to treatment or prevention by inhibition of an α9-containing nicotinic acetylcholine receptor (nAChR) in a subject comprising administering to the subject a therapeutically effective amount of a conotoxin peptide analog or pharmaceutically acceptable salt thereof, or a PEGylated conotoxin peptide analog or pharmaceutically acceptable salt thereof, or pharmaceutical composition described herein.

Also provided herein are methods of treating or preventing a condition associated with activation of an α9-containing nicotinic acetylcholine receptor (nAChR) in a subject comprising administering to the subject a therapeutically effective amount of a conotoxin peptide analog or pharmaceutically acceptable salt thereof, or a PEGylated conotoxin peptide analog or pharmaceutically acceptable salt thereof, or pharmaceutical composition described herein.

In a specific embodiment, the condition conducive to treatment or prevention by inhibition of the α9-containing nAChR is pain or inflammation.

In a specific embodiment, the condition is pain.

In a specific embodiment, the pain is selected from the group consisting of general pain, chronic pain, neuropathic pain, nociceptive pain, inflammatory pain, visceral pain, somatic pain, pain induced by peripheral nerve damage, pain induced by an inflammatory disorder, pain induced by a metabolic disorder, pain induced by cancer, pain induced by chemotherapy, pain induced by a surgical procedure, and pain induced by a burn.

In a specific embodiment, the pain is cancer-related chronic pain.

In a specific embodiment, the condition conducive to treatment or prevention by inhibition of the α9-containing nAChR is an inflammatory condition.

In a specific embodiment, the inflammatory condition is selected from the group consisting of inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, and cardiovascular disease.

In a specific embodiment, the inflammatory condition is mediated by immune cells.

In a specific embodiment, the inflammatory condition is long-term inflammation and/or peripheral neuropathy following injury.

In a specific embodiment, the condition conducive to treatment or prevention by inhibition of the α9-containing nAChR is pain and inflammation.

In a specific embodiment, the condition conducive to treatment or prevention by inhibition of the α9-containing nAChR is inflammation and neuropathy.

In a specific embodiment, the condition conducive to treatment or prevention by inhibition of an α9-containing nicotinic acetylcholine receptor (nAChR) is a condition conducive to treatment or prevention by inhibition of an α9α10 subtype of nAChR.

In a specific embodiment, the subject is a human.

Also provided herein are methods of treating or preventing pain or inflammation in a subject comprising administering to the subject a therapeutically effective amount of a conotoxin peptide analog or pharmaceutically acceptable salt thereof, or a PEGylated conotoxin peptide analog or pharmaceutically acceptable salt thereof, or pharmaceutical composition described herein.

Also provided herein are conotoxin peptide analogs or pharmaceutically acceptable salt thereof, or PEGylated conotoxin peptide analogs or pharmaceutically acceptable salt thereof, or pharmaceutical compositions described herein, for use in treating or preventing a condition conducive to treatment or prevention by inhibition of an α9-containing nicotinic acetylcholine receptor (nAChR) in a subject.

Also provided herein are pharmaceutical compositions comprising a conotoxin peptide analog or pharmaceutically acceptable salt thereof, or a PEGylated conotoxin peptide analog or pharmaceutically acceptable salt thereof, for use in treating or preventing a condition conducive to treatment or prevention by inhibition of an α9-containing nicotinic acetylcholine receptor (nAChR) in a subject.

Also provided herein are uses of a conotoxin peptide analog or pharmaceutically acceptable salt thereof, or a PEGylated conotoxin peptide analog or pharmaceutically acceptable salt thereof, or pharmaceutical composition described herein, in the preparation of a medicament for treating or preventing a condition conducive to treatment or prevention by inhibition of an α9-containing nicotinic acetylcholine receptor (nAChR) in a subject.

Also provided herein are conotoxin peptide analogs or a salt thereof, wherein the amino acid sequence of the conotoxin peptide analog is (SEQ ID NO: 106)
Gly-Cys-$X_{AA}^3$-Thr-Asp-Pro-Arg-Cys-$X_{AA}^9$-Trp-Gln-$X_{AA}^{12}$-X, wherein $X_{AA}^3$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}^9$ is Citrulline;

$X_{AA}^{12}$ is selected from the group consisting of (S)-gamma-azidohomoalanine, (S)-homopropargyl glycine, (S)-azidonorvaline, and (S)-bishomopropargyl glycine; wherein when $X_{AA}^3$ is selected from the group consisting of (S)-propargyl glycine, (S)-homopropargyl glycine, and (S)-bishomopropargyl glycine, $X_{AA}^{12}$ is (S)-gamma-azidohomoalanine or (S)-azidonorvaline; and when $X_{AA}^3$ is selected from the group consisting of (S)-azidoalanine, (S)-gamma-azidohomoalanine, and (S)-azidonorvaline, $X_AA^{12}$ is (S)-homopropargyl glycine or (S)-bishomopropargyl glycine;

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr; and wherein the C-terminus of the conotoxin peptide analog is a carboxylic acid or an amide group.

In a specific embodiment, $X_{AA}^{3}$ is (S)-propargyl glycine or (S)-azidoalanine.

In a specific embodiment, $X_{AA}^{12}$ is (S)-azidonorvaline or (S)-bishomopropargyl glycine.

In a specific embodiment, $X_{AA}^{3}$ is (S)-propargyl glycine and $X_{AA}^{12}$ is (S)-azidonorvaline.

In a specific embodiment, $X_{AA}^{3}$ is (S)-homopropargyl glycine and $X_{AA}^{12}$ is (S)-azidonorvaline.

In a specific embodiment, $X_{AA}^{3}$ is (S)-homopropargyl glycine and $X_{AA}^{12}$ is (S)-gamma-azidohomoalanine.

In a specific embodiment, $X_{AA}^{3}$ is (S)-gamma-azidohomoalanine and $X_{AA}^{12}$ is (S)-homopropargyl glycine.

In a specific embodiment, $X_{AA}^{3}$ is (S)-azidoalanine and $X_{AA}^{12}$ is (S)-bishomopropargyl glycine.

In a specific embodiment, X is $X_{AA}^{1}$.

In a specific embodiment, X is $X_{AA}^{1}X_{AA}^{2}$.

In a specific embodiment, $X_{AA}^{1}$ is selected from the group consisting of Tyr, D-Tyr and Phe.

In a specific embodiment, X is Tyr.

In a specific embodiment, the C-terminus of the conotoxin peptide analog is OH.

In a specific embodiment, the C-terminus of the conotoxin peptide analog is $NH_2$.

In a specific embodiment, $X_{AA}^{3}$ is (S)-propargyl glycine, $X_{AA}^{12}$ is (S)-azidonorvaline, X is Tyr.

In a specific embodiment, the C-terminus of the conotoxin peptide analog is a carboxylic acid group.

In a specific embodiment, the C-terminus of the conotoxin peptide analog is an amide group.

In a specific embodiment, $X_{AA}^{3}$ is (S)-homopropargyl glycine, $X_{AA}^{12}$ is (S)-azidonorvaline, X is Tyr; and wherein the C-terminus of the conotoxin peptide analog is a carboxylic acid group.

In a specific embodiment, $X_{AA}^{3}$ is (S)-homopropargyl glycine, $X_{AA}^{12}$ is (S)-gamma-azidohomoalanine, X is Tyr; and wherein the C-terminus of the conotoxin peptide analog is a carboxylic acid group.

In a specific embodiment, $X_{AA}^{3}$ is (S)-gamma-azidohomoalanine, $X_{AA}^{12}$ is (S)-homopropargyl glycine, X is Tyr; and wherein the C-terminus of the conotoxin peptide analog is a carboxylic acid group.

In a specific embodiment, $X_{AA}^{3}$ is (S)-azidoalanine, $X_{AA}^{12}$ is (S)-bishomopropargyl glycine, X is Tyr; and wherein the C-terminus of the conotoxin peptide analog is a carboxylic acid group.

In a specific embodiment, $X_{AA}^{3}$ is (S)-propargyl glycine, $X_{AA}^{12}$ is (S)-azidonorvaline, X is Phe; and wherein the C-terminus of the conotoxin peptide analog is a carboxylic acid group.

In a specific embodiment, $X_{AA}^{3}$ is (S)-propargyl glycine, $X_{AA}^{12}$ is (S)-azidonorvaline, X is D-Tyr; and wherein the C-terminus of the conotoxin peptide analog is a carboxylic acid group.

In a specific embodiment, $X_{AA}^{3}$ is (S)-propargyl glycine, $X_{AA}^{12}$ is (S)-azidonorvaline, X is Tyr-N-Me-Gly; and wherein the C-terminus of the conotoxin peptide analog is a carboxylic acid group.

In a specific embodiment, $X_{AA}^{3}$ is (S)-propargyl glycine, $X_{AA}^{12}$ is (S)-azidonorvaline, X is Tyr-D-Tyr; and wherein the C-terminus of the conotoxin peptide analog is a carboxylic acid group.

In a specific embodiment, $X_{AA}^{3}$ is (S)-propargyl glycine, $X_{AA}^{12}$ is (S)-azidonorvaline, X is Tyr-N-Me-Tyr; and wherein the C-terminus of the conotoxin peptide analog is a carboxylic acid group.

Also provided herein are conotoxin peptide analogs or a salt thereof, wherein the amino acid sequence of the conotoxin peptide analog is (SEQ ID NO: 107)
Gly-Cys-$X_{AA}^{3}$-Thr-Asp-Pro-Arg-Cys-$X_{AA}^{9}$-$X_{AA}^{10}$-Gln-$X_{AA}^{12}$-Tyr, wherein
$X_{AA}^{3}$ is (S)-propargyl glycine;
$X_{AA}^{9}$ is Citrulline;
$X_{AA}^{10}$ is 3-iodo-Tyr;
$X_{AA}^{12}$ is (S)-azidonorvaline;
wherein the C-terminus of the conotoxin peptide analog is a carboxylic acid or an amide group.

In a specific embodiment, the C-terminus of the conotoxin peptide analog is a carboxylic acid group.

In a specific embodiment, the C-terminus of the conotoxin peptide analog is an amide group.

Also provided herein are methods of making a conotoxin peptide analog of Formula (I) (SEQ ID NO:93) or a pharmaceutically acceptable salt thereof, (I)

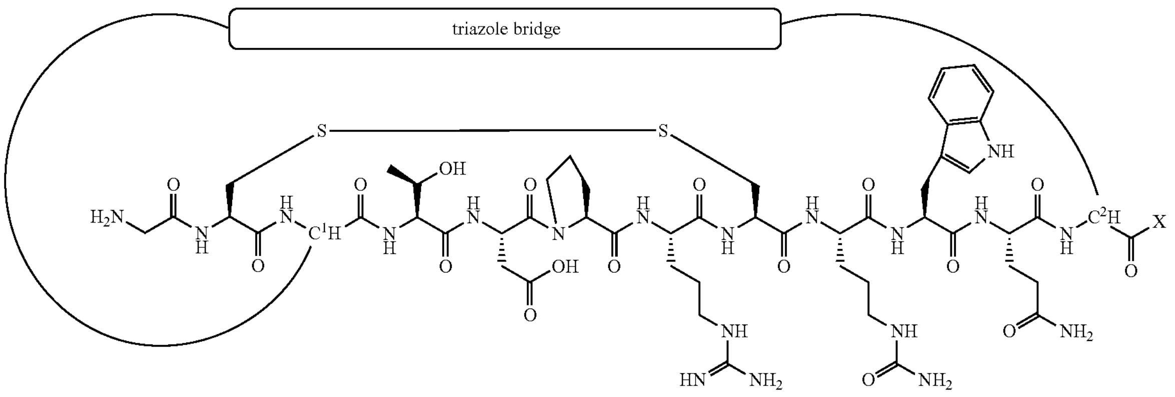

wherein

X is $X_{AA}^{1}$ or $X_{AA}^{1}X_{AA}^{2}$; wherein $X_{AA}^{1}$ is Tyr, Phe, Trp, or a D-isomer of Tyr, Phe, or Trp, and $X_{AA}^{2}$ is N-Me-Gly, D-Tyr, or N-Me-Tyr; and wherein the C-terminus of the conotoxin peptide analog of Formula (I) is a carboxylic acid or an amide group;

comprising subjecting an intermediate conotoxin peptide analog or a salt thereof to triazole formation conditions, wherein the amino acid sequence of the intermediate conotoxin peptide analog is Gly-Cys-$X_{AA}^{3}$-Thr-Asp-Pro-Arg-Cys-$X_{AA}^{9}$-Trp-Gln-$X_{AA}^{12}$-X (SEQ ID NO:106), wherein $X_{AA}^{3}$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}^{9}$ is Citrulline;

$X_{AA}^{12}$ is selected from the group consisting of (S)-gamma-azidohomoalanine, (S)-homopropargyl glycine, (S)-azidonorvaline, and (S)-bi shomopropargyl glycine;

wherein when $X_{AA}^{3}$ is selected from the group consisting of (S)-propargyl glycine, (S)-homopropargyl glycine, and (S)-bishomopropargyl glycine, $X_{AA}^{12}$ is (S)-gamma-azidohomoalanine or (S)-azidonorvaline; when $X_{AA}^{3}$ is selected from the group consisting of (S)-azidoalanine, (S)-gamma-azidohomoalanine, and (S)-azidonorvaline, $X_{AA}^{12}$ is (S)-homopropargyl glycine or (S)-bishomopropargyl glycine;

X is as defined above for the conotoxin peptide analog of Formula (I); and wherein the C-terminus of the intermediate conotoxin peptide analog is as defined above for the conotoxin peptide analog of Formula (I); and wherein under said triazole formation conditions $X_{AA}^{3}$ reacts with $X_{AA}^{12}$ to form the triazole bridge in the conotoxin peptide analog of Formula (I).

Also provided herein are methods of making a conotoxin peptide analog of Formula (Ib) (SEQ ID NO:104) or a pharmaceutically acceptable salt thereof, wherein $X_{AA}^{3}$ is (S)-propargyl glycine;

$X_{AA}^{9}$ is Citrulline;

$X_{AA}^{10}$ is 3-iodo-Tyr;

$X_{AA}^{12}$ is (S)-azidonorvaline; and wherein the C-terminus of the intermediate conotoxin peptide analog is as defined above for the conotoxin peptide analog of Formula (Ib); and wherein under said triazole formation conditions $X_{AA}^{3}$ reacts with $X_{AA}^{12}$ to form a triazole bridge as depicted in the conotoxin peptide analog of Formula (Ib).

Also provided herein are methods of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is covalently attached directly or via a linking group to the one or more PEG polymers, wherein the amino acid sequence of the conotoxin peptide analog is Gly-Cys-$X_{AA}^{3}$-Thr-Asp-Pro-Arg-Cys-$X_{AA}^{9}$-Trp-Gln-$X_{AA}^{12}$-X (SEQ ID NO106), wherein $X_{AA}^{3}$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}^{9}$ is Citrulline;

$X_{AA}^{12}$ is selected from the group consisting of (S)-gamma-azidohomoalanine, (S)-homopropargyl glycine, (S)-azidonorvaline, and (S)-bishomopropargyl glycine;

wherein when $X_{AA}^{3}$ is selected from the group consisting of (S)-propargyl glycine, (S)-homopropargyl glycine, and (S)-bishomopropargyl glycine, $X_{AA}^{12}$ is (S)-gamma-azidohomoalanine or (S)-azidonorvaline; when $X_{AA}^{3}$ is selected from the group consisting of (S)-azidoalanine, (S)-gamma-azido-homoalanine, and (S)-azidonorvaline, $X_{AA}^{12}$ is (S)-homopropargyl glycine or (S)-bishomopropargyl glycine;

X is $X_{AA}^{1}$ or $X_{AA}^{1}X_{AA}^{2}$; wherein $X_{AA}^{1}$ is Tyr, Phe, Trp, or a D-isomer of Tyr, Phe, or Trp, and $X_{AA}^{2}$ is N-Me-Gly, D-Tyr, or N-Me-Tyr; and (Ib)

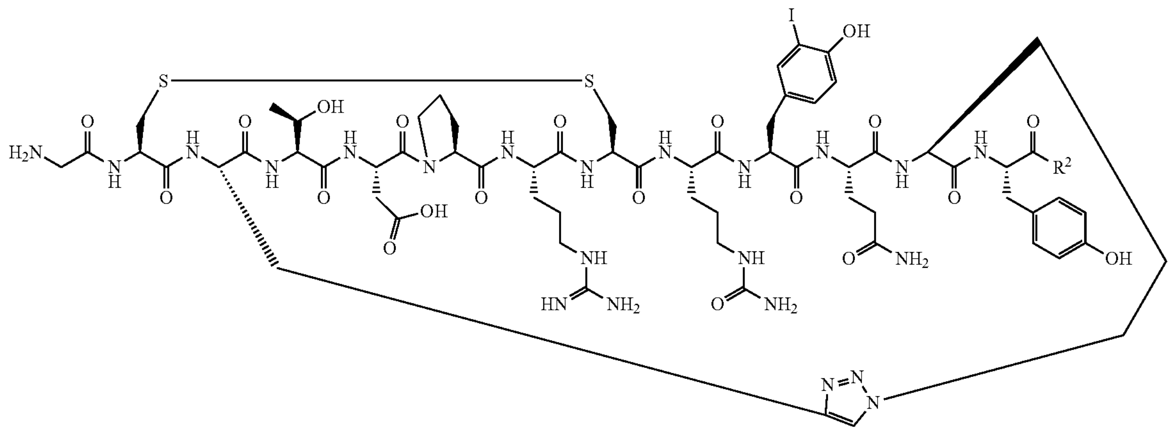

wherein the C-terminus of the conotoxin peptide analog of Formula (Ib) is a carboxylic acid or an amide group, comprising subjecting an intermediate conotoxin peptide analog or a salt thereof to triazole formation conditions, wherein the amino acid sequence of the intermediate conotoxin peptide analog is Gly-Cys-$X_{AA}^{3}$-Thr-Asp-Pro-Arg-Cys-$X_{AA}^{9}$-$X_{AA}^{10}$-Gln-$X_{AA}^{12}$-Tyr (SEQ ID NO:107), wherein the C-terminus of the conotoxin peptide analog is a carboxylic acid or an amide group.

Also provided herein are methods of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is covalently attached directly or via a linking group to the one or more PEG polymers, wherein the amino acid sequence of the conotoxin peptide analog is Gly-Cys-$X_{AA}{}^{3}$-Thr-Asp-Pro-Arg-Cys-$X_{AA}{}^{9}$-$X_{AA}{}^{10}$-Gln-$X_{AA}{}^{12}$-Tyr (SEQ ID NO107), wherein $X_{AA}{}^{3}$ is (S)-propargyl glycine;

$X_{AA}{}^{9}$ is Citrulline;

$X_{AA}{}^{10}$ is 3-iodo-Tyr;

$X_{AA}{}^{12}$ is (S)-azidonorvaline;

wherein the C-terminus of the conotoxin peptide analog is a carboxylic acid or an amide group.

4. BRIEF DESCRIPTION OF FIGURES

FIG. 1A-FIG. 10: Disulfide shuffling of CSP-4-NH2 in human serum. FIG. 1A: CSP-4-NH2 was spiked into human serum and incubated at 37° C. for the specified period, after which samples were frozen, purified by precipitation and filtration and analyzed by RP-HPLC. A time-dependent conversion of main peak to secondary peak with faster retention time was observed. FIG. 1B: Individual injections of synthetically constructed CSP-4-NH2 ribbon, bead and native isomers together with a sample of CSP-4-NH2 isolated from human serum were analyzed. Comigration of serum-derived peaks indicated conversion of the native form to the ribbon isomer. FIG. 1C: Isolation of serum-derived compound CSP-4-NH2 followed by lyophilization and mass spectrometry analysis indicated that both the native and ribbon isomer have the same mass-to-charge ratio. FIG. 1D: Conversion of the globular to ribbon form by glutathione reduction of CSP-4-NH2 indicated that disulfide shuffling underlies isomerization.

Figure 2A:
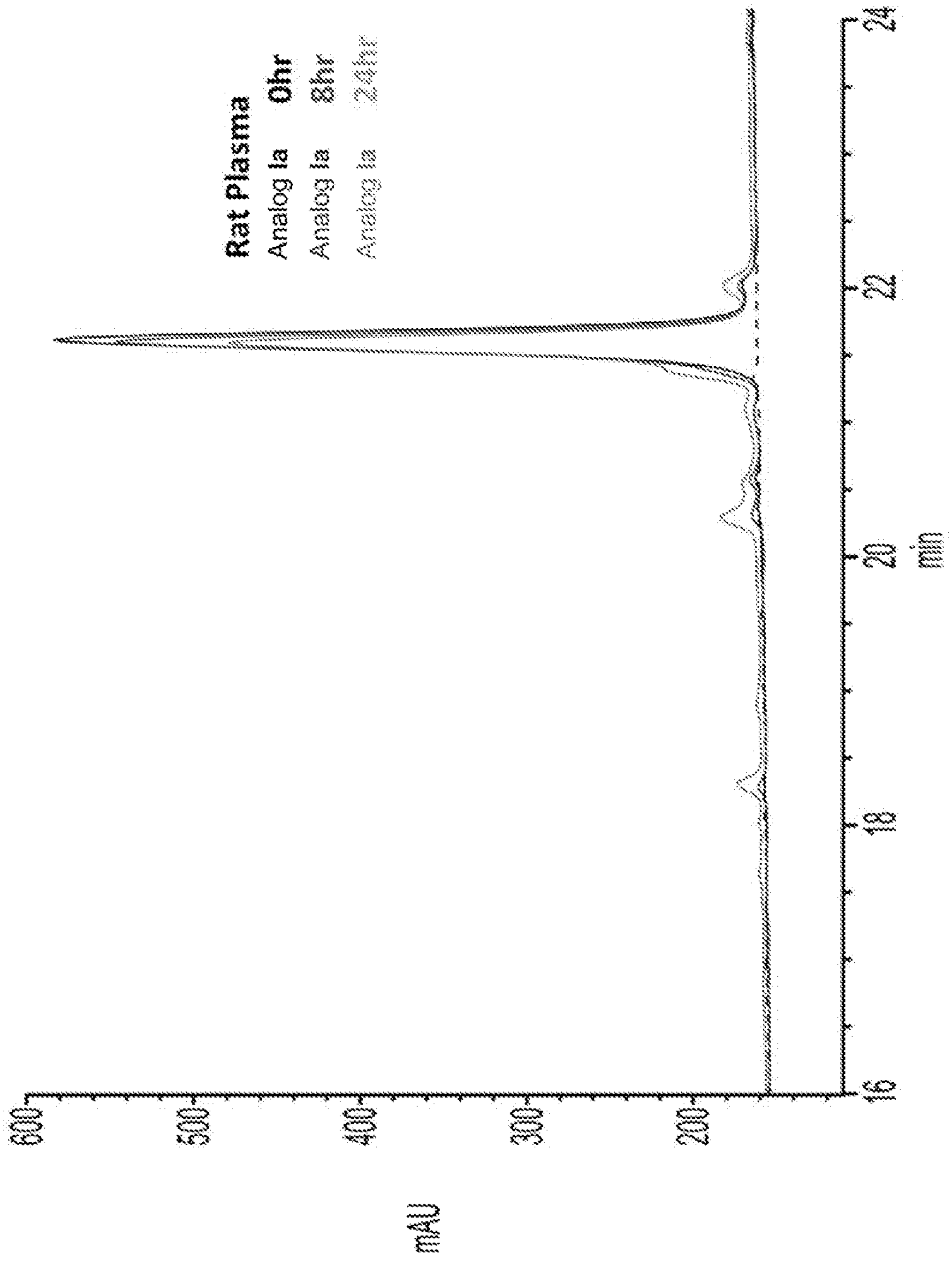
Figure 2B:
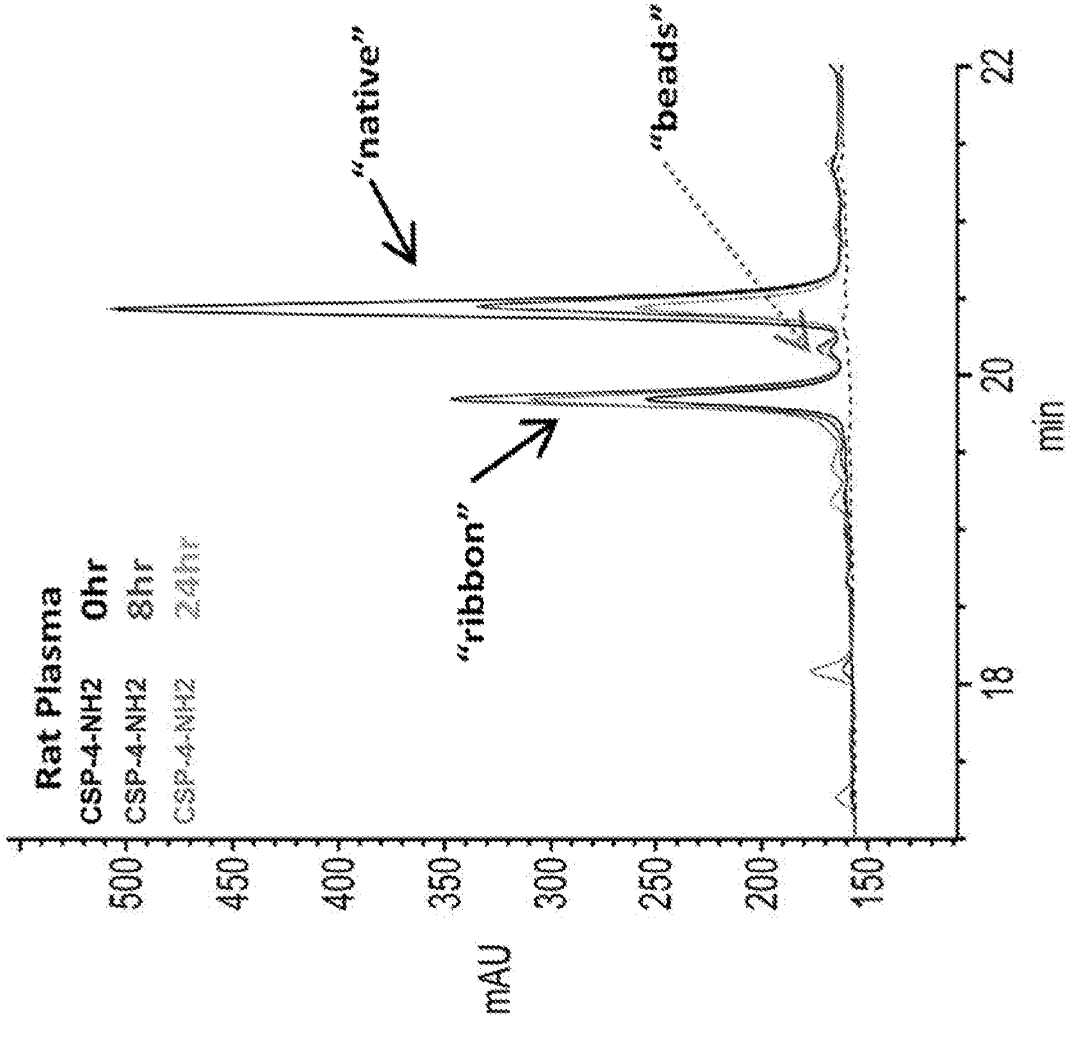

FIG. 2A-FIG. 2B: Reverse phase HPLC analyses of conotoxin peptide analog Ia and conotoxin peptide analog CSP-4-NH2 in rat plasma. FIG. 2A: reverse phase HPLC analyses of conotoxin peptide analog Ia at 0 h, 8 h and 24 h (black line: 0 h; dark grey line: 8 h; light grey line: 24 h). FIG. 2B: reverse phase HPLC analyses of conotoxin peptide analog CSP-4-$NH_2$ ("native" form, consisting of two disulfide bonds, one between Cys2 and Cys8, and a second between Cys3 and Cys12) in rat plasma at 0 h, 8 h and 24 h (black line: 0 h; dark grey line: 8 h; light grey line: 24 h).

Figure 3B:
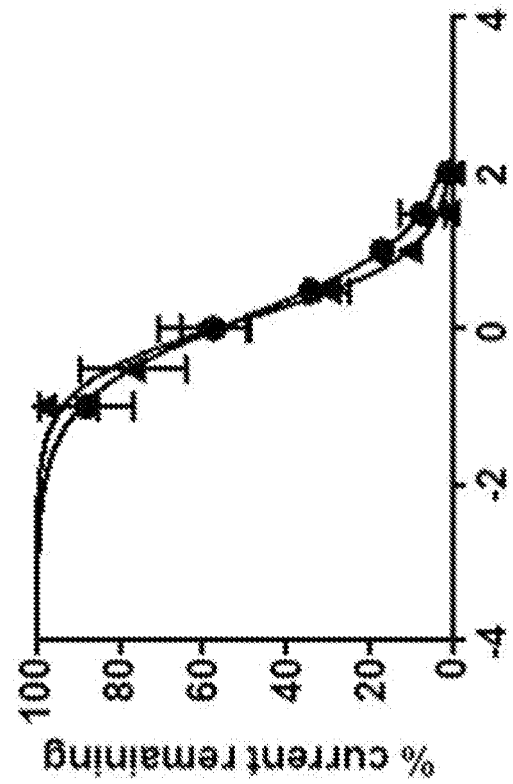
Figure 3A:
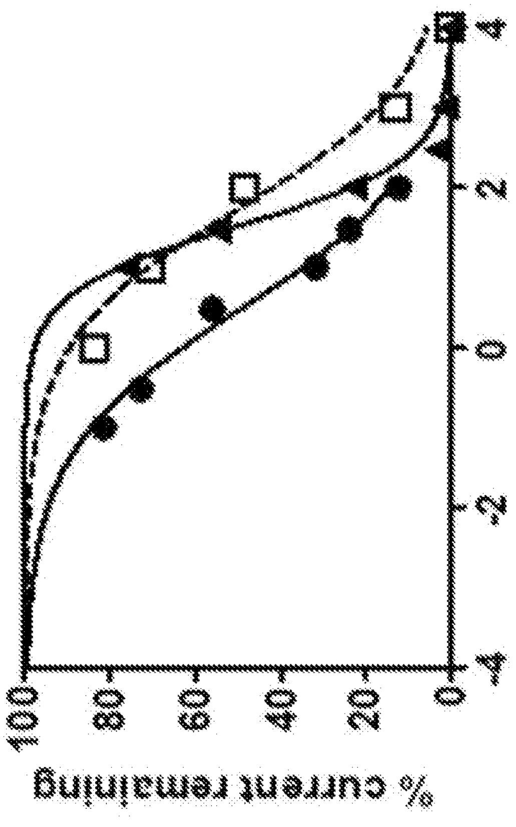

FIG. 3A-FIG. 3B: Concentration-response curves of conotoxin peptide analogs for inhibition of ACh-gated currents in the human α9α10 nAChR. FIG. 3A: Concentration-response curves of conotoxin peptide analogs Ia, Ia' and Ib' for inhibition of ACh-gated currents in the human α9α10 nAChR (●: Ia; ▲: Ia'; □: Ib'). FIG. 3B: Concentration-response curves of conotoxin peptide analogs CSP-4-NH2 and CSP-4-OH for inhibition of ACh-gated currents in the human α9α10 nAChR (●: CSP-4-NH2; ▲: CSP-4-OH).

Figure 4:
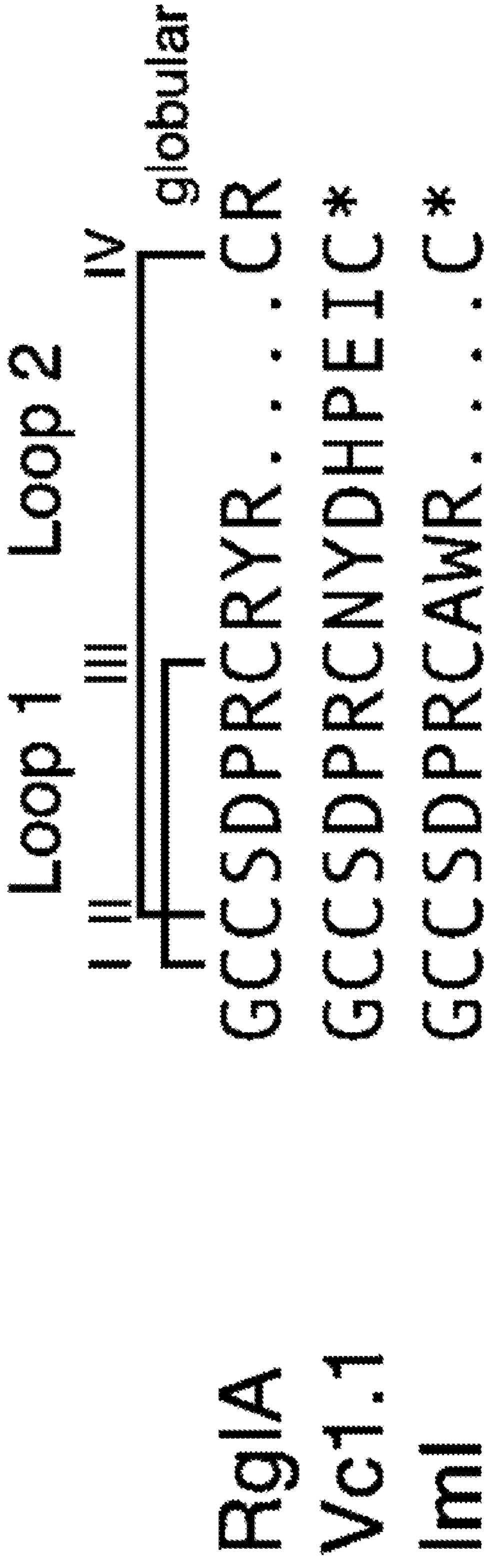

FIG. 4: Comparison of the amino acid sequences of RgIA (SEQ ID NO:1), ImI (SEQ ID NO:2) and Vc1.1 (SEQ ID NO:3).

Figure 5A:
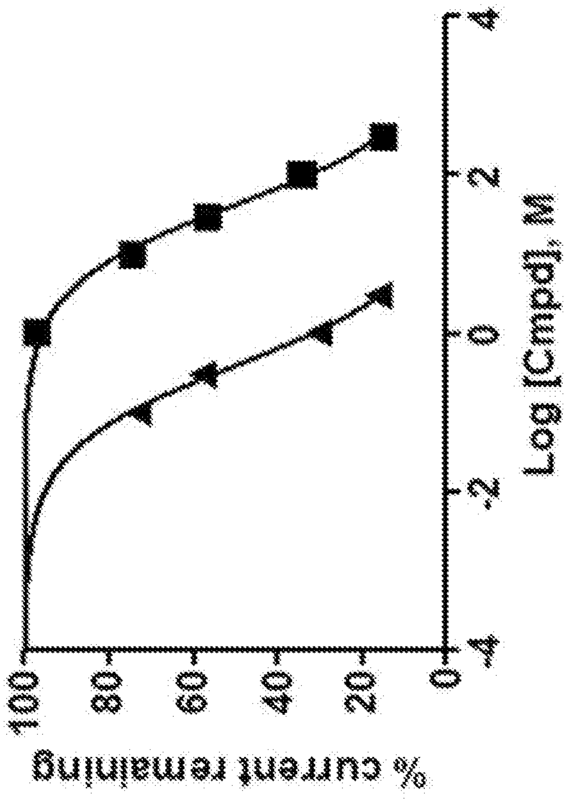
Figure 5B:
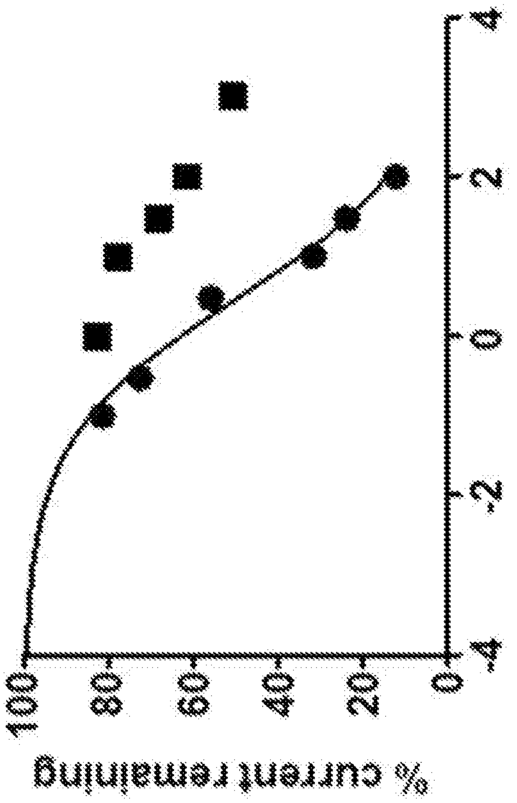

FIG. 5A-FIG. 5B: Concentration-response curves of conotoxin peptide analogs for inhibition of ACh-gated currents in the human α9α10 nAChR. FIG. 5A: Concentration-response curves of conotoxin peptide analogs CSP-4-OH and CSP-4-desTyr-OH for inhibition of ACh-gated currents in the human α9α10 nAChR (▲: CSP-4-OH; ■: CSP-4-desTyr-OH). FIG. 5B: Concentration-response curves of conotoxin peptide analogs 1a and 1q for inhibition of ACh-gated currents in the human α9α10 nAChR (●: 1a; ■: 1q).

Figure 6B:
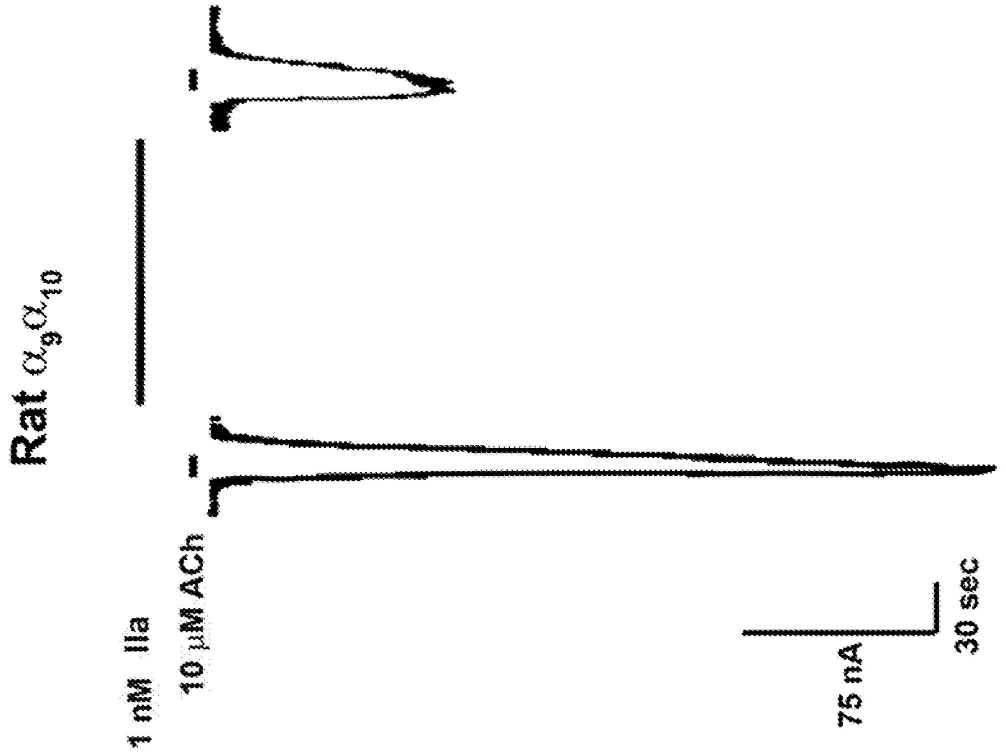
Figure 6A:
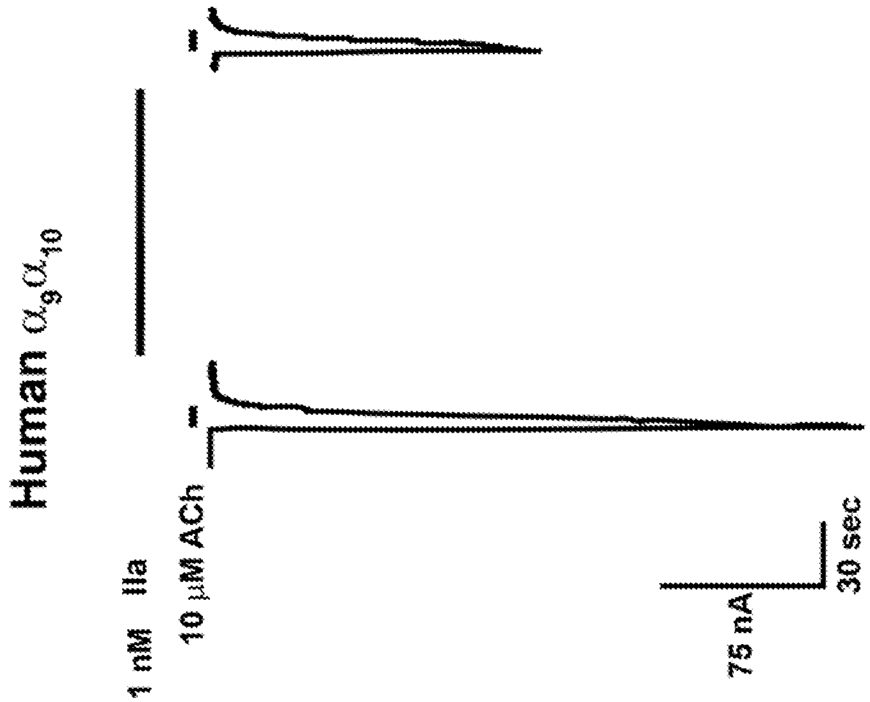

FIG. 6A-FIG. 6B: Representative traces from an oocyte injected with either the human (left) or rat (right) α9α10 nAChR. ACh-gated currents before and after exposure to compound PEGyated conotoxin peptide analog IIa. FIG. 6A: Response to ACh of the human α9α10 nAChR. FIG. 6B: Response to ACh of the rat α9α10 nAChR.

Figure 7A:
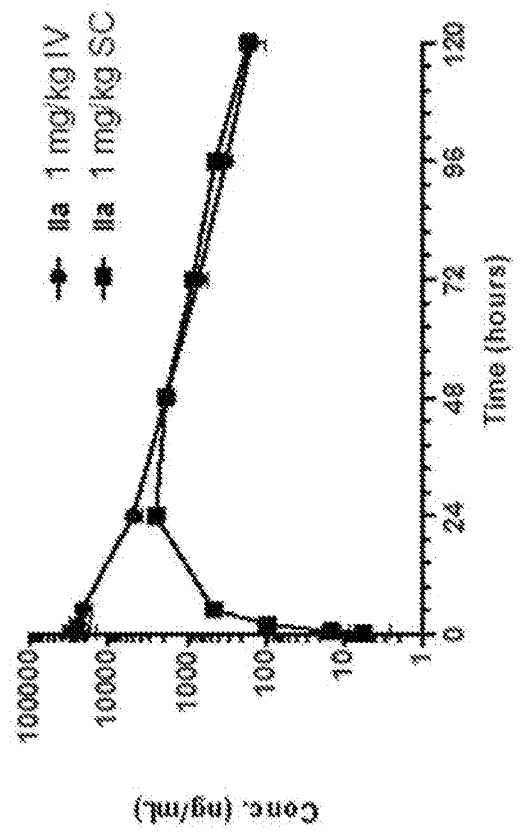
Figure 7B:
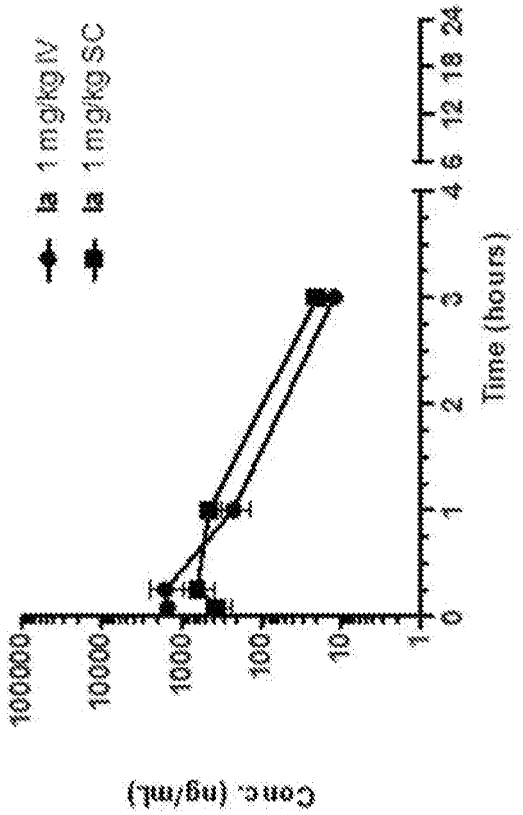

FIG. 7A-FIG. 7B: Pharmacokinetic profile of PEGylated conotoxin peptide analogs in rats. Mean concentration vs. time profiles of PEGylated conotoxin peptide analog IIa and conotoxin peptide analog Ia administered intravenously and subcutaneously to rats at 1 mg/kg (n=3). FIG. 7A: Pharmacokinetic profile of PEGylated conotoxin peptide analog IIa (-◆-: 1 mg/kg IV administration; -■-: 1 mg/kg SC administration). FIG. 7B: Pharmacokinetic profile of conotoxin peptide analog Ia (-◆-: 1 mg/kg IV administration; -■-: 1 mg/kg SC administration).

Figure 8:
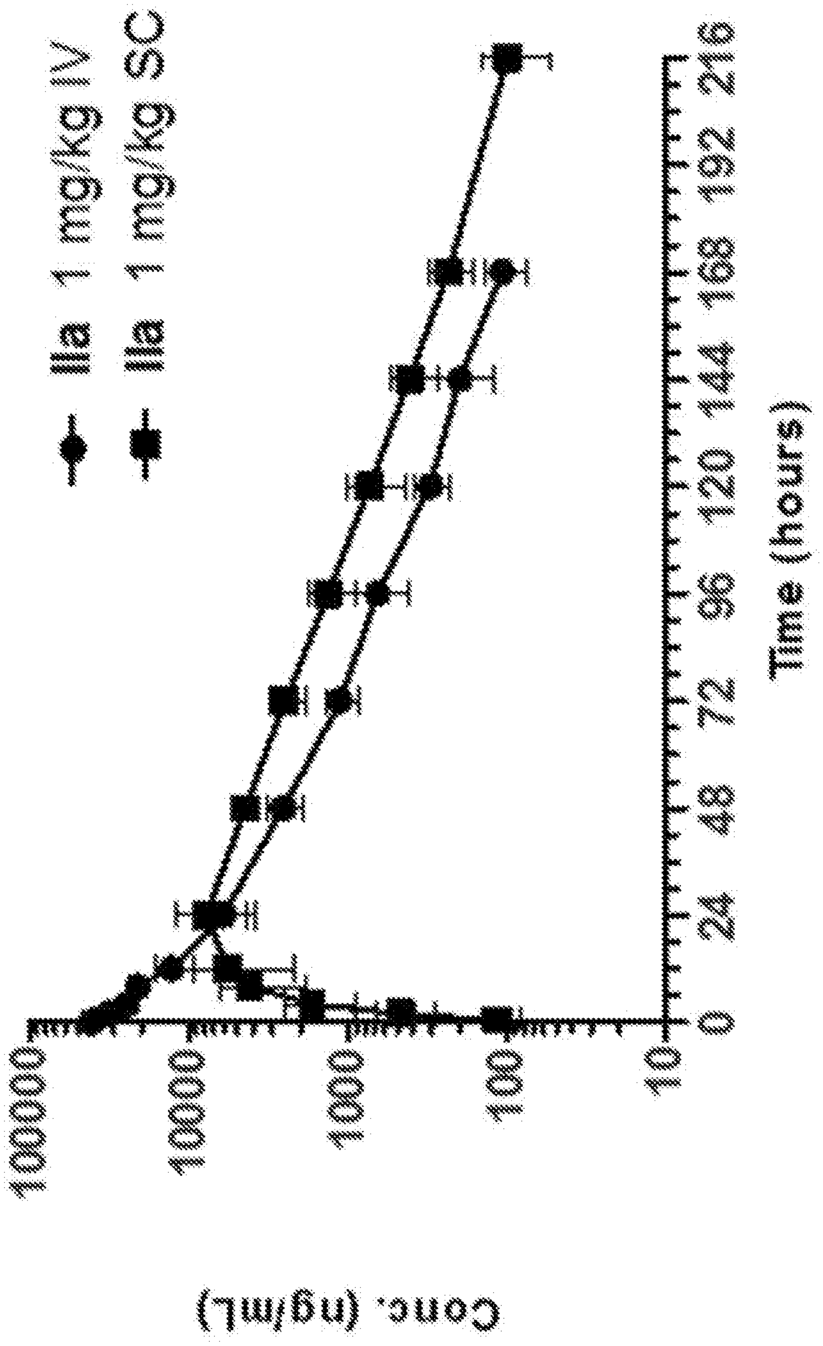

FIG. 8: Pharmacokinetic profile of PEGylated conotoxin peptide analog IIa in monkeys. Mean concentration vs time profile of compound 21 administered intravenously and subcutaneously to cynomolgus macaque monkeys at 1 mg/kg (n=3) (-◆-: 1 mg/kg IV administration; -■-: 1 mg/kg SC administration).

Figure 9:
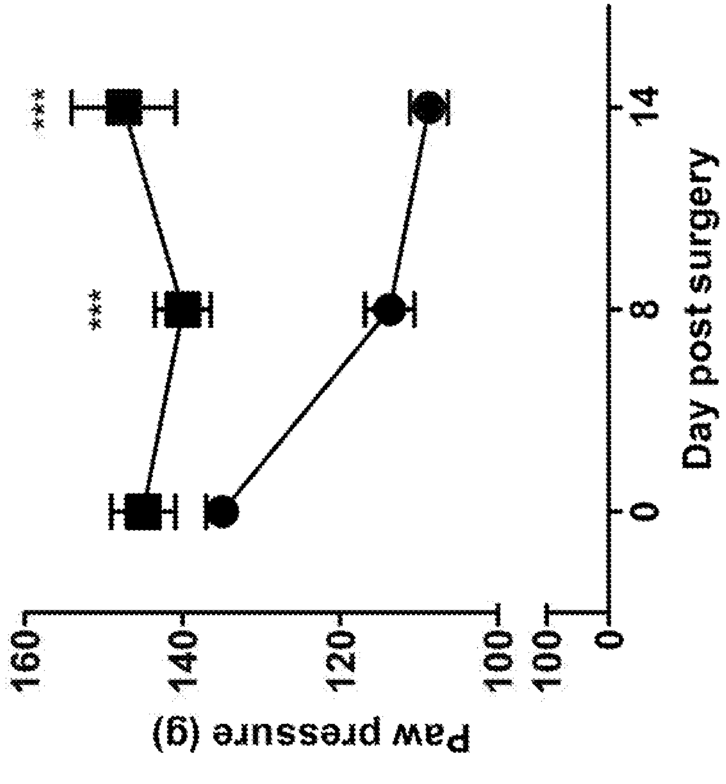

FIG. 9: Analgesic efficacy and duration of effect of conotoxin peptide analog Ib' in a rat chronic constriction injury (CCI) model (■: 0.1 mg/kg/day of conotoxin peptide analog Ib'; ●: vehicle).

Figure 10A:
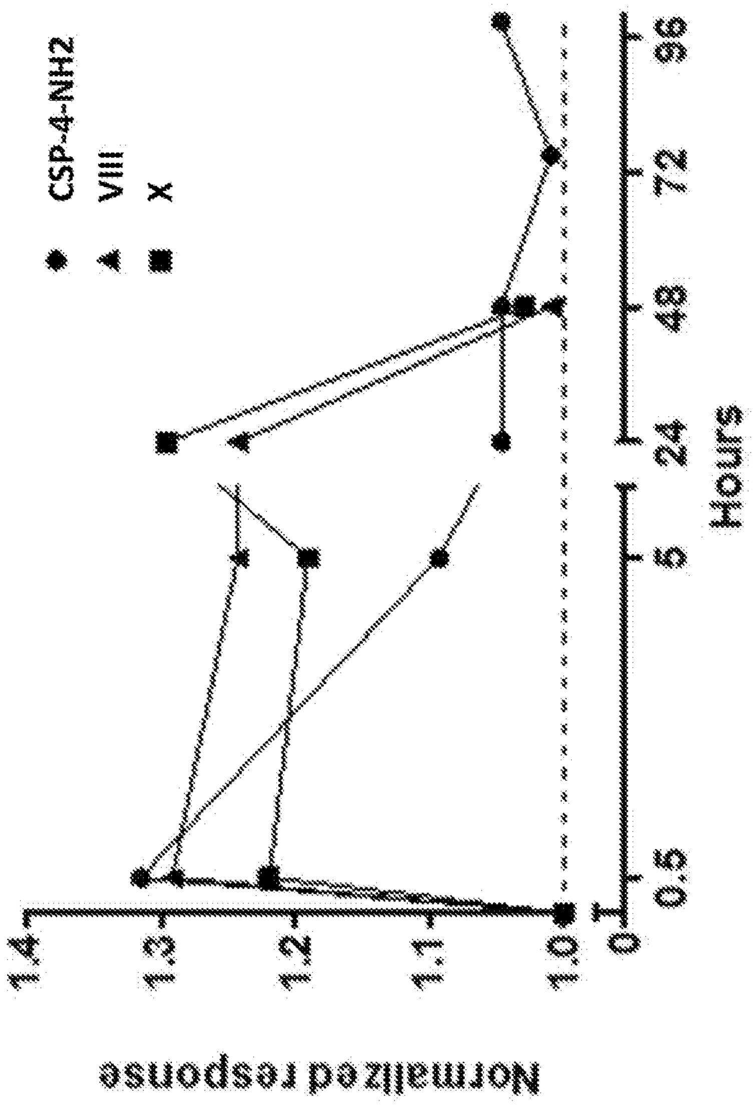
Figure 10B:
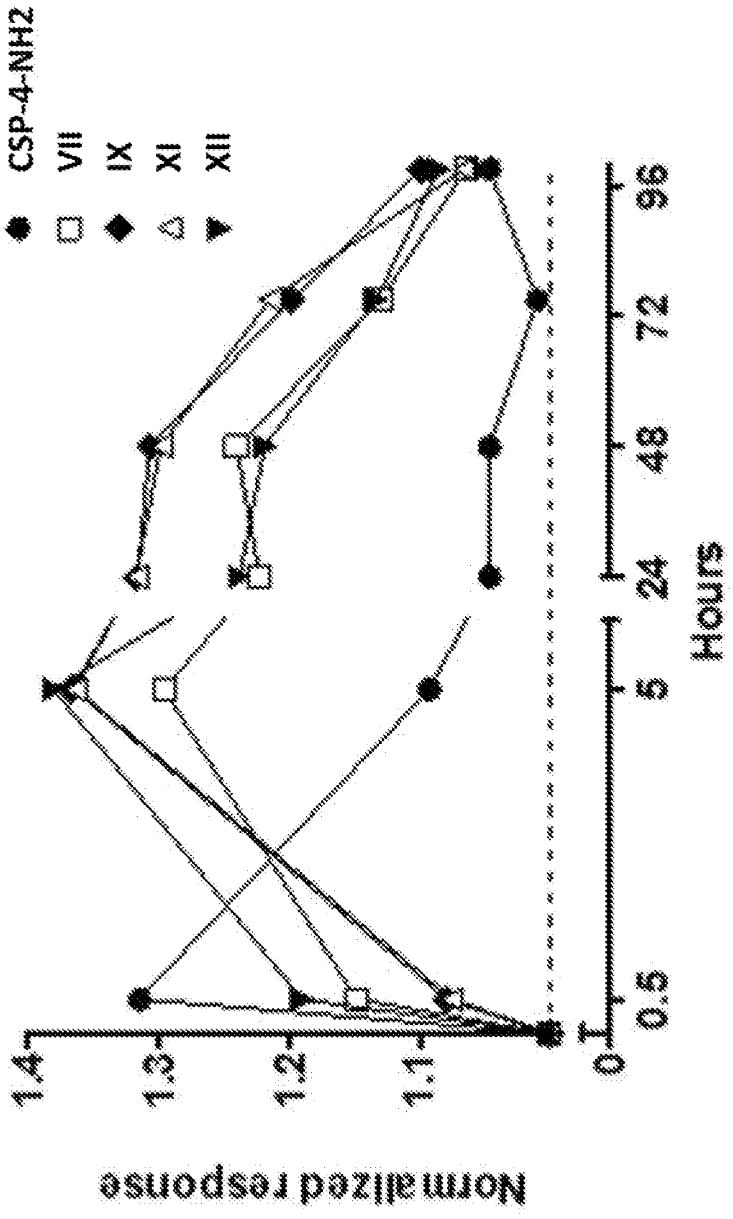
Figure 10C:
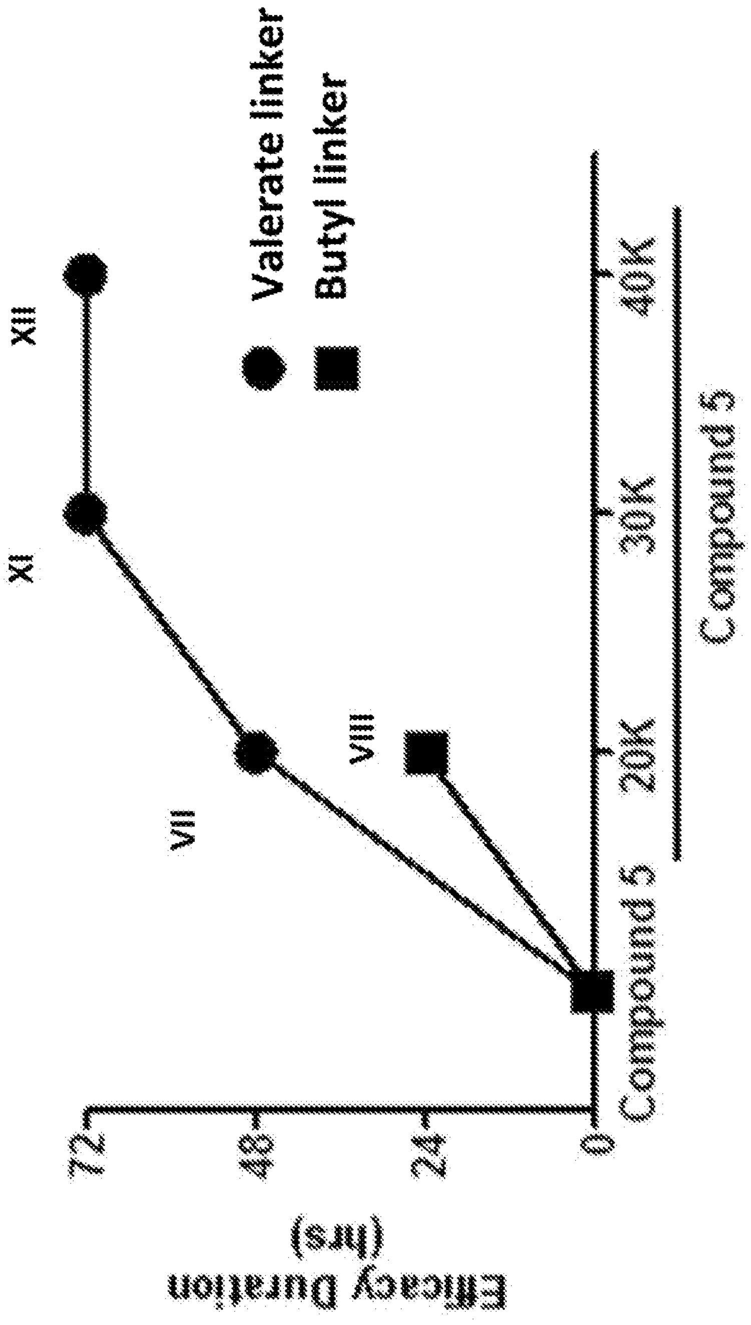

FIG. 10A-FIG. 10C: Analgesic efficacy and duration of effect of conotoxin peptide analog CSP-4-NH2 and PEGylated derivatives of CSP-4-NH2 in rat CIPN model. FIG. 10A: Mechanical hyperalgesia was measured by Randall-Selitto testing, demonstrating analgesic efficacy (normalized response) of CSP-4-NH2 and PEGylated conotoxin peptides VIII and X in the rat CIPN model over 96 h post dose. FIG. 10B: Mechanical hyperalgesia was measured by Randall-Selitto testing, demonstrating analgesic efficacy (normalized response) of CSP-4-NH2 and PEGylated conotoxin peptides VII, IX, XI and XII in the rat CIPN model over 96 h post dose. FIG. 10C: Summary plot of duration of efficacy of CSP-4-NH2 and PEGylated derivatives of CSP-4-NH2 showed that duration of efficacy correlates with both PEGylation conjugation chemistry (valerate linker vs. butyl linker) and conjugated PEG polymer size.

Figure 11A:
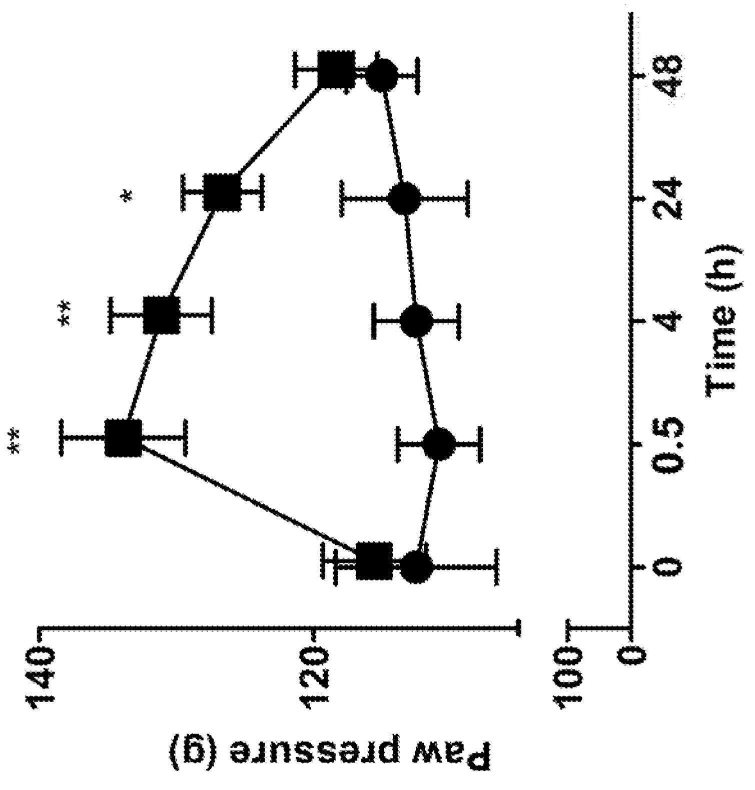
Figure 11B:
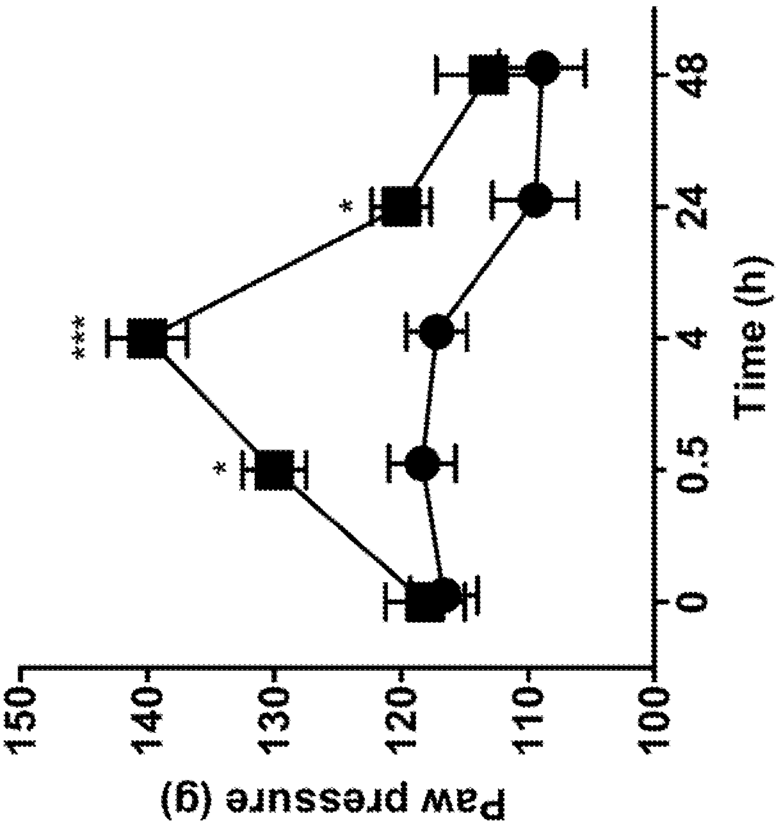
Figure 11C:
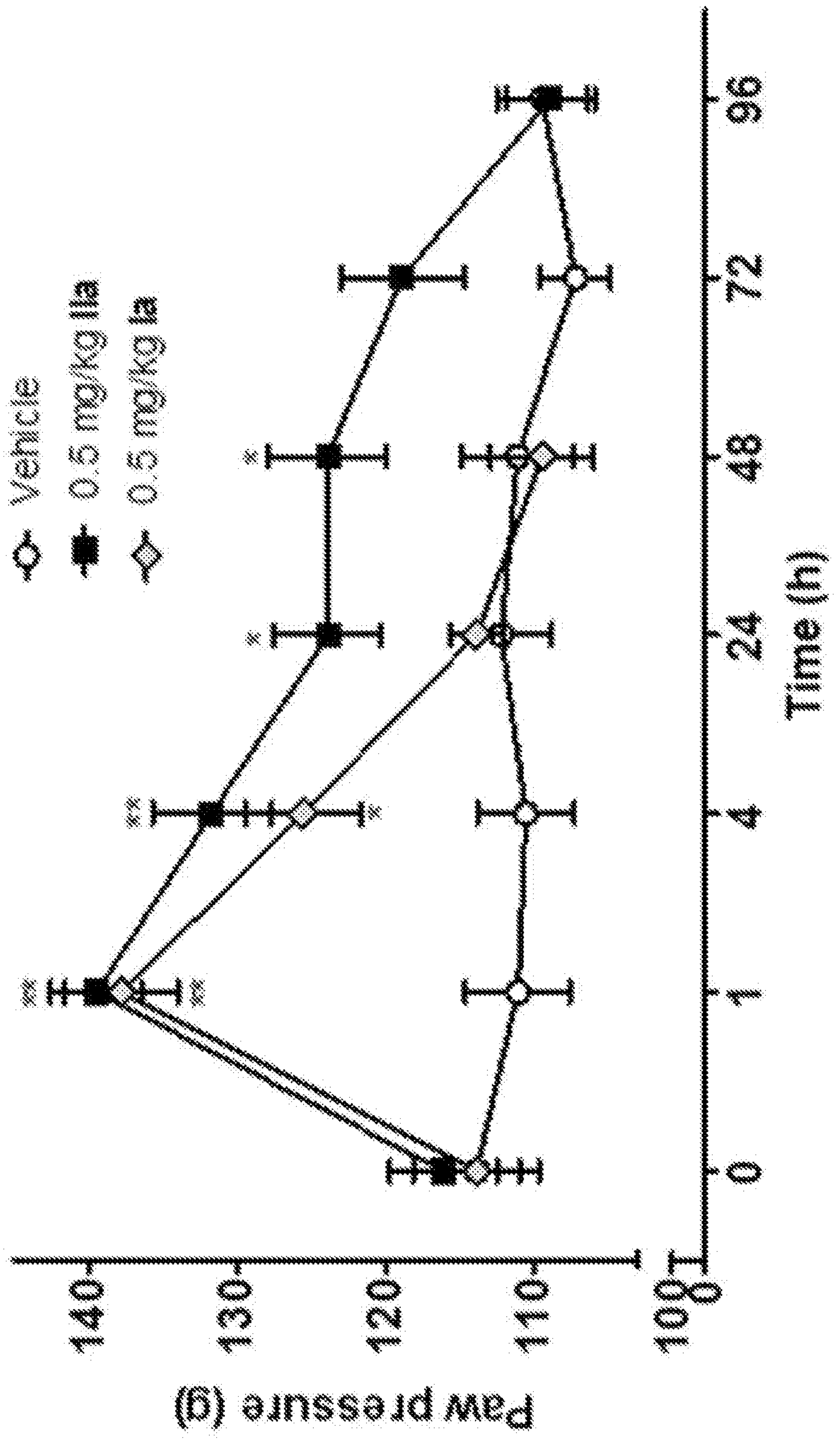

FIG. 11A-FIG. 11C: Analgesic efficacy and duration of effect of conotoxin peptide analogs Ia', Ia, and PEGylated conotoxin peptide analog IIa in a rat chemotherapy induced peripheral neuropathy (CIPN) model. FIG. 11A: Administration of a single 0.5 mg/kg dose of conotoxin peptide analog Ia' to rats having oxaliplatin-induced peripheral neuropathy, 14 days following induction of neuropathy, resulted in a statistically significant reduction in mechanical hyperalgesia compared to vehicle treated control animals for up to 24 h. (■: 0.5 mg/kg of conotoxin peptide analog Ia'; ●: vehicle). FIG. 11B: Administration of a single 0.5 mg/kg dose of Ia' to rats with spared nerve injury on day 14 following surgical induction of the model resulted in a statistically significant reduction in mechanical hyperalgesia compared to vehicle treated control animals for up to 24 h (■: 0.5 mg/kg of conotoxin peptide analog Ia'; ●: vehicle). FIG. 11C: Administration of a single 0.5 mg/kg dose of conotoxin peptide analog Ia or PEGylated conotoxin peptide analog IIa to rats with oxaliplatin-induced peripheral neuropathy, 14 days following induction of neuropathy, resulted in a significant reduction in mechanical hyperalgesia compared to vehicle treated control animals for up to 4 h (conotoxin peptide analog Ia) or 48 h (PEGylated conotoxin peptide analog IIa) post dose (-○- : vehicle; -◇- : conotoxin peptide analog Ia; -■- : PEGylated conotoxin peptide analog IIa). Mechanical hyperalgesia was measured by Randall Selitto paw withdrawal threshold in grams. The endpoint for all studies was the Randall Siletto paw withdrawal threshold in grams. Two-way ANOVA, *p<0.05, p<0.01, *p<0.001.

5. DETAILED DESCRIPTION

It is to be understood that the disclosure is not limited to the particular embodiments set forth herein, and it is also to be understood that the terminology used herein is for the purpose of describing particular embodiments only, and is not intended to be limiting.

Provided herein are alpha-conotoxin peptide analogs, including alpha-conotoxin peptide analogs that are covalently attached to polyethylene glycol (PEG), and pharmaceutical compositions of such alpha-conotoxin peptide analogs. Also provided herein are methods of treating or preventing a condition conducive to treatment or prevention by inhibition of an α9-containing nicotinic acetylcholine receptor (nAChR) (e.g., the α9α10 subtype of the nAChR) in a subject.

5.1. Abbreviations Used Herein

| Abbreviation | Meaning |
|---|---|
| AcOH | Acetic acid |
| $(Boc)_2O$ | Di-tert-butyl dicarbonate |
| tBu | tert-Butyl |
| $CH_2Cl_2$ | Dichloromethane |
| $CH_3CN$ | Acetonitrile |
| $CuSO_4$ | Copper(II) Sulfate |
| DBU | 1,8-Diazabicyclo[5.4.0]undec-7-ene |
| DIPEA | N,N-diisopropylethylamine |
| DMF | Dimethyl formamide |
| DMSO | Dimethyl sulfoxide |
| EDT | 1,2-Ethanedithiol |
| FMOC | Fluorenylmethyloxy carbonyl |
| $Et_2O$ | Diethyl Ether |
| HOAt | 1-Hydroxy-7-azabenzotriazole |
| h | Hour(s) |
| $^{i}$PrOH | Iso-propanol |
| HATU | 1-[Bis(dimethylamino)methylene]-1H-1,2,3-triazolo[4,5-b]pyridinium 3 oxid hexafluorophosphate |
| min | Minute(s) |
| MeOH | Methanol |
| PBS | Phosphate-buffered saline |
| Pbf | 2,2,4,6,7-Pentamethyldihydrobenzofuran-5-sulfonyl |

-continued

| Abbreviation | Meaning |
|---|---|
| PEG | Polyethylene glycol |
| PPTS | Pyridinium p-toluenesulfonate |
| RT | Retention Time |
| TBTU | O-(benzotriazol-1-yl)-N,N,N',N'-tetramethyluronium tetrafluoroborate |
| TEA | Triethylamine |
| TFA | Trifluoroacetic acid |
| Trt | Triphenylmethyl |

It will be appreciated that throughout this disclosure reference is made to amino acids according to the single letter or three letter codes. The amino acids forming all or a part of a peptide may be from among the known 21 naturally occurring amino acids, which are referred to by both their single letter abbreviations and their common three-letter abbreviation. In the peptide sequences provided herein, conventional amino acid residues have their conventional meaning. Thus, “Leu” is leucine, “Ile” is isoleucine, “Nle” is norleucine, and so on. To assist the reader, conventional amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

In the peptide sequences provided herein, other amino acids and their corresponding three letter abbreviations are as follows:

| | |
|---|---|
| (S)-5-azidonorvaline | 5-azidoNVa |
| (S)-propargyl glycine | Pra |
| (S)-3-azido-alanine | 3-azidoAla |
| (S)-homopropargyl glycine | homoPra |
| (S)-γ-azido-homoalanine | gamma-azidohomoAla |
| (S)-bis-homopropargyl glycine | bishomoPra |
| Citrulline | Cit |

5.2. Conotoxin Peptide RgIA Analogs

In one aspect, provided herein are conotoxin peptide analogs of Formula (I) (SEQ ID NO:93):

(I)

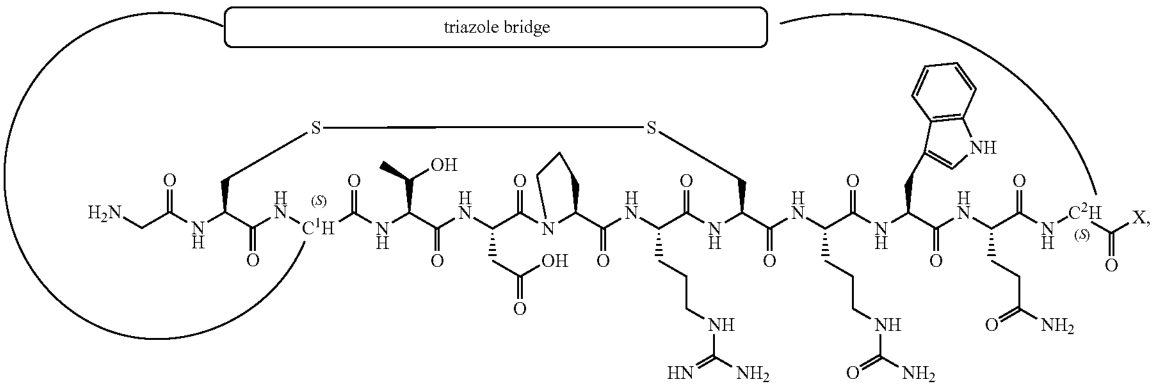

or a pharmaceutically acceptable salt thereof, wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr;

wherein the C-terminus of the conotoxin peptide analog is a carboxylic acid or an amide group.

The "(S)" notations near $C^1$ and $C^2$ carbon in Formula (I) indicate the absolute configuration of $C^1$ and $C^2$ carbon.

In various embodiments, the triazole bridge is

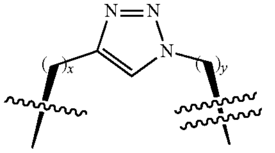

or

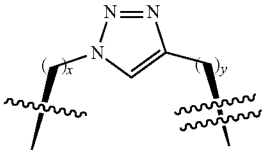

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog; and wherein x is 1, 2, 3, or 4; y is 2, 3 or 4. In a specific embodiment, the triazole bridge is

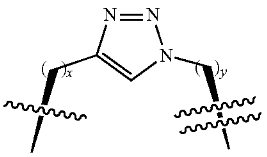

.

In a specific embodiment, the triazole bridge is

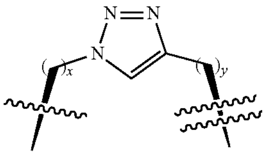

.

In a specific embodiment, x is 1, 2, 3, or 4. In one preferred embodiment, x is 1, 2, or 3. In a specific embodiment, x is 1 or 2. In one embodiment, x is 1. In another embodiment, x is 2.

In a specific embodiment, y is 2, 3, or 4. In a specific embodiment, y is 2 or 3. In one embodiment, y is 3. In another embodiment, y is 2.

In a specific embodiment, x is 1, 2 or 3, and y is 2 or 3. In a specific embodiment, x is 1, 2, or 3, and y is 2. In a specific embodiment, x is 1, 2, or 3, and y is 3. In a specific embodiment, x is 1 or 2, and y is 2 or 3. In a specific embodiment, x is 1 or 3, and y is 2 or 3. In a specific embodiment, x is 2 or 3, and y is 2 or 3. In a specific embodiment, x is 1, and y is 2 or 3. In a specific embodiment, x is 2, and y is 2 or 3. In a specific embodiment, x is 3, and y is 2 or 3. In one preferred embodiment, x is 1 and y is 3. In one preferred embodiment, x is 2 and y is 3. In one preferred embodiment, x is 2 and y is 2.

In a specific embodiment, the triazole bridge is

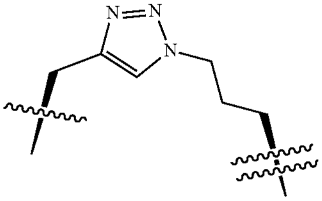

, wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog.

In a specific embodiment, the triazole bridge is

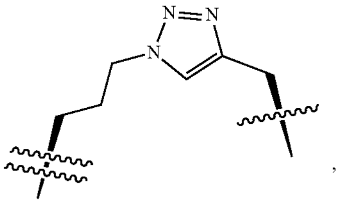

, wherein the single wavy line (  ) indicates the point of attachment of the triazole bridge to the $C^1$ carbon of the conotoxin peptide analog, and the double wavy lines ( 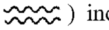 ) indicate the point of attachment of the triazole bridge to the $C^2$ carbon of the conotoxin peptide analog.

In a specific embodiment, X is $X_{AA}^1$. In a specific embodiment, X is $X_{AA}^1X_{AA}^2$.

In a specific embodiment, $X_{AA}^1$ is Tyr, Phe, Trp, or a D-isomer of Tyr, Phe, or Trp. In a specific embodiment, $X_{AA}^1$ is Tyr, Phe, or Trp. In a specific embodiment, $X_{AA}^1$ is Tyr, D-Tyr, or Phe. In a specific embodiment, $X_{AA}^1$ is Tyr or D-Tyr. In a specific embodiment, $X_{AA}^1$ is Tyr or Phe. In a specific embodiment, $X_{AA}^1$ is D-Tyr or Phe. In a specific embodiment, $X_{AA}^1$ is Phe. In a specific embodiment, $X_{AA}^1$ is D-Phe. In a specific embodiment, $X_{AA}^1$ is Trp. In a specific embodiment, $X_{AA}^1$ is D-Trp. In a specific embodiment, $X_{AA}^1$ is D-Tyr. In one preferred embodiment, $X_{AA}^1$ is Tyr.

In a specific embodiment, $X_{AA}^2$ is N-Me-Gly, D-Tyr, or N-Me-Tyr. In a specific embodiment, $X_{AA}^2$ is N-Me-Gly or D-Tyr. In a specific embodiment, $X_{AA}^2$ is D-Tyr or N-Me-Tyr. In a specific embodiment, $X_{AA}^2$ is N-Me-Gly or N-Me-Tyr. In a specific embodiment, $X_{AA}^2$ is N-Me-Gly. In a specific embodiment, $X_{AA}^2$ is N-Me-Tyr. In a specific embodiment, $X_{AA}^2$ is D-Tyr. In a specific embodiment, $X_{AA}^2$ is optionally present. In a specific embodiment, $X_{AA}^2$ is present. In a specific embodiment, $X_{AA}^2$ is absent.

In a specific embodiment, X is selected from the group consisting of Tyr, Phe, D-Tyr, (Tyr)-(D-Tyr), (Tyr)-(N-Me-Gly), (Tyr)-(N-Me-Tyr), N-Me-Tyr, D-Arg, N-Me-D-Tyr, beta-Tyr, and N-Me-Arg. In a specific embodiment, X is selected from the group consisting of Tyr, Phe, D-Tyr, (Tyr)-(D-Tyr), (Tyr)-(N-Me-Gly), and (Tyr)-(N-Me-Tyr). In a specific embodiment, X is selected from the group consisting of Tyr, Phe, and D-Tyr. In a specific embodiment, X is selected from the group consisting of (Tyr)-(D-Tyr), (Tyr)-(N-Me-Gly), and (Tyr)-(N-Me-Tyr). In a specific embodiment, X is selected from the group consisting of N-Me-Tyr, D-Arg, N-Me-D-Tyr, beta-Tyr, and N-Me-Arg. In a specific embodiment, X is Tyr. In a specific embodiment, X is Phe. In a specific embodiment, X is D-Tyr. In a specific embodiment, X is (Tyr)-(D-Tyr). In a specific embodiment, X is (Tyr)-(N-Me-Gly). In a specific embodiment, X is (Tyr)-(N-Me-Tyr). In a specific embodiment, X is N-Me-Tyr. In a specific embodiment, X is D-Arg. In a specific embodiment, X is N-Me-D-Tyr. In a specific embodiment, X is beta-Tyr. In a specific embodiment, X is N-Me-Arg.

In a specific embodiment, the C-terminus of the conotoxin peptide analog is a carboxylic acid or an amide group. In one preferred embodiment, the C-terminus of the conotoxin peptide analog is OH. In a specific embodiment, the C-terminus of the conotoxin peptide analog is $NH_2$.

In specific embodiments, the conotoxin peptide analog or pharmaceutically acceptable salt of Formula (I) is of Formula (Ia) (SEQ ID NO:94):

(Ia)

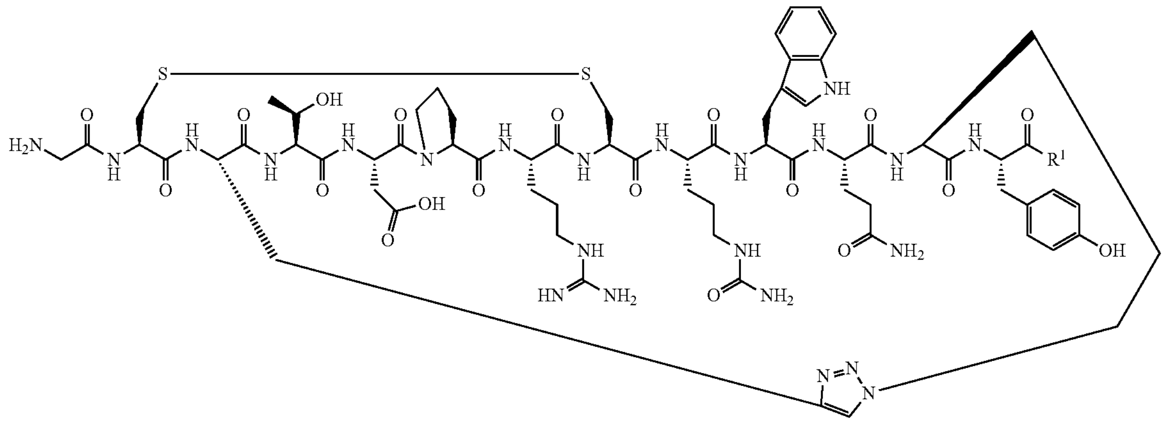

, wherein $R^1$ is OH or $NH_2$. In a specific embodiment, $R^1$ is OH. In a specific embodiment, $R^1$ is $NH_2$.

In specific embodiments, the conotoxin peptide analog or pharmaceutically acceptable salt of Formula (I) is of Formula (Ig) (SEQ ID NO:30):
(Ig)
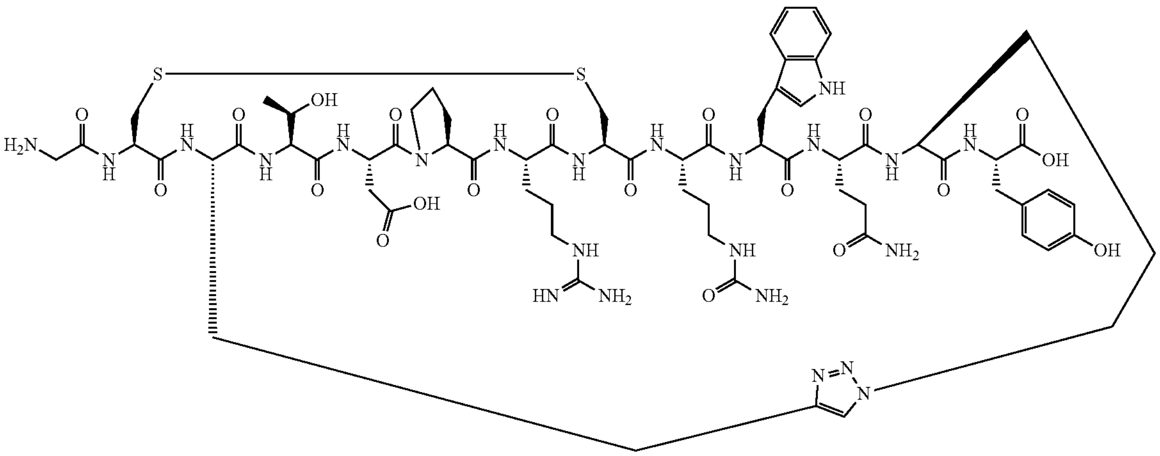
.
In specific embodiments, the conotoxin peptide analog or pharmaceutically acceptable salt of Formula (I) is of Formula (Ih) (SEQ ID NO:33):
(Ih)
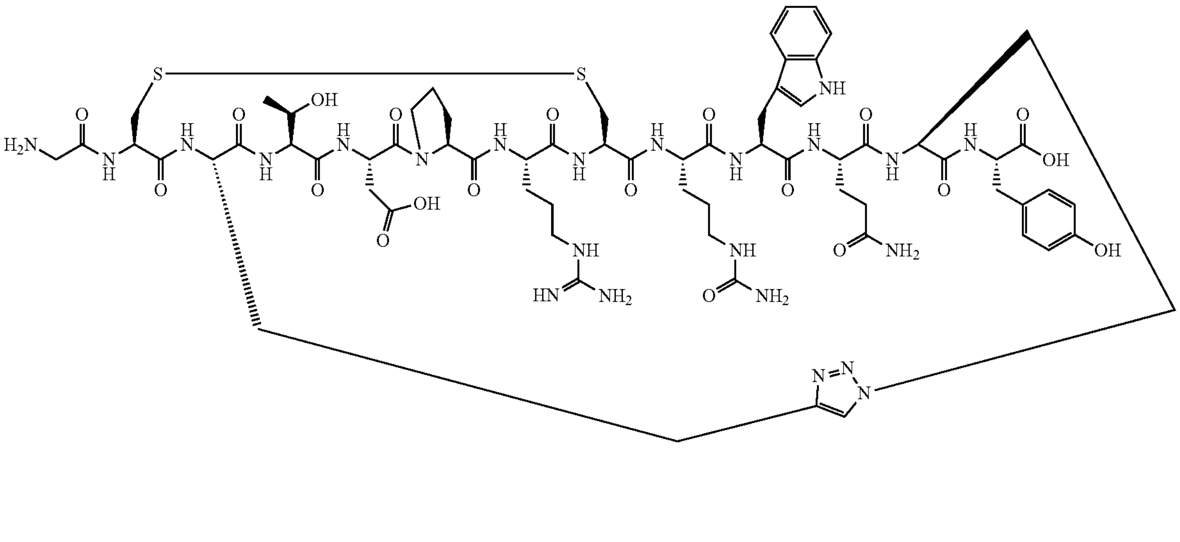
.

In specific embodiments, the conotoxin peptide analog or pharmaceutically acceptable salt of Formula (I) is of Formula (Ii) (SEQ ID NO:36):
(Ii)
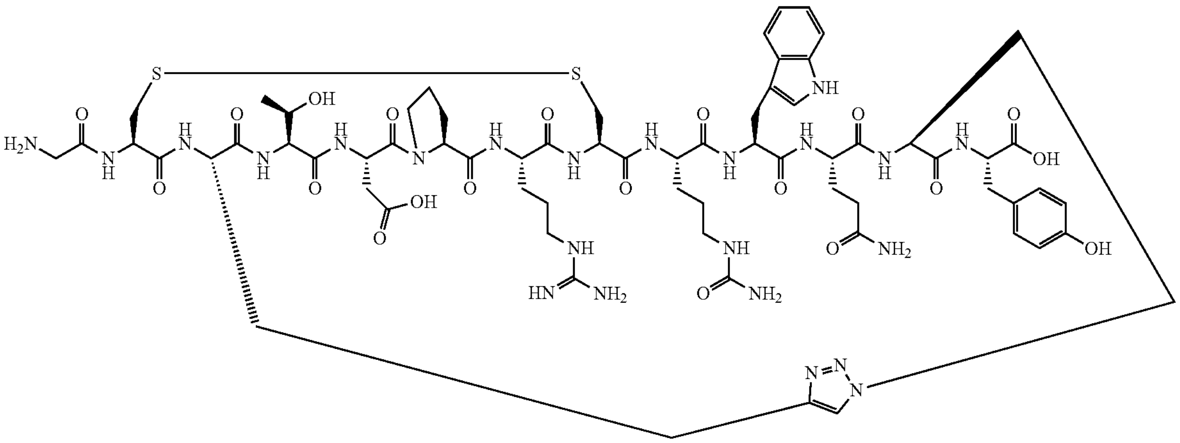
.
In specific embodiments, the conotoxin peptide analog or pharmaceutically acceptable salt of Formula (I) is of Formula (Ik) (SEQ ID NO:42):
(Ik)
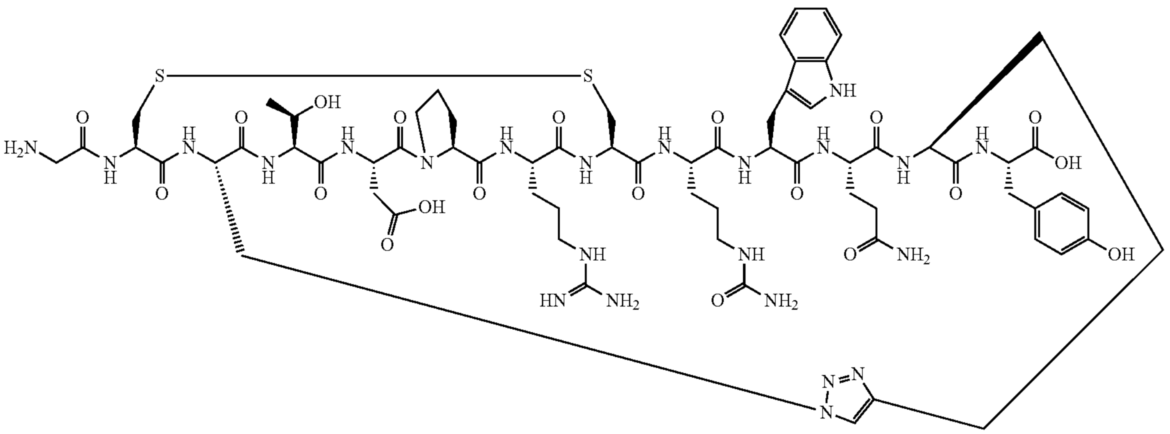
.

In specific embodiments, the conotoxin peptide analog or pharmaceutically acceptable salt of Formula (I) is of Formula (Il) (SEQ ID NO:45):
(Il)
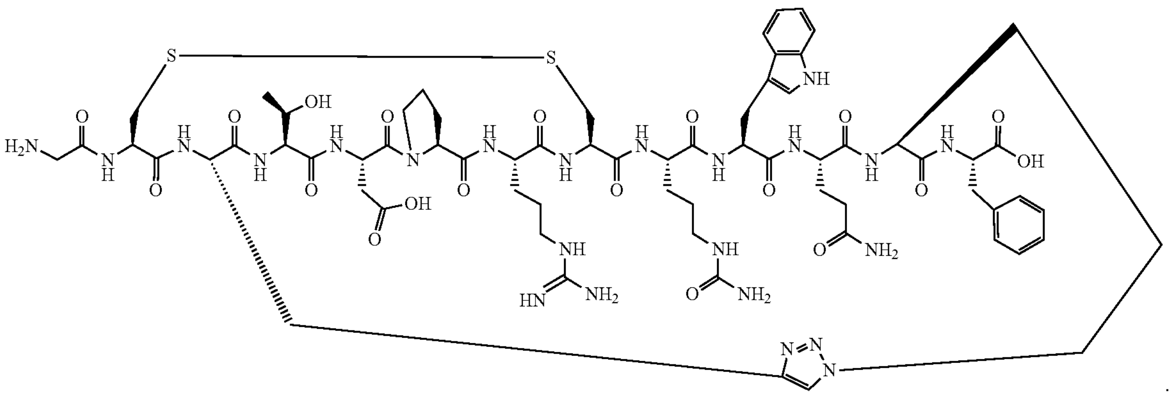
.
In specific embodiments, the conotoxin peptide analog or pharmaceutically acceptable salt of Formula (I) is of Formula (Im) (SEQ ID NO:48):
(Im)
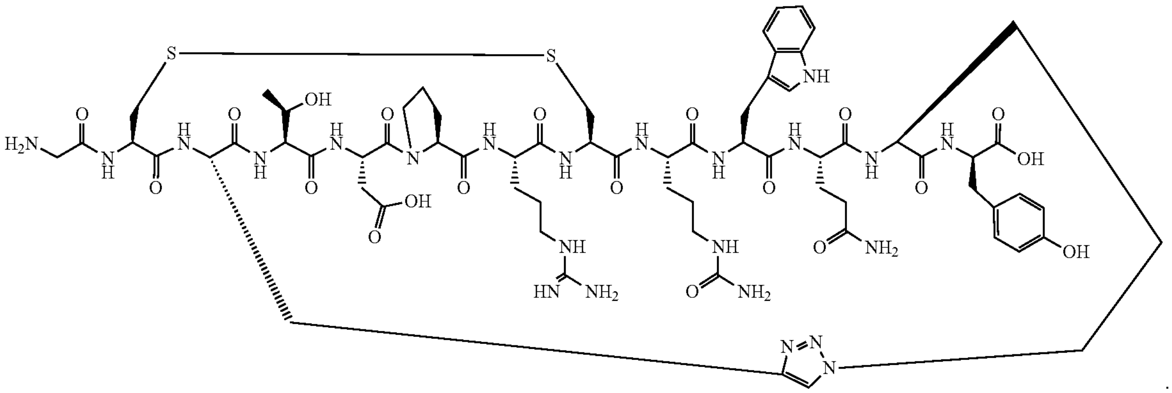
.

In specific embodiments, the conotoxin peptide analog or pharmaceutically acceptable salt of Formula (I) is of Formula (In) (SEQ ID NO:51):
(In)
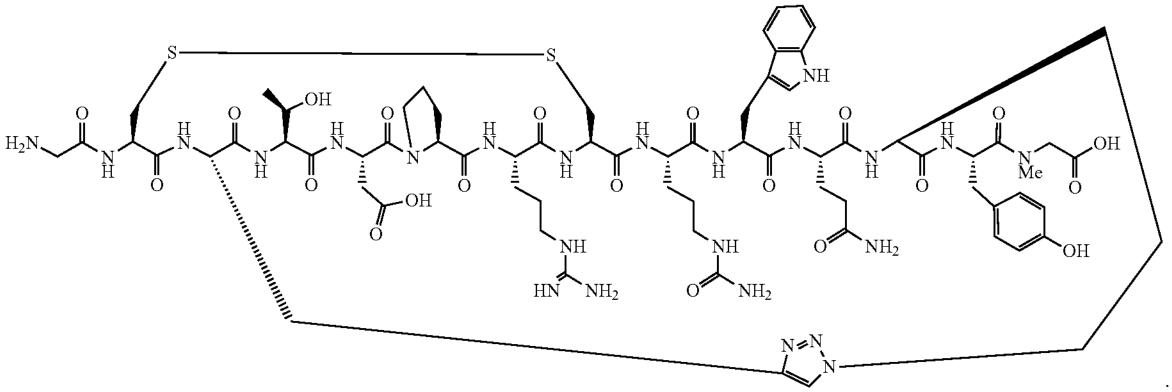
.
In specific embodiments, the conotoxin peptide analog or pharmaceutically acceptable salt of Formula (I) is of Formula (Io) (SEQ ID NO:54):
(Io)
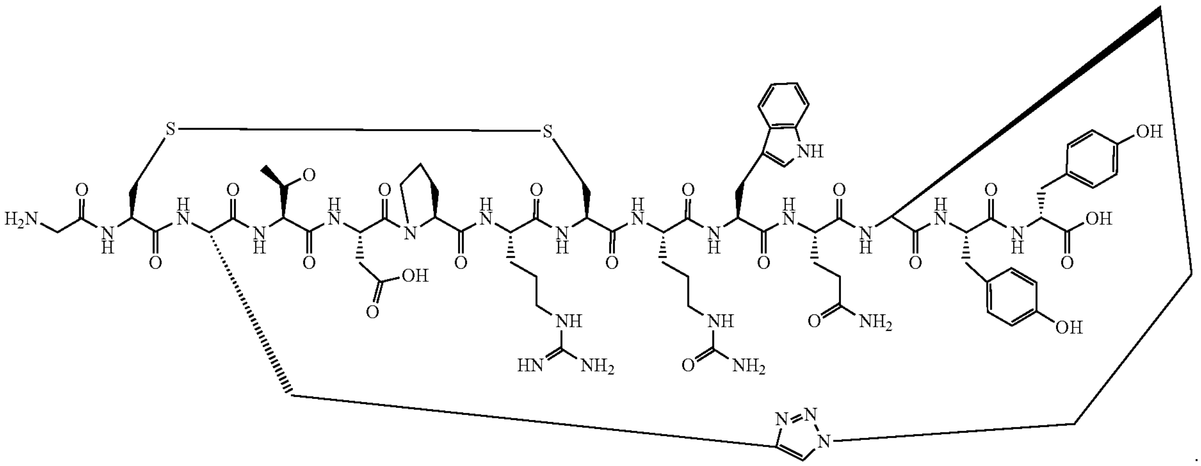
.

In specific embodiments, the conotoxin peptide analog or pharmaceutically acceptable salt of Formula (I) is of Formula (Ip) (SEQ ID NO:57):

(Ip)

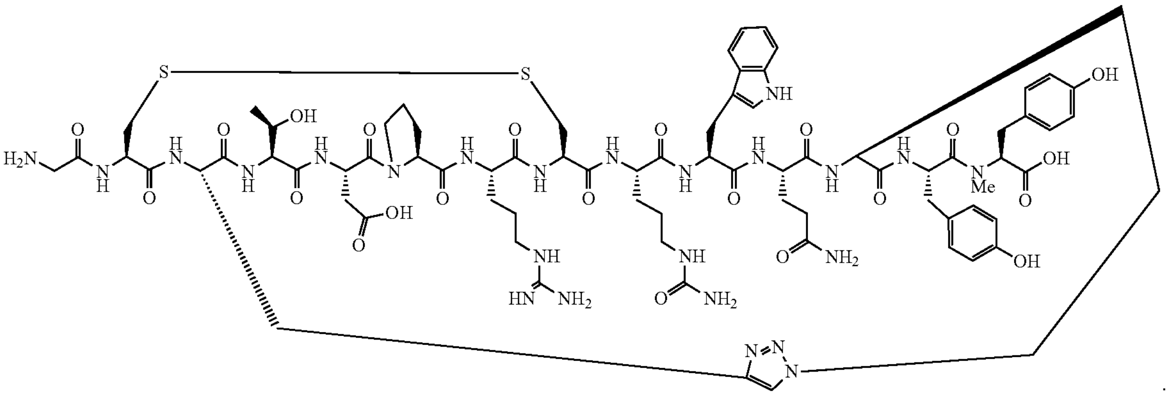

.

In another aspect, provided herein are conotoxin peptide analogs of Formula (Ib) (SEQ ID NO:104):

(Ib)

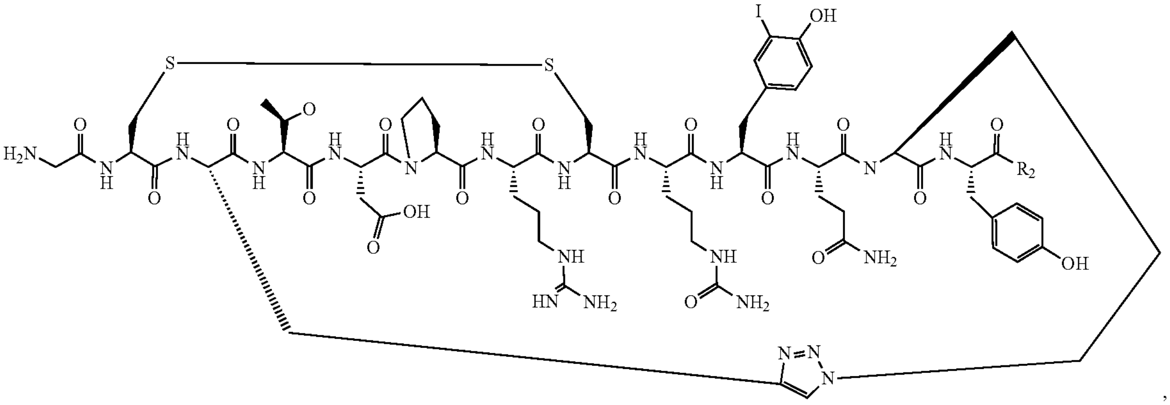

, or a pharmaceutically acceptable salt thereof, wherein $R^2$ is OH or $NH_2$.

In a specific embodiment, $R^2$ is OH. In a specific embodiment, $R^2$ is $NH_2$.

In another aspect, provided herein are conotoxin peptide analogs selected from the group consisting of conotoxin peptide analogs Ia, Ia', Ib, Ib', Ic, Id, Ie, If, Ig, Ih, Ii, Ij, Ik, Il, Im, In, Io, Ip, Iq, Ir, Is, It, Iu, and Iv, or a pharmaceutically acceptable salt thereof.

In a specific embodiment, the conotoxin peptide analog is selected from the group consisting of conotoxin peptide analogs Ia, Ia', Ib, Ib', Ig, Ih, Ii, Ik, Il, Im, In, Io, and Ip.

In a specific embodiment, the conotoxin peptide analog is selected from the group consisting of conotoxin peptide analogs Ia, Ia', Ib, and Ib'. In one preferred embodiment, the conotoxin peptide analog is conotoxin peptide analog Ia or Ia'. In one preferred embodiment, the conotoxin peptide analog is conotoxin peptide analog Ia.

5.3. PEGylated Conotoxin Peptide RgIA Analogs

In one embodiment, the conotoxin peptide analogs of the invention are PEGylated, in particular, covalently attached to one or more PEG polymers.

In a specific embodiment, a conotoxin peptide analog is covalently attached to one PEG polymer. In a specific embodiment, a conotoxin peptide analog is covalently attached to more than one PEG polymers. In a specific embodiment, a conotoxin peptide analog is covalently attached to two PEG polymers. In a specific embodiment, a conotoxin peptide analog is covalently attached to three PEG polymers.

In a preferred embodiment, a PEG polymer is covalently attached to the N-terminus of a conotoxin peptide analog, most preferably one PEG polymer is attached only to the N-terminus. In a specific embodiment, a PEG polymer is covalently attached to the C-terminus of a conotoxin peptide analog. In a specific embodiment, a PEG polymer is covalently attached to an amino acid residue position that is not the N-terminus or the C-terminus of the conotoxin peptide analog.

In a specific embodiment, a PEG polymer is covalently attached to the conotoxin peptide analog via a linking group. In a specific embodiment, a PEG polymer is covalently attached to the conotoxin peptide analog directly.

In one preferred embodiment, the linking group is a valerate linker having a formula of

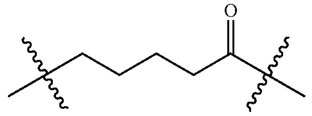

.

In a specific embodiment, the linking group is a butylene. In a specific embodiment, the linking group is a carbonyl.

In a specific embodiment, the PEG polymer is a linear or branched PEG polymer. In a specific embodiment, the PEG polymer is a branched PEG polymer. In one preferred embodiment, the PEG polymer is a linear PEG polymer.

In a specific embodiment, the PEG polymer has a molecular weight in the range of 10 kDa and 40 kDa. In one preferred embodiment, the PEG polymer is a 30 kDa PEG polymer. In specific embodiments, the PEG polymer is a linear 30 kDa PEG polymer. In specific embodiments, the PEG polymer is a linear 30 kDa mPEG polymer.

In a preferred embodiment, one PEG polymer is attached at the amino terminus of a conotoxin peptide analog, and the PEG polymer is attached via a linking group to the conotoxin peptide analog, and the linking group is a valerate linker having a formula of

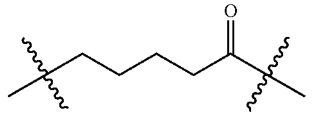

, and the PEG polymer is a linear 30 kDa mPEG polymer.

In a specific embodiment, provided herein is a PEGylated conotoxin peptide analog or pharmaceutically acceptable salt thereof, wherein the conotoxin peptide analog is of Formula (I) (SEQ ID NO:93):

wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr;

wherein the C-terminus of the conotoxin peptide analog is a carboxylic acid or an amide group; and wherein the conotoxin peptide analog is covalently attached directly or via a linking group to one or more polyethylene glycol (PEG) polymers.

In various embodiments, the triazole bridge is

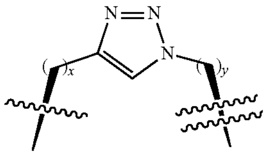

or

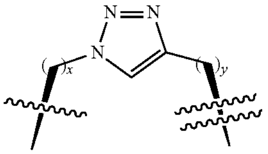

, wherein the single wavy line (  ) indicates the point of attachment of the triazole bridge to the $C^1$ carbon of the conotoxin peptide analog, and the double wavy lines (  ) indicate the point of attachment of the triazole bridge to the $C^2$ carbon of the conotoxin peptide analog; and wherein x is 1, 2, 3, or 4; y is 2, 3 or 4. In a specific embodiment, the triazole bridge is

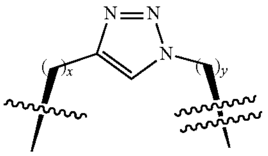

.

(I)

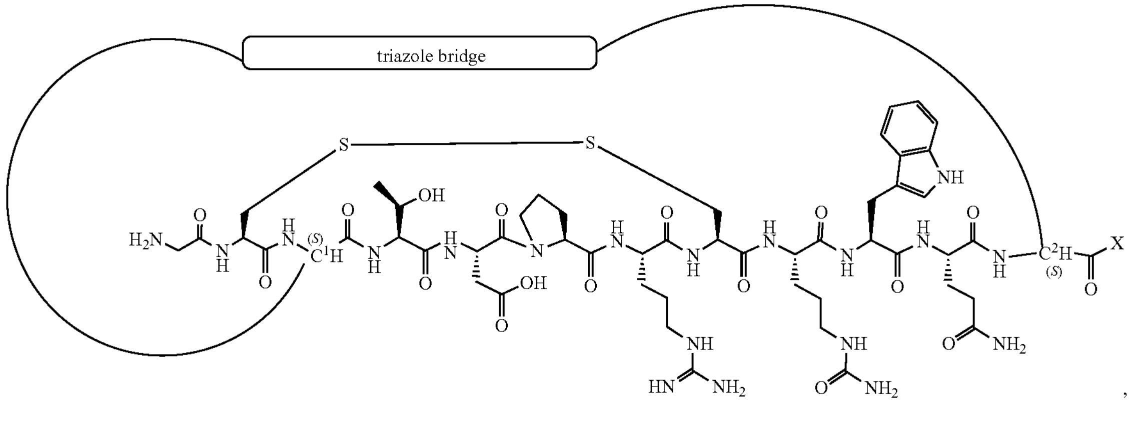

,

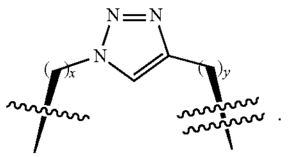

In a specific embodiment, x is 1, 2, 3, or 4. In one preferred embodiment, x is 1, 2, or 3. In a specific embodiment, x is 1 or 2. In one embodiment, x is 1. In another embodiment, x is 2.

In a specific embodiment, y is 2, 3, or 4. In a specific embodiment, y is 2 or 3. In one embodiment, y is 3. In another embodiment, y is 2.

In a specific embodiment, x is 1, 2 or 3, and y is 2 or 3. In a specific embodiment, x is 1, 2, or 3, and y is 2. In a specific embodiment, x is 1, 2, or 3, and y is 3. In a specific embodiment, x is 1 or 2, and y is 2 or 3. In a specific embodiment, x is 1 or 3, and y is 2 or 3. In a specific embodiment, x is 2 or 3, and y is 2 or 3. In a specific embodiment, x is 1, and y is 2 or 3. In a specific embodiment, x is 2, and y is 2 or 3. In a specific embodiment, x is 3, and y is 2 or 3. In one preferred embodiment, x is 1 and y is 3. In one preferred embodiment, x is 2 and y is 3. In one preferred embodiment, x is 2 and y is 2.

In a specific embodiment, the triazole bridge is

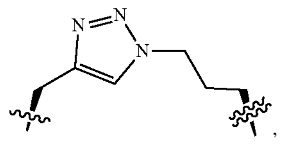

wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog.

In a specific embodiment, the triazole bridge is

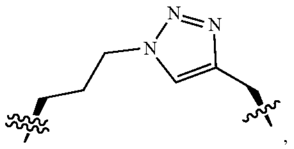

wherein the single wavy line ( ) indicates the point of attachment of the triazole bridge to the $C^1$ carbon of the conotoxin peptide analog, and the double wavy lines ( ) indicate the point of attachment of the triazole bridge to the $C^2$ carbon of the conotoxin peptide analog.

In a specific embodiment, X is $X_{AA}^1$. In a specific embodiment, X is $X_{AA}^1X_{AA}^2$.

In a specific embodiment, $X_{AA}^1$ is Tyr, Phe, Trp, or a D-isomer of Tyr, Phe, or Trp. In a specific embodiment, $X_{AA}^1$ is Tyr, Phe, or Trp. In a specific embodiment, $X_{AA}^1$ is Tyr, D-Tyr, or Phe. In a specific embodiment, $X_{AA}^1$ is Tyr or D-Tyr. In a specific embodiment, $X_{AA}^1$ is Tyr or Phe. In a specific embodiment, $X_{AA}^1$ is D-Tyr or Phe. In a specific embodiment, $X_{AA}^1$ is Phe. In a specific embodiment, $X_{AA}^1$ is D-Phe. In a specific embodiment, $X_{AA}^1$ is Trp. In a specific embodiment, $X_{AA}^1$ is D-Trp. In a specific embodiment, $X_{AA}^1$ is D-Tyr. In one preferred embodiment, $X_{AA}^1$ is Tyr.

In a specific embodiment, $X_{AA}^2$ is N-Me-Gly, D-Tyr, or N-Me-Tyr. In a specific embodiment, $X_{AA}^2$ is N-Me-Gly or D-Tyr. In a specific embodiment, $X_{AA}^2$ is D-Tyr or N-Me-Tyr. In a specific embodiment, $X_{AA}^2$ is N-Me-Gly or N-Me-Tyr. In a specific embodiment, $X_{AA}^2$ is N-Me-Gly. In a specific embodiment, $X_{AA}^2$ is N-Me-Tyr. In a specific embodiment, $X_{AA}^2$ is D-Tyr. In a specific embodiment, $X_{AA}^2$ is optionally present. In a specific embodiment, $X_{AA}^2$ is present. In a specific embodiment, $X_{AA}^2$ is absent.

In a specific embodiment, X is selected from the group consisting of Tyr, Phe, D-Tyr, (Tyr)-(D-Tyr), (Tyr)-(N-Me-Gly), (Tyr)-(N-Me-Tyr), N-Me-Tyr, D-Arg, N-Me-D-Tyr, beta-Tyr, and N-Me-Arg. In a specific embodiment, X is selected from the group consisting of Tyr, Phe, D-Tyr, (Tyr)-(D-Tyr), (Tyr)-(N-Me-Gly), and (Tyr)-(N-Me-Tyr). In a specific embodiment, X is selected from the group consisting of Tyr, Phe, and D-Tyr. In a specific embodiment, X is selected from the group consisting of (Tyr)-(D-Tyr), (Tyr)-(N-Me-Gly), and (Tyr)-(N-Me-Tyr). In a specific embodiment, X is selected from the group consisting of N-Me-Tyr, D-Arg, N-Me-D-Tyr, beta-Tyr, and N-Me-Arg. In a specific embodiment, X is Tyr. In a specific embodiment, X is Phe. In a specific embodiment, X is D-Tyr. In a specific embodiment, X is (Tyr)-(D-Tyr). In a specific embodiment, X is (Tyr)-(N-Me-Gly). In a specific embodiment, X is (Tyr)-(N-Me-Tyr). In a specific embodiment, X is N-Me-Tyr. In a specific embodiment, X is D-Arg. In a specific embodiment, X is N-Me-D-Tyr. In a specific embodiment, X is beta-Tyr. In a specific embodiment, X is N-Me-Arg.

In a specific embodiment, the C-terminus of the conotoxin peptide analog is a carboxylic acid or an amide group. In one preferred embodiment, the C-terminus of the conotoxin peptide analog is OH. In a specific embodiment, the C-terminus of the conotoxin peptide analog is $NH_2$.

In specific embodiments, the conotoxin peptide analog or pharmaceutically acceptable salt of Formula (I) is of Formula (Ia) (SEQ ID NO:94):

(Ia)

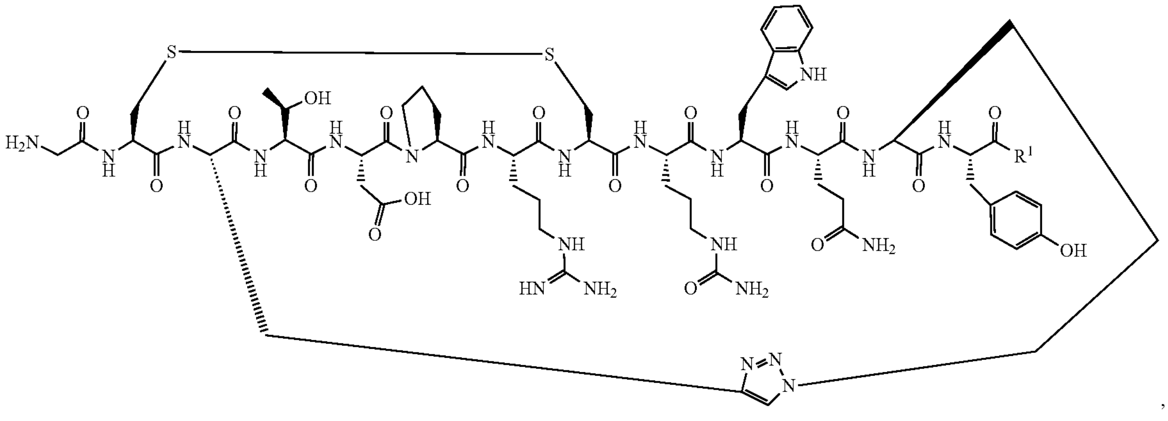

, wherein $R^1$ is OH or $NH_2$. In a specific embodiment, $R^1$ is OH. In a specific embodiment, $R^1$ is $NH_2$.

In specific embodiments, the conotoxin peptide analog or pharmaceutically acceptable salt of Formula (I) is of Formula (Ig) (SEQ ID NO:30):

(Ig)

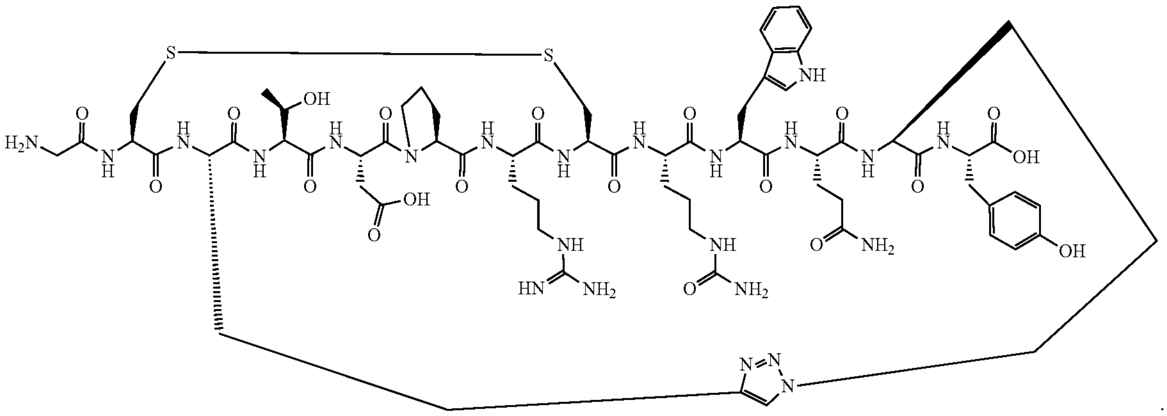

.

In specific embodiments, the conotoxin peptide analog or pharmaceutically acceptable salt of Formula (I) is of Formula (Ih) (SEQ ID NO:33):
(Ih)
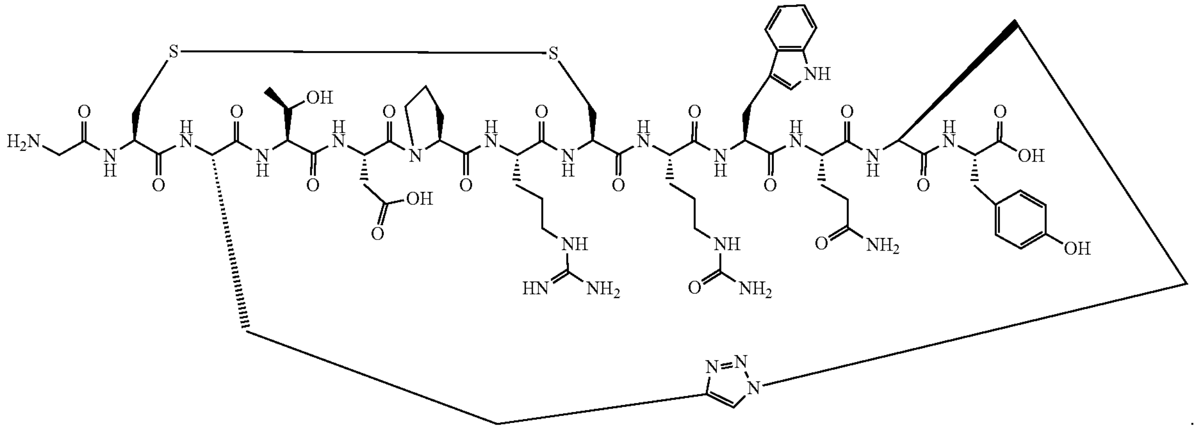
In specific embodiments, the conotoxin peptide analog or pharmaceutically acceptable salt of Formula (I) is of Formula (Ii) (SEQ ID NO:36):
(Ii)
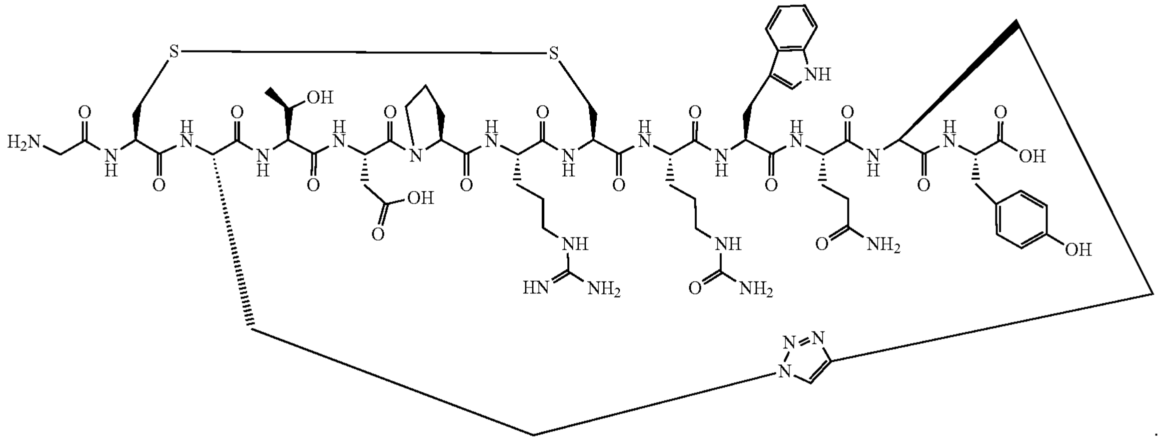

In specific embodiments, the conotoxin peptide analog or pharmaceutically acceptable salt of Formula (I) is of Formula (Ik) (SEQ ID NO:42):
(Ik)
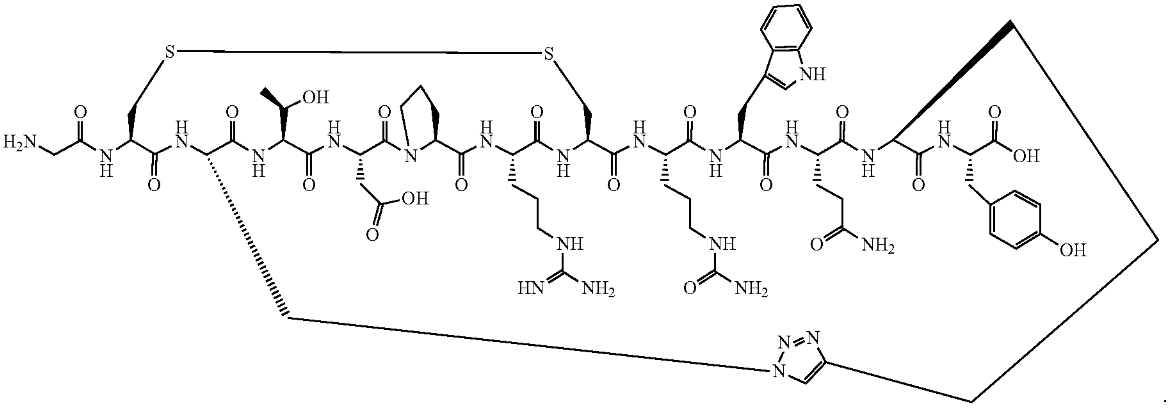
.
In specific embodiments, the conotoxin peptide analog or pharmaceutically acceptable salt of Formula (I) is of Formula (Il) (SEQ ID NO:45):
(Il)
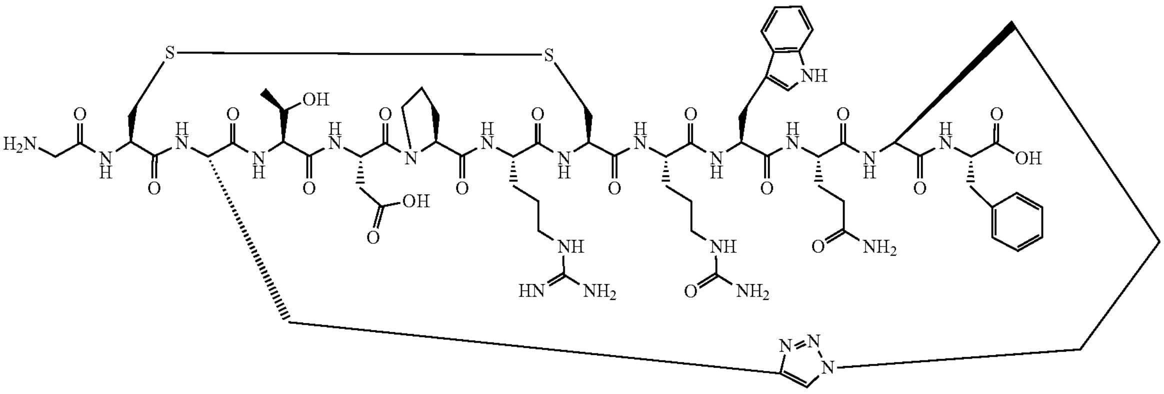
.

In specific embodiments, the conotoxin peptide analog or pharmaceutically acceptable salt of Formula (I) is of Formula (Im) (SEQ ID NO:48):
(Im)
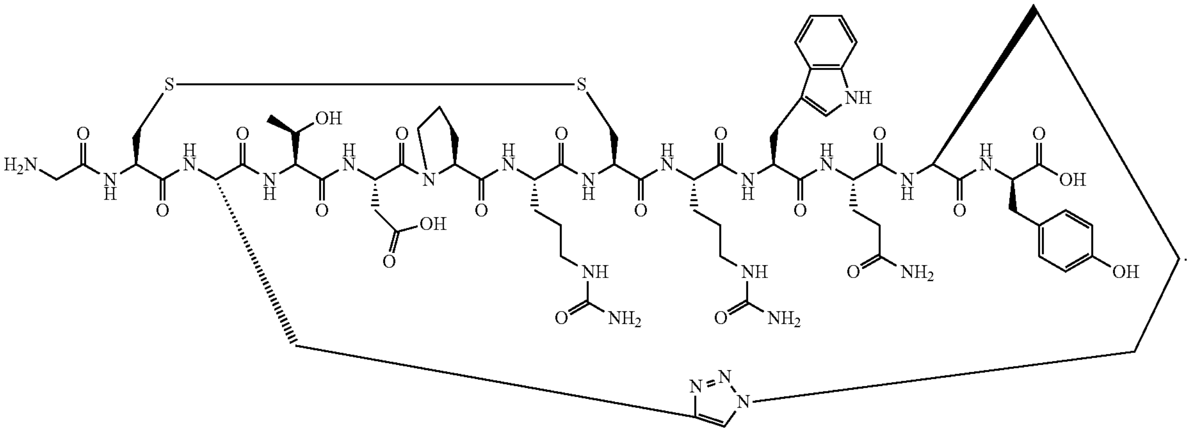
In specific embodiments, the conotoxin peptide analog or pharmaceutically acceptable salt of Formula (I) is of Formula (In) (SEQ ID NO:51):
(In)
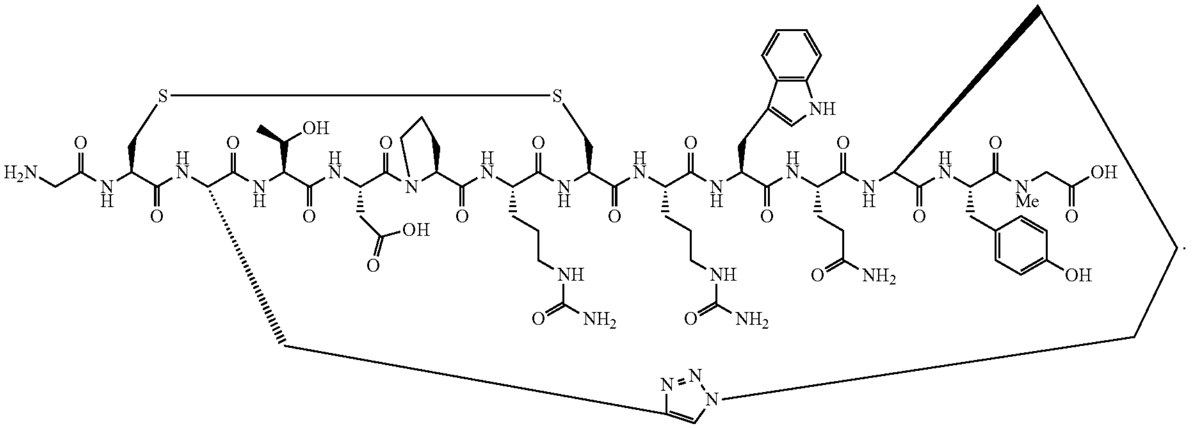

In specific embodiments, the conotoxin peptide analog or pharmaceutically acceptable salt of Formula (I) is of Formula (Io) (SEQ ID NO:54):
(Io)
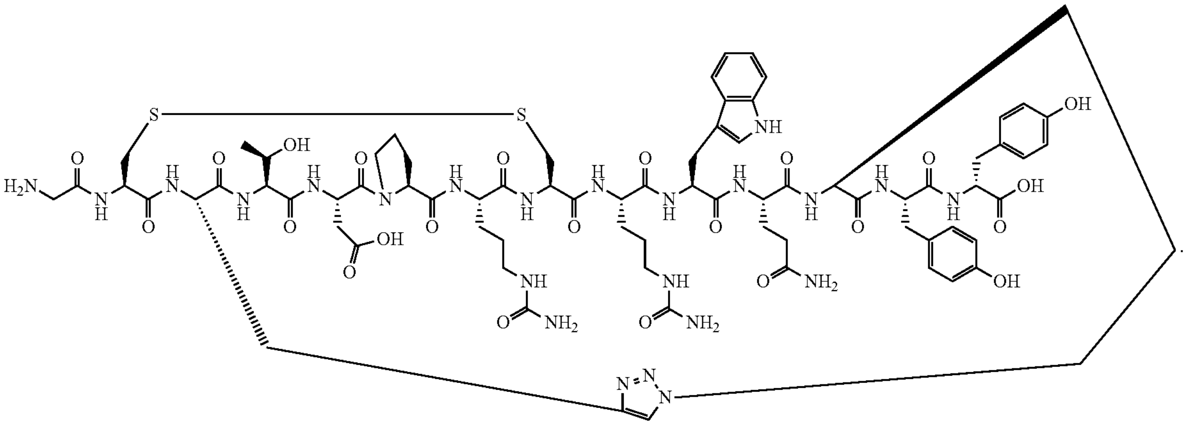
In specific embodiments, the conotoxin peptide analog or pharmaceutically acceptable salt of Formula (I) is of Formula (Ip) (SEQ ID NO:57):
(Ip)
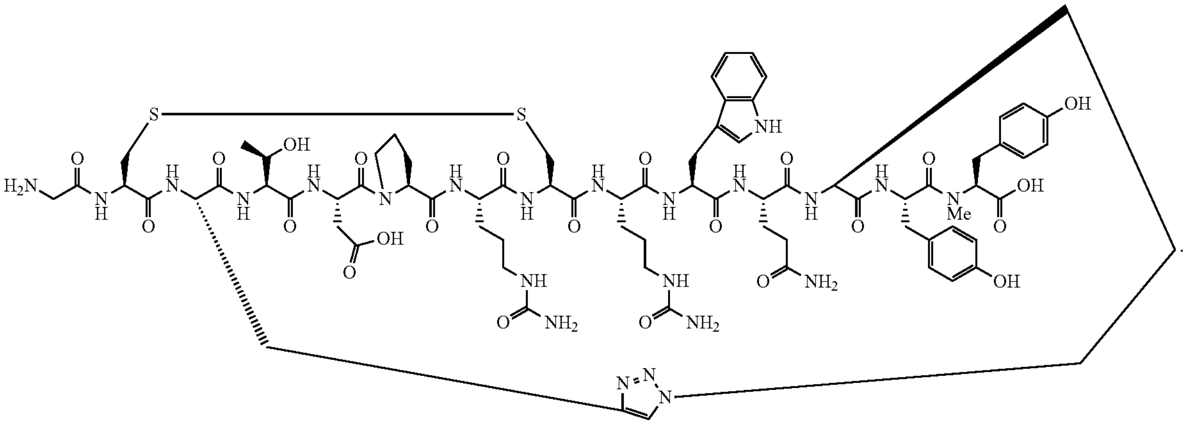
In specific embodiments, the PEGylated conotoxin peptide analog is of Formula (IIa) (SEQ ID NO:83):
(IIa)
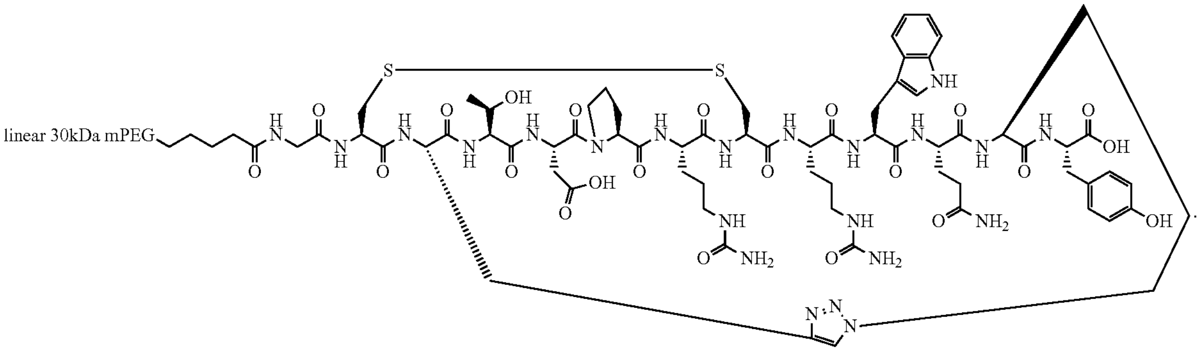

In specific embodiments, the PEGylated conotoxin peptide analog is of Formula (IIg) (SEQ ID NO:95):
(IIg)
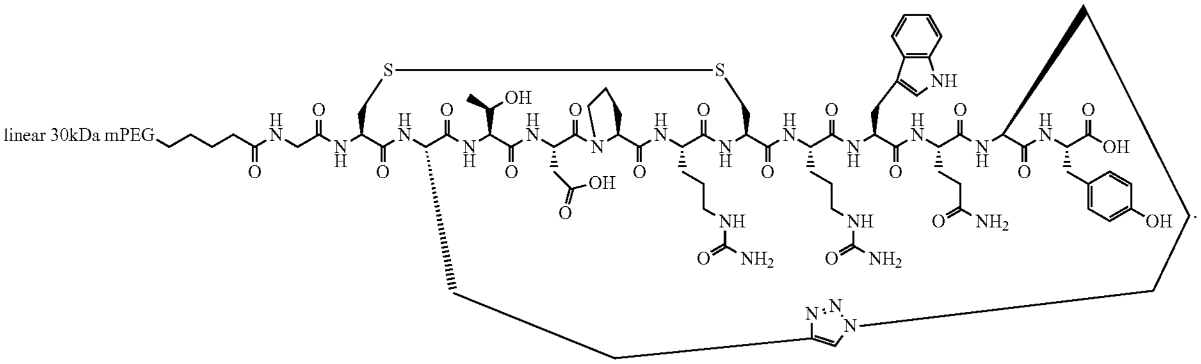
In specific embodiments, the PEGylated conotoxin peptide analog is of Formula (IIh) (SEQ ID NO:96):
(IIh)
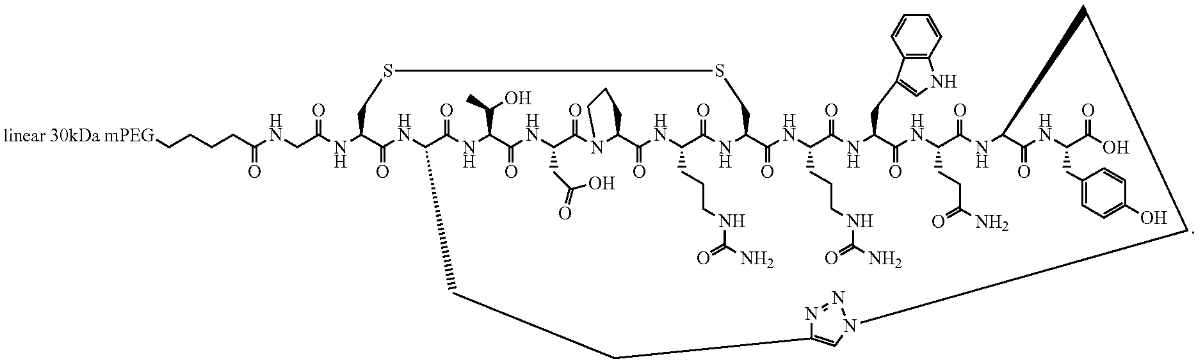
In specific embodiments, the PEGylated conotoxin peptide analog is of Formula (IIi) (SEQ ID NO:97):
(IIi)
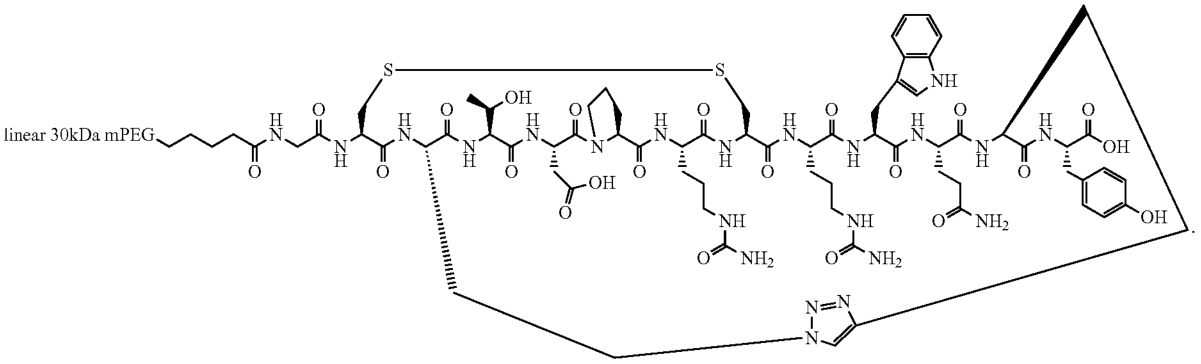

In specific embodiments, the PEGylated conotoxin peptide analog is of Formula (IIk) (SEQ ID NO:98):
(IIk)
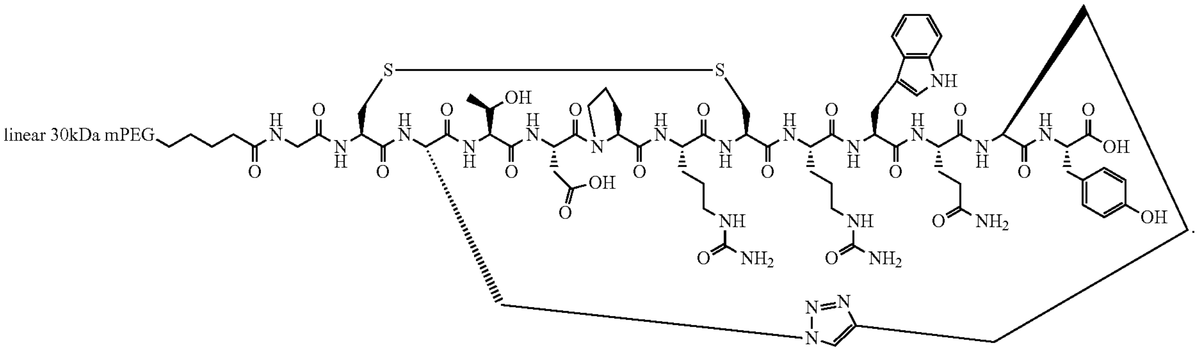
In specific embodiments, the PEGylated conotoxin peptide analog is of Formula (III) (SEQ ID NO:99):
(III)
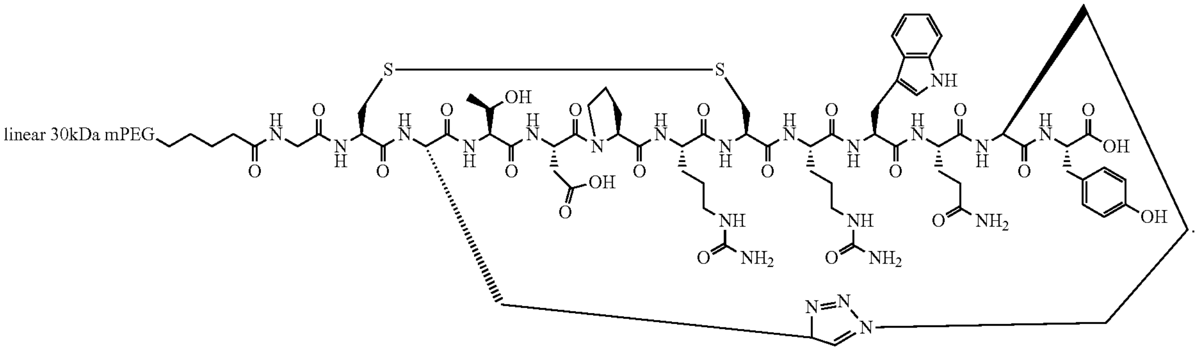
In specific embodiments, the PEGylated conotoxin peptide analog is of Formula (IIm) (SEQ ID NO:100):
(IIm)
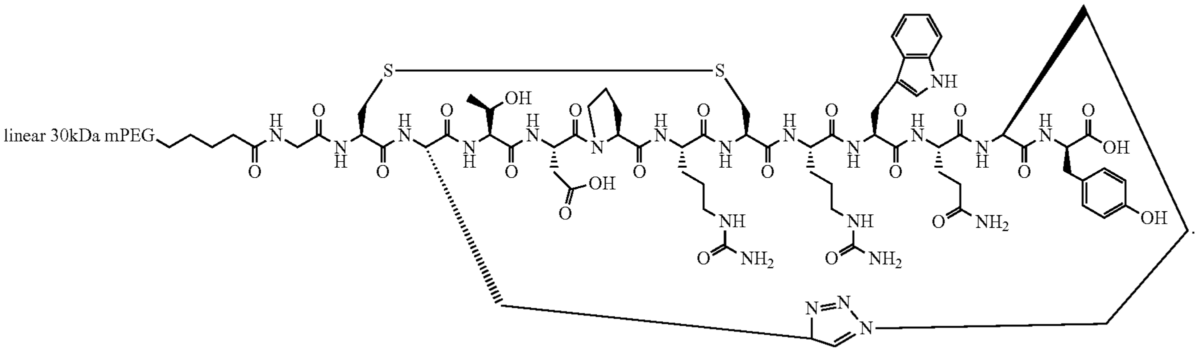

In specific embodiments, the PEGylated conotoxin peptide analog is of Formula (IIn) (SEQ ID NO:101):
(IIn)
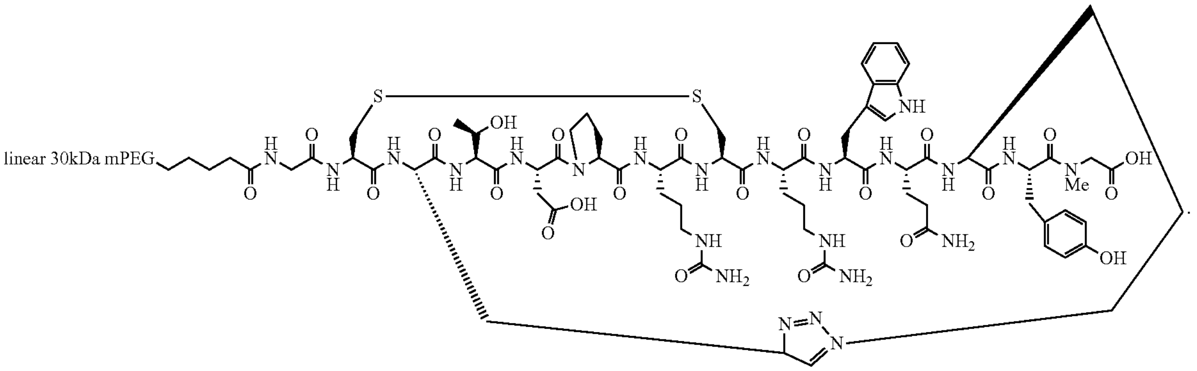
In specific embodiments, the PEGylated conotoxin peptide analog is of Formula (IIo) (SEQ ID NO:102):
(IIo)
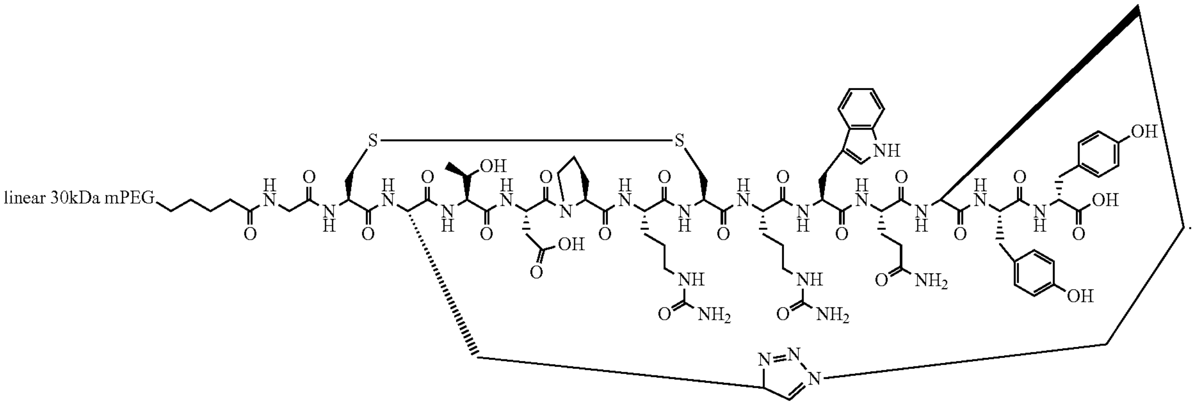
In specific embodiments, the PEGylated conotoxin peptide analog is of Formula (IIp) (SEQ ID NO:103):
(IIp)
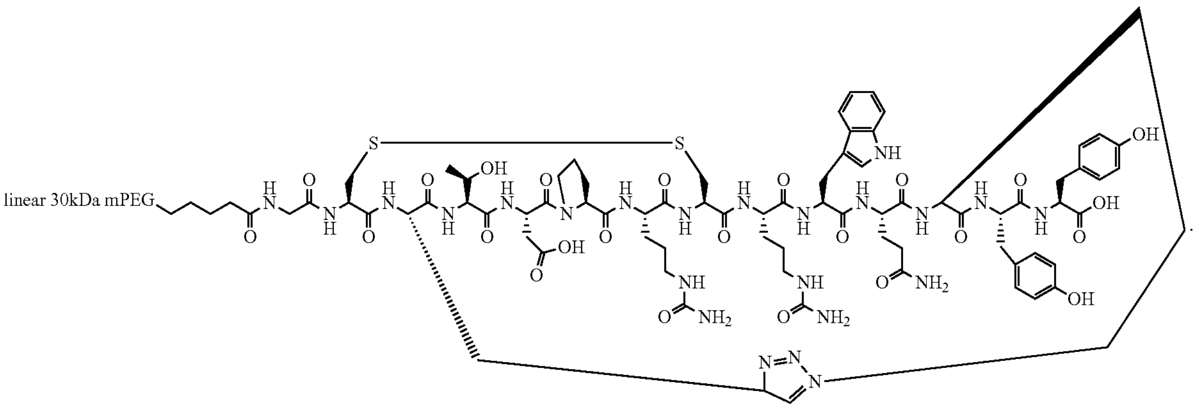

In another aspect, provided herein are PEGylated conotoxin peptide analogs or a pharmaceutically acceptable salt thereof, wherein the conotoxin peptide analog is of Formula (Ib) (SEQ ID NO:104):

(Ib)

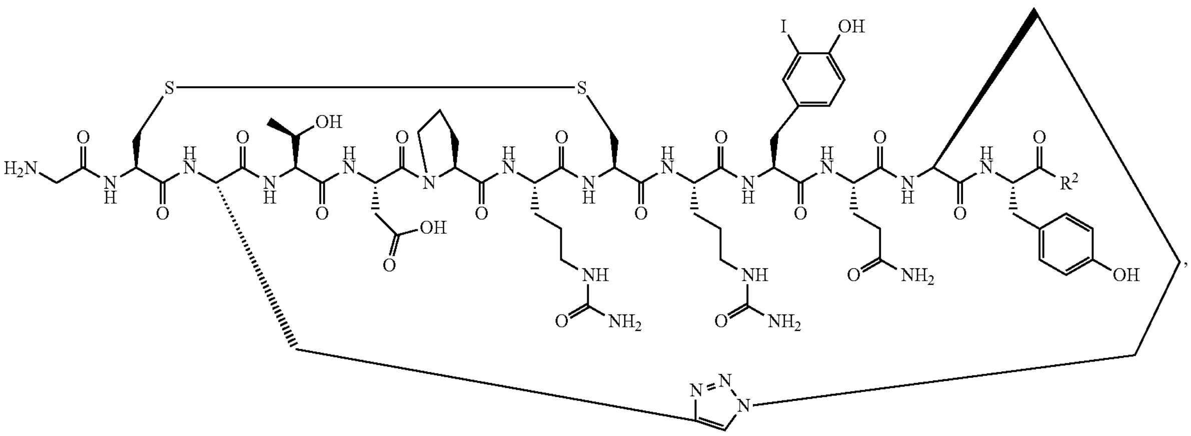

wherein $R^2$ is OH or $NH_2$; and wherein the conotoxin peptide analog is covalently attached directly or via a linking group to one or more polyethylene glycol (PEG) polymers.

In a specific embodiment of Formula (Ib), $R^2$ is OH. In a specific embodiment of Formula (Ib), $R^2$ is $NH_2$.

In specific embodiments, the PEGylated conotoxin peptide analog is of Formula (IIb) (SEQ ID NO:105):

(IIb)

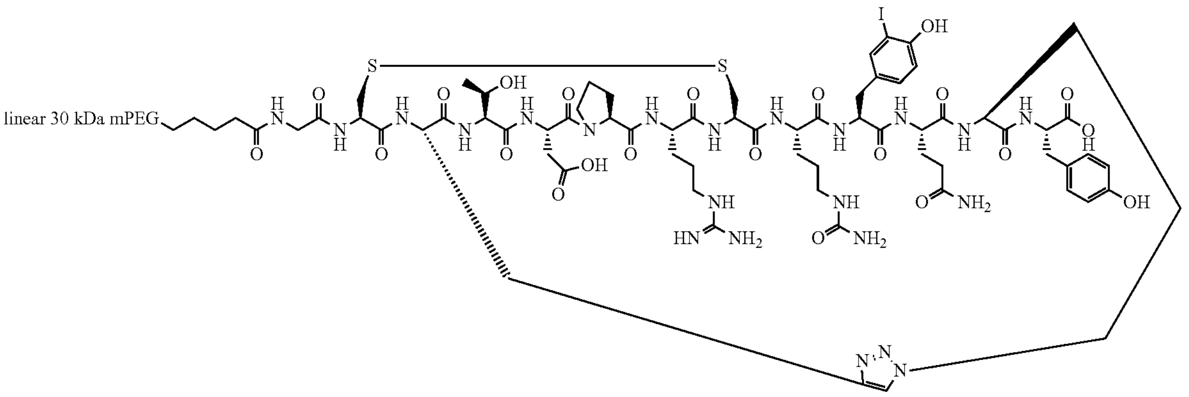

5.4. Pharmaceutical Compositions

Also provided herein are "pharmaceutical compositions," which comprise a conotoxin peptide analog provided herein or a PEGylated conotoxin peptide analog provided herein, and one or more pharmaceutically acceptable carriers. In a particular embodiment, a conotoxin peptide analog is present in a therapeutically effective amount. In a particular embodiment, a conotoxin peptide analog is present in a prophylactically effective amount. The pharmaceutical compositions can be used in accordance with the methods and uses provided herein. Thus, for example, the pharmaceutical compositions can be administered to a subject in order to practice the treatment or prevention methods and uses provided herein. Pharmaceutical compositions provided herein can be formulated to be compatible with the intended method or route of administration; exemplary routes of administration are set forth herein.

Pharmaceutical compositions typically comprise a therapeutically effective amount of at least one of the conotoxin peptide analogs or PEGylated conotoxin peptide analogs provided herein, and a pharmaceutically acceptable carrier. Suitable pharmaceutically acceptable carriers include, but are not limited to, antioxidants (e.g., ascorbic acid), preservatives (e.g., benzyl alcohol, methyl parabens, p-hydroxybenzoate), emulsifying agents, suspending agents, dispersing agents, solvents, buffers, lubricants, fillers, and/or diluents. For example, a suitable vehicle may be physiological saline solution. Typical buffers that can be used include, but are not limited to pharmaceutically acceptable weak acids, weak bases, or mixtures thereof. Buffer components can also include water soluble reagents such as phosphoric acid, tartaric acids, succinic acid, citric acid, acetic acid, and salts thereof.

A vehicle may contain other pharmaceutically acceptable excipients for modifying or maintaining the pH, osmolarity, viscosity, or stability of the pharmaceutical composition. In a specific embodiment, the vehicle is an aqueous buffer. In a specific embodiment, a vehicle comprises, for example, sodium chloride.

Pharmaceutical compositions provided herein may contain still other pharmaceutically acceptable formulation agents for modifying or maintaining the rate of release of a conotoxin peptide analog described herein. Such formulation agents include, for example, those substances known to those skilled in the art in preparing sustained-release or controlled release formulations. Regarding pharmaceutically acceptable formulation agents, see, for example, *Remington's Pharmaceutical Sciences,* 18th Ed. (1990, Mack Publishing Co., Easton, Pa. 18042) pages 1435-1712, and *The Merck Index,* 12th Ed. (1996, Merck Publishing Group, Whitehouse, N.J.).

In a specific embodiment, a pharmaceutical composition is provided in a sterile vial as a solution, suspension, gel, emulsion, or dehydrated or lyophilized powder. Such compositions may, for example, be stored either in a ready to use form, a lyophilized form requiring reconstitution prior to use, or a liquid form requiring dilution prior to use. In specific embodiments, a pharmaceutical composition is provided in a single-use container (e.g., a single-use vial, ampoule, syringe, or autoinjector). In a specific embodiment, a pharmaceutical composition is provided in a multi-use container (e.g., a multi-use vial or cartridge). Any drug delivery apparatus may be used to deliver a conotoxin peptide analog or a PEGylated conotoxin peptide analog or pharmaceutical composition described herein, including implants (e.g., implantable pumps) and catheters. In a specific embodiment, depot injections, can be utilized to release a conotoxin peptide analog or a PEGylated conotoxin peptide analog or pharmaceutical composition described herein over a defined period of time. Depot injections are generally administered subcutaneously or intramuscularly.

A pharmaceutical composition can be formulated to be compatible with its intended route of administration as described herein.

Pharmaceutical compositions may be in the form of a sterile injectable aqueous suspension. This suspension may be formulated using suitable dispersing or wetting agents and suspending agents known to those skilled in the art. The sterile injectable preparation may also be a sterile injectable solution or suspension in a non-toxic parenterally-acceptable diluent or solvent. In one embodiment, the sterile injectable solution can, for example, be a solution in 1,3-butane diol. Acceptable diluents, solvents or dispersion media that may be employed include water, Ringer's solution, saline, Cremophor EL™, phosphate buffered saline (PBS), ethanol, polyol (e.g., glycerol or liquid polyethylene glycol), and mixtures thereof. Prolonged absorption of particular injectable formulations can be achieved by including an agent that delays absorption (e.g., aluminum monostearate or gelatin).

Pharmaceutical compositions can also include carriers to protect the composition against degradation or elimination from the body. Various antibacterial and antifungal agents, for example, parabens, chlorobutanol, ascorbic acid, thimerosal, can be included in the pharmaceutical composition.

5.5. Methods of Treatment or Prevention

In one embodiment, provided herein is a method for treating or preventing a condition conducive to treatment or prevention by inhibition of an α9-containing nicotinic acetylcholine receptor (nAChR) comprising administering to a subject a therapeutically effective amount of a conotoxin peptide analog as described herein or a pharmaceutically acceptable salt thereof, or a PEGylated conotoxin peptide analog as described herein or pharmaceutically acceptable salt thereof, or a pharmaceutical composition as described herein.

In a preferred embodiment, the condition conducive to treatment or prevention by inhibition of an α9-containing nicotinic acetylcholine receptor (nAChR) is a condition conducive to treatment or prevention by inhibition of the α9α10 subtype of nAChR.

In a specific embodiment, the condition conducive to treatment or prevention by inhibition of an α9-containing nAChR, e. g., the α9α10 subtype of nAChR, is pain or inflammation.

In a preferred embodiment, the method provided herein is a method of treating a condition conducive to treatment by inhibition of an α9-containing nicotinic acetylcholine receptor (nAChR) comprising administering to a subject a therapeutically effective amount of a conotoxin peptide analog as described herein or a pharmaceutically acceptable salt thereof, or a PEGylated conotoxin peptide analog as described herein or pharmaceutically acceptable salt thereof, or a pharmaceutical composition as described herein.

In a preferred embodiment, the condition conducive to treatment by inhibition of an α9-containing nicotinic acetylcholine receptor (nAChR) is a condition conducive to treatment by inhibition of the α9α10 subtype of nAChR.

In a specific embodiment, the condition conducive to treatment by inhibition of an α9-containing nAChR, e. g., the α9α10 subtype of nAChR, is pain or inflammation.

In a preferred embodiment, the method provided herein is a method of preventing a condition conducive to prevention by inhibition of an α9-containing nicotinic acetylcholine receptor (nAChR) comprising administering to a subject a therapeutically effective amount of a conotoxin peptide analog as described herein or a pharmaceutically acceptable salt thereof, or a PEGylated conotoxin peptide analog as described herein or pharmaceutically acceptable salt thereof, or a pharmaceutical composition as described herein.

In a preferred embodiment, the condition conducive to prevention by inhibition of an α9-containing nicotinic acetylcholine receptor (nAChR) is a condition conducive to treatment by inhibition of the α9α10 subtype of nAChR.

In a specific embodiment, the condition conducive to prevention by inhibition of an α9-containing nAChR, e. g., the α9α10 subtype of nAChR, is pain or inflammation.

In a specific embodiment, the condition conducive to treatment or prevention by inhibition of an α9-containing nicotinic acetylcholine receptor, e. g., the α9α10 subtype of nAChR, is pain. In a specific embodiment, the pain is selected from the group consisting of general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and pain induced by a burn. In a specific embodiment, the pain is cancer-related chronic pain. In a specific embodiment, the pain is pain associated with neuropathy, which, by way of example, can be drug (e.g., cancer chemotherapeutic)-induced neuropathy or infection-induced neuropathy. In a specific embodiment, the pain is neuralgia, including but not limited to postherpetic neuralgia, for example, postherpetic neuralgia due to shingles.

In a specific embodiment, the condition conducive to treatment or prevention by inhibition of an α9-containing nicotinic acetylcholine receptor, e. g., the α9α10 subtype of nAChR, is an inflammatory condition. In a specific embodiment, the inflammatory condition is selected from the group consisting of is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, and cardiovascular disease. In a specific embodiment, the inflammatory condition is mediated by immune cells. In a specific embodiment, the inflammatory condition is long-term inflammation and/or peripheral neuropathy following injury.

In a specific embodiment, the condition associated with the α9-containing nicotinic acetylcholine receptor, e. g., the α9α10 subtype of nAChR, is pain and inflammation. In a specific embodiment, the condition associated with the α9α10 subtype of nAChR condition is inflammation and neuropathy.

In another aspect, provided herein is a method of treating or preventing a condition associated with activation of an α9-containing nAChR, e. g., the α9α10 subtype of nAChR, in a subject comprising administering to the subject a therapeutically effective amount of a conotoxin peptide analog as described herein or pharmaceutically acceptable salt thereof, or a PEGylated conotoxin peptide analog as described herein or pharmaceutically acceptable salt thereof, or a pharmaceutical composition as described herein.

In another aspect, provided herein is a method of treating or preventing pain or inflammation in a subject comprising administering to the subject a therapeutically effective amount of a conotoxin peptide analog as described herein or pharmaceutically acceptable salt thereof, or a PEGylated conotoxin peptide analog as described herein or pharmaceutically acceptable salt thereof, or pharmaceutical composition as described herein. In a specific embodiment of a method of treating or preventing pain, the pain is pain associated with neuropathy, which, by way of example, can be drug (e.g., cancer chemotherapeutic)-induced neuropathy or infection-induced neuropathy. In a specific embodiment, the pain is neuralgia, including but not limited to postherpetic neuralgia, for example, postherpetic neuralgia due to shingles.

In a specific embodiment, the method provided herein is a method of treating pain or inflammation. In a specific embodiment, the method provided herein is a method of treating pain. In a specific embodiment, the method provided herein is a method of treating inflammation.

In a specific embodiment, the method provided herein is a method of preventing pain or inflammation. In a specific embodiment, the method provided herein is a method of preventing pain. In a specific embodiment, the method provided herein is a method of preventing inflammation.

In a specific embodiment, the method of preventing pain is to prevent pain associated with neuropathy. In a specific embodiment of such method, the pain associated with neuropathy is neuralgia. In a specific embodiment, the neuralgia is postherpetic neuralgia. In a specific embodiment, the method of preventing pain is to prevent pain induced by cancer chemotherapy (and thus a conotoxin peptide analog or pharmaceutically acceptable salt thereof is administered to the patient prior to the patient being administered cancer chemotherapy). In a specific embodiment, the method of preventing pain is to prevent pain induced by a surgical procedure; in a specific embodiment of such method, a conotoxin peptide analog or pharmaceutically acceptable salt thereof is administered prior to and/or concurrently with the surgical procedure, in particular, where the surgical procedure is reasonably expected to result in pain and/or inflammation.

In another aspect, provided herein is a method of inhibiting an α9-containing nicotinic acetylcholine receptor (nAChR), e.g., the α9α10 subtype of nAChR, in a subject comprising administering to the subject a therapeutically effective amount of a conotoxin peptide analog as described herein or a pharmaceutically acceptable salt thereof, or a pharmaceutical composition as described herein.

In specific embodiments, "treat", "treating", treatment" and the like refer to an action (such as administering a conotoxin peptide analog or pharmaceutically acceptable salt thereof or a pharmaceutical composition comprising a conotoxin peptide analog or pharmaceutically acceptable salt thereof) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment can include inhibiting (i.e., arresting the development or further development of the disease, disorder or condition or clinical symptoms associated therewith) an active disease.

In specific embodiments of the invention in which a method of prevention is carried out, the prevention need not be complete; in a specific embodiment, the prevention is partial inhibition or partial prevention or a reduction in the disease, condition or disorder relative to that which would otherwise be expected to occur absent the administration of the conotoxin peptide analog or pharmaceutically acceptable salt thereof.

In specific embodiments, the administering can be by injecting or otherwise physically delivering a conotoxin peptide analog into a patient, such as by mucosal, intradermal, intravenous, intramuscular delivery and/or any other method of physical delivery described herein or known in the art. When a disease, disorder or condition, or a symptom thereof, is being treated, administration of the conotoxin peptide analog or pharmaceutically acceptable salt thereof typically occurs after the onset of disease, disorder or condition or symptom thereof. When a disease, disorder or condition, or a symptom thereof, is being prevented, administration of the conotoxin peptide analog or pharmaceutically acceptable salt thereof typically occurs before the onset of the disease, disorder or condition or symptom thereof. In a specific embodiment, a conotoxin peptide analog or pharmaceutically acceptable salt thereof is administered prior to and after the onset of pain and/or inflammation to both prevent and treat the pain and/or inflammation.

In various embodiments, a conotoxin peptide analog, including but not limited to a PEGylated conotoxin peptide analog, or a pharmaceutically acceptable salt thereof, or a pharmaceutical composition, as described herein, is used in any of the methods provided herein. For example, a conotoxin peptide analog, including but not limited to a PEGylated conotoxin peptide analog, or a pharmaceutically acceptable salt thereof, or a pharmaceutical composition, provided herein can be used in a method for treatment or prevention of a disease or disorder or condition described herein. Thus, a conotoxin peptide analog, including but not limited to a PEGylated conotoxin peptide analog, or a pharmaceutically acceptable salt thereof, or a pharmaceutical composition, provided herein can be for use as a medicament. A conotoxin peptide analog, including but not limited to a PEGylated conotoxin peptide analog, or a pharmaceutically acceptable salt thereof, or a pharmaceutical composition, provided herein can be for use in a method for the treatment or prevention of a condition conducive to treatment or prevention by inhibition of an α9-containing nicotinic acetylcholine receptor (nAChR), e.g. the α9α10 subtype of nAChR. A conotoxin peptide analog, including but not limited to a PEGylated conotoxin peptide analog, or a pharmaceutically acceptable salt thereof, or a pharmaceutical composition, provided herein can be for use in a method for the treatment or prevention of a condition conducive to treatment or prevention by inhibition of an α9-containing nicotinic acetylcholine receptor (nAChR), e.g. the α9α10 subtype of nAChR. For example, a conotoxin peptide analog, including but not limited to a PEGylated conotoxin peptide analog, or a pharmaceutically acceptable salt thereof, or a pharmaceutical composition, provided herein can be for use in a method for the treatment or prevention of pain or inflammation.

5.6. Routes of Administration and Dosage

A conotoxin peptide analog, including but not limited to a PEGylated conotoxin peptide analog, or a pharmaceutically acceptable salt thereof, or a pharmaceutical composition, described herein may be administered to a patient by any of a variety of routes. These include, but are not limited to, parenteral, intra-articular, intranasal, intratracheal, oral, intradermal, topical, intramuscular, intraperitoneal, transdermal, intravenous, intratumoral, conjunctival, subcutaneous, and pulmonary routes. In a specific embodiment, a conotoxin peptide analog, including but not limited to a PEGylated conotoxin peptide analog, or a pharmaceutically acceptable salt thereof, or a pharmaceutical composition, described herein is administered via subcutaneous administration. In a specific embodiment, a conotoxin peptide analog, including but not limited to a PEGylated conotoxin peptide analog, or a pharmaceutically acceptable salt thereof, or a pharmaceutical composition, described herein is administered via intravenous administration. In a specific embodiment, a conotoxin peptide analog, including but not limited to a PEGylated conotoxin peptide analog, or a pharmaceutically acceptable salt thereof, or a pharmaceutical composition, described herein is administered via intra-articular administration.

The amount of a conotoxin peptide analog, including but not limited to a PEGylated conotoxin peptide analog, or a pharmaceutically acceptable salt thereof, to be administered to the patient will depend on the nature of the disease and the condition of the patient, and can be determined by standard clinical techniques and the knowledge of the physician.

The precise dose and regime to be employed in a composition will also depend on the route of administration, and the seriousness of the disease, and should be decided according to the judgment of the physician and each patient's circumstance. Determination of the proper dosage can be determined by one skilled in the medical arts. The total daily dosage may be divided and administered in portions throughout the day or by means providing continuous delivery.

In a specific embodiment, a conotoxin peptide analog or pharmaceutically acceptable salt thereof is administered to a human subject at a dosage of between 0.01 to about 50 mg/kg of body weight. In a specific embodiment, a conotoxin peptide analog, e.g., a PEGylated conotoxin peptide analog, or a pharmaceutically acceptable salt thereof, is administered to a human subject at a dosage of about 0.5 mg/kg of body weight. In specific embodiments, the human dose is from 1 to 1000 mg/day. In specific embodiments, the human daily dose is from 1 to 750 mg/day; or from 10 to 500 mg/day.

A conotoxin peptide analog, e.g., a PEGylated conotoxin peptide analog, or a pharmaceutically acceptable salt thereof, or a pharmaceutical composition, disclosed herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens may be adjusted over time according to the individual need and the professional judgment of the person administering or supervising the administration of the formulations.

5.7. Patients

The patient referred to in this disclosure, can be, but is not limited to, a human or non-human vertebrate such as a wild, domestic or farm animal. In a specific embodiment, the patient is a mammal, e.g., a human, a cow, a dog, a cat, a goat, a horse, a sheep, a pig, a rabbit, a rat, or a mouse. In a preferred embodiment, the patient is a human patient.

In a specific embodiment, the human patient is an adult (at least age 16). In another specific embodiment, the human patient is an adolescent (age 12-15). In another specific embodiment, the patient is a child (under age 12).

5.8. Methods of Making Conotoxin Peptide Analogs

This disclosure provides methods of making conotoxin peptide analogs, in which intermediate conotoxin peptide analogs (prior to triazole bridge formation) are subjected to triazole formation conditions to form the conotoxin peptide analogs of the invention.

5.8.1. Intermediate Conotoxin Peptide Analogs

This disclosure provides syntheses of intermediate conotoxin peptide analogs for synthesizing conotoxin peptide analogs with a triazole bridge. An intermediate conotoxin peptide analog can, for example, be synthesized using solid phase peptide synthesis. When carrying out the solid phase peptide synthesis, necessary amino acids with appropriate reaction groups (for example, an azide group or an acetylene group) for forming a triazole bridge can be introduced into the peptide (e.g., a conotoxin peptide of RgIA). The necessary amino acids can be introduced into the 3- and 12-position of the conotoxin peptide analog of RgIA.

Into one of the 3- and 12-positions is introduced an amino acid residue bearing an acetylene group (e.g., (S)-propargyl glycine, (S)-homopropargyl glycine, or (S)-bishomopropargyl glycine), and into the other position is introduced an amino acid bearing an azide group (e.g., (S)-azidoalanine, (S)-gamma-azidohomoalanine, (S)-azidonorvaline), whereby the acetylene group and the azide group within the same intermediate conotoxin peptide can form a triazole ring when the intermediate conotoxin peptide is subjected to triazole formation conditions, thereby forming a triazole bridge in the resulting conotoxin peptide analog.

In a specific embodiment, the necessary amino acids for forming the triazole bridge are, for example, selected from the group of (S)-propargyl glycine, (S)-azidoalanine, (S)-homopropargyl glycine, (S)-gamma-azidohomoalanine, (S)-azidonorvaline, and (S)-bishomopropargyl glycine.

In another aspect, provided herein is an intermediate conotoxin peptide analog or a salt thereof, wherein the amino acid sequence of the conotoxin peptide analog is (SEQ ID NO: 106)
Gly-Cys-$X_{AA}^3$-Thr-Asp-Pro-Arg-Cys-$X_{AA}^9$-Trp-Gln-$X_{AA}^{12}$-X, wherein $X_{AA}^3$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}^9$ is Citrulline;

$X_{AA}^{12}$ is selected from the group consisting of (S)-gamma-azidohomoalanine, (S)-homopropargyl glycine, (S)-azidonorvaline, and (S)-bishomopropargyl glycine;

wherein when $X_{AA}^3$ is selected from the group consisting of (S)-propargyl glycine, (S)-homopropargyl glycine, and (S)-bishomopropargyl glycine, $X_{AA}^{12}$ is (S)-gamma-azidohomoalanine or (S)-azidonorvaline; and when $X_{AA}^3$ is selected from the group consisting of (S)-azidoalanine, (S)-gamma-azidohomoalanine, and (S)-azidonorvaline, $X_{AA}^{12}$ is (S)-homopropargyl glycine or (S)-bishomopropargyl glycine;

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr; and wherein the C-terminus of the intermediate conotoxin peptide analog is a carboxylic acid or an amide group.

In a specific embodiment, $X_{AA}^3$ is (S)-propargyl glycine or (S)-azidoalanine. In a specific embodiment, wherein $X_{AA}^{12}$ is (S)-azidonorvaline or (S)-bishomopropargyl glycine. In a specific embodiment, $X_{AA}^3$ is (S)-propargyl glycine and $X_{AA}^{12}$ is (S)-azidonorvaline. In a specific embodiment, $X_{AA}^3$ is (S)-homopropargyl glycine and $X_{AA}^{12}$ is (S)-azidonorvaline. In a specific embodiment, $X_{AA}^3$ is (S)-homopropargyl glycine and $X_{AA}^{12}$ is (S)-gamma-azidohomoalanine. In a specific embodiment, $X_{AA}^3$ is (S)-gamma-azidohomoalanine and $X_{AA}^{12}$ is (S)-homopropargyl glycine. In a specific embodiment, $X_{AA}^3$ is (S)-gamma-azidohomoalanine and $X_{AA}^{12}$ is (S)-homopropargyl glycine.

In a specific embodiment, X is $X_{AA}^1$. In a specific embodiment, X is $X_{AA}^1X_{AA}^2$.

In a specific embodiment, $X_{AA}^1$ is Tyr, Phe, Trp, or a D-isomer of Tyr, Phe, or Trp.

In a specific embodiment, $X_{AA}^1$ is Tyr, Phe, or Trp. In a specific embodiment, $X_{AA}^1$ is Tyr, D-Tyr, or Phe. In a specific embodiment, $X_{AA}^1$ is Tyr or D-Tyr. In a specific embodiment, $X_{AA}^1$ is Tyr or Phe. In a specific embodiment, $X_{AA}^1$ is D-Tyr or Phe. In a specific embodiment, $X_{AA}^1$ is Phe. In a specific embodiment, $X_{AA}^1$ is D-Phe. In a specific embodiment, $X_{AA}^1$ is Trp. In a specific embodiment, $X_{AA}^1$ is D-Trp. In a specific embodiment, $X_{AA}^1$ is D-Tyr. In a preferred embodiment, $X_{AA}^2$ is Tyr.

In a specific embodiment, $X_{AA}^2$ is N-Me-Gly, D-Tyr, or N-Me-Tyr. In a specific embodiment, $X_{AA}^2$ is N-Me-Gly or D-Tyr. In a specific embodiment, $X_{AA}^2$ is D-Tyr or N-Me-Tyr. In a specific embodiment, $X_{AA}^2$ is N-Me-Gly or N-Me-Tyr. In a specific embodiment, $X_{AA}^2$ is N-Me-Gly. In a specific embodiment, $X_{AA}^2$ is N-Me-Tyr. In a specific embodiment, $X_{AA}^2$ is D-Tyr. In a specific embodiment, $X_{AA}^2$ is optionally present. In a specific embodiment, $X_{AA}^2$ is present. In a specific embodiment, $X_{AA}^2$ is absent.

In a specific embodiment, X is selected from the group consisting of Tyr, Phe, D-Tyr, (Tyr)-(D-Tyr), (Tyr)-(N-Me-Gly), (Tyr)-(N-Me-Tyr), N-Me-Tyr, D-Arg, N-Me-D-Tyr, beta-Tyr, and N-Me-Arg. In a specific embodiment, X is selected from the group consisting of Tyr, Phe, D-Tyr, (Tyr)-(D-Tyr), (Tyr)-(N-Me-Gly), and (Tyr)-(N-Me-Tyr). In a specific embodiment, X is selected from the group consisting of Tyr, Phe, and D-Tyr. In a specific embodiment, X is selected from the group consisting of (Tyr)-(D-Tyr), (Tyr)-(N-Me-Gly), and (Tyr)-(N-Me-Tyr). In a specific embodiment, X is selected from the group consisting of N-Me-Tyr, D-Arg, N-Me-D-Tyr, beta-Tyr, and N-Me-Arg. In a specific embodiment, X is Tyr. In a specific embodiment, X is Phe. In a specific embodiment, X is D-Tyr. In a specific embodiment, X is (Tyr)-(D-Tyr). In a specific embodiment, X is (Tyr)-(N-Me-Gly). In a specific embodiment, X is (Tyr)-(N-Me-Tyr). In a specific embodiment, X is N-Me-Tyr. In a specific embodiment, X is D-Arg. In a specific embodiment, X is N-Me-D-Tyr. In a specific embodiment, X is beta-Tyr. In a specific embodiment, X is N-Me-Arg.

In a specific embodiment, the C-terminus of the conotoxin peptide analog is a carboxylic acid or an amide group. In one preferred embodiment, the C-terminus of the conotoxin peptide analog is OH. In a specific embodiment, the C-terminus of the conotoxin peptide analog is $NH_2$.

In specific embodiments, $X_{AA}^3$ is (S)-propargyl glycine, $X_{AA}^{12}$ is (S)-azidonorvaline, X is Tyr. In one embodiment, the C-terminus of the conotoxin peptide analog is a carboxylic acid group. In another embodiment, the C-terminus of the conotoxin peptide analog is an amide group.

In specific embodiments, $X_{AA}^3$ is (S)-homopropargyl glycine, $X_{AA}^{12}$ is (S)-azidonorvaline, X is Tyr; and wherein the C-terminus of the conotoxin peptide analog is a carboxylic acid group.

In specific embodiments, $X_{AA}^3$ is (S)-homopropargyl glycine, $X_{AA}^{12}$ is (S)-gamma-azidohomoalanine, X is Tyr; and wherein the C-terminus of the conotoxin peptide analog is a carboxylic acid group.

In specific embodiments, $X_{AA}^3$ is (S)-gamma-azidohomoalanine, $X_{AA}^{12}$ is (S)-homopropargyl glycine, X is Tyr; and wherein the C-terminus of the conotoxin peptide analog is a carboxylic acid group.

In specific embodiments, $X_{AA}^3$ is (S)-azidoalanine, $X_{AA}^{12}$ is (S)-bishomopropargyl glycine, X is Tyr; and wherein the C-terminus of the conotoxin peptide analog is a carboxylic acid group.

In specific embodiments, $X_{AA}^3$ is (S)-propargyl glycine, $X_{AA}^{12}$ is (S)-azidonorvaline, X is Phe; and wherein the C-terminus of the conotoxin peptide analog is a carboxylic acid group.

In specific embodiments, $X_{AA}^3$ is (S)-propargyl glycine, $X_{AA}^{12}$ is (S)-azidonorvaline, X is D-Tyr; and wherein the C-terminus of the conotoxin peptide analog is a carboxylic acid group.

In specific embodiments, $X_{AA}^3$ is (S)-propargyl glycine, $X_{AA}^{12}$ is (S)-azidonorvaline, X is Tyr-N-Me-Gly; and wherein the C-terminus of the conotoxin peptide analog is a carboxylic acid group.

In specific embodiments, $X_{AA}^3$ is (S)-propargyl glycine, $X_{AA}^{12}$ is (S)-azidonorvaline, X is Tyr-D-Tyr; and wherein the C-terminus of the conotoxin peptide analog is a carboxylic acid group.

In specific embodiments, $X_{AA}^3$ is (S)-propargyl glycine, $X_{AA}^{12}$ is (S)-azidonorvaline, X is Tyr-N-Me-Tyr; and wherein the C-terminus of the conotoxin peptide analog is a carboxylic acid group.

5.8.2. Triazole Bridge Formation

Following the synthesis of an intermediate conotoxin peptide with the necessary groups for forming a triazole bridge at the 3- and 12-positions (bearing one acetylene group and one azide group, respectively), the acetylene group and the azide group react under triazole formation conditions to afford a triazole thereby forming a triazole bridge in the resulting conotoxin peptide analog.

In a specific embodiment, provided herein is a method of making a conotoxin peptide analog of Formula (I) (SEQ ID NO:93) or a pharmaceutically acceptable salt thereof, (I)

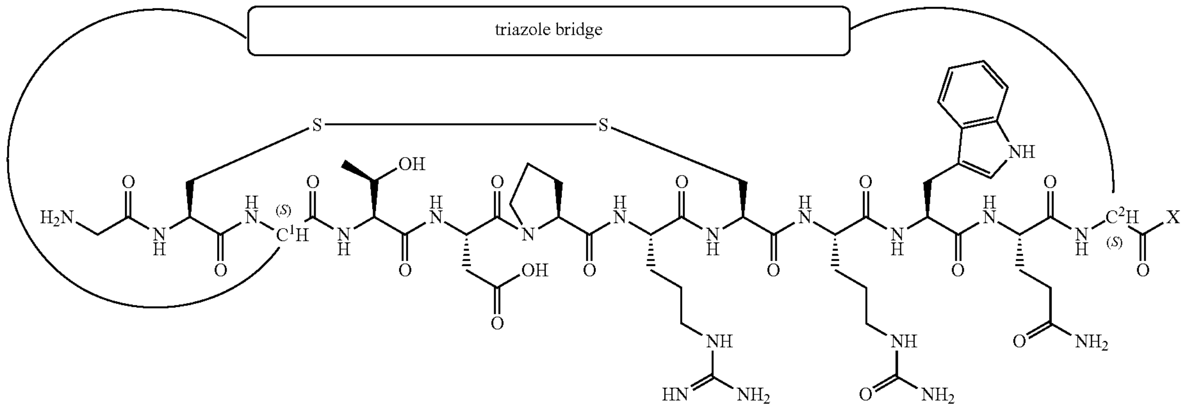

In another aspect, provided herein is an intermediate conotoxin peptide analog or a salt thereof, wherein the amino acid sequence of the conotoxin peptide analog is (SEQ ID NO: 107)
Gly-Cys-$X_{AA}^3$-Thr-Asp-Pro-Arg-Cys-$X_{AA}^9$-$X_{AA}^{10}$-Gln-$X_{AA}^{12}$-Tyr, wherein $X_{AA}^3$ is (S)-propargyl glycine;

$X_{AA}^9$ is Citrulline;

$X_{AA}^{10}$ is 3-iodo-Tyr;

$X_{AA}^{12}$ is (S)-azidonorvaline;

wherein the C-terminus of the intermediate conotoxin peptide analog is a carboxylic acid or an amide group.

In a specific embodiment, the C-terminus of the intermediate conotoxin peptide analog is a carboxylic acid group.

In a specific embodiment, the C-terminus of the intermediate conotoxin peptide analog is an amide group.

wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr; and wherein the C-terminus of the conotoxin peptide analog of Formula (I) is a carboxylic acid or an amide group;

comprising subjecting an intermediate conotoxin peptide analog or a salt thereof to triazole formation conditions, wherein the amino acid sequence of the intermediate conotoxin peptide analog is Gly-Cys-$X_{AA}^3$-Thr-Asp-Pro-Arg-Cys-$X_{AA}^9$-Trp-Gln-$X_{AA}^{12}$-X (SEQ ID NO:106), wherein $X_{AA}^3$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}^9$ is Citrulline;

$X_{AA}^{12}$ is selected from the group consisting of (S)-gamma-azidohomoalanine, (S)-homopropargyl glycine, (S)-azidonorvaline, and (S)-bishomopropargyl glycine; wherein when $X_{AA}^3$ is selected from the group consisting of (S)-propargyl glycine, (S)-homopropargyl glycine, and (S)-bishomopropargyl glycine, $X_{AA}^{12}$ is (S)-gamma-azidohomoalanine or (S)-azidonorvaline; when $X_{AA}^3$ is selected from the group consisting of (S)-azidoalanine, (S)-gamma-azidohomoalanine, and (S)-azidonorvaline, $X_{AA}^{12}$ is (S)-homopropargyl glycine or (S)-bishomopropargyl glycine;

X is as defined above for the conotoxin peptide analog of Formula (I); and wherein the C-terminus of the intermediate conotoxin peptide analog is as defined above for the conotoxin peptide analog of Formula (I); and wherein under said triazole formation conditions $X_{AA}^3$ reacts with $X_{AA}^{12}$ to form the triazole bridge in the conotoxin peptide analog of Formula (I).

In yet another aspect, provided herein is a method of making a conotoxin peptide analog of Formula (Ib) (SEQ ID NO:104) or a pharmaceutically acceptable salt thereof, (Ib)

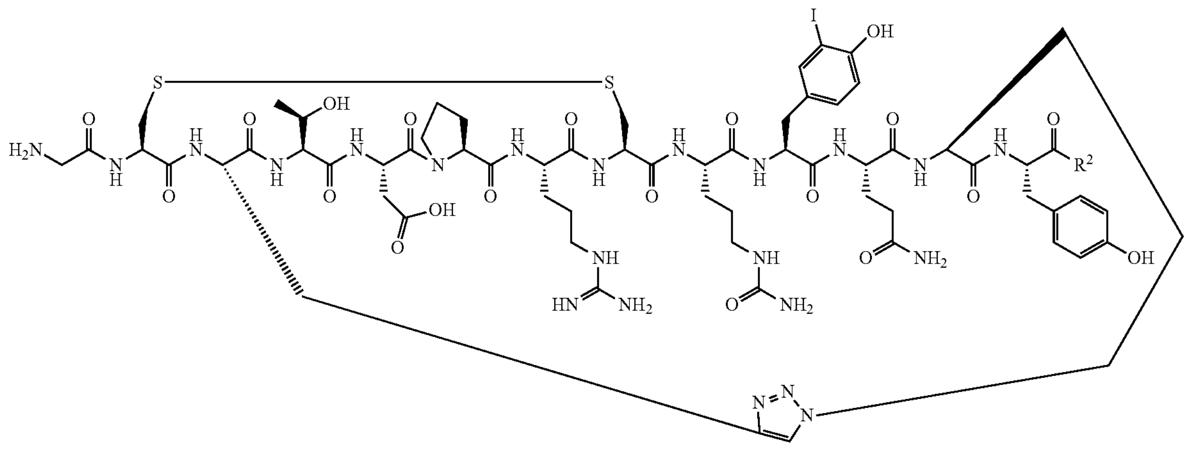

wherein the C-terminus of the conotoxin peptide analog of Formula (Ib) is a carboxylic acid or an amide group, comprising subjecting an intermediate conotoxin peptide analog or a salt thereof to triazole formation conditions, wherein the amino acid sequence of the intermediate conotoxin peptide analog is Gly-Cys-$X_{AA}^3$-Thr-Asp-Pro-Arg-Cys-$X_{AA}^9$-$X_{AA}^{10}$-Gln-$X_{AA}^{12}$-Tyr (SEQ ID NO:107), wherein $X_{AA}^3$ is (S)-propargyl glycine;

$X_{AA}^9$ is Citrulline;

$X_{AA}^{10}$ is 3-iodo-Tyr;

$X_{AA}^{12}$ is (S)-azidonorvaline; and wherein the C-terminus of the intermediate conotoxin peptide analog is as defined above for the conotoxin peptide analog of Formula (Ib); and wherein under said triazole formation conditions $X_{AA}^3$ reacts with $X_{AA}^{12}$ to form a triazole bridge as depicted in the conotoxin peptide analog of Formula (Ib).

In a specific embodiment, the triazole formation conditions are conditions for "Click Chemistry" (i.e., 1,3-dipolar cycloaddition of azides and terminal alkynes) described in Hein et al. Pharm. Res. 2008, 25(10): 2216-2230. In a specific embodiment, the triazole formation conditions include presence of a copper catalyst. In a specific embodiment, the triazole formation conditions include presence of a copper catalyst and a reducing reagent. In one embodiment, the copper catalyst is a Cu(II) salt. In one embodiment, the copper catalyst is $CuSO_4$. In one embodiment, the reducing reagent is L-ascorbic acid. In another embodiment, the reducing reagent is sodium ascorbate. In one embodiment, the triazole formation conditions include presence of a ruthenium catalyst. In one embodiment, the ruthenium catalyst is Cp*RuCl($PPh_3$). In certain embodiments, the triazole formation conditions are catalyst-free conditions.

In a specific embodiment, a salt of the conotoxin peptide analog of Formula (I) or (Ib) can be subjected to salt exchange steps to afford a pharmaceutically acceptable salt. In one embodiment, for example, a TFA salt of a conotoxin peptide analog of Formula (I) reacts with a base in an aqueous solution (pH 7.0-8.0) and then reacts with an appropriate acid to afford a pharmaceutically acceptable salt of the conotoxin peptide analog of Formula (I). In one embodiment, the base is $NH_4HCO_3$ (aq.). In one embodiment, after reaction with a base in an aqueous solution, the conotoxin peptide analog reacts with acetic acid to afford an acetate salt of the conotoxin peptide analog.

5.8.3. PEGylation

The synthesized conotoxin peptide analogs can further be covalently conjugated to one or more polyethylene glycol (PEG) polymers. The conotoxin peptide analogs can, for example, be attached directly or via a linking group to one or more PEG polymers.

In a specific embodiment, provided herein is a method of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is attached directly or via a linking group to the one or more PEG polymers. In one embodiment, the conotoxin peptide analog is the conotoxin peptide analog is of Formula (I) (SEQ ID NO:93):

(I)

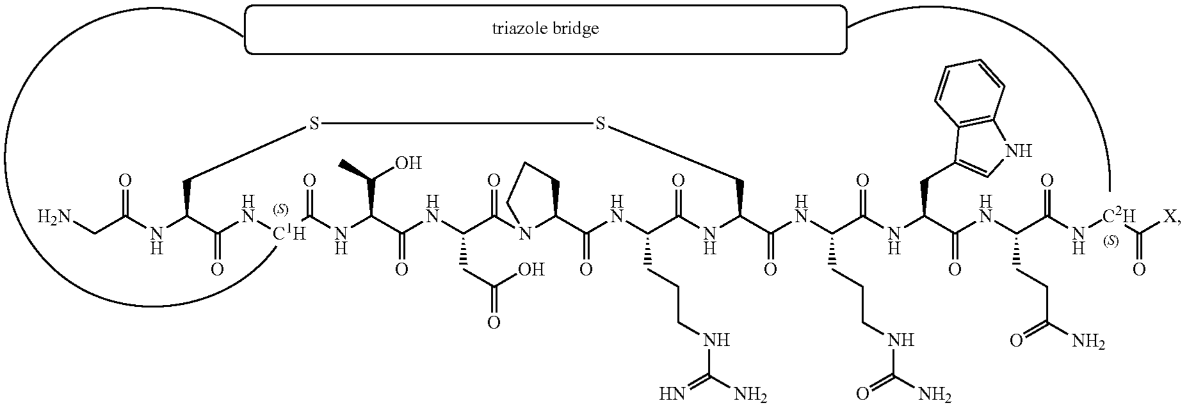

wherein

X is $X_{AA}^1$ or $X_{AA}^1X_{AA}^2$; wherein $X_{AA}^1$ is Tyr, Phe, Trp, or a D-isomer of Tyr, Phe, or Trp, and $X_{AA}^2$ is N-Me-Gly, D-Tyr, or N-Me-Tyr;

wherein the C-terminus of the conotoxin peptide analog is a carboxylic acid or an amide group; and wherein the conotoxin peptide analog is covalently attached directly or via a linking group to one or more polyethylene glycol (PEG) polymers.

In a specific embodiment, provided herein is a method of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is covalently attached directly or via a linking group to the one or more PEG polymers, wherein the conotoxin peptide analog is the conotoxin peptide analog is of Formula (Ib) (SEQ ID NO:104):

(Ib)

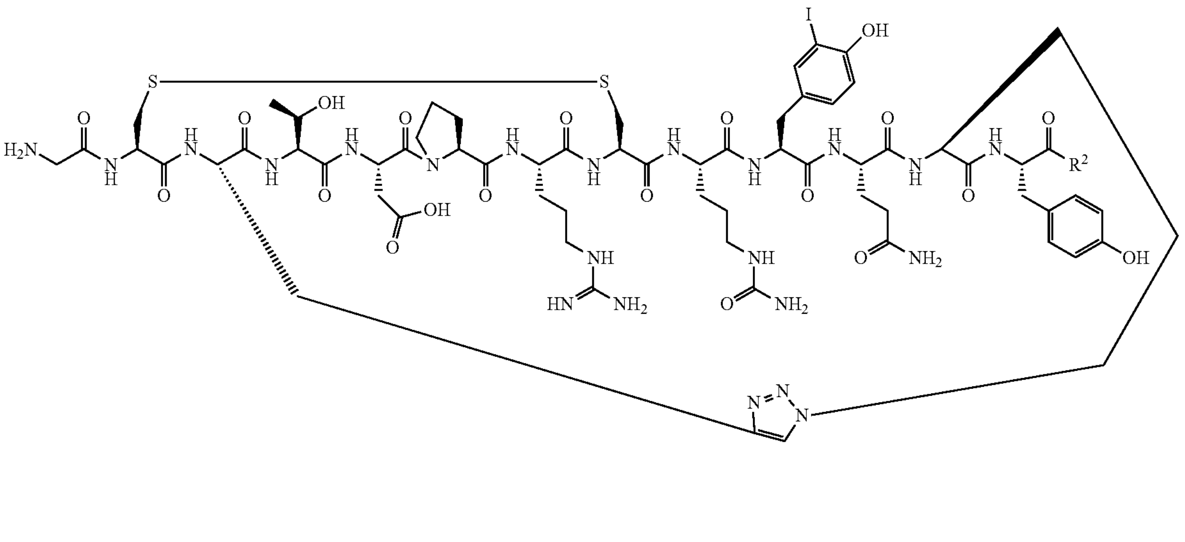
, wherein $R^2$ is OH or $NH_2$.

In a specific embodiment, provided herein is a method of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is covalently attached directly or via a linking group to the one or more PEG polymers, wherein the amino acid sequence of the conotoxin peptide analog is Gly-Cys-$X_{AA}{}^3$-Thr-Asp-Pro-Arg-Cys-$X_{AA}{}^9$-Trp-Gln-$X_{AA}{}^{12}$-X (SEQ ID NO:106), wherein $X_{AA}{}^3$ is selected from the group consisting of (S)-propargyl glycine, (S)-azidoalanine, (S)-homopropargyl glycine, (S)-gamma-azidohomoalanine, (S)-azidonorvaline and (S)-bishomopropargyl glycine;

$X_{AA}{}^9$ is Citrulline;

$X_{AA}12$ is selected from the group consisting of (S)-gamma-azidohomoalanine, (S)-homopropargyl glycine, (S)-azidonorvaline, and (S)-bishomopropargyl glycine;

wherein when $X_{AA}{}^3$ is selected from the group consisting of (S)-propargyl glycine, (S)-homopropargyl glycine, and (S)-bishomopropargyl glycine, $X_{AA}{}^{12}$ is (S)-gamma-azidohomoalanine or (S)-azidonorvaline; when $X_{AA}{}^3$ is selected from the group consisting of (S)-azidoalanine, (S)-gamma-azidohomoalanine, and (S)-azidonorvaline, $X_{AA}{}^{12}$ is (S)-homopropargyl glycine or (S)-bishomopropargyl glycine;

X is $X_{AA}{}^1$ or $X_{AA}{}^1X_{AA}{}^2$; wherein $X_{AA}{}^1$ is Tyr, Phe, Trp, or a D-isomer of Tyr, Phe, or Trp, and $X_{AA}{}^2$ is N-Me-Gly, D-Tyr, or N-Me-Tyr; and wherein the C-terminus of the conotoxin peptide analog is a carboxylic acid or an amide group.

In yet another aspect, provided herein is a method of making a PEGylated conotoxin peptide analog or a pharmaceutically acceptable salt thereof, comprising contacting under reaction conditions a conotoxin peptide analog or a salt thereof, with one or more reactive polyethylene glycol (PEG) polymers to form a PEGylated conotoxin peptide analog, wherein the reactive PEG polymers each comprise a reactive group covalently linked, optionally via a linking group, to a PEG polymer, and wherein each reactive group reacts under the reaction conditions to form a covalent bond with the conotoxin peptide analog whereby the conotoxin peptide analog is covalently attached directly or via a linking group to the one or more PEG polymers, wherein the amino acid sequence of the conotoxin peptide analog is Gly-Cys-$X_{AA}{}^3$-Thr-Asp-Pro-Arg-Cys-$X_{AA}{}^9$-$X_{AA}{}^{10}$-Gln-$X_{AA}{}^{12}$-Tyr (SEQ ID NO:107), wherein $X_{AA}{}^3$ is (S)-propargyl glycine;

$X_{AA}{}^9$ is Citrulline;

$X_{AA}{}^{10}$ is 3-iodo-Tyr;

$X_{AA}{}^{12}$ is (S)-azidonorvaline;

wherein the C-terminus of the conotoxin peptide analog is a carboxylic acid or an amide group.

In a specific embodiment, the reaction conditions are standard PEGylation conditions. In one embodiments, the reaction conditions are conditions are standard amide formation conditions. Certain standard amide formation conditions are described in Valour and Bradley, Chemical Society Reviews, 2009, 38:606-631. In one embodiment, the amide formation conditions include presence of a coupling reagent such as dicyclohexylcarbodiimide (DCC), 1-hydroxy-1H-benzotriazole (HOBt), 1-ethyl-3-(3-dimethylaminopropyl)carbodiimide (EDC), or 1-[Bis(dimethylamino)methylene]-1H-1,2,3-triazolo[4,5-b]pyridinium 3-oxid hexafluorophosphate (HATU). In another embodiment, the reaction conditions are conditions are standard amine formation conditions. In one embodiment, the amine formation conditions are reductive amination conditions.

6. EXAMPLES

The following non-limiting examples disclose preparations and tests of conotoxin peptide analogs of conotoxin RgIA and PEGylated conotoxin peptide analogs of conotoxin RgIA.

It should be understood that the following examples are illustrative and not limiting.

6.1. Example 1: Disulfide Shuffling of RgIA Conotoxin Peptide Analogs CSP-4-OH and CSP-4-NH2

RgIA conotoxin peptide analogs CSP-4-OH and CSP-4-NH2 have an amino acid sequence of Gly-Cys-Cys-Thr-Asp-Pro-Arg-Cys-(Cit)-(3-iodo-Tyr)-Gln-Cys-Tyr; where CSP-4-OH (SEQ ID NO:4) has a carboxylic acid group at the C-terminus and CSP-4-NH2 has an amide group at the C-terminus. CSP-4-desTyr-OH has an amino acid sequence of Gly-Cys-Cys-Thr-Asp-Pro-Arg-Cys-(Cit)-(3-iodo-Tyr)-Gln-Cys (SEQ ID NO:5), with a carboxylic acid at the C-terminus.

When incubated in human and rat plasma and serum, conotoxin peptide analogs CSP-4-OH and CSP-4-NH2 were found to be susceptible to disulfide shuffling. Such disulfide rearrangement resulted in the formation of isomers of the RgIA derivatives that lose activity on the α9α10 nAChR.

The active conformation of CSP-4-NH2 consist of two disulfide bonds, one between Cys2 and Cys8, and a second between Cys3 and Cys12. The Cys2-8, Cys3-12 "native" form of CSP-4-NH2 is active on both the human and rat α9α10 nAChR. Upon exposure to human and rat serum or plasma, a significant portion of the native form of CSP-4-NH2 underwent isomerization into a "ribbon" form, containing alternative disulfide bonds Cys2-Cys12 and Cys3-Cys8 and a "bead" form containing alternative Cys2-Cys3 and Cys8-Cys12 disulfide bonds.

In plasma and serum samples, CSP-4-NH2 principally isomerized between the native and ribbon forms, with very little bead formation (FIG. 1A, B). Neither the ribbon nor bead form were active on the human or rat α9α10 nAChR, suggesting that disulfide shuffling contributes to a reduction in potency of the molecule. Furthermore, the presence of a C-terminal amide in CSP-4-NH2 did not reduce isomerization relative to a C-terminal carboxylic acid in CSP-4-OH. Finally, disulfide isomerization also occurred in vivo following intravenous and subcutaneous injection of a 1 mg/kg dose of compound 6 (CSP-4-NH2) to Sprague Dawley rats. At 1 h following injection, only 40-50% of the recovered peptide from blood remained in the native form by HPLC-MS/MS analysis, indicating that disulfide isomerization occurs in vivo similar to observations in vitro.

Figure 1B:
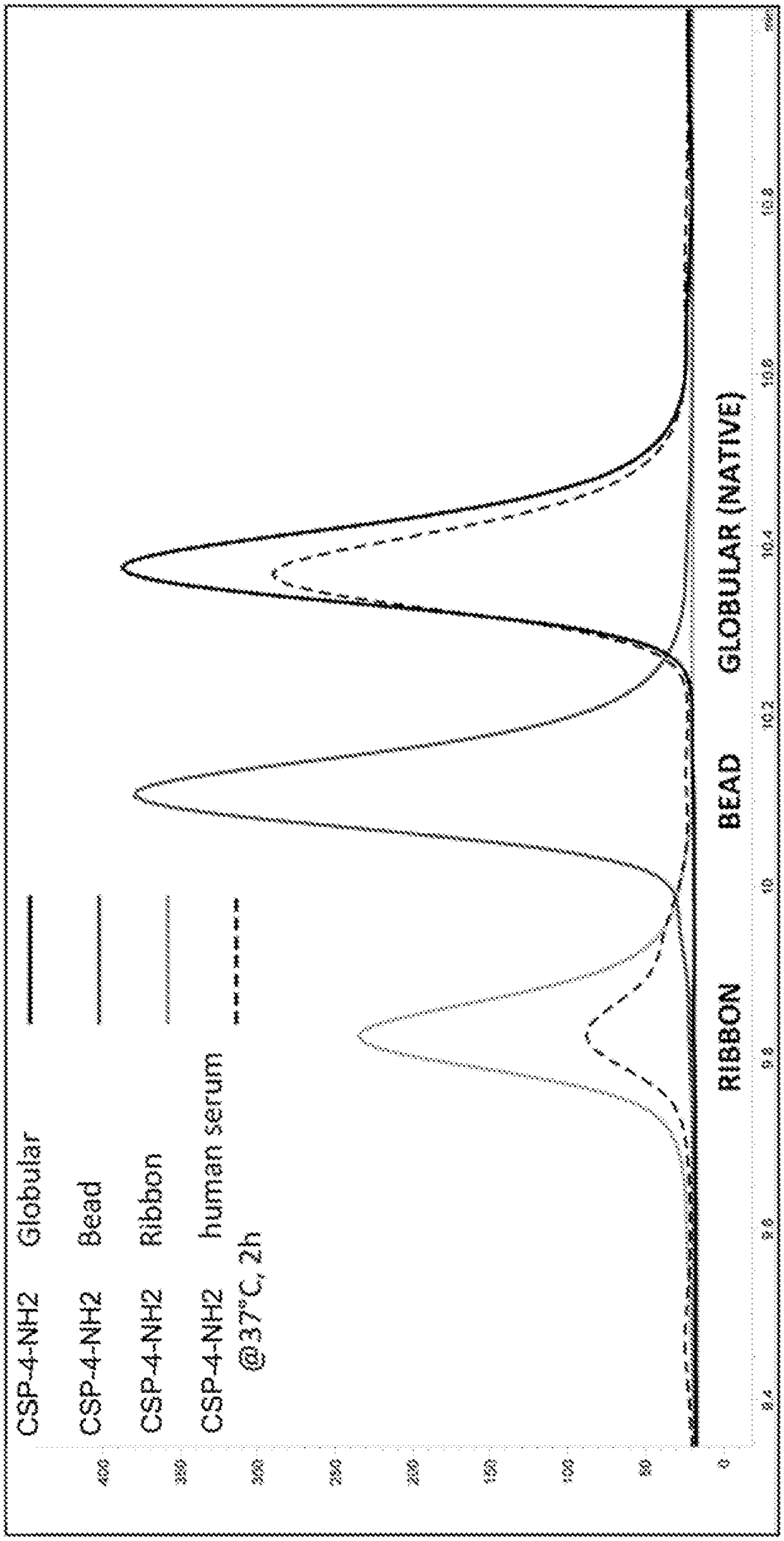
Figure 1D:
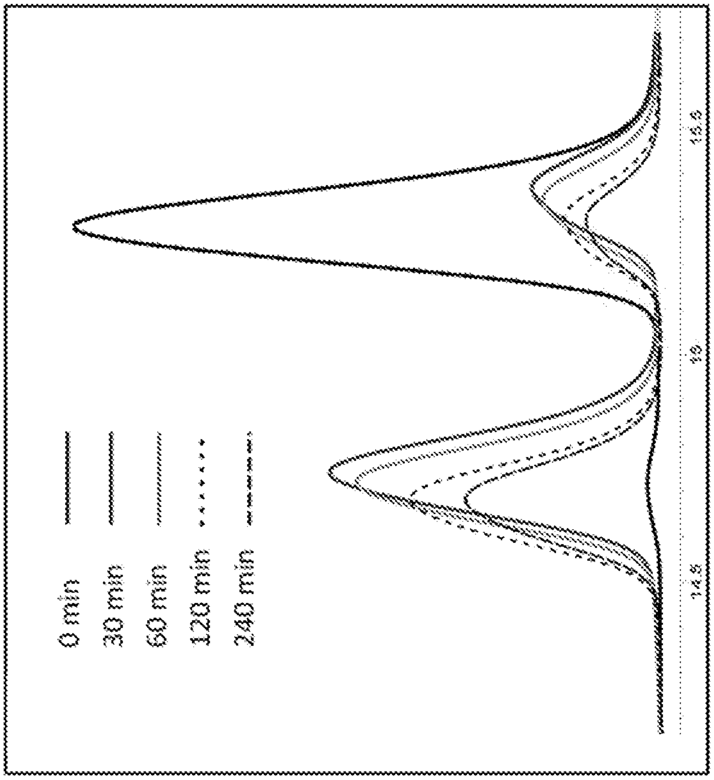

Disulfide shuffling of conotoxin peptide analogs CSP-4-OH and CSP-4-NH2 was demonstrated by incubating the peptides at a final concentration of 0.1-0.5 mg/mL in serum or plasma from Sprague Dawley rat and human in vitro at 37° C. up to 24 h. Plasma samples were treated with anticoagulants including citrate, $K_2EDTA$ and heparin. Samples of the incubations were removed at several timepoints and for each timepoint, the resulting peptide isomers were extracted from the matrix by protein precipitation (3 volumes of methanol) followed by centrifugation of the precipitated sample at 10,000×g through a Millipore Ultrafree-MC GV centrifugal filter. The resulting clarified sample was recovered and 5 μL was injected on an Agilent 1260 Infinity HPLC fitted with a Phenomenex *Aeris* C-18 column (2.1×150 mm, 3.6 μm). Peptides were separated by gradient elution at 0.3 mL/min with 0 to 50% B over 45 min; mobile phase A (19:1:0.01 $H_2O/CH_3CN$/TFA) and mobile phase B ($CH_3CN$ with 0.05% TFA). Under these conditions, the relative retention time of the various isomers of CSP-4-NH2 was as follows: ribbon<bead<native (FIG. 1B).

Treatment of CSP-4-NH2 (40 μg/mL) with a 1:1 mixture of oxidized glutathione and reduced glutathione (10 mM each) for 1 h, followed by treatment (quenching) with 8% formic acid, resulted in formation of the ribbon isomer with the same mass and chromatography retention time as the product observed in serum or plasma, indicating that disulfide isomerization mediated peptide instability in biological matrices (FIG. 10). Glutathione reduction resulted in a mixture of native and ribbon form.

Figure 1C:
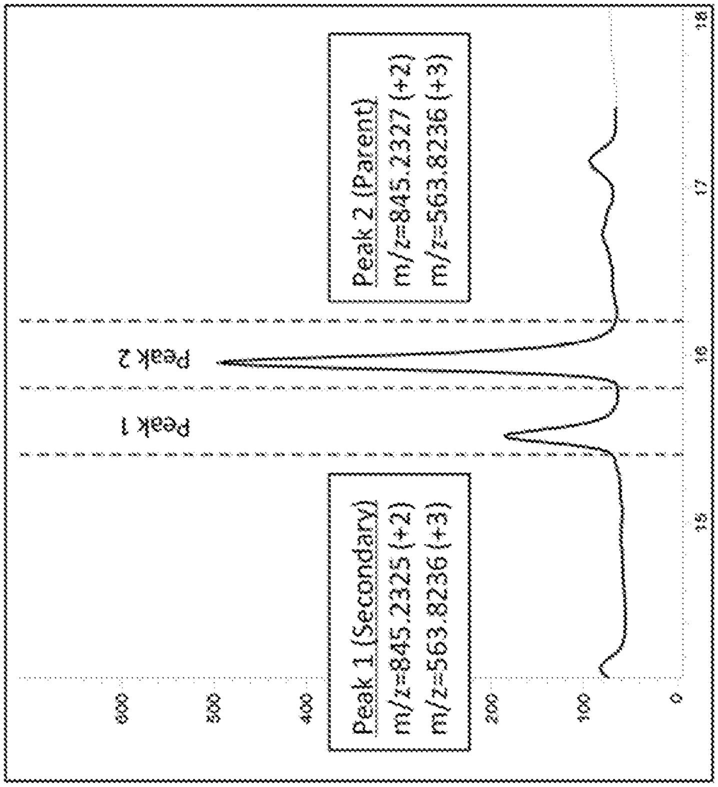

Following the resolution, collection and lyophilization of each HPLC peak as above, the identity of each CSP-4-OH and CSP-4-NH2 isomer was determined using LC-MS analysis on an Orbitrap Elite (FIG. 1C). Aliquots of non-reduced sample were diluted 1:100 in water:acetonitrile: formic acid (98:2:0.1%) to an estimated concentration of 1.2-1.5 pmol/μL. A 10 μL injection was made by an Easy-nLC II HPLC system (Thermo Scientific) onto a 75 μm i.d. PicoTip™ 25 cm long fused silica nano-column (New Objective) coupled to a 2 cm long, 100 μm i.d. IntegraFrit™trap (New Objective). The column and the trap were configured in a vented configuration (Licklider, et al., Analytical Chemistry, 2002, 74, 3076-3082), with the column packed with 5 μm size Magic C18 AQ reverse-phased media (100 Å pore size, Michrom Bioresources, Auburn, Calif.) and the trap packed with the same material (200 Å pore size, Michrom). Samples were resolved on the column using a gradient consisting Mobile Phase A [ultrapure grade water/formic acid (0.1% by volume)] and Mobile Phase B [acetonitrile/formic acid (0.1% by volume)] at a flow rate of 400 nL/min according to the following: beginning with 95% “A” and 5% “B”, 0 to 2 minutes where Mobile Phase “B” is ramped from 5% to 7%, followed by a ramp of 7% “B” to 35% “B” over 60 minutes, followed by a ramp of 35% “B” to 50% “B” over 2 minutes where “B” is held for 1 minute, followed by a ramp of 50% “B” to 90% “B” over 5 minutes and held for 8 minutes, and finally followed by a period where “B” is ramped back down to 5% over 1 minute for re-equilibration to starting conditions. The mass spectrometer was operated in the data dependent mode over the range of 400-1800 m/z. For each cycle of the instrument, the top 3 most abundant ions were selected from a precursor scan (with the orbitrap resolution set at 120 k in the profile mode). MS/MS data were collected in the centroid mode using the same settings as listed above, with the exception that the isolation width was set to 2.0 m/z. The dynamic exclusion settings used were as follows: repeat count of 1, a 15 second count duration, an exclusion list size of 500 and an exclusion duration of 30 seconds. The native and ribbon isomers had the same mass-to-charge ratio as determined using mass spectrometry, indicating that the two HPLC peaks have the same identity (FIG. 1C).

Isolated ribbon isomer of CSP-4-NH2 was found to have no blocking activity on the human α9α10 nAChR. CSP-4-NH2 was incubated in human serum for one hour as described above, followed by preparative HPLC and collection of the peak corresponding to the ribbon isomer. The ribbon isomer was also chemically synthesized with the Cyst-Cys12 and Cys3-Cys8 disulfide connectivity. Chemically synthesized ribbon isomer and isomer isolated following incubation in human serum were tested for activity on the human α9α10 nAChR using two electrode voltage clamp electrophysiology.

The ability of each analog to block acetylcholine-induced α9α10 nAChR currents in *Xenopus* oocytes was measured. As shown in the Table 1, native CSP-4-NH2 at a concentration of 100 nM blocked >99% of ACh-evoked currents, whereas both the chemically synthesized and serum-derived ribbon isomers of CSP-4-NH2 were inactive at concentrations of 0.1-10 μM. As shown in FIGS. 1A and 1B, in plasma and serum samples, conotoxin peptide analog CSP-4-$NH_2$ isomerized between the native and ribbon forms, with very little bead formation.

The reduced activity of the ribbon form on the human or rat α9α10 nAChR suggested that disulfide shuffling contributes to a reduction in potency of the molecule. Furthermore, the presence of a C-terminal amide in CSP-4-NH2 did not reduce isomerization relative to a C-terminal carboxylic acid in CSP-4-OH. Finally, disulfide isomerization also occured in vivo following intravenous and subcutaneous injection of a 1 mg/kg dose of CSP-4-OH to Sprague Dawley rats. At 1 h following injection, only 40-50% of the recovered peptide from blood remains in the native form by HPLC-MS/MS analysis, indicating that disulfide isomerization occurs in vivo similar to observations in vitro.

TABLE 1

Activity of native and ribbon isomers of CSP-4-NH2 on human α9α10 nAChR expressed in *Xenopus* oocytes (Percent of 100 μM acetylcholine-induced current remaining in the presence of compound compared to control response in the absence of compound) human α9α10 nAChRs

| Compound | Oocyte Number | | | | |
|---|---|---|---|---|---|
| (μM) | 1 | 2 | 3 | 4 | Mean ± SEM |
| 0.1 μM native CSP-4-NH2 | 0.4 | 0.21 | 0.59 | | 0.4 ± 0.11 |
| 0.1 μM synthetic ribbon CSP-4-NH2 | 112.25 | 102.48 | | | 107.4 ± 4.9 |
| 10 μM synthetic ribbon CSP-4-NH2 | 95 | 102.48 | 84.56 | 105.07 | 96.8 ± 4.6 |
| 1 μM serum-isolated ribbon CSP-4-NH2 | 130.35 | 98.77 | 101.21 | | 110.1 ± 10.1 |

6.2. Example 2: Preparation of Conotoxin Peptide Analogs

Example 1.1 Conotoxin Peptide Analog Ia (L-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8) disulfide-cyclic $3^3$,$12^5$-(1H-1,2,3-triazole-4,1-diyl)) (SEQ ID NO:6)

(Ia)

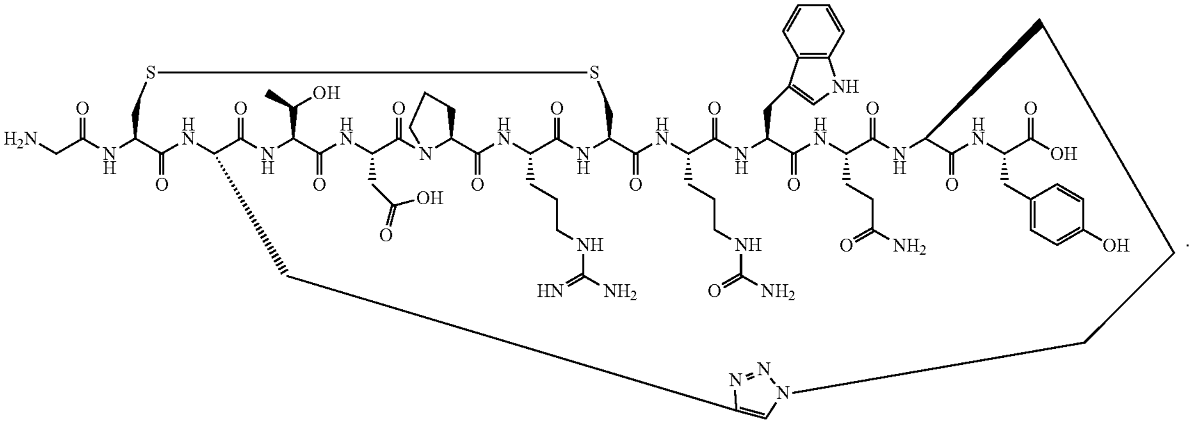

2-Chlorotrityl resin loaded with FMOC-Tyr(OtBu)—OH (1): 2-Chlorotrityl chloride resin (MFCD00040399, 15.0 g, 18 mmol) was added to a reaction vessel and was washed with $CH_2Cl_2$ (100 mL) and then swelled in $CH_2Cl_2$ (100 mL) for 10 min. After draining the reaction vessel, a solution of FMOC-Tyr(OtBu)—OH (2.5 g, 5.4 mmol) in $CH_2Cl_2$ (150 mL) was added, followed by dropwise addition of DIPEA (1.8 mL, 10.8 mmol). The reaction vessel was then shaken at room temperature for 1.5 h. The solvent was drained from the resin, which was subsequently washed with DMF (6×100 mL), followed by MeOH (2×100 mL) and finally $Et_2O$ (2×100 mL). The resin was dried under vacuum for 2 h and the FMOC loading test indicated that peptide loading was 0.29 mmol/g.

Solid phase peptide synthesis (SPPS) of peptide sequence FMOC-Gly-Cys(Trt)-Pra-Thr(tBu)-Asp(OtBu)-Pro-Arg (Pbf)-Cys(Trt)-Cit-Trp(Boc)-Gln(Trt)-5-azido-NVa-Tyr (tBu)-O-(2-Chlorotrityl) on polystyrene support (2): The FMOC-Tyr(OtBu)-loaded 2-chlorotrityl resin (1, 17.3 g, 5 mmol) was washed with DMF (100 ml) and then drained completely. The FMOC group was removed from the tethered Tyr group by treatment with 1:4 piperidine/DMF (2×100 mL, 15 min each), and then the resin was washed with DMF (6×100 mL). Then, HATU (3.80 g, 10 mmol), HOAt (1.35 g, 10 mmol), and DIPEA (2.5 mL, 15 mmol) were added with FMOC-5-azido-Nva-OH (CAS #1097192-04-5, 3.80 g, 10 mmol) in DMF (100 mL). The reaction vessel was shaken for a minimum of 2.5 h, followed by washing with DMF (6×100 mL). Reaction completeness was determined by the Ninhydrin test. If negative (colorless), the coupling was considered complete and the synthesis was continued. If positive (blue), a second equivalent of the same FMOC-amino acid (10 mmol) in DMF (100 mL) was coupled using the resin and HATU/HOAt (10 mmol/10 mmol) as described above. Once the Ninhydrin test indicated the reaction was complete, the FMOC was removed from each of the sequentially added amino acid, followed by coupling of the subsequent FMOC-amino acid-OH in the peptide sequence as described above. This was successively carried out in the following order with FMOC-Gln(Trt)-OH (CAS #132327-80-1, 6.1 g, 10 mmol), FMOC-Trp(Boc)-OH (CAS #143824-78-6, 5.2 g, 10 mmol), FMOC-Cit-OH (CAS #133174-15-9, 3.9 g, 10 mmol), FMOC-Cys(Trt)-OH (CAS #103213-32-7, 5.8 g, 10 mmol), FMOC-Arg(Pbf)-OH (CAS #154445-77-9, 6.4 g, 10 mmol), FMOC-Pro-OH (CAS #71989-31-6, 3.3 g, 10 mmol), FMOC-Asp(OtBu)—OH (CAS #71989-14-5, 4.1 g, 10 mmol), FMOC-Thr(tBu)—OH (CAS #71989-35-0, 3.9 g, 10 mmol), FMOC-Pra-OH (CAS #198561-07-8, 3.3 g, 10 mmol), FMOC-Cys(Trt)-OH (5.8 g, 10 mmol), and FMOC-Gly-OH (CAS #29022-11-5, 2.9 g, 10 mmol). After the linear peptide couplings were complete, the resin was washed with DMF (100 mL×6), followed by MeOH (100 mL×2) and finally $Et_2O$ (100 mL×2), and then dried under vacuum for 2 h.

Resin cleavage of amino acid sequence H-Gly-Cys-Pra-Thr-Asp-Pro-Arg-Cys-Cit-Trp-Gln-S-azidoNVa-Tyr-OH (3) (SEQ ID NO:7): To the dry resin (2, 28.0 g, 5.0 mmol) in a flask was added 230 mL of cleavage solution (TFA/EDT/Thioanisole/Anisole: 90:3:5:2) and the mixture was shaken for 2 h at room temperature. After this time, the resin was filtered and washed with TFA (2×50 mL). The filtrates were combined, and 10-fold volume of cold (0° C.) $Et_2O$ was added, which resulted in precipitation of the peptide. The precipitated peptide was centrifuged at 5,000 rpm for 10 min and washed with cold (0° C.) $Et_2O$ (3×50 mL). The crude product was dried under vacuum for 2 h to obtain 3 (6.8 g, 4.2 mmol, 84%), which was used without further purification for the next step.

Cysteine disulfide bridge formation to produce H-Gly-Cys-Pra-Thr-Asp-Pro-Arg-Cys-Cit-Trp-Gln-5-azidoNva-Tyr-OH, (Cys2→Cys8) disulfide bridge (4) (SEQ ID NO:8): Peptide 3 (2.0 g, 1.2 mmol) was dissolved in $CH_3CN$ (100 mL), DMSO (100 mL) and $H_2O$ (1800 mL). Then $H_2O_2$ (30% in $H_2O$, 0.25 mL) was added dropwise and the mixture was stirred at room temperature for 1.5 h. After this time, the mixture was filtered, and the filtrate was purified by HPLC Method J to afford 800 mg of the title compound 4 as a white solid (yield: 38%, TFA salt). LC-MS (ESI) m/z: 540.7 $[M+3H]/3^+$, 810.3 $[M+2H]/2^+$, Purity 95% (214 nm). The remaining 4.8 g of 3 was distributed into two batches and oxidized and purified as described to obtain a total of 2.5 g of 4 (overall yield: 35%).

1,3-Dipolar cyclization/Click reaction (triazole bridge formation) to produce conotoxin peptide analog Ia: Peptide 4 (400 mg, 0.25 mmol) was dissolved in iPrOH (100 mL) and $H_2O$ (300 mL). Then a solution of $CuSO_4$ (157 mg, 1 mmol) in $H_2O$ (2 mL) was added, followed by the dropwise addition of L-ascorbic acid (176 mg, 1 mmol) in $H_2O$ (2 mL). The mixture was stirred at room temperature for 2 h. Then, the solution was loaded directly onto a flash column (e.g. Biotage® SNAP Ultra C18, 120 g) and eluted with water (0.1% TFA) and $CH_3CN$. The eluate fractions containing conotoxin peptide analog Ia were combined and lyophilized to obtain 305 mg of the TFA salt of conotoxin peptide analog Ia as a white solid (305 mg, TFA salt, yield: 69%). LC-MS (ESI) m/z: 540.7 $[M+3H]/3^+$, 810.3 $[M+2H]/2^+$, Purity 90% (214 nm). The remaining 2.1 g of 4 was distributed into three batches and each was treated with the conditions described above, affording 1.7 g of the title conotoxin peptide analog Ia (overall combined yield: 61%, TFA salt).

The obtained TFA salt of conotoxin peptide analog Ia (1.0 g) was dissolved in $H_2O$ (20 mL) and $CH_3CN$ (2 mL). Then a 20 mM solution of $NH_4HCO_3$ (aq.) was added drop wise to adjust the pH 7.0-8.0. The mixture was then purified using HPLC method H. Product containing fractions were lyophilized to give the acetate salt of conotoxin peptide analog Ia a white solid (650 mg, acetate salt, overall yield: 62%). The remaining 700 mg of conotoxin peptide analog Ia-TFA salt was purified and converted to the acetate salt in same manner to afford 350 mg (48%, acetate salt). The overall combined amount obtained was 1.0 g acetate salt of conotoxin peptide analog Ia (56%). LC-MS (ESI-TOF) m/z: 540.2 $[M+3H]/3^+$, 810.0 $[M+2H]/2^+$, 1617.66 $[M+H]/^+$; HPLC method A; retention time: 10.1 min; purity 95.7%.

The synthesis of Conotoxin Peptide Analog Ia is illustration in Scheme 1.

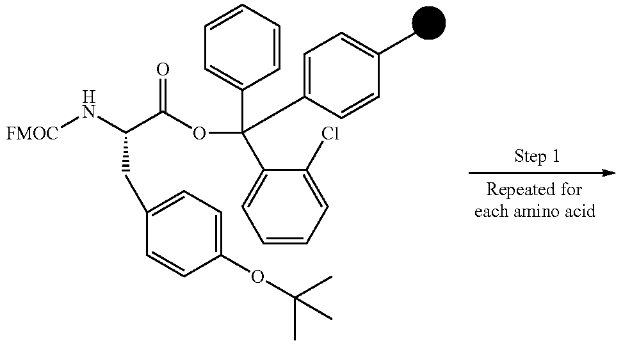

1

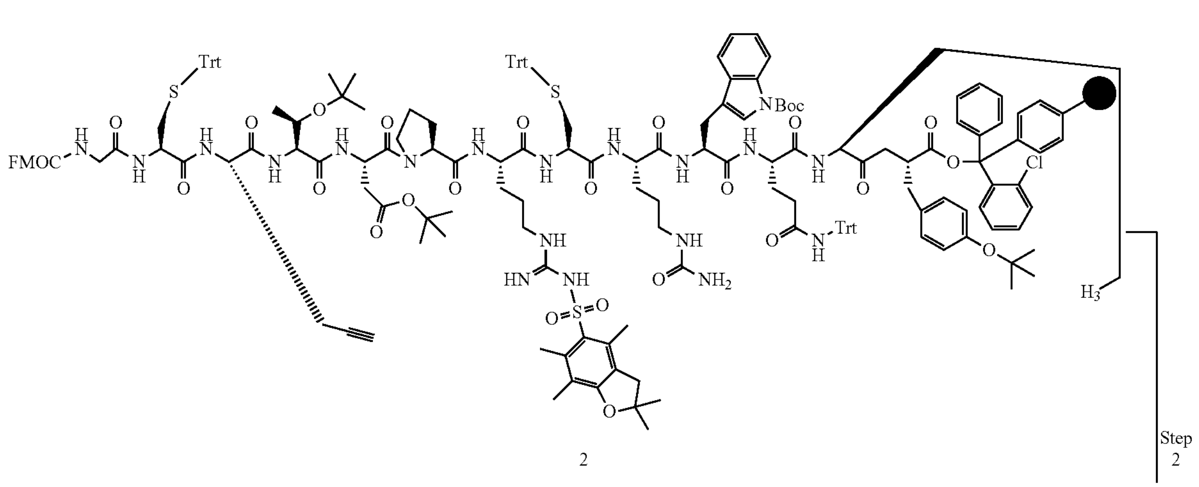

2

-continued
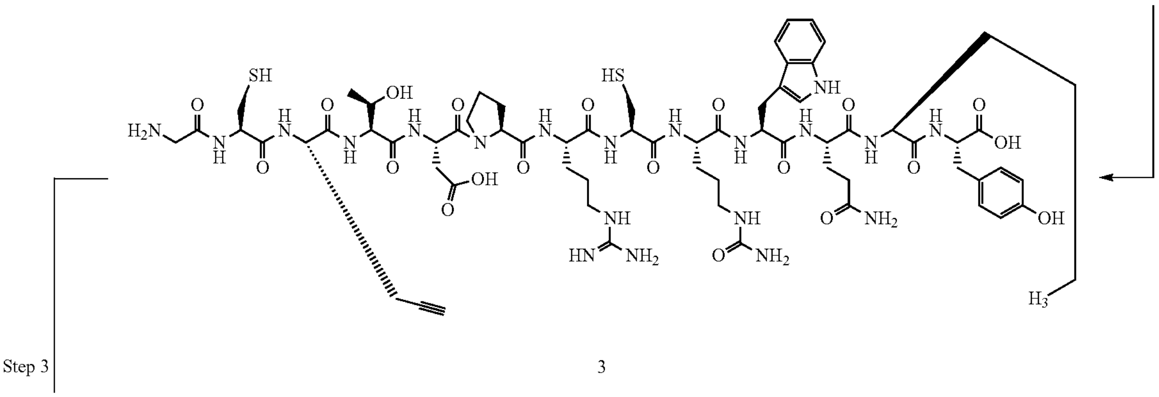
Step 3
3
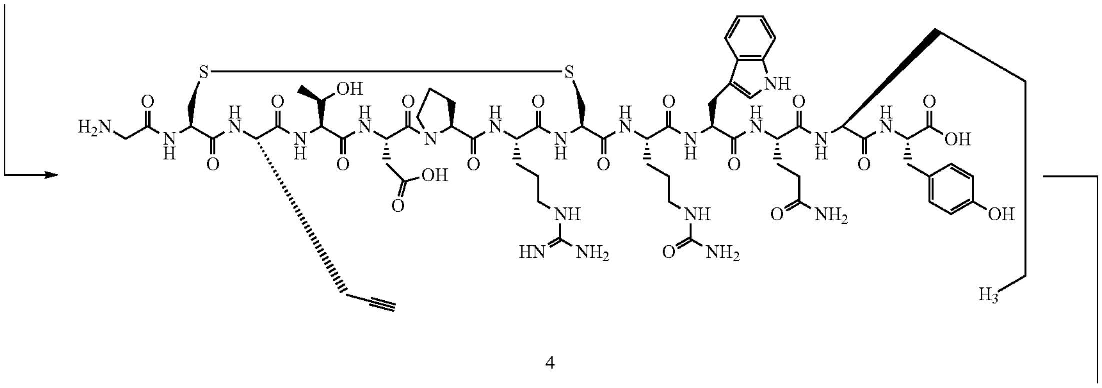
4
Step 4
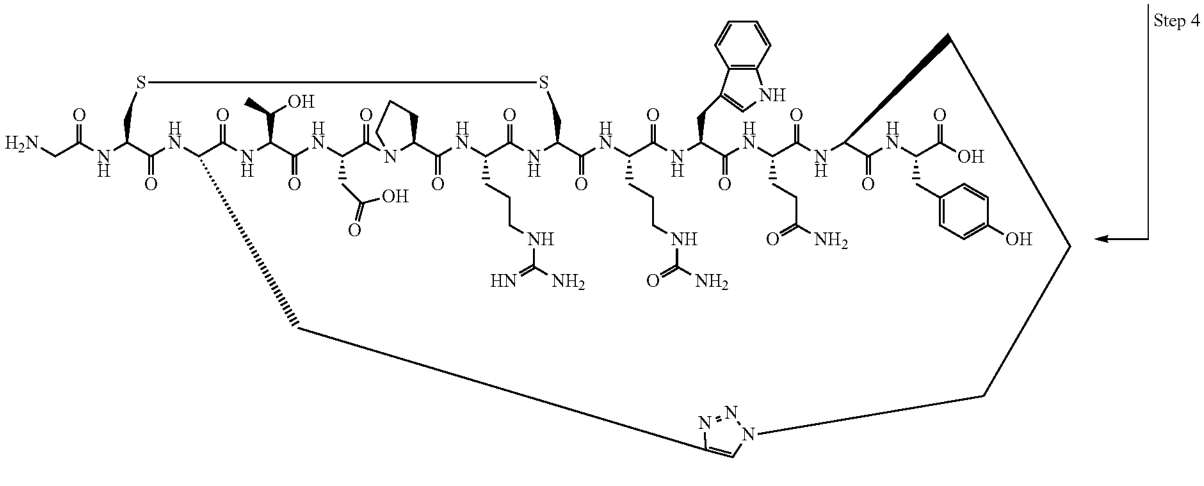
15

Example 1.2 Conotoxin Peptide Analog Ia' (L-tyrosinamide, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^3$,$12^5$-(1H-1,2,3-triazole-4,1-diyl)) (SEQ ID NO:9)

(Ia')

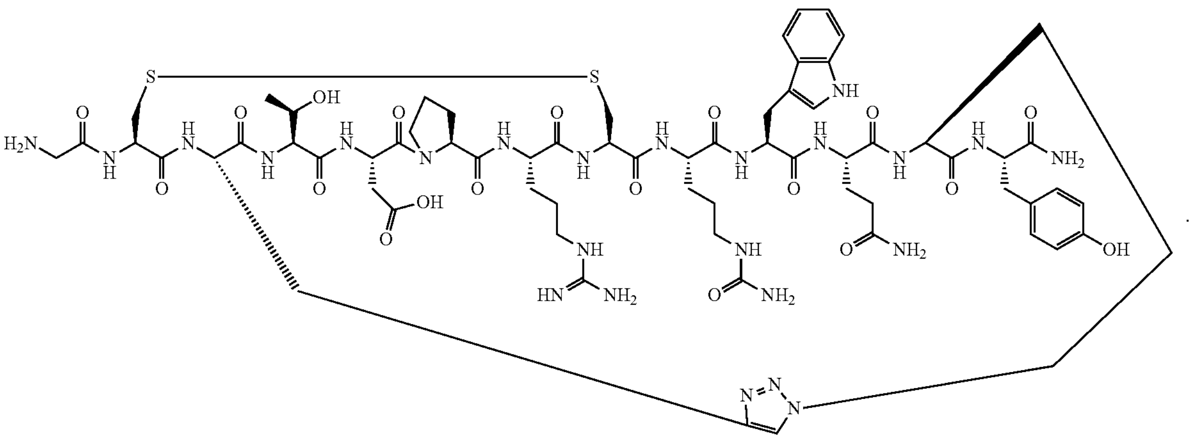

Intermediate conotoxin peptide analog Ya' (H-Gly-Cys-Pra-Thr-Asp-Pro-Arg-Cys-Cit-Trp-Gln-5-azidoNVa-Tyr-NH2) (SEQ ID NO:10): Intermediate conotoxin peptide analog Ya' was synthesized by employing the same procedure described for compound 3 using a Rink Amide resin MFCD00677976 in lieu of 2-Chlorotrityl chloride resin MFCD00040399.

Intermediate conotoxin peptide analog Za' (H-Gly-Cys-Pra-Thr-Asp-Pro-Arg-Cys-Cit-Trp-Gln-5-azidoNVa-Tyr-NH2, (Cys2→Cys8) disulfide bridge) (SEQ ID NO:11): Intermediate conotoxin peptide analog Za' was synthesized by employing the same procedure described for compound 4 using intermediate conotoxin peptide analog Ya' in lieu of compound 3.

Conotoxin peptide analog Ia' was synthesized by employing the same procedure described for Conotoxin peptide analog Ia using intermediate conotoxin peptide analog Za' in lieu of compound 4. LC-MS (single quad ESI) m/z: 1617.5 $(M+1H)^{+}$ (calculated MW: 1616.5); HPLC method E; retention time: 14.0 min; purity 96.9%.

Example 1.3 Conotoxin Peptide Analog Ib (L-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-3-iodotyrosyl-L-glutaminyl-L-norvalyl-cyclic (2→8)-disulfide-cyclic $3^3$,$12^5$-(1H-1,2,3-triazole-4,1-diyl)) (SEQ ID NO:12)

(Ib)

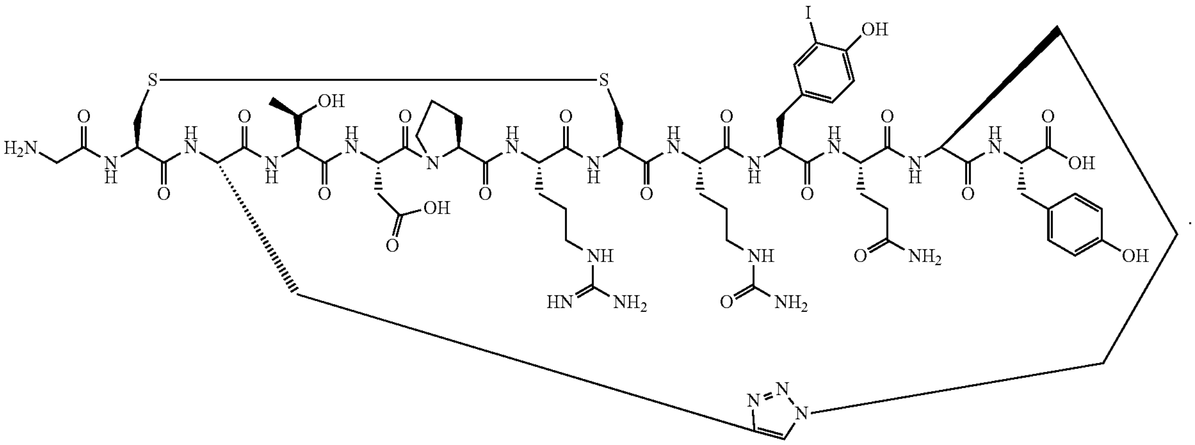

Intermediate conotoxin peptide analog Yb (H-Gly-Cys-Pra-Thr-Asp-Pro-Arg-Cys-Cit-3-I-Tyr-Gln-5-azidoNVa-Tyr-OH) (SEQ ID NO:13): Intermediate conotoxin peptide analog Yb was synthesized by employing the same procedure described for compound 3 using FMOC-3-I-Tyr-OH in lieu of FMOC-Trp(Boc)-OH in the peptide synthesis of the 10-position residue.

Intermediate conotoxin peptide analog Zb (H-Gly-Cys-Pra-Thr-Asp-Pro-Arg-Cys-Cit-3-I-Tyr-Gln-5-azidoNVa-Tyr-OH, (Cys2→Cys8) disulfide bridge) (SEQ ID NO:14): Intermediate conotoxin peptide analog Zb was synthesized by employing the same procedure described for compound 4 using intermediate conotoxin peptide analog Yb in lieu of compound 3.

Conotoxin peptide analog Ib was synthesized by employing the same procedure described for conotoxin peptide analog Ia using intermediate conotoxin peptide analog Zb in lieu of compound 4. LC-MS (ESI-TOF) m/z: 574.7 [M+3H]/$3^+$, 861.5 [M+2H]/$2^+$ (calculated MW: 1720.54); HPLC method C; retention time: 11.7 min; purity 94.8%.

Example 1.4 Conotoxin Peptide Analog Ib' (L-tyrosinamide, glycyl-L-cysteinyl-L-alanyl-L-threonyl-L-α-aspartyl-L-prolyl-L-arginyl-L-cysteinyl-N5-(aminocarbonyl)-L-ornithyl-L-3-iodotyrosyl-L-glutaminyl-L-norvalyl-cyclic (2→8)-disulfide-cyclic $3^3$,$12^5$-(1H-1,2,3-triazole-4,1-diyl)) (SEQ ID NO:15)

Intermediate conotoxin peptide analog Yb' (H-Gly-Cys-Pra-Thr-Asp-Pro-Arg-Cys-Cit-3-I-Tyr-Gln-5-azidoNVa-Tyr-NH2) (SEQ ID NO:16): Intermediate conotoxin peptide analog Yb' was synthesized by employing the same procedure described for intermediate conotoxin peptide analog Yb using a Rink Amide resin MFCD00677976 in lieu of 2-Chlorotrityl chloride resin MFCD00040399 in the solid phase peptide sythesis.

Intermediate conotoxin peptide analog Zb' (H-Gly-Cys-Pra-Thr-Asp-Pro-Arg-Cys-Cit-3-I-Tyr-Gln-5-azidoNVa-Tyr-NH2, (Cys2→Cys8) disulfide bridge) (SEQ ID NO:17): Intermediate conotoxin peptide analog Zb' was synthesized by employing the same procedure described for compound 4 using intermediate conotoxin peptide analog Yb' in lieu of compound 3.

Conotoxin peptide analog Ib' was synthesized by employing the same procedure described for conotoxin peptide analog Ia using intermediate conotoxin peptide analog Zb' in lieu of compound 4. LC-MS (ESI-TOF) m/z: 574.2 [M+3H]/$3^+$, 860.8 [M+2H]/$2^+$ (calculated MW: 1719.55); HPLC method B; retention time: 10.5 min; purity 93.8%.

(Ib')

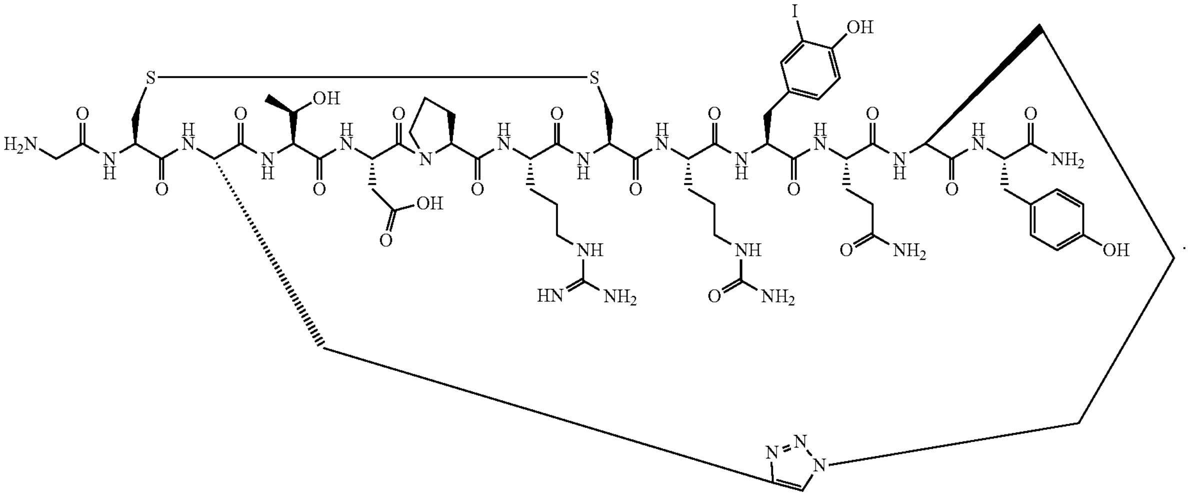

Example 1.5 Conotoxin Peptide Analog Ic (L-tyrosinamide, glycyl-L-alanyl-L-cysteinyl-L-threonyl-L-α-aspartyl-L-prolyl-L-arginyl-L-norvalyl-N5-(aminocarbonyl)-L-ornithyl-L-3-iodotyrosyl-L-glutaminyl-L-cysteinyl-cyclic $2^3,8^5$-(1H-1,2,3-triazole-4,1-diyl)-cyclic-(3→12)-disulfide) (SEQ ID NO:18)

(Ic)

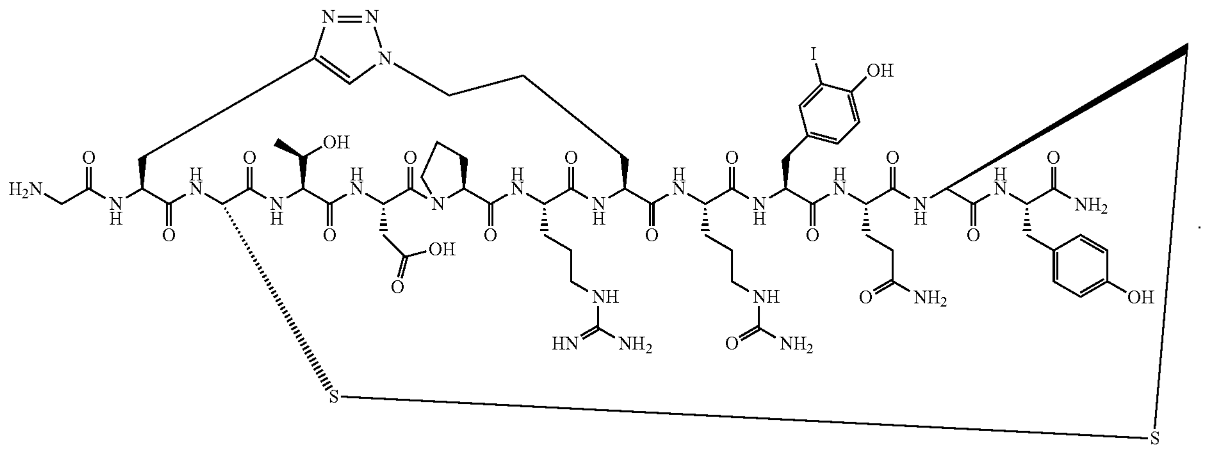

Intermediate conotoxin peptide analog Yc (H-Gly-Pra-Cys-Thr-Asp-Pro-Arg-5-azidoNVa-Cit-3-I-Tyr-Gln-Cys-Tyr-NH2) (SEQ ID NO:19): Intermediate conotoxin peptide analog Yc was synthesized by employing the same procedure described for intermediate conotoxin peptide analog Yb' using FMOC-Cys(Trt)-OH in lieu of FMOC-5-azido-Nva-OH (the 12-position residue), FMOC-5-azido-Nva-OH in lieu of FMOC-Cys(Trt)-OH (the 8-position residue), FMOC-Cys(Trt)-OH in lieu of FMOC-Pra-OH (the 3-position residue), and FMOC-Pra-OH in lieu of FMOC-Cys (Trt)-OH (the 2-position residue) in the solid phase peptide synthesis.

Intermediate conotoxin peptide analog Zc (H-Gly-Pra-Cys-Thr-Asp-Pro-Arg-5-azidoNVa-Cit-3-I-Tyr-Gln-Cys-Tyr-NH2, (Cys3→Cys12) disulfide bridge) (SEQ ID NO:20): Intermediate conotoxin peptide analog Zc was synthesized by employing the same procedure described for compound 4 using intermediate conotoxin peptide analog Yc in lieu of compound 3.

Conotoxin peptide analog Ic was synthesized by employing the same procedure described for conotoxin peptide analog Ib' using intermediate conotoxin peptide analog Zc in lieu of Intermediate conotoxin peptide analog Zb'. LC-MS (ESI-TOF) m/z: 574.2 $[M+3H]/3^+$, 860.7 $[M+2H]/2^+$ (calculated MW: 1719.55); HPLC method B; retention time: 10.2 min; Purity 98.3%.

Example 1.6 Conotoxin Peptide Analog Id (L-tyrosinamide, glycyl-L-norvalyl-L-cysteinyl-L-threonyl-L-α-aspartyl-L-prolyl-L-arginyl-L-alanyl-N5-(aminocarbonyl)-L-ornithyl-L-3-iodotyrosyl-L-glutaminyl-L-cysteinyl-cyclic $2^5,8^3$-(1H-1,2,3-triazole-1,4-diyl)-cyclic-(3→12)-disulfide) (SEQ ID NO:21)

(Id)

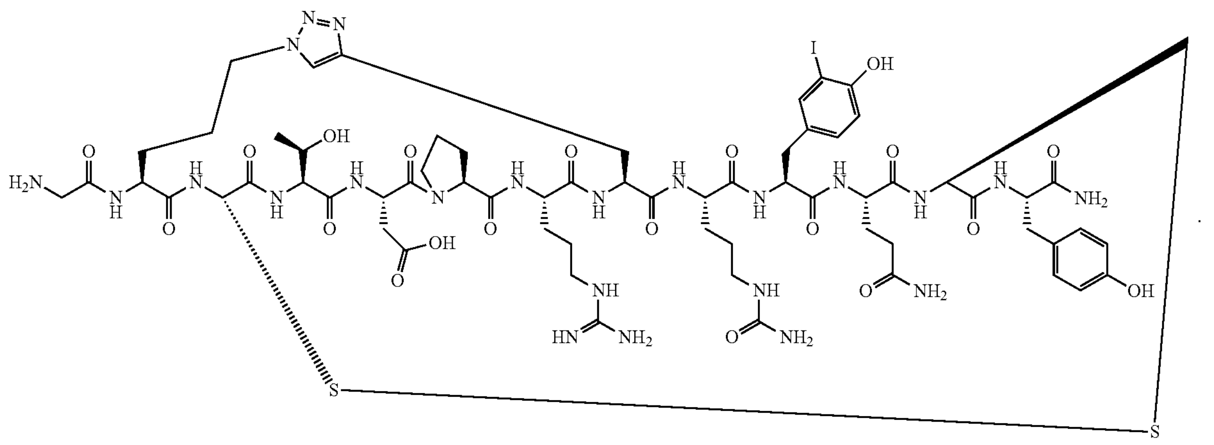

Intermediate conotoxin peptide analog Yd (H-Gly-5-azidoNVa-Cys-Thr-Asp-Pro-Arg-Pra-Cit-3-I-Tyr-Gln-Cys-Tyr-NH2) (SEQ ID NO:22): Intermediate conotoxin peptide analog Yd was synthesized by employing the same procedure described for intermediate conotoxin peptide analog Yb' using FMOC-Cys(Trt)-OH in lieu of FMOC-5-azido-Nva-OH (the 12-position residue), FMOC-Pra-OH in lieu of FMOC-Cys(Trt)-OH (the 8-position residue), FMOC-Cys (Trt)-OH in lieu of FMOC-Pra-OH (the 3-position residue), and FMOC-5-azido-Nva-OH in lieu of FMOC-Cys(Trt)-OH (the 2-position residue) in the solid phase peptide synthesis.

Intermediate conotoxin peptide analog Zd (H-Gly-5-azidoNVa-Cys-Thr-Asp-Pro-Arg-Pra-Cit-3-I-Tyr-Gln-Cys-Tyr-NH2, (Cys3→Cys12) disulfide bridge) (SEQ ID NO:23): Intermediate conotoxin peptide analog Zd was synthesized by employing the same procedure described for intermediate conotoxin peptide analog Zb' using intermediate conotoxin peptide analog Yd in lieu of intermediate conotoxin peptide analog Yb'.

Conotoxin peptide analog Id was synthesized by employing the same procedure described for conotoxin peptide analog Ib' using intermediate conotoxin peptide analog Zd in lieu of intermediate conotoxin peptide analog Zb'. LC-MS (ESI-TOF) m/z: 860.7 $[M+2H]/2^{+}$ (calculated MW: 1719.55); HPLC method B; retention time: 10.2 min; purity 99.2%.

Example 1.7 Conotoxin Peptide Analog Ie (L-tyrosinamide, glycyl-L-cysteinyl-L-norvalyl-L-threonyl-L-α-aspartyl-L-prolyl-L-arginyl-L-cysteinyl-N5-(aminocarbonyl)-L-ornithyl-L-3-iodotyrosyl-L-glutaminyl-L-alanyl-cyclic (2→8)-disulfide-cyclic $3^5,12^3$-(1H-1,2,3-triazole-1,4-diyl)) (SEQ ID NO:24)

Intermediate conotoxin peptide analog Ye (H-Gly-Cys-5-azidoNVa-Thr-Asp-Pro-Arg-Cys-Cit-3-I-Tyr-Gln-Pra-Tyr-NH2) (SEQ ID NO:25): Intermediate conotoxin peptide analog Ye was synthesized by employing the same procedure described for intermediate conotoxin peptide analog Yb' using FMOC-Pra-OH in lieu of FMOC-5-azido-Nva-OH (the 12-position residue) and FMOC-5-azido-Nva-OH in lieu of FMOC-Pra-OH (the 3-position residue) in the solid phase peptide synthesis.

Intermediate conotoxin peptide analog Ze (H-Gly-Cys-5-azidoNVa-Thr-Asp-Pro-Arg-Cys-Cit-3-I-Tyr-Gln-Pra-Tyr-NH2, (Cys2→Cys8) disulfide bridge) (SEQ ID NO:26): Intermediate conotoxin peptide analog Ze was synthesized by employing the same procedure described for intermediate conotoxin peptide analog Zb' using intermediate conotoxin peptide analog Ye in lieu of intermediate conotoxin peptide analog Yb'.

Conotoxin peptide analog Ie was synthesized by employing the same procedure described for conotoxin peptide analog Ib' using intermediate conotoxin peptide analog Ze in lieu of intermediate conotoxin peptide analog Zb'. LC-MS (ESI-TOF) m/z: 574.4 $[M+3H]/3^{+}$, 861.1 $[M+2H]/2^{+}$ (calculated MW: 1719.55); HPLC method C; retention time: 12.6 min; purity 92.1%.

(Ie)

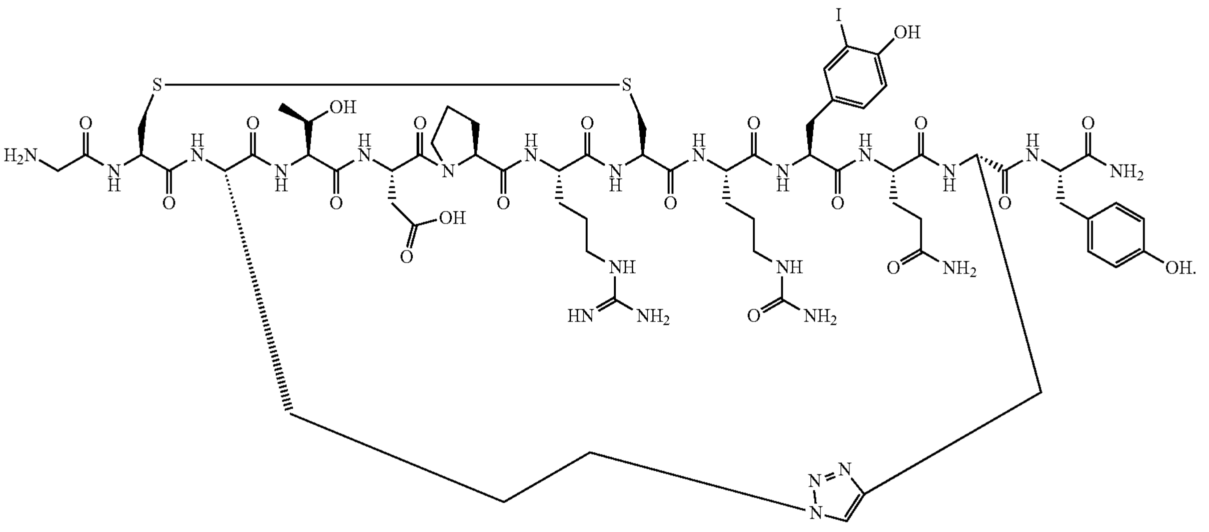

Example 1.8 Conotoxin Peptide Analog If (L-tyrosinamide, glycyl-L-cysteinyl-L-alanyl-L-threonyl-L-α-aspartyl-L-prolyl-L-arginyl-L-cysteinyl-N5-(aminocarbonyl)-L-ornithyl-L-3-iodotyrosyl-L-glutaminyl-L-alanyl-cyclic (2→8)-disulfide-cyclic $3^3$,$12^3$-(1H-1,2,3-triazole-4,1-diyl)) (SEQ ID NO:27)

Intermediate conotoxin peptide analog Zf was synthesized by employing the same procedure described for intermediate conotoxin peptide analog Zb' using intermediate conotoxin peptide analog Yf in lieu of intermediate conotoxin peptide analog Yb'.

Conotoxin peptide analog If was synthesized by employing the same procedure described for conotoxin peptide analog Ib' using intermediate conotoxin peptide analog Zf in (If)

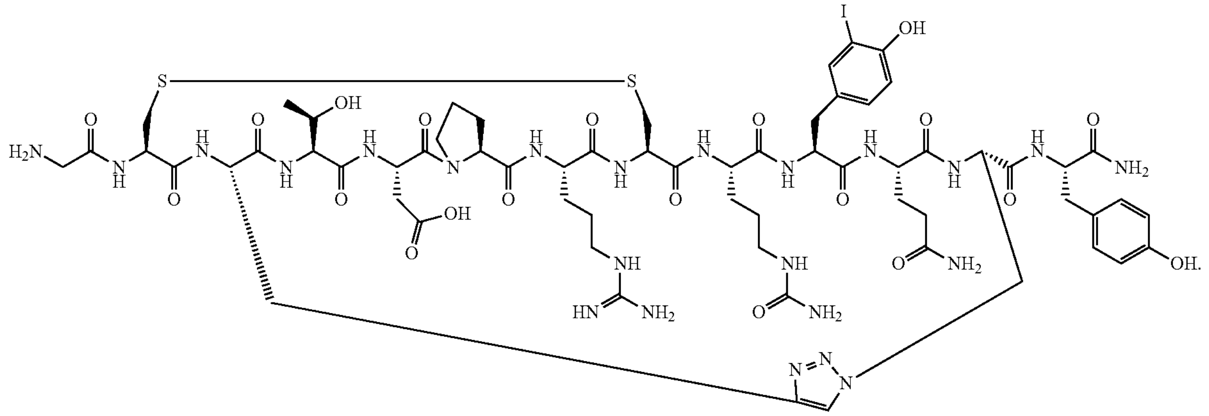

Intermediate conotoxin peptide analog Yf (H-Gly-Cys-Pra-Thr-Asp-Pro-Arg-Cys-Cit-3-I-Tyr-Gln-3-azidoAla-Tyr-NH2) (SEQ ID NO:28): Intermediate conotoxin peptide analog Yf was synthesized by employing the same procedure described for intermediate conotoxin peptide analog Yb' using FMOC-3-azido-Ala-OH in lieu of FMOC-Pra-OH (the 12-position residue) and FMOC-Pra-OH in lieu of FMOC-5-azido-Nva-OH (the 3-position residue) in the solid phase peptide synthesis.

Intermediate conotoxin peptide analog Zf (H-Gly-Cys-Pra-Thr-Asp-Pro-Arg-Cys-Cit-3-I-Tyr-Gln-3-azidoAla-Tyr-NH2, (Cys2→Cys8) disulfide bridge) (SEQ ID NO:29):

lieu of intermediate conotoxin peptide analog Zb'. LC-MS (ESI-TOF) m/z: 847.1 $[M+2H]/2^+$; $[M+1H]/^+$ (calculated MW: 1691.52); HPLC method E; retention time: 12.3 min; purity 94.6%.

Example 1.9 Conotoxin Peptide Analog Ig (L-tyrosine, glycyl-L-cysteinyl-(2S)-2-aminobutanoyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^4$,$12^5$-(1H-1,2,3-triazole-4,1-diyl)) (SEQ ID NO:30)

(Ig)

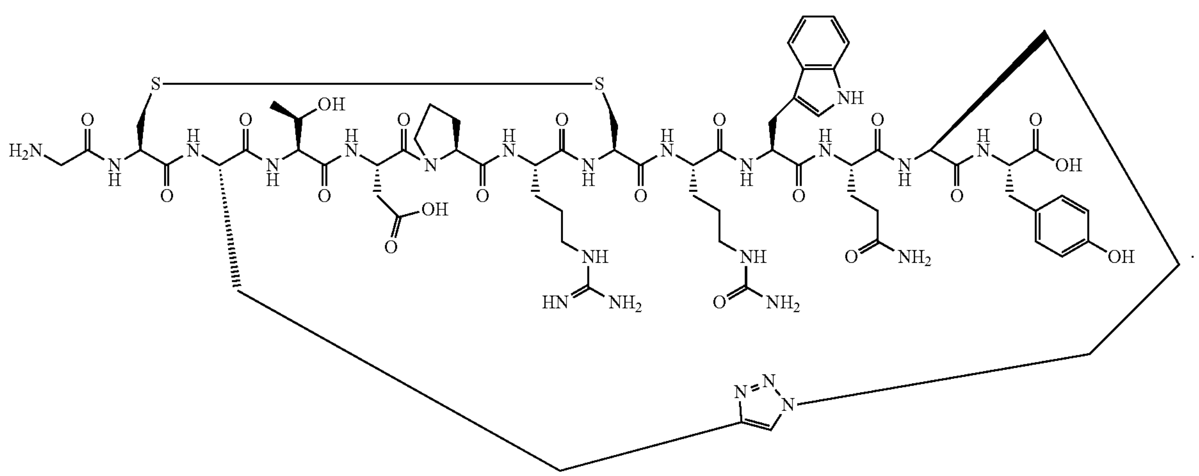

Intermediate conotoxin peptide analog Yg (H-Gly-Cys-homoPra-Thr-Asp-Pro-Arg-Cys-Cit-Trp-Gln-5-azidoNva-Tyr-OH) (SEQ ID NO:31): Intermediate conotoxin peptide analog Yg was synthesized by employing the same procedure described for compound 3 using FMOC-homopropargyl glycine in lieu of FMOC-Pra-OH (the 3-position residue) in the solid phase peptide synthesis.

Intermediate conotoxin peptide analog Zg (H-Gly-Cys-homoPra-Thr-Asp-Pro-Arg-Cys-Cit-Trp-Gln-5-azidoNva-Tyr-OH, (Cys2→Cys8) disulfide bridge) (SEQ ID NO:32): Intermediate conotoxin peptide analog Zg was synthesized by employing the same procedure described for compound 4 using intermediate conotoxin peptide analog Yg in lieu of compound 3.

Conotoxin peptide analog Ig was synthesized by employing the same procedure described for conotoxin peptide analog Ia using intermediate conotoxin peptide analog Zg in lieu of compound 4. LC-MS (single quad ESI) m/z: 545.0 $[M+3H]/3^+$, 817.3 $[M+2H]/2^+$ (calculated MW: 1631.67); HPLC method A; retention time: 12.5 min; purity 98.2%.

Example 1.10 Conotoxin Peptide Analog Ih (L-tyrosine, glycyl-L-cysteinyl-(2S)-2-aminobutanoyl-L-threonyl-L-α-aspartyl-L-prolyl-L-arginyl-L-cysteinyl-N5-(aminocarbonyl)-L-ornithyl-L-tryptophyl-L-glutaminyl-L-(2S)-2-aminobutanoyl-cyclic (2→8)-disulfide-cyclic $3^4,12^4$-(1H-1,2,3-triazole-4,1-diyl)) (SEQ ID NO:33)

Intermediate conotoxin peptide analog Yh (H-Gly-Cys-homoPra-Thr-Asp-Pro-Arg-Cys-Cit-Trp-Gln-gamma-azidohomoAla-Tyr-OH) (SEQ ID NO:34): Intermediate conotoxin peptide analog Yh was synthesized by employing the same procedure described for compound 3 using FMOC-homopropargyl glycine in lieu of FMOC-Pra-OH (the 3-position residue) and FMOC-γ-azido-homoalanine in lieu of FMOC-5-azido-Nva-OH (the 12-position residue) in the solid phase peptide synthesis.

Intermediate conotoxin peptide analog Zh (H-Gly-Cys-homoPra-Thr-Asp-Pro-Arg-Cys-Cit-Trp-Gln-gamma-azidohomoAla-Tyr-OH, (Cys2→Cys8) disulfide bridge) (SEQ ID NO:35): Intermediate conotoxin peptide analog Zh was synthesized by employing the same procedure described for compound 4 using intermediate conotoxin peptide analog Yh in lieu of compound 3.

Conotoxin peptide analog Ih was synthesized by employing the same procedure described for conotoxin peptide analog Ia using intermediate conotoxin peptide analog Zh in lieu of compound 4. LC-MS (single quad ESI) m/z: 540.6 $[M+3H]/3^+$, 809.9 $[M+2H]/2^+$ (calculated MW: 1617.66); HPLC method A; retention time: 12.4 min; purity 83.9%.

(Ih)

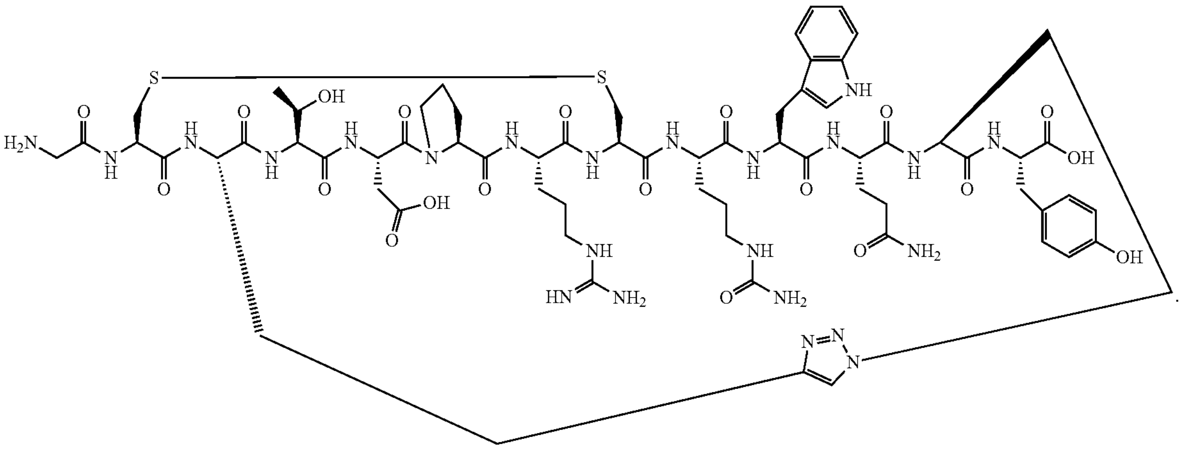

Example 1.11 Conotoxin Peptide Analog Ii (L-tyrosine, glycyl-L-cysteinyl-(2S)-2-aminobutanoyl-L-threonyl-L-α-aspartyl-L-prolyl-L-arginyl-L-cysteinyl-N5-(aminocarbonyl)-L-ornithyl-L-tryptophyl-L-glutaminyl-L-(2S)-2-aminobutanoyl-cyclic (2→8)-disulfide-cyclic $3^4$,$12^4$-(1H-1,2,3-triazole-1,4-diyl)) (SEQ ID NO:36)

(Ii)

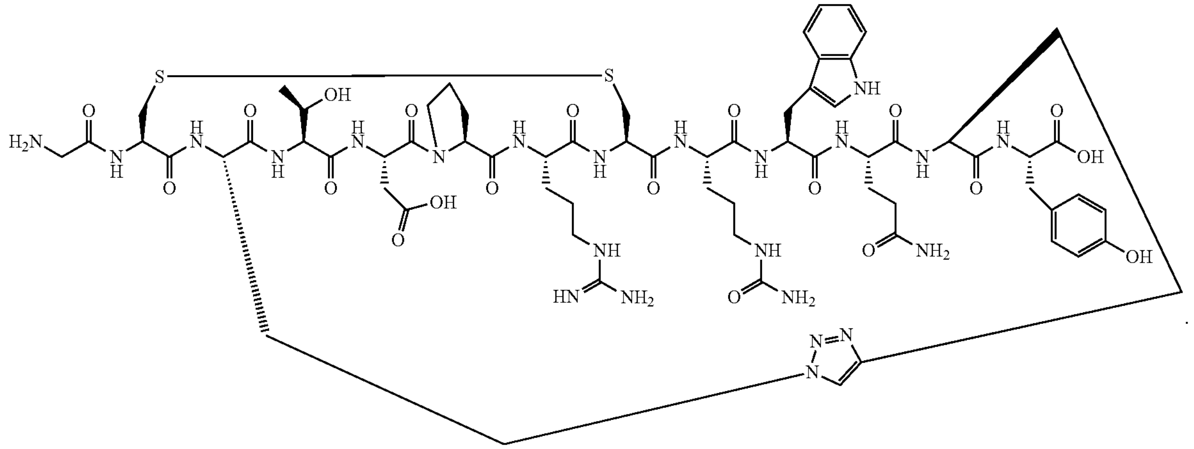

Intermediate conotoxin peptide analog Yi (H-Gly-Cys-gamma-azidohomoAla-Thr-Asp-Pro-Arg-Cys-Cit-Trp-Gln-homoPra-Tyr-OH) (SEQ ID NO:37): Intermediate conotoxin peptide analog Yi was synthesized by employing the same procedure described for compound 3 using FMOC-γ-azido-homoalanine in lieu of FMOC-Pra-OH (the 3-position residue) and FMOC-homopropargyl glycine in lieu of FMOC-5-azido-Nva-OH (the 12-position residue) in the solid phase peptide synthesis.

Intermediate conotoxin peptide analog Zi (H-Gly-Cys-gamma-azidohomoAla-Thr-Asp-Pro-Arg-Cys-Cit-Trp-Gln-homoPra-Tyr-OH, (Cys2→Cys8) disulfide bridge) (SEQ ID NO:38): Intermediate conotoxin peptide analog Zi was synthesized by employing the same procedure described for compound 4 using intermediate conotoxin peptide analog Yi in lieu of compound 3.

Conotoxin peptide analog Ii was synthesized by employing the same procedure described for conotoxin peptide analog Ia using intermediate conotoxin peptide analog Zi in lieu of compound 4. LC-MS (single quad ESI) m/z: 540.7 $[M+3H]/3^+$, 810.5 $[M+2H]/2^+$ (calculated MW: 1617.66); HPLC method A; retention time: 12.3 min; purity 85.8%.

Example 1.12 Conotoxin Peptide Analog Ij (L-tyrosine, glycyl-L-cysteinyl-(2S)-2-aminopentanoyl-L-alanyl-L-threonyl-L-α-aspartyl-L-prolyl-L-arginyl-L-cysteinyl-N5-(aminocarbonyl)-L-ornithyl-L-3-iodotyrosyl-L-glutaminyl-L-alanyl-cyclic (2→8)-disulfide-cyclic $3^5$,$12^3$-(1H-1,2,3-triazole-4,1-diyl)) (SEQ ID NO:39)

(Ij)

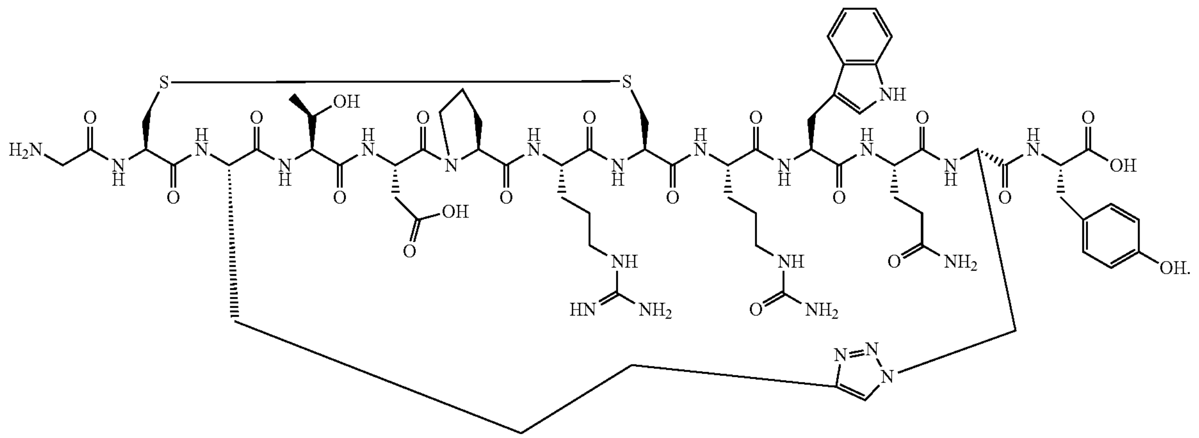

Intermediate conotoxin peptide analog Yj (H-Gly-Cys-bishomoPra-Thr-Asp-Pro-Arg-Cys-Cit-Trp-Gln-3-azidoAla-Tyr-OH) (SEQ ID NO:40): Intermediate conotoxin peptide analog Yj was synthesized by employing the same procedure described for compound 3 using FMOC-bis-homopropargyl glycine in lieu of FMOC-Pra-OH (the 3-position residue) and FMOC-3-azido-Ala-OH in lieu of FMOC-5-azido-Nva-OH (the 12-position residue) in the solid phase peptide synthesis.

Intermediate conotoxin peptide analog Zj (H-Gly-Cys-bishomoPra-Thr-Asp-Pro-Arg-Cys-Cit-Trp-Gln-3-azidoAla-Tyr-OH, (Cys2→Cys8) disulfide bridge) (SEQ ID NO:41): Intermediate conotoxin peptide analog Zj was synthesized by employing the same procedure described for compound 4 using intermediate conotoxin peptide analog Yj in lieu of compound 3.

Conotoxin peptide analog Ij was synthesized by employing the same procedure described for conotoxin peptide analog Ia using intermediate conotoxin peptide analog Zj in lieu of compound 4. LC-MS (single quad ESI) m/z: 540.5 $[M+3H]/3^+$, 810.1 $[M+2H]/2^+$ (calculated MW: 1617.66); HPLC method A; retention time: 12.04 min; purity 97.6%.

Example 1.13 Conotoxin Peptide Analog Ik (L-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-(2S)-2-aminopentanoyl-cyclic (2→8)-disulfide-cyclic $3^3,12^5$-(1H-1,2,3-triazole-1,4-diyl)) (SEQ ID NO:42)

Intermediate conotoxin peptide analog Yk (H-Gly-Cys-3-azidoAla-Thr-Asp-Pro-Arg-Cys-Cit-Trp-Gln-bishomoPra-Tyr-OH) (SEQ ID NO:43): Intermediate conotoxin peptide analog Yk was synthesized by employing the same procedure described for compound 3 using FMOC-3-azido-Ala-OH in lieu of FMOC-Pra-OH (the 3-position residue) and FMOC-bis-homopropargyl glycine in lieu of FMOC-5-azido-Nva-OH (the 12-position residue) in the solid phase peptide synthesis.

Intermediate conotoxin peptide analog Zk (H-Gly-Cys-3-azidoAla-Thr-Asp-Pro-Arg-Cys-Cit-Trp-Gln-bishomoPra-Tyr-OH, (Cys2→Cys8) disulfide bridge) (SEQ ID NO:44): Intermediate conotoxin peptide analog Zk was synthesized by employing the same procedure described for compound 4 using intermediate conotoxin peptide analog Yk in lieu of compound 3.

Conotoxin peptide analog Ik was synthesized by employing the same procedure described for conotoxin peptide analog Ia using intermediate conotoxin peptide analog Zk in lieu of compound 4. LC-MS (single quad ESI) m/z: 540.6 $[M+3H]/3^+$, 810.0 $[M+2H]/2^+$ (calculated MW: 1617.66); HPLC method A; retention time: 12.24 min; purity 97.6%.

(Ik)

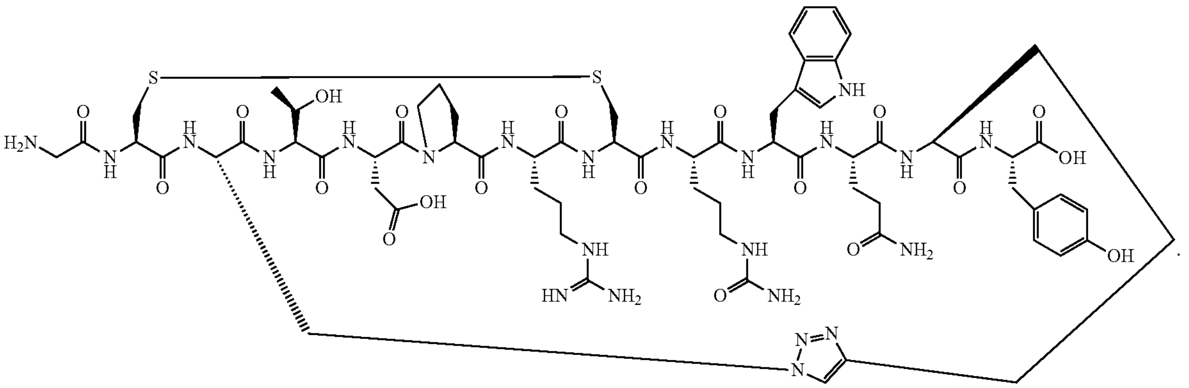

Example 1.14 Conotoxin Peptide Analog Il (L-phenylalanine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^3$,$12^5$-(1H-1,2,3-triazole-4,1-diyl)) (SEQ ID NO:45)

employing the same procedure described for compound 4 using intermediate conotoxin peptide analog Yl in lieu of compound 3.

Conotoxin peptide analog Il was synthesized by employing the same procedure described for conotoxin peptide analog Ia using intermediate conotoxin peptide analog Zl in lieu of compound 4. LC-MS (single quad ESI) m/z: 535.2 $[M+3H]/3^+$, 802.2 $[M+2H]/2^+$ (calculated MW: 1601.66); HPLC method A; retention time: 13.47 min; purity 95.6%.

(Il)

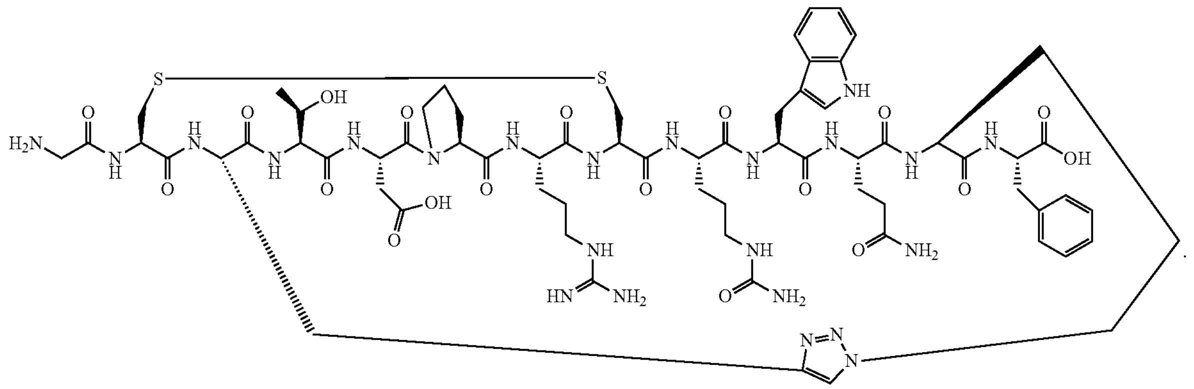

2-Chlorotrityl resin loaded FMOC-Phe(OtBu)—OH (5): 2-Chlorotrityl resin loaded FMOC-Phe(OtBu)—OH was synthesized by employing the same procedure described for 2-Chlorotrityl resin 1 using FMOC-Phe(OtBu)—OH in lieu of FMOC-Tyr(OtBu)—OH.

Intermediate conotoxin peptide analog Yl (H-Gly-Cys-Pra-Thr-Asp-Pro-Arg-Cys-Cit-Trp-Gln-5-azidoNVa-Phe-OH) (SEQ ID NO:46): Intermediate conotoxin peptide analog Yl was synthesized by employing the same procedure described for compound 3 using FMOC-Phe(OtBu)—OH-loaded 2-chlorotrityl resin (5) in lieu of the FMOC-Tyr(OtBu)-loaded 2-chlorotrityl resin (1) as the C-terminus start in the solid phase peptide synthesis.

Intermediate conotoxin peptide analog Zl (H-Gly-Cys-Pra-Thr-Asp-Pro-Arg-Cys-Cit-Trp-Gln-5-azidoNVa-Phe-OH, (Cys2→Cys8) disulfide bridge) (SEQ ID NO:47): Intermediate conotoxin peptide analog Zl was synthesized by Example 1.15 Conotoxin Peptide Analog Im (D-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^3$,$12^5$-(1H-1,2,3-triazole-4,1-diyl)) (SEQ ID NO:48)

(Im)

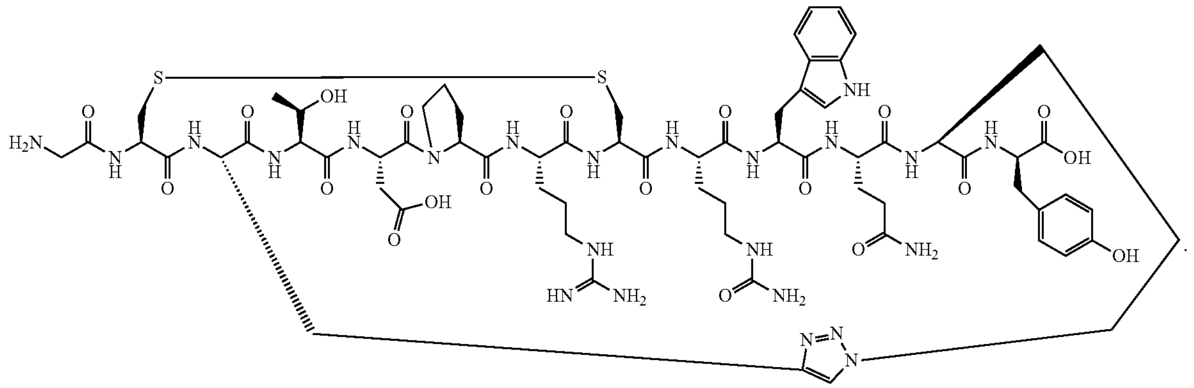

2-Chlorotrityl resin loaded FMOC-D-Tyr(OtBu)—OH (6): 2-Chlorotrityl resin loaded FMOC-D-Tyr(OtBu)—OH was synthesized by employing the same procedure described for 2-Chlorotrityl resin 1 using FMOC-D-Tyr(OtBu)—OH in lieu of FMOC-Tyr(OtBu)—OH.

Intermediate conotoxin peptide analog Ym (H-Gly-Cys-Pra-Thr-Asp-Pro-Arg-Cys-Cit-Trp-Gln-5-azidoNVa-D-Tyr-OH) (SEQ ID NO:49): Intermediate conotoxin peptide analog Ym was synthesized by employing the same procedure described for compound 3 using FMOC-D-Tyr(OtBu)—OH-loaded 2-chlorotrityl resin (6) in lieu of the FMOC-Tyr (OtBu)-loaded 2-chlorotrityl resin (1) as the C-terminus start in the solid phase peptide synthesis.

Intermediate conotoxin peptide analog Zm (H-Gly-Cys-Pra-Thr-Asp-Pro-Arg-Cys-Cit-Trp-Gln-5-azidoNVa-D-Tyr-OH, (Cys2→Cys8) disulfide bridge) (SEQ ID NO:50): Intermediate conotoxin peptide analog Zm was synthesized by employing the same procedure described for compound 4 using intermediate conotoxin peptide analog Ym in lieu of compound 3.

Conotoxin peptide analog Im was synthesized by employing the same procedure described for conotoxin peptide analog Ia using intermediate conotoxin peptide analog Zm in lieu of compound 4. LC-MS (single quad ESI) m/z: 540.6 $[M+3H]/3^+$, 810.0 $[M+2H]/2^+$ (calculated MW: 1617.66); HPLC method A; retention time: 12.07 min; purity 86.6%.

Example 1.16 Conotoxin Peptide Analog In (glycine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-L-tyrosyl-N-methyl-cyclic (2→8)-disulfide-cyclic $3^3,12^5$-(1H-1,2,3-triazole-4,1-diyl)) (SEQ ID NO:51)

(In)

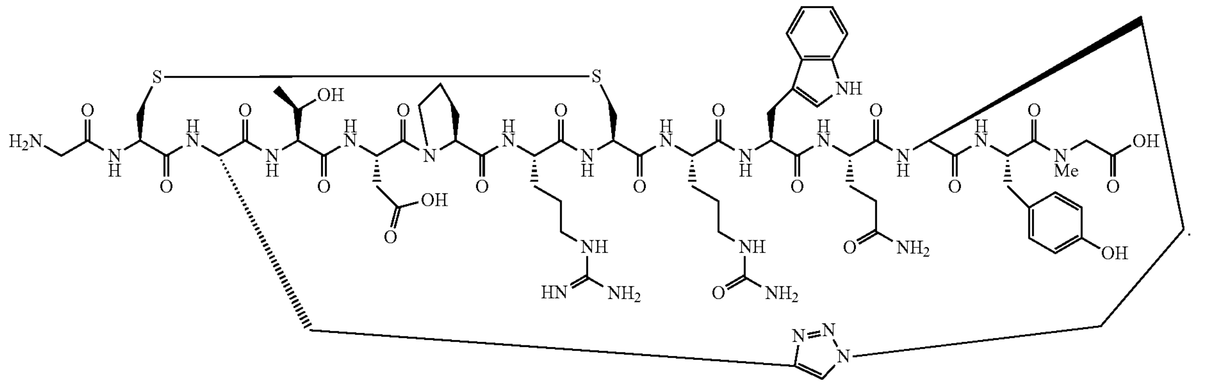

2-Chlorotrityl resin loaded FMOC—N-Me-Gly-OH (7): 2-Chlorotrityl resin loaded FMOC—N-Me-Gly-OH was synthesized by employing the same procedure described for 2-Chlorotrityl resin 1 using FMOC—N-Me-Gly-OH in lieu of FMOC-Tyr(OtBu)—OH.

Intermediate conotoxin peptide analog Yn (H-Gly-Cys-Pra-Thr-Asp-Pro-Arg-Cys-Cit-Trp-Gln-5-azidoNVa-Tyr-N-Me-Gly-OH) (SEQ ID NO:52): Intermediate conotoxin peptide analog Yn was synthesized by employing the same procedure described for compound 3 using FMOC—N-Me-Gly-OH-loaded 2-chlorotrityl resin (7) to sequentially add amino acid, carried out in the following order with FMOC-Tyr(OtBu)—OH, FMOC-5-azido-Nva-OH, FMOC-Gln (Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zn (H-Gly-Cys-Pra-Thr-Asp-Pro-Arg-Cys-Cit-Trp-Gln-5-azidoNVa-Tyr-N-Me-Gly-OH, (Cys2→Cys8) disulfide bridge) (SEQ ID NO:53): Intermediate conotoxin peptide analog Zn was synthesized by employing the same procedure described for compound 4 using intermediate conotoxin peptide analog Yn in lieu of compound 3.

Conotoxin peptide analog In was synthesized by employing the same procedure described for conotoxin peptide analog Ia using intermediate conotoxin peptide analog Zn in lieu of compound 4. LC-MS (single quad ESI) m/z: 564.2 $[M+3H]/3^+$, 846.0 $[M+2H]/2^+$ (calculated MW: 1688.69); HPLC method A; retention time: 11.63 min; purity 95.8%.

Example 1.17 Conotoxin Peptide Analog Io (D-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-L-tyrosyl-cyclic (2→8)-disulfide-cyclic $3^3,12^5$-(1H-1,2,3-triazole-4,1-diyl)) (SEQ ID NO:54)

(Io)

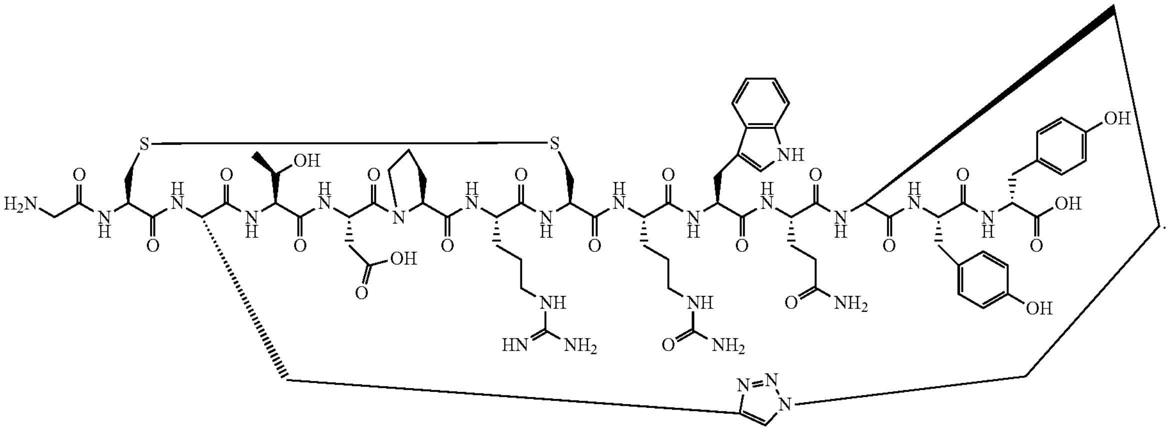

Intermediate conotoxin peptide analog Yo (H-Gly-Cys-Pra-Thr-Asp-Pro-Arg-Cys-Cit-Trp-Gln-5-azidoNVa-Tyr-D-Tyr-OH) (SEQ ID NO:55): Intermediate conotoxin peptide analog Yo was synthesized by employing the same procedure described for compound 3 using FMOC-D-Tyr (OtBu)—OH-loaded 2-chlorotrityl resin to sequentially add amino acid, carried out in the following order with FMOC-Tyr(OtBu)—OH, FMOC-5-azido-Nva-OH, FMOC-Gln (Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zo (H-Gly-Cys-Pra-Thr-Asp-Pro-Arg-Cys-Cit-Trp-Gln-5-azidoNVa-Tyr-D-Tyr-OH, (Cys2→Cys8) disulfide bridge) (SEQ ID NO:56): Intermediate conotoxin peptide analog Zo was synthesized by employing the same procedure described for compound 4 using intermediate conotoxin peptide analog Yo in lieu of compound 3.

Conotoxin peptide analog Io was synthesized by employing the same procedures described for conotoxin peptide analog Ia using intermediate conotoxin peptide analog Zo in lieu of compound 4. LC-MS (single quad ESI) m/z: 595.0 $[M+3H]/3^+$, 891.7 $[M+2H]/2^+$ (calculated MW: 1780.72); HPLC method A; retention time: 12.43 min; purity 97.4%.

Example 1.18 Conotoxin Peptide Analog Ip (L-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-L-tyrosyl-N-methyl-cyclic (2→8)-disulfide-cyclic $3^3,12^5$-(1H-1,2,3-triazole-4,1-diyl)) (SEQ ID NO:57)

(Ip)

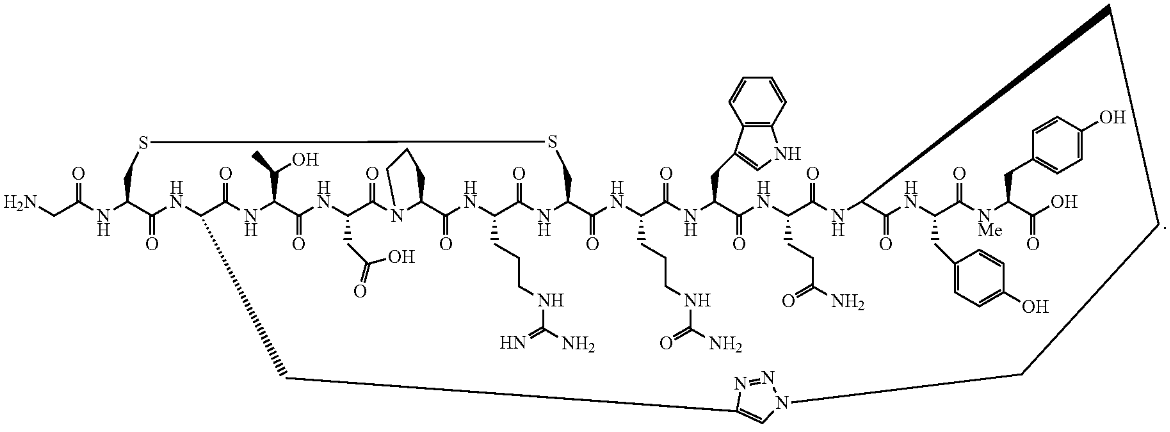

2-Chlorotrityl resin loaded FMOC—N-Me-Tyr-OH (8): 2-Chlorotrityl resin loaded FMOC—N-Me-Tyr-OH was synthesized by employing the same procedure described for 2-Chlorotrityl resin 1 using FMOC—N-Me-Tyr-OH in lieu of FMOC-Tyr(OtBu)—OH.

Intermediate conotoxin peptide analog Yp (H-Gly-Cys-Pra-Thr-Asp-Pro-Arg-Cys-Cit-Trp-Gln-5-azidoNVa-Tyr-N-Me-Tyr-OH) (SEQ ID NO:58): Intermediate conotoxin peptide analog Yp was synthesized by employing the same procedure described for compound 3 using FMOC—N-Me-Tyr-OH-loaded 2-chlorotrityl resin (8) to sequentially add amino acid, carried out in the following order with FMOC-Tyr(OtBu)—OH, FMOC-5-azido-Nva-OH, FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zp (H-Gly-Cys-Pra-Thr-Asp-Pro-Arg-Cys-Cit-Trp-Gln-5-azidoNVa-Tyr-N-Me-Tyr-OH, (Cys2→Cys8) disulfide bridge) (SEQ ID NO:59): Intermediate conotoxin peptide analog Zp was synthesized by employing the same procedure described for compound 4 using intermediate conotoxin peptide analog Yp in lieu of compound 3.

Conotoxin peptide analog Ip was synthesized by employing the same procedures described for conotoxin peptide analog Ia using intermediate conotoxin peptide analog Zp in lieu of compound 4. LC-MS (single quad ESI) m/z: 599.7 $[M+3H]/3^+$, 898.7 $[M+2H]/2^+$ (calculated MW: 1794.74); HPLC method A; retention time: 12.56 min; purity 95.5%.

Example 1.19 Conotoxin Peptide Analog Iq (L-norvaline, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-cyclic (2→8)-disulfide-cyclic $3^3,12^5$-(1H-1,2,3-triazole-4,1-diyl)) (SEQ ID NO:60)

2-Chlorotrityl resin loaded FMOC-5-azido-Nva-OH (9): 2-Chlorotrityl resin loaded FMOC-5-azido-Nva-OH was synthesized by employing the same procedure described for 2-Chlorotrityl resin 1 using FMOC-5-azido-Nva-OH in lieu of FMOC-Tyr(OtBu)—OH.

Intermediate conotoxin peptide analog Yq (H-Gly-Cys-Pra-Thr-Asp-Pro-Arg-Cys-Cit-Trp-Gln-5-azidoNVa-OH) (SEQ ID NO:61): Intermediate conotoxin peptide analog Yq was synthesized by employing the same procedure described for compound 3 using FMOC-5-azido-Nva-OH-loaded 2-chlorotrityl resin (9) to sequentially add amino acid, carried out in the following order with FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zq (H-Gly-Cys-Pra-Thr-Asp-Pro-Arg-Cys-Cit-Trp-Gln-5-azidoNVa-OH, (Cys2→Cys8) disulfide bridge) (SEQ ID NO:62): Intermediate conotoxin peptide analog Zq was synthesized by employing the same procedure described for compound 4 using intermediate conotoxin peptide analog Yq in lieu of compound 3.

Conotoxin peptide analog Iq was synthesized by employing the same procedures described for conotoxin peptide analog Ia using intermediate conotoxin peptide analog Zq in lieu of compound 4. LC-MS (ESI-TOF) m/z: 1455.5 $[M+1H]/^+$ (calculated MW: 1454.59); HPLC method A; retention time: 11.4 min; purity 95.0%.

(Iq)

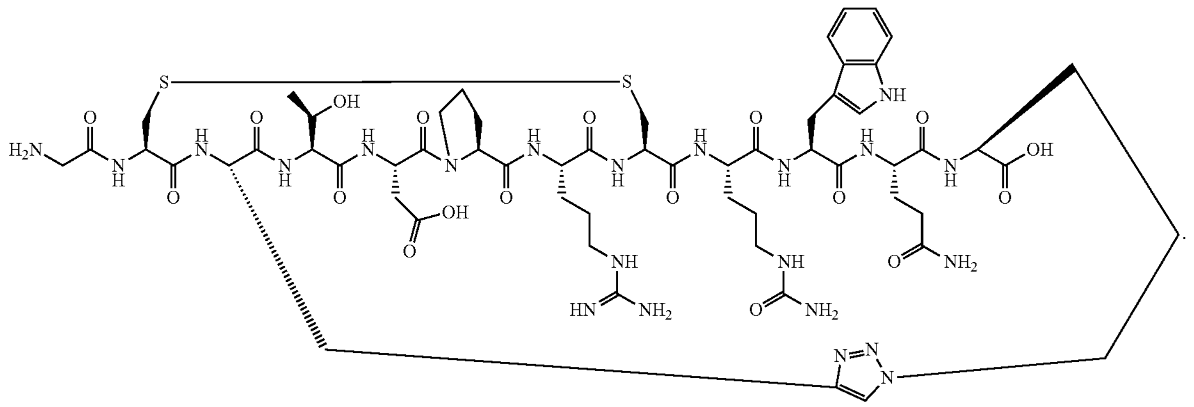

Example 1.20 Conotoxin Peptide Analog Ir (L-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-N-methyl-cyclic (2→8)-disulfide-cyclic $3^3,12^5$-(1H-1,2,3-triazole-4,1-diyl)) (SEQ ID NO:63)

(Ir)

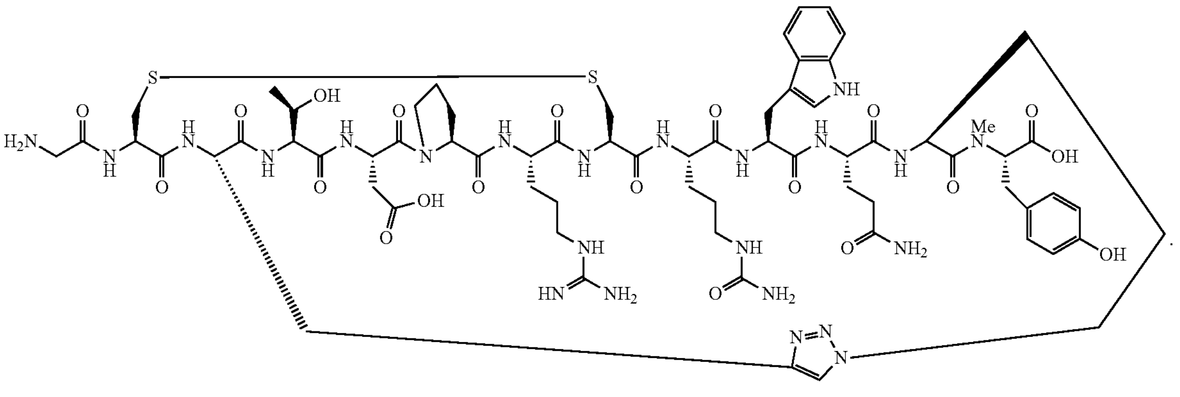

Intermediate conotoxin peptide analog Yr (H-Gly-Cys-Pra-Thr-Asp-Pro-Arg-Cys-Cit-Trp-Gln-5-azidoNVa-N-Me-Tyr-OH) (SEQ ID NO:64): Intermediate conotoxin peptide analog Yr was synthesized by employing the same procedure described for compound 3 using FMOC—N-Me-Tyr-OH-loaded 2-chlorotrityl resin to sequentially add amino acid, carried out in the following order with FMOC-5-azido-Nva-OH, FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zr (H-Gly-Cys-Pra-Thr-Asp-Pro-Arg-Cys-Cit-Trp-Gln-5-azidoNVa-N-Me-Tyr-OH, (Cys2→Cys8) disulfide bridge) (SEQ ID NO:65): Intermediate conotoxin peptide analog Zr was synthesized by employing the same procedure described for compound 4 using intermediate conotoxin peptide analog Yr in lieu of compound 3.

Conotoxin peptide analog Ir was synthesized by employing the same procedures described for conotoxin peptide analog Ia using intermediate conotoxin peptide analog Zr in lieu of compound 4. LC-MS (single quad ESI) m/z: 545.3 $[M+3H]/3^+$, 817.0 $[M+2H]/2^+$ (calculated MW: 1631.67); HPLC method A; retention time: 12.01 min; purity 96.4%.

Example 1.21 Conotoxin Peptide Analog Is (D-arginine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^3,12^5$-(1H-1,2,3-triazole-4,1-diyl)) (SEQ ID NO:66)

(Is)

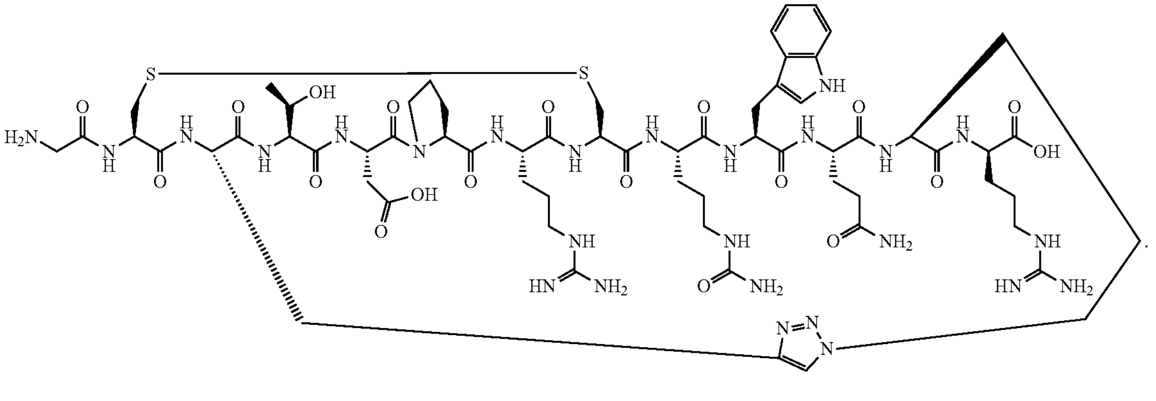

2-Chlorotrityl resin loaded FMOC-D-Arg-OH (10): 2-Chlorotrityl resin loaded FMOC-D-Arg-OH was synthesized by employing the same procedure described for 2-Chlorotrityl resin 1 using FMOC-D-Arg-OH in lieu of FMOC-Tyr(OtBu)—OH.

Intermediate conotoxin peptide analog Ys (H-Gly-Cys-Pra-Thr-Asp-Pro-Arg-Cys-Cit-Trp-Gln-5-azidoNVa-D-Arg-OH) (SEQ ID NO:67): Intermediate conotoxin peptide analog Ys was synthesized by employing the same procedure described for compound 3 using FMOC-D-Arg-OH-loaded 2-chlorotrityl resin (10) to sequentially add amino acid, carried out in the following order with FMOC-5-azido-Nva-OH, FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zs (H-Gly-Cys-Pra-Thr-Asp-Pro-Arg-Cys-Cit-Trp-Gln-5-azidoNVa-D-Arg-OH, (Cys2→Cys8) disulfide bridge) (SEQ ID NO:68): Intermediate conotoxin peptide analog Zs was synthesized by employing the same procedure described for compound 4 using intermediate conotoxin peptide analog Ys in lieu of compound 3.

Conotoxin peptide analog Is was synthesized by employing the same procedures described for conotoxin peptide analog Ia using intermediate conotoxin peptide analog Zs in lieu of compound 4. LC-MS (single quad ESI) m/z: 539.2 $[M+3H]/3^+$, 807.0 $[M+2H]/2^+$ (calculated MW: 1610.69); HPLC method A; retention time: 10.52 min; purity 97.1%.

Example 1.22 Conotoxin Peptide Analog It (D-tyrosine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-N-methyl-cyclic (2→8)-disulfide-cyclic $3^3$,$12^5$-(1H-1,2,3-triazole-4,1-diyl)) (SEQ ID NO:69)

2-Chlorotrityl resin loaded FMOC—N-Me-D-Tyr-OH (11): 2-Chlorotrityl resin loaded FMOC—N-Me-D-Tyr-OH was synthesized by employing the same procedure described for 2-Chlorotrityl resin 1 using FMOC—N-Me-D-Tyr-OH in lieu of FMOC-Tyr(OtBu)—OH.

Intermediate conotoxin peptide analog Yt (H-Gly-Cys-Pra-Thr-Asp-Pro-Arg-Cys-Cit-Trp-Gln-5-azidoNVa-N-Me-D-Tyr-OH) (SEQ ID NO:70): Intermediate conotoxin peptide analog Yt was synthesized by employing the same procedure described for compound 3 using FMOC—N-Me-D-Tyr-OH-loaded 2-chlorotrityl resin (11) to sequentially add amino acid, carried out in the following order with FMOC-5-azido-Nva-OH, FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zt (H-Gly-Cys-Pra-Thr-Asp-Pro-Arg-Cys-Cit-Trp-Gln-5-azidoNVa-N-Me-D-Tyr-OH, (Cys2→Cys8) disulfide bridge) (SEQ ID NO:71): Intermediate conotoxin peptide analog Zt was synthesized by employing the same procedure described for compound 4 using intermediate conotoxin peptide analog Yt in lieu of compound 3.

Conotoxin peptide analog It was synthesized by employing the same procedures described for conotoxin peptide analog Ia using intermediate conotoxin peptide analog Zt in lieu of compound 4. LC-MS (single quad ESI) m/z: 545.3 $[M+3H]/3^+$, 817.0 $[M+2H]/2^+$ (calculated MW: 1631.67); HPLC method A; retention time: 10.72 min; purity 96.6%.

(It)

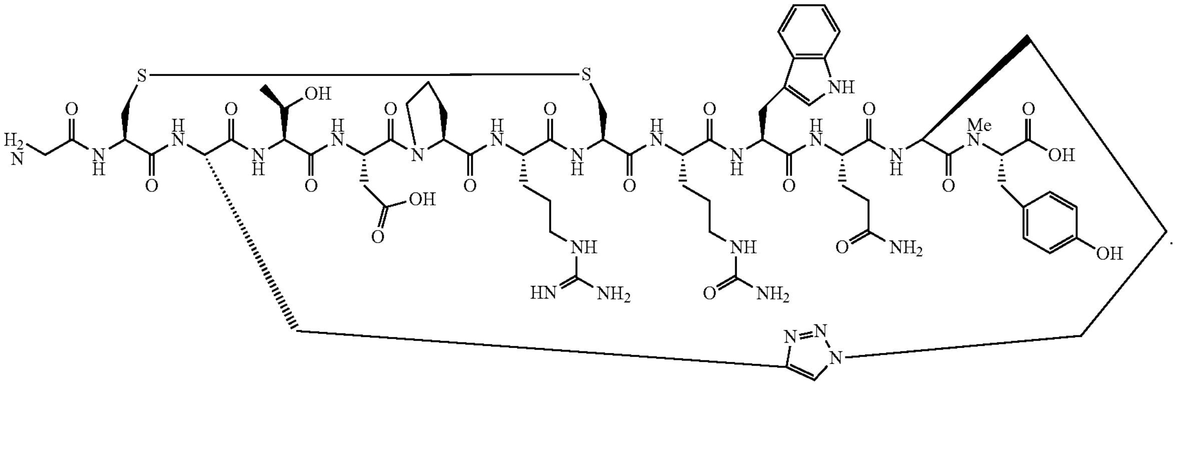

Example 1.23 Conotoxin Peptide Analog Iu ((R)-3-(amino)-3-(4-hydroxyphenyl)propionic acid, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-cyclic (2→8)-disulfide-cyclic $3^3$,$12^5$-(1H-1,2,3-triazole-4,1-diyl)) (SEQ ID NO:72)

(Iu)

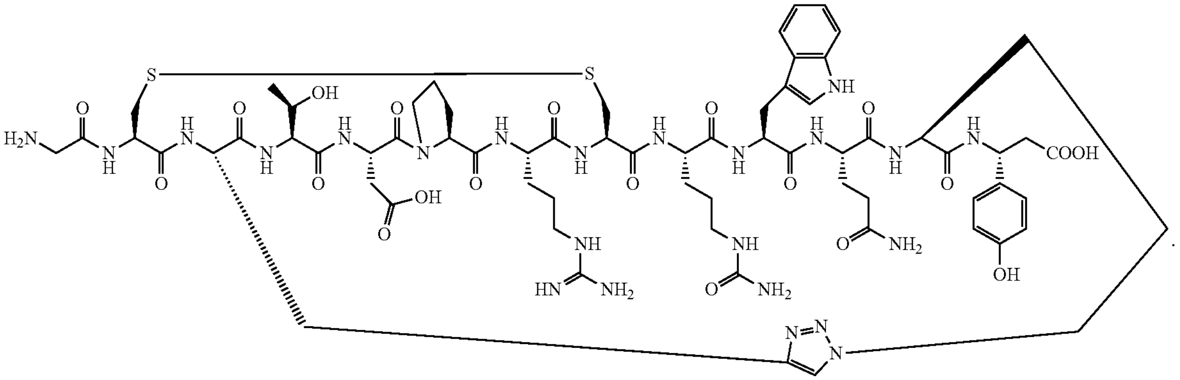

2-Chlorotrityl resin loaded FMOC-beta-Tyr-OH (12): 2-Chlorotrityl resin loaded FMOC-beta-Tyr-OH was synthesized by employing the same procedure described for 2-Chlorotrityl resin 1 using FMOC-beta-Tyr-OH in lieu of FMOC-Tyr(OtBu)—OH.

Intermediate conotoxin peptide analog Yu (H-Gly-Cys-Pra-Thr-Asp-Pro-Arg-Cys-Cit-Trp-Gln-5-azidoNVa-beta-Tyr-OH) (SEQ ID NO:73): Intermediate conotoxin peptide analog Yu was synthesized by employing the same procedure described for compound 3 using FMOC-beta-Tyr-OH-loaded 2-chlorotrityl resin (12) to sequentially add amino acid, carried out in the following order with FMOC-5-azido-Nva-OH, FMOC-Gln(Trt)-OH, FMOC-Trp(Boc)-OH, FMOC-Cit-OH, FMOC-Cys(Trt)-OH, FMOC-Arg(Pbf)-OH, FMOC-Pro-OH, FMOC-Asp(OtBu)—OH, FMOC-Thr (tBu)—OH, FMOC-Pra-OH, FMOC-Cys(Trt)-OH, and FMOC-Gly-OH.

Intermediate conotoxin peptide analog Zu (H-Gly-Cys-Pra-Thr-Asp-Pro-Arg-Cys-Cit-Trp-Gln-5-azidoNVa-beta-Tyr-OH, (Cys2→Cys8) disulfide bridge) (SEQ ID NO:74): Intermediate conotoxin peptide analog Zu was synthesized by employing the same procedure described for compound 4 using intermediate conotoxin peptide analog Yu in lieu of compound 3.

Conotoxin peptide analog Iu was synthesized by employing the same procedures described for conotoxin peptide analog Ia using intermediate conotoxin peptide analog Zu in lieu of compound 4. LC-MS (single quad ESI) m/z: 544.5 $[M+3H]/3^+$, 816.3 $[M+2H]/2^+$ (calculated MW: 1631.67); HPLC method A; retention time: 10.28 min; purity 98.8%.

Example 1.24 Conotoxin Peptide Analog Iv (L-arginine, glycyl-L-cysteinyl-L-alanyl-L-threonyl-L-α-aspartyl-L-prolyl-L-arginyl-L-cysteinyl-N5-(aminocarbonyl)-L-ornithyl-L-tryptophyl-L-glutaminyl-L-norvalyl-N-methyl-cyclic (2→8)-disulfide-cyclic $3^3$,$12^5$-(1H-1,2,3-triazole-4,1-diyl)) (SEQ ID NO:75)

(Iv)

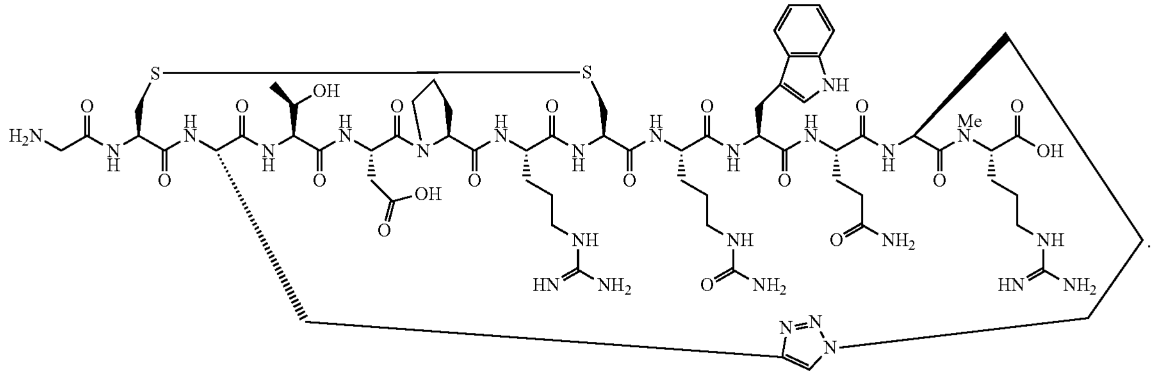

2-Chlorotrityl resin loaded FMOC—N-Me-Arg-OH (13): 2-Chlorotrityl resin loaded FMOC—N-Me-Arg-OH was synthesized by employing the same procedure described for 2-Chlorotrityl resin 1 using FMOC—N-Me-Arg-OH in lieu of FMOC-Tyr(OtBu)—OH.

Intermediate conotoxin peptide analog Yv (H-Gly-Cys-Pra-Thr-Asp-Pro-Arg-Cys-Cit-Trp-Gln-5-azidoNVa-N-Me-Arg-OH) (SEQ ID NO:76): Intermediate conotoxin peptide analog Yv was synthesized by employing the same procedure described for compound 3 using FMOC—N-Me-Arg-OH-loaded 2-chlorotrityl resin (13) to sequentially add amino acid, carried out in the following order with FMOC-5-azido-Nva-OH, FMOC-Gln(Trt)-OH, FMOC-Trp(Boc)-OH, FMOC-Cit-OH, FMOC-Cys(Trt)-OH, FMOC-Arg (Pbf)-OH, FMOC-Pro-OH, FMOC-Asp(OtBu)—OH, FMOC-Thr(tBu)—OH, FMOC-Pra-OH, FMOC-Cys(Trt)-OH, and FMOC-Gly-OH.

Intermediate conotoxin peptide analog Zv (H-Gly-Cys-Pra-Thr-Asp-Pro-Arg-Cys-Cit-Trp-Gln-5-azidoNVa-N-Me-Arg-OH, (Cys2→Cys8) disulfide bridge) (SEQ ID NO:77): Intermediate conotoxin peptide analog Zv was synthesized by employing the same procedure described for compound 4 using intermediate conotoxin peptide analog Yv in lieu of compound 3.

Conotoxin peptide analog Iv was synthesized by employing the same procedures described for conotoxin peptide analog Ia using intermediate conotoxin peptide analog Zv in lieu of compound 4. LC-MS (single quad ESI) m/z: 542.9 $[M+3H]/3^+$, 813.5 $[M+2H]/2^+$ (calculated MW: 1624.71); HPLC method A; retention time: 9.29 min; purity 95.9%.

Example 1.25 Conotoxin Peptide Analogs Iw (L-tyrosinamide, glycyl-L-cysteinyl-L-glutamyl-L-threonyl-L-α-aspartyl-L-prolyl-L-arginyl-L-cysteinyl-N5-(aminocarbonyl)-L-ornithyl-L-3-iodotyrosyl-L-glutaminyl-L-lysyl-cyclic (2→8)-disulfide-cyclic-(3→12)-lactam) (SEQ ID NO:78)

Synthesis of Linear Peptide Intermediate (X1) (SEQ ID NO:79): FMOC-Tyr(OtBu)-loaded Rink amide MBHA resin (1.7 g, 0.5 mmol) was washed with DMF (10 ml) and then drained completely. The FMOC group was removed from the tethered Tyr group by treatment with 1:4 piperidine/DMF (2×10 mL, 15 min each), and then the resin was washed with DMF (6×10 mL). Then, HATU (CAS #148893-10-1, 0.38 g, 1 mmol), HOAt (CAS #39968-33-7, 0.14 g, 1 mmol), and DIPEA (0.25 mL, 1.5 mmol) were added with FMOC-Lys(ivDde)-OH (CAS #204777-78-6, 0.57 g, 1 mmol) in DMF (10 mL). The reaction vessel was shaken for a minimum of 2.5 h, followed by washing with DMF (6×10 mL). Reaction completeness was determined by the Ninhydrin test. If negative (colorless), the coupling was considered complete and the synthesis was continued. If positive (blue), a second equivalent of the same FMOC-amino acid (1 mmol) in DMF (10 mL) was coupled using the resin and HATU/HOAt (1 mmol/1 mmol) as described above. Once the Ninhydrin test indicated the reaction was complete, the FMOC was removed from each of the sequentially added amino acid, followed by coupling of the subsequent FMOC-amino acid-OH in the peptide sequence as described above. This was successively carried out in the following order with FMOC-Gln(Trt)-OH (CAS #132327-80-1, 0.61 g, 1 mmol), FMOC-(3-I-Tyr)-OH (CAS #134486-00-3, 0.53 g, 1 mmol), FMOC-Cit-OH (CAS #133174-15-9, 0.39 g, 1 mmol), FMOC-Cys(Trt)-OH (CAS #103213-32-7, 0.58 g, 1 mmol), FMOC-Arg(Pbf)-OH (CAS #154445-77-9, 0.64 g, 1 mmol), FMOC-Pro-OH (CAS #71989-31-6, 0.33 g, 1 mmol), FMOC-Asp(OtBu)—OH (CAS #71989-14-5, 0.41 g, 1 mmol), FMOC-Thr(tBu)—OH (CAS #71989-35-0, 0.39 g, 1 mmol), FMOC-Glu(ODmab) (CAS #268730-86-5, 0.68 g, 1 mmol), FMOC-Cys(Trt)-OH (0.58 g, 1 mmol), and FMOC-Gly-OH (CAS #29022-11-5, 0.29 g, 1 mmol). After the linear peptide couplings were complete, the resin was washed with DMF (10 mL×6), followed by MeOH (10 mL×2) and finally $Et_2O$ (10 mL×2), and then dried under vacuum for 2 h.

(Iw)

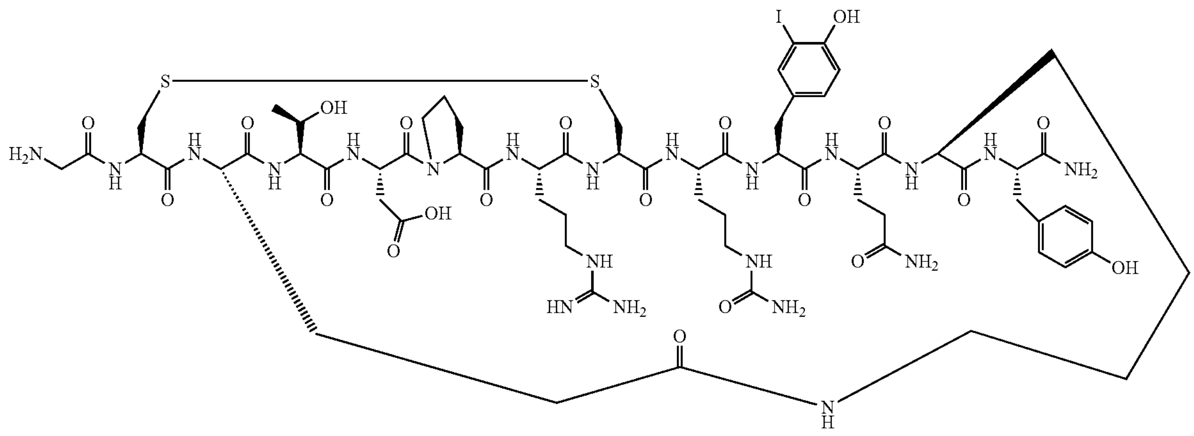

.

X1
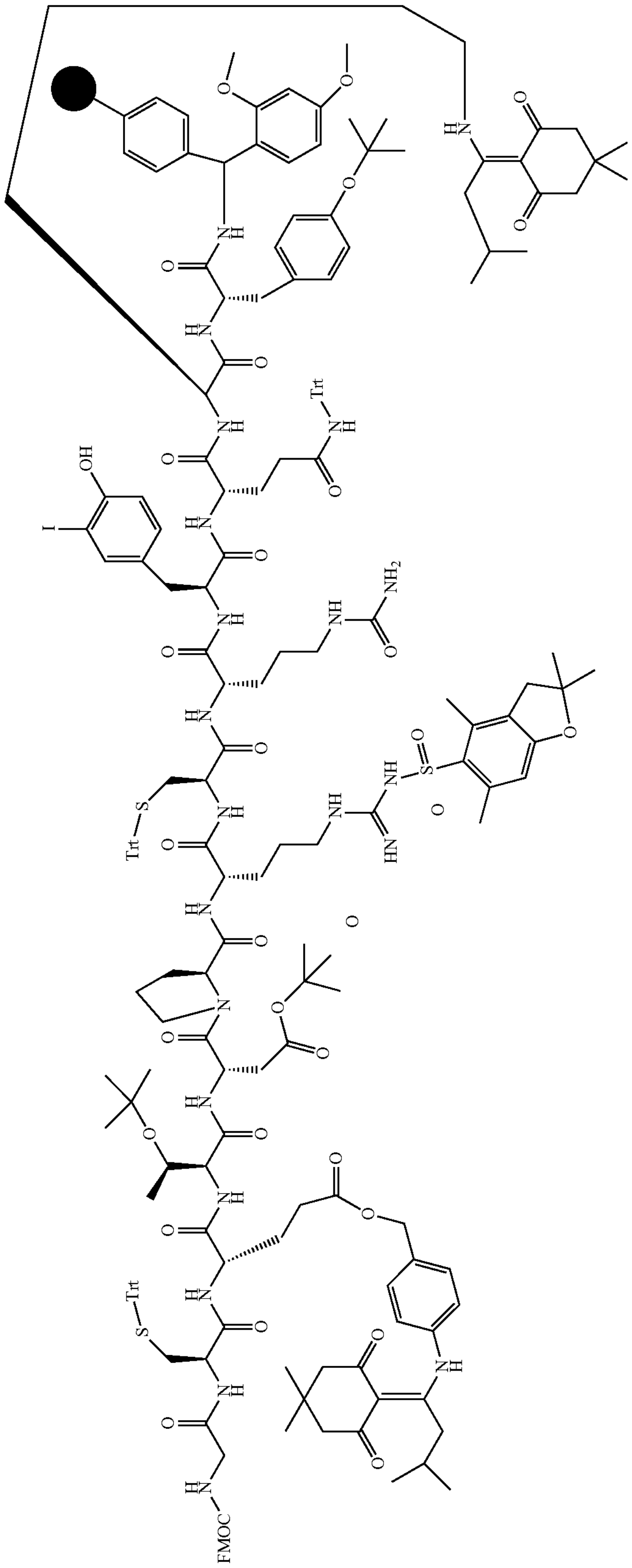

Lactam formation to produce Intermediate X2 on resin (SEQ ID NO:80): To remove the ivDde and ODmab protecting groups from the Lys 12 and Glu3 residues, respectively, the peptide resin was washed with DMF (10 mL) and then drained completely, then the resin was incubated with 2% hydrazine hydrate in DMF (10 mL) for 1 h at rt. The resin was subsequently washed with DMF (6×10 mL) and then resuspended in DMF (10 mL) followed by treatment with HATU (0.38 g, 1 mmol), HOAt (0.14 g, 1 mmol), and DIPEA (0.25 mL, 1.5 mmol). The reaction vessel was shaken for a minimum of 2.5 h, followed by washing with DMF (6×10 mL), then MeOH (10 mL×2) and finally $Et_2O$ (10 mL×2), and then dried under vacuum for 2 h.

X2

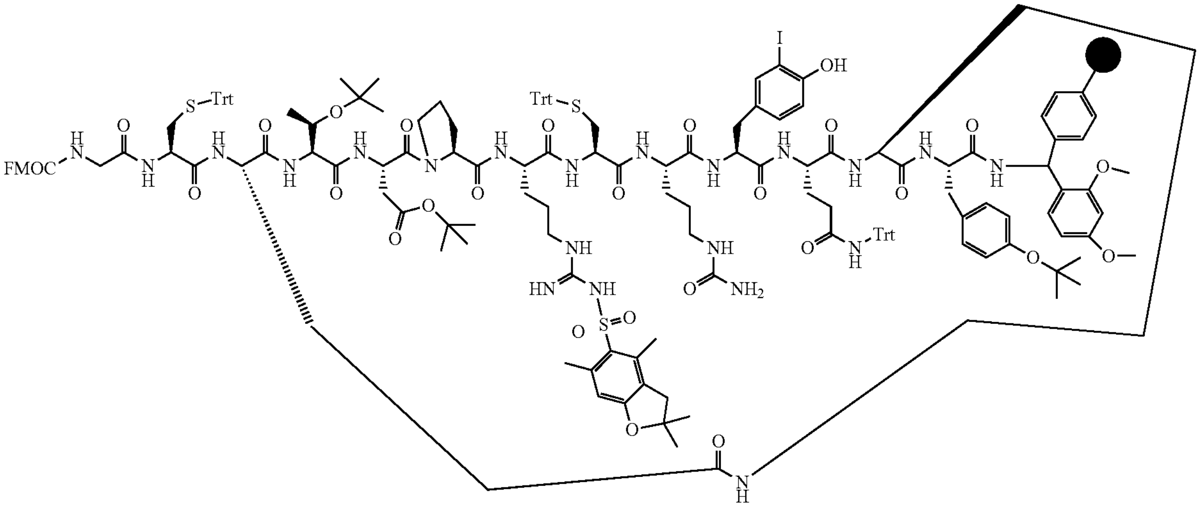

Cleavage from resin to afford Intermediate X3 (SEQ ID NO:81): The lactam was cleaved from the resin by incubating Intermediate X2 in 23 mL of cleavage solution (TFA/EDT/Thioanisole/Anisole: 30:3:5:2) and the mixture was shaken for 2 h at room temperature. After this time the resin was filtered and washed with TFA (2×5 mL). The filtrates were combined, and 10-fold volume of cold (0° C.) $Et_2O$ was added, which resulted in precipitation of the peptide. The precipitated peptide was centrifuged at 5,000 rpm for 10 min and washed with cold (0° C.) $Et_2O$ (3×5 mL). The crude X3 was dried under vacuum for 2 h to obtain the crude monocyclic 3-12 lactampeptide intermediate (X3, MW=1727.7 g/mol, 0.4 g, 0.23 mmol, 46%), which was used without further purification.

X3

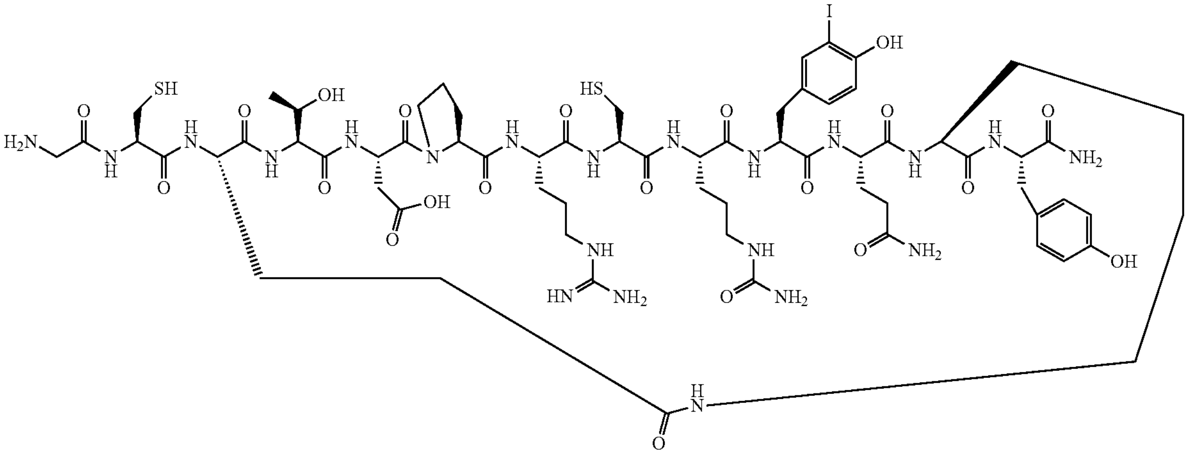

Disulfide bridge formation to afford conotoxin peptide analog Iw: Intermediate X3 (0.4 g, 0.23 mmol) was dissolved in $CH_3CN$ (10 mL), DMSO (10 mL) and $H_2O$ (180 mL). Then $H_2O_2$ (30% in $H_2O$, 25 μL) was added dropwise and the mixture was stirred at room temperature for 1.5 h. After this time, the mixture was filtered, and the filtrate was purified by HPLC Method J to afford 50 mg of the conotoxin peptide analog Iw as a white solid (MW 1725.6 g/mol, 29 μmol, yield this step: 12.6%, TFA salt). Purity 82% (230 nm).

The peptide was purified further while exchanging the TFA anion for acetate by preparative HPLC according to the method described for conotoxin peptide analogs Ia. The isolated yield of conotoxin peptide analog Iw (acetate salt) was 20 mg (12 μmol, 2.4% overall yield). LC-MS (single quad ESI) m/z: 576.1 $[M+3H]/3^+$, 863.5 $[M+2H]/2^+$, (calculated MW: 1723.56); HPLC method K; retention time: 7.0 min; purity 97%.

Example 1.26 Conotoxin Peptide Analogs Ix (L-tyrosinamide, glycyl-L-cysteinyl-L-lysyl-L-threonyl-L-α-aspartyl-L-prolyl-L-arginyl-L-cysteinyl-N5-(aminocarbonyl)-L-ornithyl-L-3-iodotyrosyl-L-glutaminyl-L-glutamyl-cyclic (2→8)-disulfide-cyclic-(3→12)-lactam) (SEQ ID NO:82)

(Ix)

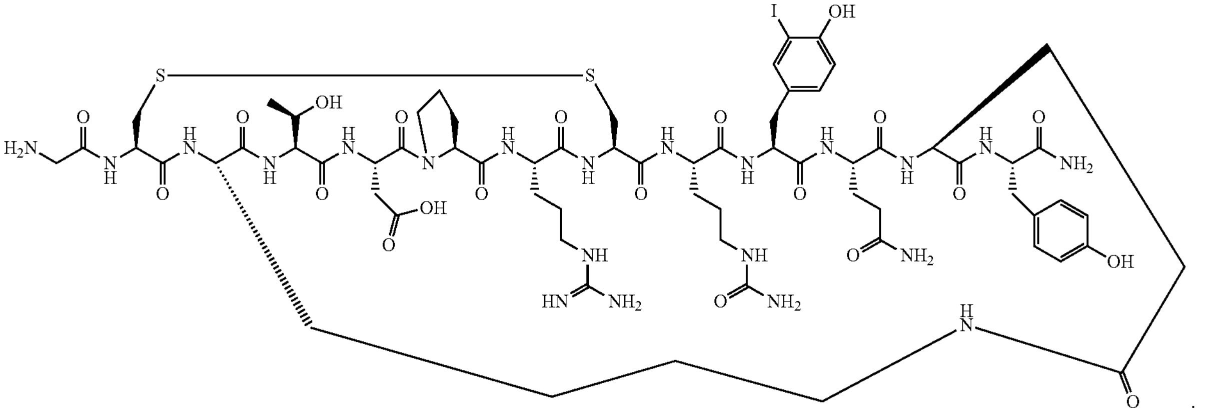

Conotoxin peptide analog Ix was synthesized by employing the same procedures described for conotoxin peptide analog Iw using FMOC-Glu(ODmab) in lieu of FMOC-Lys(ivDde)-OH and FMOC-Lys(ivDde)-OH in lieu of FMOC-Glu(ODmab). LC-MS (ESI-ion trap) m/z: 862.9 $[M+2H]/2^+$, 1724.3 $[M+H]/^+$, (calculated MW: 1723.56); HPLC method K; retention time: 7.1 min; purity 95%.

6.3. Example 2: Preparation of PEGylated Conotoxin Peptide Analogs

Example 2.1 PEGylated Conotoxin Peptide Analog IIa (SEQ ID NO:83) (30 kDa-mPEG-valerate (VA)-Conotoxin Peptide Analog Ia)

(IIa)

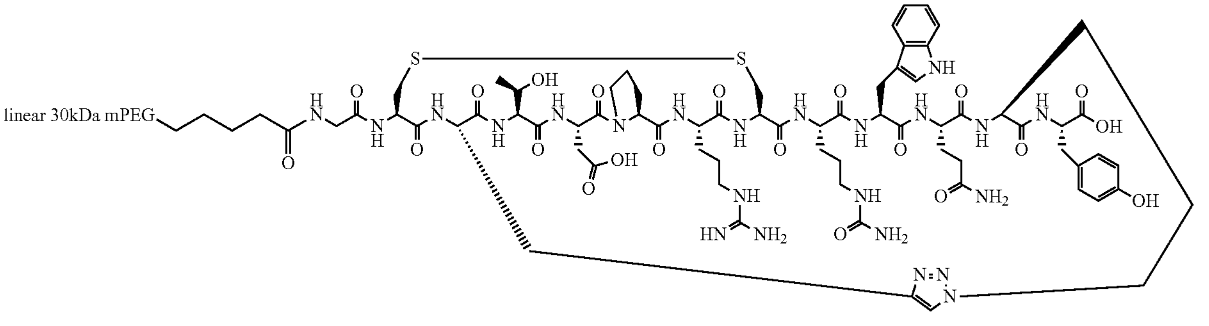

The acetate salt of conotoxin peptide analog Ia (25 mg, 0.015 mmol) was dissolved in PBS buffer (pH=8.0, 12.5 mL) followed by the addition of mPEG-30 kDa-VA-NHS ester (560 mg, 0.018 mmol; NOF America, SUNBRIGHT ME-30011S; Final linker=valeric acid amide ("VA");

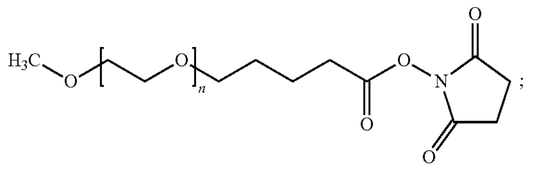

average n=675) in $H_2O$ (20 mL). After shaking the reaction vessel for 2 h at room temperature, the reaction progress was monitored using analytical HPLC. When >90% of conotoxin peptide analog Ia had been consumed, as determined by HPLC analysis, the resulting PEGylated peptide, PEGylated conotoxin peptide analog IIa was purified by HPLC Method I to remove unreacted conotoxin peptide analog Ia (RT=5.0 min). The HPLC peak for PEGylated conotoxin peptide analog IIa was fractionated into thirds and each fraction was analyzed by the HPLC Method I with ELSD detection (in-line, post UV detector) to determine the peptide purity (UV RT=16.65 min, ELSD retention time=16.75 min) amount of residual free PEG (ELSD RT=17.00 min). Fractions with >95% peptide purity that contained <5% free PEG, based on the ELSD signal (free PEG relative to the ELSD signal of peptide), were combined and lyophilized. Overall isolated yield 0.21 g (44%); HPLC Method I: purity: 95% (UV 214 nm), 97% (ELSD). The characterization data for PEGylated conotoxin peptide analog IIa are listed in Table 2 below.

TABLE 2

Characterization Data for PEGylated conotoxin peptide analog IIa

| Analysis | Result | Method |
|---|---|---|
| Experimentally Determined Mass | 32254.6 | MALDI-TOF |
| Copper content | <11 ppm | ICP-AES |
| Karl Fischer Water content | 0.40% | Coulometric KF analysis |

TABLE 2-continued

Characterization Data for PEGylated conotoxin peptide analog IIa

| Analysis | Result | Method |
|---|---|---|
| Nitrogen content | 0.93% | Elemental Analysis |
| Peptide content | 91.0% (based on calculated MW: 31512) | Calculation using nitrogen content in elemental analysis |
| AcOH content | 0.549% | Ion Chromatography |
| TFA content | 0.361% | Ion Chromatography |

Example 2.2 PEGylated Conotoxin Peptide Analog IVa (SEQ ID NO:84) (30 kDa-mPEG-bAmine-Conotoxin Peptide Analog Ia)

(IVa)

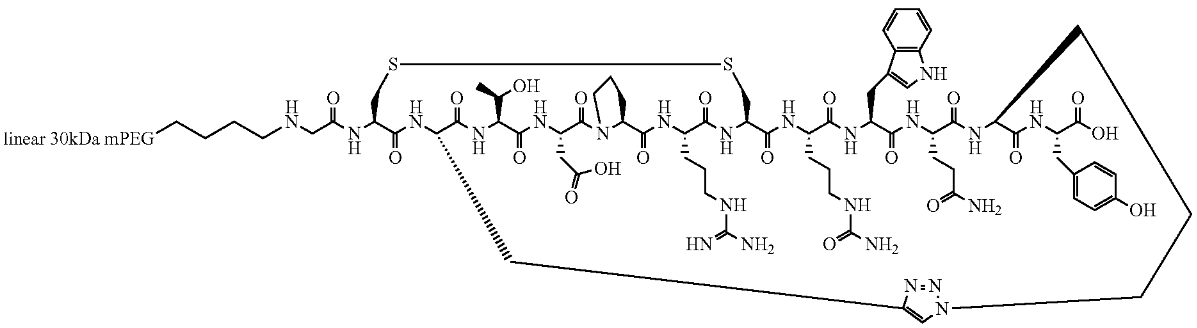

The acetate salt of conotoxin peptide analog Ia (25 mg, 0.013 mmol) was dissolved in MeOH (10 mL) followed by the addition of a solution of mPEG-30 kDa-butyraldehyde (CAS No. 9004-74-4, 414 mg, 0.013 mmol) in MeOH (10 mL). The mixture was shaken at room temperature for 3 h. After this time, a solution of PPTS (3.3 mg, 0.013 mmol) in MeOH (0.1 mL) was added, followed by addition of a solution of $NaCNBH_3$ (1.6 mg, 0.026 mmol) in MeOH (0.1 mL). Shaking was continued for 12 h, after this time the reaction mixture was purified directly by prep-HPLC method G to provide the TFA salt of PEGylated conotoxin peptide analog IVa (92 mg, overall yield, 21%, TFA salt). HPLC Purity: 95.7% (UV 214 nm).

A subsequent salt exchange was achieved by dissolving the TFA salt of PEGylated conotoxin peptide analog IVa (92 mg, 0.0027 mmol) from above in 3 mL of water. To this solution, the dropwise addition of $NH_4HCO_3$ (aq) was added to adjust the pH 7.0-8.0. The mixture was then purified directly by preparative RP-HPLC (Mobile Phase: A: 0.1% AcOH in Water, B: 0.1% AcOH in ACN), and lyophilized to provide the acetate salt of PEGylated conotoxin peptide analog IVa as white solid (31 mg, overall yield, 7%, acetate salt). LC/MS Purity: 95.5% (UV 214 nm), 98.7% (ELSD). The characterization data for PEGylated conotoxin peptide analog IVa are listed in Table 3 below.

TABLE 3

| Characterization Data for PEGylated conotoxin peptide analog IVa | | |
|---|---|---|
| Analysis | Result | Method |
| Experimentally Determined Mass | 33465.4 | MALDI-TOF |
| Nitrogen content | 1.00% | C, H, N Combustion Analysis |
| Peptide content | 98.05% (based on calculated MW: 31571.8) | Calculation using nitrogen content in elemental analysis |

Example 2.3 C-Terminus PEGylated Conotoxin Peptide Analog Va (SEQ ID NO:85) (Conotoxin Peptide Analog Ia-30 kDa-PEG)

(458 μL, 26 μmol) in anhydrous DMF (45 mL) were each added. The mixture was stirred at room temperature for 2 h then purified by HPLC method G (Table 7). Lyophilization of the purified product afforded a salt of C-terminus PEGylated conotoxin peptide analog Va (100 mg, 3.1 μmol, 35% yield), as a TFA salt (Purity 91% at 214 nm). This TFA salt was then dissolved in $H_2O$:$CH_3CN$ (3 mL: 1 mL), then a dilute solution of $NH_4HCO_3$ (aq.) was added dropwise to obtain a pH=7.0-8.0. The mixture was then purified by HPLC method H (Table 7) to afford the acetate salt of C-terminus PEGylated conotoxin peptide analog Va. After lyophilization, a white solid was obtained, (50 mg, yield: 15.8 μcool, 17.5%, acetate salt). LC-Purity: 90.4% (UV 214 nm), 99.3% (ELSD). The characterization data for PEGylated conotoxin peptide analog Va are listed in Table 4 below.

(Va)

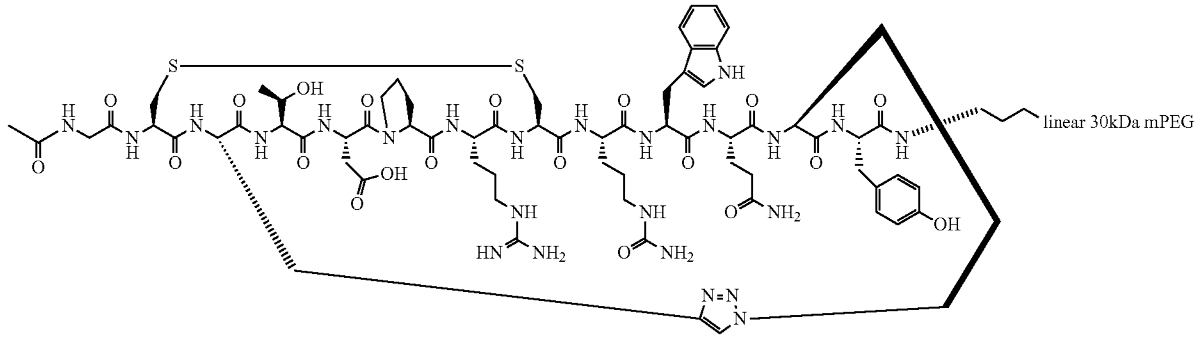

N-terminus N-acetyl conotoxin peptide analog Ia intermediate (14): conotoxin peptide analog Ia (75 mg, 46 μmol) was dissolved in anhydrous DMF (35 mL) and then $Ac_2O$ (7.5 μL, 0.3 mmol) and anhydrous pyridine (32 μL, 0.4 mmol) were added. The solution stirred for 2 h at room temperature. Then, the product was purified by preparative HPLC method G (Table 7). After lyophilization of the product containing fractions, compound 14 was obtained as an off-white solid (44.5 mg, 27 μmol, 98% purity, 59% yield). LC-MS (ESI) m/z: 554.6 $[M+3H]/3^+$, 831.0 $[M+2H]/2^+$, Purity 98% (UV 214 nm).

C-Terminus PEGylated Conotoxin Peptide Analog Va: Compound 14 (15 mg, 9.0 μmot) was dissolved in anhydrous DMF (2.5 mL) and a solution of 30 kDa-mPEG-propylamine (300 mg, 10 μmol, 1.1 equiv.) in anhydrous DMF (2.5 mL) was added. Then, a solution of HBTU (3.7 mg, 9.7 μmol) in DMF (0.3 mL) and a solution of DIPEA

TABLE 4

| Characterization Data for PEGylated conotoxin peptide analog Va | | |
|---|---|---|
| Analysis | Result | Method |
| Experimentally Determined Mass | 31307.7 | MALDI-TOF |
| Nitrogen content | 0.71% | C, H, N Combustion Analysis |
| Peptide content | 66.77% (based on calculated MW: 31598.8) | Calculation using nitrogen content in elemental analysis |

Example 2.4 7-Arg-PEGylated Conotoxin Peptide Analog VIa (SEQ ID NO:86) (Ac-conotoxin peptide analog Ia (Arg7-VA-30 kDa-PEG)

(VIa)

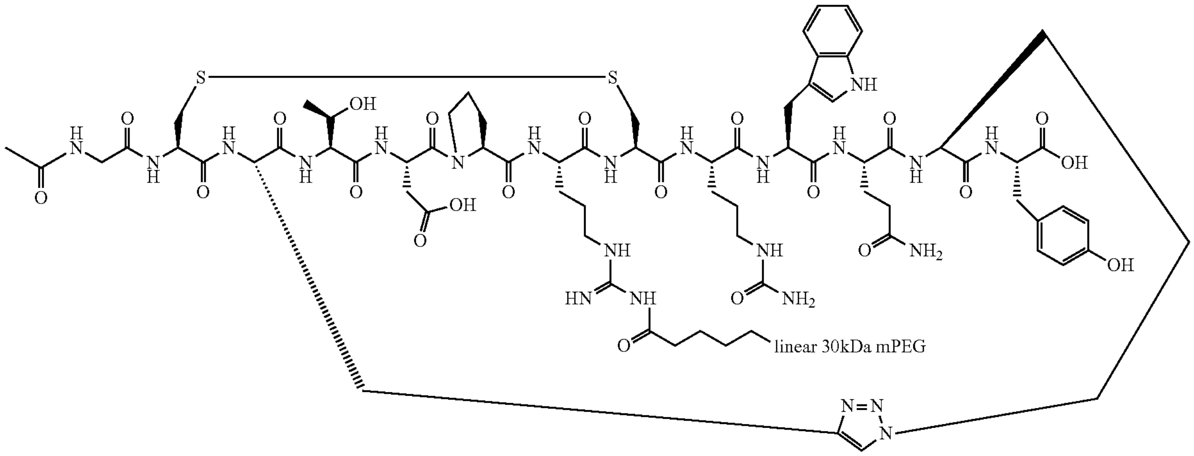

N-terminus N-acetyl conotoxin peptide analog Ia intermediate 14 (15 mg, 9.0 μmot) was dissolved in anhydrous DMF (2.5 mL) followed by addition of a solution of the mPEG-30 kDa-valeric Acid-NHS ester reagent (0.54 g, 18 μmol) in anhydrous DMF (2.5 mL). Then, a solution of DBU (4 μL, 27 μmol) in DMF (0.3 mL) was added. The mixture was heated to 40° C. for 4 h and then the product was purified by HPLC method G (Table 7). Subsequent lyophilization afforded 35 mg of the acetate salt of 7-Arg-PEGylated conotoxin peptide analog VIa (Table 6; 35 mg, 1.1 μmot, 12.2%, TFA salt). Purity 80% (UV 214 nm). The salt exchange was carried out as described for the acetate salt of conotoxin peptide analog Ia to afford the acetate salt of 7-Arg-PEGylated conotoxin peptide analog VIa as a white solid (28 mg, 9.8% overall yield, acetate salt). Purity: 99.1% (UV 214 nm), 81.4% (ELSD). The characterization data for PEGylated conotoxin peptide analog VIa are listed in Table 5 below.

TABLE 5

Characterization Data for PEGylated conotoxin peptide analog Via

| Analysis | Result | Method |
|---|---|---|
| Experimentally Determined Mass | 32102.8 | MALDI-TOF |
| Nitrogen content | 0.55% | C, H, N Combustion Analysis |
| Peptide content | 54.0% (based on calculated MW: 31641.9) | Calculation using nitrogen content in elemental analysis |

TABLE 6

PEGylation reagents

| PEGylation reagent | Structure |
|---|---|
| mPEG-30 kDa-valeric acid-NHS ester<br>average n = 675.<br>Final linker = valeric acid amide ("VA") | 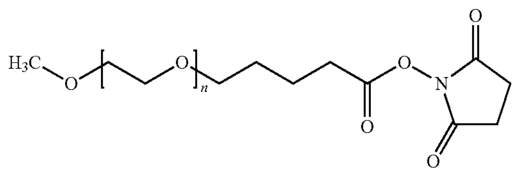 |
| mPEG-30 kDa-butyraldehyde<br>Final linker = butylamine linker ("bAmine")<br>average n = 678 | 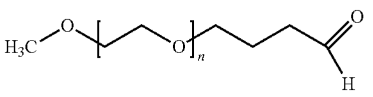 |
| mPEG-30 kDa-propylamine<br>Final linker = propylamide ("pAmide")<br>average n = 678 | 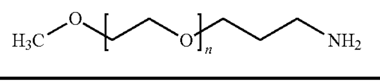 |

The HPLC methods described herein are summarized in Table 7 below.

TABLE 7

Summary of HPLC Methods

| HPLC Method | Description |
|---|---|
| A | UV 214 nm; Column: XBridge Peptide BEH C18, 4.6 × 150 mm, 3.5 μm; Eluent A: 0.05% TFA in water; Eluent B: 0.05% TFA in $CH_3CN$; Time (% B): 0 min (5), 20 min (65); Flow rate: 1.0 mL/min; 40° C. column temperature. |
| B | UV 220 nm; Column: Phenomenex Jupiter, 4.6 × 250 mm, 5 μm, C18, 300 Å; Eluent A: 0.05% TFA in water; Eluent B: 0.05% TFA in $CH_3CN$; Time (% B): 0 min (10), 30 min (70); Flow rate 1.0 mL/min; room temperature. |
| C | UV 220 nm; Column: YMC-Pack-ODS-A, 4.6 × 250 mm, 5 μm, C18, 200 Å; Eluent A: 0.05% TFA in water; Eluent B: 0.05% TFA in $CH_3CN$; Time (% B): 0 min (5), 30 min (65); 1.0 mL/min; room temperature. |
| D | UV 220 nm; Column: Phenomenex Jupiter, 4.6 × 250 mm, 5 μm, C18, 300 Å; Eluent A: 0.05% TFA in water; Eluent B: 0.05% TFA in $CH_3CN$; Time (% B): 0 min (10), 30 min (70); Flow rate 1.0 mL/min; room temperature. |
| E | UV 220 nm; Column: YMC-Pack-ODS-A, 4.6 × 250 mm, 5 μm, C18, 200 Å; Eluent A: 0.05% TFA in water; Eluent B: 0.05% TFA in $CH_3CN$; Time (% B): 0 min (5), 30 min (65); 1.0 mL/min; room temperature. |
| F | UV 215 nm; Column: YMC-Pack-ODS-A, 4.6 × 250 mm, 5 μm, C18, 200 Å; Eluent A: 0.1% TFA in water; Eluent B: 0.1% TFA in $CH_3CN$; Time (% B): 0 min (10), 30 min (40); 1.0 mL/min; room temperature. |
| G | UV 215 nm; Column: XBridge Peptide BEH C18, 19 × 250 mm, 10 μm, 300 Å; Eluent A: 0.05% TFA in water; Eluent B: 0.05% TFA in $CH_3CN$; Time (% B): 0 min (17), 3 min (32), 23 min (42), 28 (95); Flow rate: 25 mL/min; room temperature. |
| H | UV 215 nm; Column: XBridge Peptide BEH C18, 19 × 250 mm, 10 μm, 300 Å; Eluent A: 0.1% AcOH in water; Eluent B: 0.1% AcOH in $CH_3CN$; Time (% B): 0 min (5), 5 min (25), 15 min (80), 20 (95); Flow rate: 20 mL/min; room temperature. |
| I | UV 214 nm and ELSD detection; Column: XBridge Peptide BEH C18, 4.6 × 150 mm, 3.5 μm, 300 Å; Eluent A: 0.05% TFA in water; Eluent B: 0.05% TFA in $CH_3CN$; Time (% B): 0 min (15), 3 min (15), 20 min (75); Flow rate: 1.0 mL/min; 40° C. column temperature. |
| J | UV 215 nm; Column: XBridge Peptide BEH C18, 19 × 250 mm, 10 μm, 130 Å; Eluent A: 0.05% TFA in water; Eluent B: 0.05% TFA in $CH_3CN$; Flow rate: 20.0 mL/min; gradient elution 5 to 100% B; room temperature. |
| K | UV 230 nm; Column: XBridge Peptide BEH C18, 2.1 × 150 mm, 3.5 μm; Eluent A: 0.05% TFA in water; Eluent B: 0.05% TFA in $CH_3CN$; Time (% B): 0 min (5), 8 min (100); Flow rate: 0.3 mL/min; 25° C. column temperature. |

6.4. Stability Analysis

To address disulfide instability in the RgIA derivatives, conotoxin peptide analogs with a disulfide bridge replaced by a triazole bridge were synthesized and were evaluated in human and Sprague Dawley rat plasma and serum.

Reverse phase HPLC analysis of samples from each of the triazole-stabilized conotoxin peptide analogs revealed a single isolated peak consistent with the native conformation of the peptide. For example, FIG. 2A shows that conotoxin peptide analog Ia shows a single isolated peak on reverse phase HPLC in rat plasma at 0 h, 8 h and 24 h. There was no evidence for disulfide rearrangement, suggesting that substitution of one native disulfide bond with a triazole mimetic is adequate to prevent disulfide shuffling of RgIA derivatives in plasma.

In contrast, as shown in the reverse phase HPLC traces of conotoxin peptide analog CSP-4-$NH_2$ in FIG. 2B, a significant portion of conotoxin peptide analog CSP-4-$NH_2$ ("native" form, consisting of two disulfide bonds, one between Cys2 and Cys8, and a second between Cys3 and Cys12) underwent isomerization into a "ribbon" form, containing alternative disulfide bonds Cys2-Cys12 and Cys3-Cys8 and a "bead" form containing alternative Cys2-Cys3 and Cys8-Cys12 disulfide bonds. In plasma and serum samples, conotoxin peptide analog CSP-4-$NH_2$ principally isomerized between the native and ribbon forms, with very little bead formation (FIG. 2B).

6.5. Biological Assays

6.5.1. Two-Electrode Voltage Clamp Method for Rat and Human nAChRs

Example 4.1

Assay:

*Xenopus laevis* oocytes (*Xenopus* 1, MI) were used to heterologously express cloned rat or human nAChR subtypes. Recordings were made 1-5 days post-injection. Briefly, an oocyte was placed in a 100 μL chamber (4 mm diameter 62 mm deep) fabricated from Sylgard and gravity-perfused with ND96 (96 mM NaCl, 1.8 mM $CaCl_2$, 2.0 mM KCl, 1.0 mM $MgCl_2$, 5 mM HEPES, pH 7.1-7.5) at a constant flow rate (2 mL/min). The oocyte's membrane potential was held at −70 mV using a GeneClamp 500 two-electrode voltage clamp amplifier. nAChRs were stimulated with 1-sec pulses of 100 μM acetylcholine (ACh) once every minute and ACh-gated currents were acquired. After a steady baseline of ACh pulses was achieved using ND96, the solution was switched to ND96 containing various compound concentrations and ACh pulses were observed for a blocking response. Responses to ACh of nAChRs after peptide application were calculated as the "% response" of that observed at baseline. Concentration-response curves for inhibition of ACh-gated currents were generated by fitting each oocyte data to the Hill equation: % response=100/{1+([toxin]/$IC_{50}$}$^{nH}$} by non-linear regression analysis and using constraining at bottom equal to 0 and top equal to 100 (GraphPad Prism). Independent concentration response curves were fitted per oocyte and the $IC_{50}$ values were averaged. $IC_{50}$ average values were reported as means±SEM. Two-tailed unpaired t-test was used for significance differences (GraphPad Prism).

Results:

6.5.1.1. Replacement of Disulfide Bridge with a Triazole Bridge Improves Stability and Maintains Adequate Activity on Both Rat and Human nAChRs

TABLE 8

Inhibition of the rat and human α9α10 nicotinic acetylcholine receptors (nAChRs) by conotoxin peptide RgIA and its analogs

| Conotoxin Peptide/Analog | α9α10 nAChR $IC_{50}$ (nM) Rat | Human |
|---|---|---|
| RgIA | 2.4 ± 0.7 | >10,000 |
| CSP-4-OH | 0.9 ± 0.6 | 1.5 ± 0.5 |
| CSP-4-NH2 | 0.4 ± 0.2 | 3.5 ± 1.5 |
| CSP-4-desTyr | NT | 42 ± 0.1 |
| Ia | 14.3 ± 1.8 | 0.7 ± 0.03 |
| Ia' | 12.61 ± 0.08 | 26 ± 4 |
| Ib | 7 ± 0.7 | 37 ± 1.3 |
| Ib' | 2.3 ± 0.5 | 48 ± 9 |
| Ic | 69 ± 8.5 | 152 ± 71 |
| Id | ≥1000 | ≥1000 |
| Ie | 6.6 ± 1.7 | 115 ± 56 |
| If | 12.5 ± 8.7 | 1521 ± 116 |
| Ig | 22 ± 1.1 | 19 ± 1.2 |
| Ih | 8.5 ± 1.1 | 8 ± 1.5 |
| Ii | 1.6 ± 0.6 | 3.4 ± 1.4 |
| Ij | 69 ± 8.5 | 152 ± 71 |
| Ik | 9.5 ± 1.3 | 16.6 ± 1.1 |
| Il | NT | 11 ± 1.4 |
| Im | NT | 50 ± 1.2 |
| In | ≤10 nM | 37 ± 15 |
| Io | ≤10 nM | 59 |
| Ip | ≤10 nM | 26 ± 1.4 |
| Iq | 69 ± 2 | >300 nM |
| Ir | 31 ± 0.7 | ~100 |
| Is | NT | 59 ± 1.7 |
| It | NT | ~100 nM |
| Iu | <30 | ~100 nM |
| Iv | <30 | ~100 nM |
| Iw | 36 ± 9 | >300 |
| Ix | 21 ± 1.4 | 123 ± 22 |

Note:
NT = not tested.

The activities of the conotoxin peptide analogs and the PEGylated conotoxin peptide analogs prepared in Sections 6.2 and 6.3 on both rat and human nAChRs were determined and the results are summarized in Tables 8 and 9 respectively.

As shown in Table 8, CSP-4-NH2 showed nanomolar activities on both rat and human nAChRs ($IC_{50}$; 0.4±0.2 nM on rat α9α10 nAChR and 3.5±1.5 nM on human α9α10 nAChR). Nevetheless, because CSP-4-NH2 has two disulfide bridges (one disulfide bridge between cysteine residues at 2- and 8-positions; another one disulfide bridge between cysteine residues at 3- and 8-positions), CSP-4-NH2 suffered from a disulfide shuffling issue and has poor stability (see FIG. 1A-FIG. 1D and FIG. 2B).

As shown in Table 8, conotoxin peptide analogs Iw and Ix with the 3- and 12-position disulfide bridge replaced by a lactam bridge, did not maintain adequate activities on the human α9α10 nAChR. Conotoxin peptide analogs Iw and Ix showed $IC_{50}$'s of >300 nM and 123±22 nM, respectively. Certain conotoxin peptide analogs that had a triazole bridge formed between a Pra at 3-position and an AzidoNva at 12-position maintained adequate biological activities on the human α9α10 nAChR (e. g., $IC_{50}$<100 nM). For example, the $IC_{50}$'s of conotoxin peptide analogs Ia and Ia' on the human α9α10 nAChR were measured to be 0.7±0.03 nM and 26±4 nM, respectively. The $IC_{50}$'s of conotoxin peptide analogs Ib and Ib' on the human α9α10 nAChR were measured to be 37±1.3 nM and 48±9 nM, respectively. Conotoxin peptide analogs Ia and Ib, with a carboxylic acid at the C-terminus, and conotoxin peptide analogs Ia' and Ib', with an amide group at the C-terminus, maintained adequate activities. Conotoxin peptide analogs Ia and Ib, both of which have an amide group at the C-terminus, each showed lower $IC_{50}$'s than the corresponding conotoxin peptide analog with a carboxylic acid at the C-terminus (Ia vs. Ia' and Ib vs. Ib').

In contrast, conotoxin peptide analogs Ic and Id having a triazole bridge formed between the 2- and 8-positions, did not maintain adequate activity on the human α9α10 nAChR. The $IC_{50}$'s of conotoxin peptide analogs Ic and Id were measured to be 152±71 nM and ≥1000 nM, respectively. Also in contrast, conotoxin peptide analogs If and Ij having a triazole bridge formed between the 3- and 12-positions, but having a triazole bridge formed from a Pra or an AzidoAla, respectively, at the 12-position did not maintain adequate activity on the human α9α10 nAChR. The $IC_{50}$'s of conotoxin peptide analogs If and Ij were measured to be 1521±116 nM and 152±71 nM, respectively.

Deletion of the terminal amino acid of RgIA and replacement with an amide (Cys12-amide) has previously been demonstrated to have no substantial impact on binding of the peptide to the rat α9α10 nAChR (Ellison et al, 2008, J. Mol. Biol. 377:1216-1227; Armishaw, 2010, Toxins 2:1471-1499; US 20120220539 A 1). Further, other alpha-conotoxins such as Vc1.1 and ImI do not have an amino acid at position 13 (see FIG. 4), suggesting that this residue would not be essential for channel binding.

However, C-terminal amino acid deletion or replacement was found unexpectedly to affect human α9α10 nAChR potency in the context of conotoxin peptide analog Ia. Specifically, as shown in Table 8, when the Tyr at the 13-position was replaced with a Phe (conotoxin peptide analog Il) or D-Tyr (conotoxin peptide analog Im), the potency was reduced. The $IC_{50}$'s of conotoxin peptide analogs Il and Im were measured to be 11±1.4 nM and 50±1.2 nM, respectively. In contrast, when the Tyr at the 13-position was deleted (conotoxin peptide analog Iq), replaced by an N-Me-Tyr (conotoxin peptide analog Ir), replaced by a D-Arg (conotoxin peptide analog Is), replaced by an N-Me-D-Tyr (conotoxin peptide analog It), replaced by a beta-Tyr (conotoxin peptide analog Iu) or replaced by N-Me-Arg (conotoxin peptide analog Iv), it afforded conotoxin peptide analogs with lower potencies on the human α9α10 nAChR.

The impact of deletion of the amino acid residue at the 13-position of conotoxin peptide analogs with a triazole bridge formed between the 3- and 12-positions on their potency on the human α9α10 nAChR was evaluated relative to the impact of deletion of the 13-position residue of CSP-4-OH (the corresponding conotoxin peptide analog with a disulfide bridge between the 3- and 12-positions). Unexpectedly, with respect to CSP-4-OH (Cys3,12 disulfide bridge), deletion of Tyr at 13-position was found to result in a greater than 20-fold reduction in binding affinity for the human α9α10 nAChr (FIG. 5A). However, with respect to conotoxin peptide analog 1a (replacement with a triazole bridge between 3- and 12-position), deletion of amino acid 13 resulted in an approximately 10-fold loss in activity on the rat channel and a greater than 100-fold loss of activity on the human channel (conotoxin peptide analogs 1a vs 1q) (Table 8, FIG. 5B). These data showed that deletion of an amino acid at C-terminus (position 13) decreased the activities of conotoxin peptide analogs with a triazole bridge between the 3- and 12-positions, but not for those with a disulfide bridge between the 3- and 12-positions. These data suggested that interactions throughout loop 2 and the carboxy-terminus of the peptide are important for determining human channel potency in the context of a stabilized disulfide mimetic and that changes to the secondary structure of loop 2 and the carboxy terminus create unpredictable interactions between conotoxin peptide RgIA analogs and the α9α10 nAChR.

Moreover, addition of one additional amino acid to C-terminus of conotoxin peptide analog Ia (e.g., an N-Me-Gly, D-Tyr, or N-Me-Tyr) to afford conotoxin peptide analogs In, Io, and Ip of 14 residues maintained potency on the human α9α10 nAChR. As illustrated in Table 8, for example, the $IC_{50}$'s of conotoxin peptide analogs In (additional an N-Me-Gly at the 14-position compared to Ia), Io (additional a D-Tyr at the 14-position compared to Ia) and Ip (additional an N-Me-Tyr at the 14-position compared to Ia) were measured to be 37±15 nM, 59 nM and 26±1.4 nM, respectively.

Channel binding selectivity: in an evaluation of potential off-target effects involving 88 receptors, transporters, enzymes and kinases, triazole-containing conotoxin peptide analogs Ia' and Ib' demonstrated no off-target effects at 10 μM, except for partial inhibition (52% and 56%, respectively) of the α7 nAChR. In this respect, triazole bridge replacement of disulfide bridge in conotoxin peptide RgIA did not significantly alter the selectivity of the conotoxin peptide analogs. 6.5.1.2. PEGylation of conotoxin peptide analog Ia at the N-terminus unexpectedly retains adequate activity on both rat and human nAChRs The addition of a 30 kDa valerate-linear PEG (N-terminal acylation) to the N-terminus of conotoxin peptide analog Ia resulted in PEGylated conotoxin peptide analog IIa. When evaluated in its activity against the human and rat nAChRs, PEGylated conotoxin peptide analog IIa produced similar blockade on the rat and human α9α10 nAChRs (FIG. 6A and FIG. 6B) with low nanomolar potencies. On the human α9α10 nAChR, PEGylated conotoxin peptide analog IIa resulted in nearly identical $IC_{50}$ (Table 9; 0.7±0.1 nM) to the unconjugated conotoxin peptide analog Ia (0.7±0.03 nM). In contrast to the literature teaching that PEGyation would potentially create a structural constraint resulting in a reduction of peptide binding potency to rodent and human channels (Fishburn, 2008, J. Pharm. Sci. 97:4167-4183; Parrott and DeSimone, 2011, Nat. Chem. 4:13-14), the PEGyated conotoxin peptide analog IIa with an about 18.5-fold molecular weight increase by the attachment to the PEG polymer unexpectedly retained the potency of conotoxin peptide Ia (0.7±0.1 nM on human α9α10 nAChR)

TABLE 9

Inhibition of the rat and human α9α10 nicotinic acetylcholine receptors (nAChRs) by conotoxin peptide analog Ia and its PEGylated conotoxin peptide analogs IIa, IIIa, IVa, Va and VIa

| Conotoxin | α9α10 nAChR $IC_{50}$ (nM) | |
|---|---|---|
| Peptide/Analog | Rat | Human |
| RgIA | 2.4 ± 0.7 | >10,000 |
| CSP-4-OH | 1.5 ± 0.5 | 0.9 ± 0.6 |
| CSP-4-NH2 | 0.4 ± 0.2 | 3.5 ± 1.5 |
| Ia | 14.3 ± 1.8 | 0.7 ± 0.03 |
| Ia' | 7.7 ± 0.7 | 26 ± 4 |
| IIa | NT | 0.7 ± 0.1 |
| IVa | NT | 100 |
| Va | NT | ~300 |
| VIa | NT | 300 |

Note:
NT = not tested.

The impact of PEGylation at different attachment positions was evaluated by testing the activities of PEGylated conotoxin peptide analogs Va (in which a linear mPEG polymer is covalently attached to the C-terminus of conotoxin peptide analog Ia) and VIa (in which a linear mPEG polymer is covalently attached to the Arginine at the 7-position of conotoxin peptide analog Ia) against the human α9α10 nAChR. Substantially higher $IC_{50}$ against the human nAChR was observed for both PEGylated conotoxin peptide analogs Va ($IC_{50}$=~300 nM) and VIa ($IC_{50}$=300 nM), compared to that of PEGylated conotoxin peptide analogs IIa ($IC_{50}$=0.7±0.1 nM), which has a linear mPEG polymer covalently attached to the N-terminus of conotoxin peptide analog Ia. Conjugating to the PEG at the C-terminus (Va) or at position 7 (VIa) of conotoxin peptide analog Ia did not afford PEGylated conotoxin peptide analogs with adequate activities.

The potency of a PEGylated conotoxin peptide analog with a different linker was also studied. The activity of the PEGylated conotoxin peptide analog IVa, with a linear mPEG polymer attached to the N-terminus of conotoxin peptide analog Ia via a butylene linker) against the human α9α10 nAChR was tested. As shown in Table 9, the $IC_{50}$ of PEGylated conotoxin peptide analog IVa was more than 100-fold higher ($IC_{50}$=~100 nM) than that of PEGylated conotoxin peptide analogs IIa ($IC_{50}$=0.7±0.1 nM), in which the PEG polymer is attached to the N-terminus of the peptide (conotoxin peptide analog Ia) via a valerate linker. These results illustrated that the choice of linker type and of the position on the peptide to which the PEG polymer is attached can be crucial to the PEGylation derivatization of conotoxin peptide analog Ia for retaining its potency against the human α9α10 nAChR. Unexpectedly, the PEGylated conotoxin peptide analog IIa, with a 30 kDa linear mPEG covalently attached to the N-terminus of conotoxin peptide analog Ia via a valerate linker was found to be the optimal PEGylated conotoxin peptide analog.

A similar unexpected result was also demonstrated with PEGylated CSP-4-NH2. With the addition of a 30 KDa PEG to the N-terminus of CSP-4-NH2 via a valerate linker, the resulting PEGylated conotoxin peptide analog XI (linear 30 kDa mPEG-VA-CSP-4-NH2) maintained low nanomolar potency on the rat α9α10 nAChR ($IC_{50}$=6.0±0.1 nM), suggesting that the N-termini of these peptides are permissive to the addition of bulky molecules without significantly altering their in vitro biological potency.

6.5.2. Pharmacokinetics Studies of Conotoxin Peptide Analogs and PEGylated Conotoxin Peptide Analogs in Rats Pharmacokinetics Studies of Conotoxin Peptide Analog Ia in rats: conotoxin peptide analog Ia was injected intravenously or subcutaneously in 10-week-old male Sprague Dawley rats (n=3 per group) at 1 mg/kg in vehicle (10 mM sodium phosphate, 0.8% sodium chloride, 0.05% Tween 20, pH 6.0). Blood was collected at various time points (pre-dose and from 0.083 to 24 hours post dose) via tail vein into $K_2$EDTA collection tubes, centrifuged and plasma was stored at −60 to −90° C. until analysis. The concentrations of conotoxin peptide analog 1a were determined using a peptide specific LC-MS/MS assay as described below. Raw data were generated and plotted using a nonlinear regression with a sigmoidal dose-response (variable slope) with GraphPad Prism. Pharmacokinetic parameters were calculated using PKSolver 2.0 software.

LC-MS/MS analysis for conotoxin peptide analog 1a plasma PK samples: conotoxin peptide analog 1a sample analyses were carried out with a Shimadzu liquid chromatography system (Shimadzu UFLC-XR) and an AB Sciex API 5000 triple quadrupole tandem mass spectrometer. The HPLC system consisted of Shimadzu liquid chromatography system equipped with two LC-20AC XR pumps, a CBM-20A Communication Module, a SIL-20AC XR auto-sampler, a CTO-20A Column Thermostat and in-line SPD-20A UV detector. Chromatographic separation was carried out on a Thermo Scientific Fluophase PFP column (2.1×50 mm, 5 μm, 100 Å) at 40° C. The mobile phase A was water with 0.05% acetic acid and mobile phase B was acetonitrile with 0.05% acetic acid. At a flow rate of 0.3 mL/min, a linear gradient of B (5%-90%) was applied over 0-6 min, then 90% over 6.0-7.8 min, and then returned to 5% B for 2 min for column equilibration. The samples were kept at 4° C. in the auto-sampler and a volume of 5 μL was injected onto the HPLC system for each analysis.

Mass spectrometric detection was performed on a triple quadrupole tandem mass spectrometer API 5000) equipped with a turbo ion spray source operated in the negative ionization mode. The MS operating conditions were optimized as follows: The ion spray voltage was set at −4500 KV and the source temperature was maintained at 500° C.; The collision energy was set at −35V. Nitrogen was used as the collision gas. The flow rates of the curtain gas, ion source gas1 and gas2 were set at 10, 40 and 40 L/min, respectively. The operation of the LC-MS/MS and data analysis were performed using the Analyst 2.1 software (AB Sciex). Quantification data was obtained by using multiple reaction monitoring (MRM) mode of conotoxin peptide analog Ia transition at m/z 809.0/792.5.

A standard curve of conotoxin peptide analog Ia (10-5000 ng/mL) was made in $K_2$EDTA rat plasma (Bioreclamation) from a 1.0 mg/mL stock solution of accurately weighed, purity corrected peptide in DMSO using a HP D300 Digital Dispenser (Tecan). 50 μL of PK sample plasma, conotoxin peptide analog Ia standards, and conotoxin peptide analog Ia QC samples were aliquoted onto a Phree Phospholipid Removal Plate (Phenomenex), treated with 450 μL of methanol (1:10 dilution) and thoroughly mixed. Samples were then filtered through the Phree Plate into 96-deep-well sample plate with a vacuum manifold and analyzed using the LC-MS/MS methods described. The concentration of conotoxin peptide analog Ia was derived from the standard curve using one parameter nonlinear regression with AB-Sciex MultiQuant software, and PK parameters were calculated using PKSolver 2.0 software.

Pharmacokinetics (PK) studies of PEGylated conotoxin peptide analog IIa in rats: PEGylated conotoxin peptide analog IIa was injected intravenously ("IV") or subcutaneously ("SC") in 10-week-old male Sprague Dawley rats (n=3 per group) at 1 mg/kg (core peptide content, ~19 mg/kg PEGylated peptide content) in vehicle (10 mM sodium phosphate, 0.8% sodium chloride, 0.05% Tween 20, pH 6.0). Blood was collected at various time points (pre-dose and from 0.083-120 h post dose) via tail vein into $K_2$EDTA collection tubes, centrifuged and plasma was stored at −60 to −90° C. until analysis. Amount of conotoxin peptide analog IIa was quantified by a PEG-conjugate specific ELISA assay as described below. Derived plasma concentrations (net peptide) were generated using a nonlinear regression with a sigmoidal dose-response (variable slope) with GraphPad Prism. PK parameters were calculated using PKSolver 2.0 software.

ELISA antibodies, reagents and methods for PEGylated conotoxin peptide analog IIa PK sample analysis: Rabbit polyclonal anti-conopeptide capture antibodies were generated by immunizing naïve NZW rabbits with conotoxin peptide analog Ia conjugated to a KLH carrier protein and boosted with conotoxin peptide analog Ia. Polyclonal IgG antibodies were then purified from immune serum using an affinity Protein G Sepharose (GE Healthcare Life Sciences) gravity column followed by polishing and buffer exchange on a 16/600 Superdex 75 pG Size-Exclusion Chromatography (SEC) column (GE Healthcare Life Sciences) using PBS as the mobile phase. SEC fractions containing purified antibody were pooled and concentrations were calculated by bicinchoninic acid assay (BCA assay). The purified polyclonal antibodies have demonstrated cross reactivity to recognize conotoxin peptide analog Ia and conotoxin peptide analog IIa. The microtiter plate wells were coated with 50 μL per well of capture antibody (Purified anti-conotoxin peptide analog Ia 7626R pAb, Lot #26R-1-D54-0618, 5 μg/mL) in coating buffer (0.1M NaHCO3 pH 9.6) for 12 h at 4° C. or at 37° C. with shaking for 1 h and then blocked with 200 μL per well of 5% BSA in PBS for 2 h at room temperature. Plasma samples, QC samples and standards (50 μL) were loaded in duplicate and incubated for 1.5-2 h at room temperature with shaking, followed by the addition of 50 μL per well of anti-PEG antibody (1 ug/mL) in diluent buffer (0.5% BSA in PBS) for an additional 1 h at room temperature with shaking. 50 per well of streptavidin HRP diluted 1:200 in diluent buffer was added to the plate and incubated for 1 h at room temperature with shaking, followed by the addition of 50 μL of the chromogenic substrate (TMB) which was incubated at room temperature for 5-6 min. The reaction was stopped with 100 μL $H_2SO_4$ and absorbance at 450 nm was measured using ELISA plate reader. Plates were washed 3 times with washing buffer (PBST, pH 7.4, containing 0.1% (v/v) Tween 20) then 3-6 times with PBS after each step. As a reference for quantification, a standard curve was established by a serial dilution of PEGlyated conotoxin peptide analog IIa in 10% $K_2$EDTA plasma (rat or monkey) (400 ng/mL-0.06 ng/mL, weight based on core peptide content). The amount of PEGyated conotoxin peptide analog IIa in each sample was quantified by extrapolating the signal of the sample into the linear range (signal vs concentration) of the standard curve.

Results: As discussed below, PEGylation of conotoxin peptide analog Ia was shown to prolong its circulation time.

The pharmacokinetic profile of PEGylated conotoxin peptide IIa was evaluated in rats and compared to the PK profile and clearance of conotoxin peptide analog Ia. Plots of mean concentrations of conotoxin peptide analog Ia and PEGylated conotoxin peptide IIa vs. time in plasma following a single 1 mg/kg IV or SC dose are shown in FIG. 7A and FIG. 7B. Two enhancements due to PEGylation were clear when comparing the PEG-conjugate PK profile to the profile of the unconjugated conotoxin peptide analog Ia alone: (i) the half-life of conotoxin peptide analog Ia was substantially increased by the addition of a PEG group, and (ii) the total exposure of PEGylated conotoxin peptide IIa was much greater than that for unconjugated conotoxin peptide analog Ia. For SC administered compounds, the elimination half-life of PEGylated conotoxin peptide IIa was approximately 42-times greater than the unconjugated conotoxin peptide analog Ia (21 h vs 0.5 h respectively). The Cmax and AUC for PEGylated conotoxin peptide IIa were also improved, with the Cmax of PEGylated conotoxin peptide IIa being nearly four-fold that of the unconjugated conotoxin peptide analog Ia and the AUC for PEGylated conotoxin peptide IIa being nearly 140-times greater than the AUC for conotoxin peptide analog Ia (Cmax: PEGylated conotoxin peptide IIa: 2518 ng/mL; conotoxin peptide analog Ia: 648 ng/mL) ($AUC_{0-t}$: PEGylated conotoxin peptide IIa: 137729 ng/mL*hr; conotoxin peptide analog Ia: 981 ng/mL*hr). Pharmacokinetics (PK) and pharmacodynamics (PD) parameters for conotoxin peptide analog Ia: and PEGylated conotoxin peptide IIa in rats are shown in Table 10 below.

TABLE 10

Pharmacokinetics (PK) and pharmacodynamics (PD) parameters for conotoxin peptide analog Ia: and PEGylated conotoxin peptide IIa in rats

| Parameter | Conotoxin peptide analog Ia | PEGylated Conotoxin peptide analog IIa |
|---|---|---|
| In vitro potency (TEVC Human α9α10) | 0.7 nM | 0.7 nM |
| PK (Rat, SC - 1 mg/kg) Cmax | 648 ng/ml | 2518 ng/ml |
| PK (Rat, SC - 1 mg/kg) Clast | 20 ng/ml | 166 ng/ml |
| PK (Rat, SC - 1 mg/kg) Tmax | 0.25 h | 24 h |
| PK (Rat, SC - 1 mg/kg) Tlast | 3 h | 120 h |
| PK (Rat, SC - 1 mg/kg) AUC | 981 ng/mL*h | 137729 ng/mL*h |
| PK (Rat, SC - 1 mg/kg) T½ | 0.5 h | 21 h |
| PD (Rat CIPN) Required dose to reach max efficacy | 0.5 mg/kg (net peptide) | 0.5 mg/kg (net peptide) |
| PD (Rat CIPN) Duration of PD effect | 4-24 h | 48-72 h |
| Metabolic stability (Rat SC dose, % intact peptide remaining at Tmax relative to loss of Tyr13) | 66% (percent intact peptide at 0.25 h) | 82% (percent intact peptide at 104 h) |

The enhancement of PK profile by PEGylation of conotoxin peptide analog Ia was also observed in monkeys. Male cynomolgus macaque monkeys were administered PEGylated conotoxin peptide IIa at 1 mg/kg (net peptide concentration) IV and SC for a PK study. After IV administration, the PEGylated conotoxin peptide IIa highest exposure was at 0.083 h post-dose with a Cmax of 42,200 ng/mL and decreased to 109 ng/mL at 168 h post-dose. The AUC was 603,594 ng/ml*h. After SC administration, the PEGylated conotoxin peptide IIa highest exposure was at 24 h post-dose with a Cmax of 7,867 ng/mL and decreased to 216 ng/mL at 168 h post-dose. The AUC was 453,077 ng/ml*h and the bioavailability of PEGylated conotoxin peptide IIa after SC dosing was 75%. PK profiles and parameters for PEGylated conotoxin peptide IIa in monkeys are shown in FIG. 8 and Table 11.

TABLE 11

Pharmacokinetic parameters of PEGylated conotoxin peptide IIa after a single 1 mg/kg dose administration (IV or SC) in monkeys

| Parameter | | Unit | PEGylated conotoxin peptide IIa 1 mg/kg IV | PEGylated conotoxin peptide IIa 1 mg/kg SC |
|---|---|---|---|---|
| Peak plasma concentration | $C_{max}$ | ng/mL | 41764 | 7867 |
| Last plasma concentration | $C_{last}$ | ng/mL | 109 | 101 |
| Time of peak plasma concentration | $T_{max}$ | h | 0.083 | 24 |
| Time of last plasma concentration | $T_{last}$ | h | 168 | 216 |
| Elimination half life | $T_{1/2}$ | h | 28.3 | 29.8 |
| Area under the curve | $AUC_{0-t}$ | ng/mL*h | 599144 | 448716 |
| AUC extrapolated to infinity | $AUC_{0-inf\ obs}$ | ng/mL*h | 448716 | 453077 |
| Bioavailability | F | % | NT | 87 |

Note:
NT = not tested.

6.5.3. Analgesic Activity in Animal Pain Models

The chronic constriction injury (CCI) model is a model of mononeuropathy induced by ligation to the sciatic nerve (Bennett and Xie, 1988, Pain, 33(1):87-107). Damage to the peripheral nerves is involved, with infiltration by mast cells, granulocytes, macrophages and T lymphocytes. These cells, via secretion of inflammatory mediators (e.g. proinflammatory cytokines and chemokines), can contribute to the generation and maintenance of neuropathic pain. The CCI is one of the common models for peripheral nerve injury.

Assay: male Sprague Dawley rats were anesthetized in an induction chamber using 5% Isoflurane (O2 at 1 L/min) on Day 0. Once the appropriate anesthetic plane had been reached, a constant flow of isoflurane at a maintenance level of 3% was administered by nose cone. A 2 cm skin incision was made on the left hind leg parallel to the femur. The sciatic nerve was exposed, and proximal to the trifurcation of the sciatic nerve, four loose ligatures of 4-0 chromic gut were tied approximately 1 mm apart. The muscle and skin were closed, and animals were allowed to recover. Beginning on the day of surgery and daily for 14 days thereafter, 0.1 mg/kg of conotoxin peptide analog 1b' was administered in a vehicle composed of 10 mM sodium phosphate, 0.8% NaCl, 0.05% tween 20 by subcutaneous injection.

Results: Data from animals treated with conotoxin peptide analog 1b' were compared to animals treated with vehicle control. Mechanical hyperalgesia was measured in the left hind paw (n=3 times) using an Ugo Basile Analgesimeter 7 and 14 days post-surgery. Statistical analysis was performed by two-way ANOVA. As shown in FIG. 9, daily treatment with 0.1 mg/kg conotoxin peptide analog 1b' resulted in a statistically significant improvement in paw withdrawal thresholds relative to vehicle-treated control animals on both measurement days. These data indicated that a triazole-substituted RgIA analog effectively treated neuropathic pain in the rat CCI model.

6.5.4. Chemotherapy Induced Peripheral Neuropathy Model

Assay: Chemotherapy induced peripheral neuropathy (CIPN) is common in patients undergoing chemotherapy with platinum salts. Chemotherapy induced neuropathy in male Sprague Dawley rats was induced by treatment with 2.4 mg/kg intravenous (i.v.) oxaliplatin twice per week for 3 weeks (6 i.v. injections). The nociceptive thresholds in rats were determined with an analgesimeter (Ugo Basile, Varese, Italy). Briefly, a constantly increasing pressure was applied to a small area of the dorsal surface of the hind paw using a blunt conical probe. Mechanical pressure was increased until vocalization or a withdrawal reflex occurred. Vocalization or withdrawal reflex thresholds were expressed in grams. For analgesia measures, mechanical pressure application was stopped at 120 g. Throughout the study period, experimenters were blinded as to the identity of the injected compounds. Data were analyzed with one-way ANOVA using Dunnett's multiple comparison test (GraphPad Prism). Neuropathic pain was measured on day 14 following administration of a single subcutaneous dose (e.g., 0.5 mg/kg) of conotoxin peptide analog.

6.5.4.1. Evaluation of PEGylated Conotoxin Peptide Analog Derivatives with Different PEG Polymers Different PEGylated derivates of CSP-4-NH2 were prepared, including linear 20 kDa mPEG-VA-CSP-4-NH2 (PEGylated conotoxin peptide analog VII, Formula (VII), SEQ ID NO:87), linear 20 kDa mPEG-bAmine-CSP-4-NH2 (PEGylated conotoxin peptide analog VIII, Formula (VIII), SEQ ID NO:88), branched 2×10 kDa mPEG-amine-CSP-4-NH2 (PEGylated conotoxin peptide analog IX, Formula (IX), SEQ ID NO:89), branched 2×10 kDa mPEG-carbonate-CSP-4-NH2 (PEGylated conotoxin peptide analog X, Formula (X), SEQ ID NO:90), linear 30 kDa mPEG-VA-CSP-4-NH2 (PEGylated conotoxin peptide analog XI, Formula (XI), SEQ ID NO:91), and linear 40 kDa mPEG-VA-CSP-4-NH2 (PEGylated conotoxin peptide analog XII, Formula (XII), SEQ ID NO:92).

(VII)

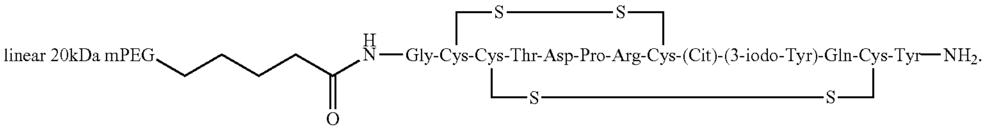

(VIII)

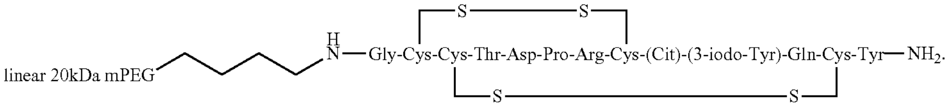

(IX)

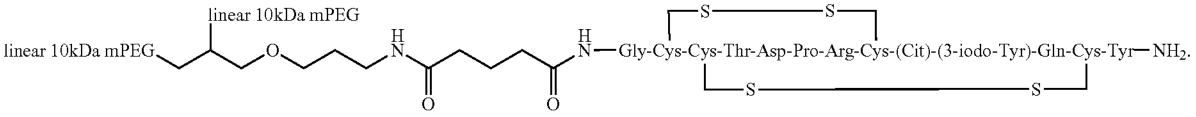

(X)

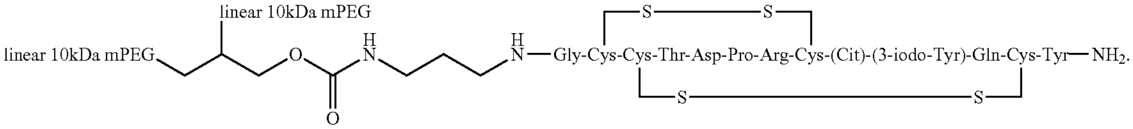

(XI)

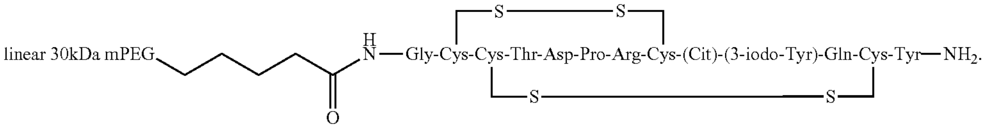

(XII)

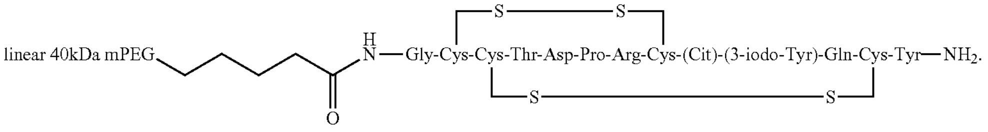

The duration of analgesic effect of various PEGylated derivatives of CSP-4-NH2 in the rat CIPN model were evaluated. The PEGylated derivatives tested varied in size (from 20 kDa to 40 kDa) and configuration (covalently attached to linear or branched PEG polymers). Analgesic efficacy and duration of the pharmacodynamic effect was determined in the rat CIPN model after a single 500 μg/kg subcutaneous dose of CSP-4-NH2, PEGylated conotoxins VII, VIII, IX, X, XI and XII. Analgesic efficacy was tested 30 min, 5 h, 24 h, 48 h, 72 h and 96 h after dosing. Mechanical hyperalgesia was measured by Randall-Selitto test. Pain thresholds decreased over time after IV administration of oxaliplatin twice a week, with mechanical hyperalgesia being significantly induced by day 7 post Oxaliplatin dosing and continuing to increase by day 14. The efficacy of CSP-4-NH2 and PEG-derivatives of CSP-4-NH2 in reducing mechanical hyperalgesia was tested on Day 14. Randall Selitto mechanical hyperalgesia measurements reached pre-chemotherapy levels from 0.5-5 h following drug administration. The duration of analgesic efficacy increased as the molecular weight of the added PEG increased up to a 30 kDa linear PEG. The duration of efficacy of PEGylated CSP-4-NH2 using the n-butyl linker (VIII) was significantly shorter than the duration of efficacy of PEGylated CSP-4-NH2 via the valeric acid linker (VII), (XI), (XII) (FIGS. 10A-10C). There was no additional benefit obtained by conjugation with a PEG molecule larger than a 30 kDa linear PEG (XII) or with a branched chain PEG (IX and X) (FIG. 10C).

6.5.4.2. Evaluation of Efficacy of Conotoxin Peptide Analogs Ia and Ia' and PEGylated Conotoxin Peptide Analog IIa As shown in FIG. 11A, a single subcutaneous dose (0.5 mg/kg) of conotoxin peptide analog Ia' resulted in statistically significant improvements in mechanical hyperalgesia at 0.5 h, 4 h and 24 h post-dose. As shown in FIG. 11B, single subcutaneous injection of conotoxin peptide analog Ia' resulted in a statistically significant improvement in mechanical hyperalgesia at 0.5 h, 4 h and 24 h post-dose relative to vehicle treated animals. FIG. 11C shows administration of a single 0.5 mg/kg dose of conotoxin peptide analog Ia or PEGylated conotoxin peptide analog IIa to rats 14 days following induction of oxaliplatin-induced peripheral neuropathy resulted in a significant reduction in mechanical hyperalgesia (up to 4 h for Ia or up to 48 h for IIa). These data further indicated the therapeutic potential for treating or preventing neuropathic pain with these triazole stabilized RgIA derivatives.

7. INCORPORATION BY REFERENCE

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A PEGylated conotoxin peptide analog or pharmaceutically acceptable salt thereof, wherein the conotoxin peptide analog is of Formula (Ia) (SEQ ID NO:94)

(Ia)

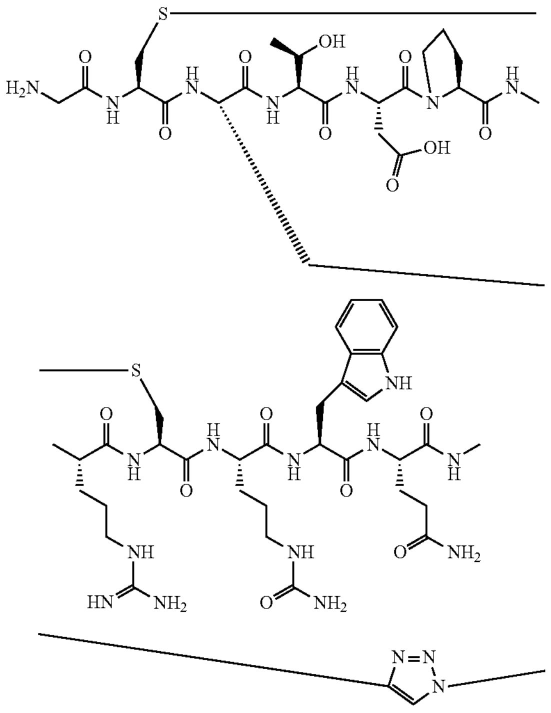

-continued

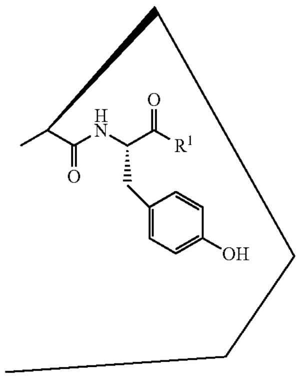

, wherein $R^1$ is OH, wherein the conotoxin peptide analog is covalently attached directly or via a linking group to one polyethylene glycol (PEG) polymer;

wherein the PEG polymer is covalently attached to the N-terminus of the conotoxin peptide analog; and wherein the PEG polymer has a molecular weight in the range of 10 kDa to 40 kDa.

2. The PEGylated conotoxin peptide analog or pharmaceutically acceptable salt of claim 1, wherein the PEG polymer is covalently attached to the conotoxin peptide analog via a linking group.

3. The PEGylated conotoxin peptide analog or pharmaceutically acceptable salt of claim 2, wherein the linking group is a valerate linker having a formula of

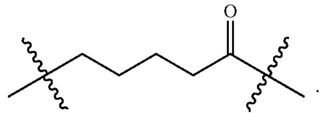 [SMILES: *CCCCC(*)=O]

4. The PEGylated conotoxin peptide analog or pharmaceutically acceptable salt of claim 1, wherein the PEG polymer is a linear PEG polymer.

5. The PEGylated conotoxin peptide analog or pharmaceutically acceptable salt of claim 1, wherein the PEG polymer has a molecular weight of 30 kDa.

6. The PEGylated conotoxin peptide analog or pharmaceutically acceptable salt of claim 5, wherein the PEG polymer is a linear PEG polymer.

7. The PEGylated conotoxin peptide analog or pharmaceutically acceptable salt of claim 1, wherein the PEGylated conotoxin peptide analog is of Formula (IIa) (SEQ ID NO:83):

(IIa)

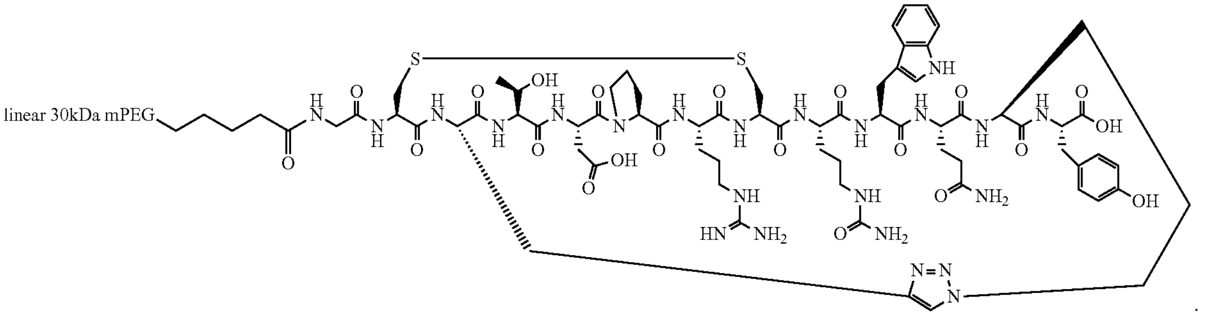

8. A pharmaceutical composition comprising the PEGylated conotoxin peptide analog or pharmaceutically acceptable salt of claim 7, and a pharmaceutically acceptable carrier.

9. A method of treating pain in a subject comprising administering to the subject a therapeutically effective amount of the PEGylated conotoxin peptide analog or pharmaceutically acceptable salt of claim 7.

10. A pharmaceutical composition comprising the PEGylated conotoxin peptide analog or pharmaceutically acceptable salt of claim 1, and a pharmaceutically acceptable carrier.

11. A method of treating pain in a subject comprising administering to the subject a therapeutically effective amount of the PEGylated conotoxin peptide analog or pharmaceutically acceptable salt of claim 1.

12. A pharmaceutical composition comprising the PEGylated conotoxin peptide analog or pharmaceutically acceptable salt of claim 2, and a pharmaceutically acceptable carrier.

13. A method of treating pain in a subject comprising administering to the subject a therapeutically effective amount of the PEGylated conotoxin peptide analog or pharmaceutically acceptable salt of claim 2.

14. A pharmaceutical composition comprising the PEGylated conotoxin peptide analog or pharmaceutically acceptable salt of claim 3, and a pharmaceutically acceptable carrier.

15. A pharmaceutical composition comprising the PEGylated conotoxin peptide analog or pharmaceutically acceptable salt of claim 4, and a pharmaceutically acceptable carrier.

16. A pharmaceutical composition comprising the PEGylated conotoxin peptide analog or pharmaceutically acceptable salt of claim 5, and a pharmaceutically acceptable carrier.

17. A pharmaceutical composition comprising the PEGylated conotoxin peptide analog or pharmaceutically acceptable salt of claim 6, and a pharmaceutically acceptable carrier.

18. A method of treating pain in a subject comprising administering to the subject a therapeutically effective amount of the PEGylated conotoxin peptide analog or pharmaceutically acceptable salt of claim 3.

19. A method of treating pain in a subject comprising administering to the subject a therapeutically effective amount of the PEGylated conotoxin peptide analog or pharmaceutically acceptable salt of claim 4.

20. A method of treating pain in a subject comprising administering to the subject a therapeutically effective amount of the PEGylated conotoxin peptide analog or pharmaceutically acceptable salt of claim 5.

21. A method of treating pain in a subject comprising administering to the subject a therapeutically effective amount of the PEGylated conotoxin peptide analog or pharmaceutically acceptable salt of claim 6.

22. A method of treating inflammation in a subject comprising administering to the subject a therapeutically effective amount of the PEGylated conotoxin peptide analog or pharmaceutically acceptable salt of claim 1.

23. A method of treating inflammation in a subject comprising administering to the subject a therapeutically effective amount of the PEGylated conotoxin peptide analog or pharmaceutically acceptable salt of claim 7.

24. A method of treating inflammation in a subject comprising administering to the subject a therapeutically effective amount of the PEGylated conotoxin peptide analog or pharmaceutically acceptable salt of claim 2.

25. A method of treating inflammation in a subject comprising administering to the subject a therapeutically effective amount of the PEGylated conotoxin peptide analog or pharmaceutically acceptable salt of claim 3.

26. A method of treating inflammation in a subject comprising administering to the subject a therapeutically effective amount of the PEGylated conotoxin peptide analog or pharmaceutically acceptable salt of claim 4.

27. A method of treating inflammation in a subject comprising administering to the subject a therapeutically effective amount of the PEGylated conotoxin peptide analog or pharmaceutically acceptable salt of claim 5.

28. A method of treating inflammation in a subject comprising administering to the subject a therapeutically effective amount of the PEGylated conotoxin peptide analog or pharmaceutically acceptable salt of claim 6.

* * * * *